(12) United States Patent
Wong et al.

(10) Patent No.: US 9,981,030 B2
(45) Date of Patent: May 29, 2018

(54) GLYCAN CONJUGATES AND USE THEREOF

(71) Applicant: ACADEMIA SINICA, Taipei (TW)

(72) Inventors: Chi-Huey Wong, Rancho Santa Fe, CA (US); Chung-Yi Wu, New Taipei (TW); Chia-Hung Wang, Hsinchu (TW); Shiou-Ting Li, Kouhu Township (TW)

(73) Assignee: Academia Sinica, Taipei (TW)

( * ) Notice: Subject to any disclaimer, the term of this patent is extended or adjusted under 35 U.S.C. 154(b) by 100 days.

(21) Appl. No.: 14/392,333

(22) PCT Filed: Jun. 27, 2014

(86) PCT No.: PCT/US2014/044740
§ 371 (c)(1),
(2) Date: Dec. 23, 2015

(87) PCT Pub. No.: WO2014/210564
PCT Pub. Date: Dec. 31, 2014

(65) Prior Publication Data
US 2016/0175421 A1    Jun. 23, 2016

Related U.S. Application Data

(60) Provisional application No. 61/840,324, filed on Jun. 27, 2013.

(51) Int. Cl.
| | |
|---|---|
| *A61K 31/715* | (2006.01) |
| *C08B 37/00* | (2006.01) |
| *A61K 39/095* | (2006.01) |
| *C07H 1/00* | (2006.01) |
| *C07H 15/04* | (2006.01) |
| *C07H 15/18* | (2006.01) |
| *A61K 39/385* | (2006.01) |
| *A61K 39/39* | (2006.01) |
| *A61K 39/00* | (2006.01) |

(52) U.S. Cl.
CPC .......... *A61K 39/095* (2013.01); *A61K 31/715* (2013.01); *A61K 39/385* (2013.01); *A61K 39/39* (2013.01); *C07H 1/00* (2013.01); *C07H 15/04* (2013.01); *C07H 15/18* (2013.01); *C08B 37/006* (2013.01); *A61K 2039/55505* (2013.01); *A61K 2039/55511* (2013.01); *A61K 2039/55566* (2013.01); *A61K 2039/55577* (2013.01); *A61K 2039/6037* (2013.01); *A61K 2039/627* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 3,896,111 A | 7/1975 | Kupchan et al. |
| 4,137,230 A | 1/1979 | Hashimoto et al. |
| 4,151,042 A | 4/1979 | Higashide et al. |
| 4,248,870 A | 2/1981 | Miyashita et al. |
| 4,256,746 A | 3/1981 | Miyashita et al. |
| 4,260,608 A | 4/1981 | Miyashita et al. |

(Continued)

FOREIGN PATENT DOCUMENTS

| | | |
|---|---|---|
| EP | 404097 A2 | 12/1990 |
| EP | 0341735 B1 | 9/1992 |

(Continued)

OTHER PUBLICATIONS

Torres-Sanchez et al., "Synthesis and Biological Evaluation of Phosphono Analogues of Capsular Polysaccharide Fragments from Neisseria meningitidis A" Chem Eur J (2007) vol. 13 pp. 6623-6635.*

(Continued)

*Primary Examiner* — Eric Olson
(74) *Attorney, Agent, or Firm* — Duane Morris LLP; Vicki G. Norton; Johann Y. Lin

(57) ABSTRACT

Described herein are synthetic glycan conjugates comprising a carrier and a glycan moiety derived from *Neisseria meningitidis*, wherein the glycan moiety is covalently linked to the carrier through a linker. Also provided herein are a mixture of the glycan conjugates thereof, immmunogenic compositions thereof, and kits thereof. The invention further provides methods of using the synthetic glycan conjugates and immunogenic compositions thereof to treat and/or reduce the risk of infectious diseases such as bacterial infections.

33 Claims, 8 Drawing Sheets

(I)

(56) References Cited

U.S. PATENT DOCUMENTS

| | | |
|---|---|---|
| 4,265,814 A | 5/1981 | Hashimoto et al. |
| 4,270,537 A | 6/1981 | Romaine |
| 4,294,757 A | 10/1981 | Asai |
| 4,307,016 A | 12/1981 | Asai et al. |
| 4,308,268 A | 12/1981 | Miyashita et al. |
| 4,308,269 A | 12/1981 | Miyashita et al. |
| 4,309,428 A | 1/1982 | Miyashita et al. |
| 4,313,946 A | 2/1982 | Powell et al. |
| 4,315,929 A | 2/1982 | Freedman et al. |
| 4,317,821 A | 3/1982 | Miyashita et al. |
| 4,322,348 A | 3/1982 | Asai et al. |
| 4,331,598 A | 5/1982 | Hasegawa et al. |
| RE30,985 E | 6/1982 | Cartaya |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,376,110 A | 3/1983 | David et al. |
| 4,419,446 A | 12/1983 | Howley et al. |
| 4,424,219 A | 1/1984 | Hashimoto et al. |
| 4,450,254 A | 5/1984 | Isley et al. |
| 4,560,655 A | 12/1985 | Baker |
| 4,596,556 A | 6/1986 | Morrow et al. |
| 4,596,792 A | 6/1986 | Vyas |
| 4,599,230 A | 7/1986 | Milich et al. |
| 4,599,231 A | 7/1986 | Milich et al. |
| 4,601,903 A | 7/1986 | Frasch |
| 4,601,978 A | 7/1986 | Karin |
| 4,657,866 A | 4/1987 | Kumar |
| 4,676,980 A | 6/1987 | Segal et al. |
| 4,741,900 A | 5/1988 | Alvarez et al. |
| 4,767,704 A | 8/1988 | Cleveland et al. |
| 4,790,824 A | 12/1988 | Morrow et al. |
| 4,816,567 A | 3/1989 | Cabilly et al. |
| 4,849,222 A | 7/1989 | Broaddus |
| 4,886,499 A | 12/1989 | Cirelli et al. |
| 4,927,762 A | 5/1990 | Darfler |
| 4,940,460 A | 7/1990 | Casey et al. |
| 4,941,880 A | 7/1990 | Burns |
| 4,965,199 A | 10/1990 | Capon et al. |
| 4,970,198 A | 11/1990 | Lee et al. |
| 4,975,278 A | 12/1990 | Senter et al. |
| 5,004,697 A | 4/1991 | Pardridge |
| 5,015,235 A | 5/1991 | Crossman |
| 5,053,394 A | 10/1991 | Ellestad et al. |
| 5,061,620 A | 10/1991 | Tsukamoto et al. |
| 5,064,413 A | 11/1991 | McKinnon et al. |
| 5,075,109 A | 12/1991 | Tice et al. |
| 5,079,233 A | 1/1992 | Lee |
| 5,100,669 A | 3/1992 | Hyon et al. |
| 5,112,596 A | 5/1992 | Malfroy-Camine |
| 5,122,469 A | 6/1992 | Mather et al. |
| 5,141,496 A | 8/1992 | Dalto et al. |
| 5,190,521 A | 3/1993 | Hubbard et al. |
| 5,208,020 A | 5/1993 | Chari et al. |
| 5,229,275 A | 7/1993 | Goroff |
| 5,264,365 A | 11/1993 | Georgiou et al. |
| 5,268,164 A | 12/1993 | Kozarich et al. |
| 5,312,335 A | 5/1994 | McKinnon et al. |
| 5,326,856 A | 7/1994 | Coughlin et al. |
| 5,328,483 A | 7/1994 | Jacoby |
| 5,334,144 A | 8/1994 | Alchas et al. |
| 5,339,163 A | 8/1994 | Homma et al. |
| 5,362,852 A | 11/1994 | Geoghegan |
| 5,369,017 A | 11/1994 | Wong et al. |
| 5,374,541 A | 12/1994 | Wong et al. |
| 5,383,851 A | 1/1995 | McKinnon, Jr. et al. |
| 5,395,541 A | 3/1995 | Carpenter et al. |
| 5,416,064 A | 5/1995 | Chari et al. |
| 5,417,662 A | 5/1995 | Hjertman et al. |
| 5,466,220 A | 11/1995 | Brenneman |
| 5,480,381 A | 1/1996 | Weston |
| 5,500,362 A | 3/1996 | Robinson et al. |
| 5,503,627 A | 4/1996 | McKinnon et al. |
| 5,506,206 A | 4/1996 | Kozarich et al. |
| 5,508,192 A | 4/1996 | Georgiou et al. |
| 5,518,725 A | 5/1996 | Daynes et al. |
| 5,520,639 A | 5/1996 | Peterson et al. |
| 5,527,288 A | 6/1996 | Gross et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,569,189 A | 10/1996 | Parsons |
| 5,569,825 A | 10/1996 | Lonberg et al. |
| 5,571,894 A | 11/1996 | Wels et al. |
| 5,580,717 A | 12/1996 | Dower et al. |
| 5,585,089 A | 12/1996 | Queen et al. |
| 5,587,458 A | 12/1996 | King et al. |
| 5,591,669 A | 1/1997 | Krimpenfort et al. |
| 5,591,828 A | 1/1997 | Bosslet et al. |
| 5,599,302 A | 2/1997 | Lilley et al. |
| 5,606,040 A | 2/1997 | McGahren et al. |
| 5,624,821 A | 4/1997 | Winter et al. |
| 5,625,126 A | 4/1997 | Lonberg et al. |
| 5,633,425 A | 5/1997 | Lonberg et al. |
| 5,635,483 A | 6/1997 | Pettit et al. |
| 5,639,635 A | 6/1997 | Joly et al. |
| 5,641,870 A | 6/1997 | Rinderknecht et al. |
| 5,643,577 A | 7/1997 | Pang et al. |
| 5,648,237 A | 7/1997 | Carter |
| 5,648,260 A | 7/1997 | Winter et al. |
| 5,649,912 A | 7/1997 | Peterson |
| 5,661,016 A | 8/1997 | Lonberg et al. |
| 5,663,149 A | 9/1997 | Pettit et al. |
| 5,674,988 A | 10/1997 | Sabesan |
| 5,677,180 A | 10/1997 | Robinson et al. |
| 5,686,416 A | 11/1997 | Kozarich et al. |
| 5,690,938 A | 11/1997 | Ermak et al. |
| 5,693,762 A | 12/1997 | Queen et al. |
| 5,704,911 A | 1/1998 | Parsons |
| 5,712,374 A | 1/1998 | Kuntsman et al. |
| 5,714,374 A | 2/1998 | Arnold et al. |
| 5,714,586 A | 2/1998 | Kunstman et al. |
| 5,731,168 A | 3/1998 | Cater et al. |
| 5,733,743 A | 3/1998 | Johnson et al. |
| 5,736,137 A | 4/1998 | Anderson et al. |
| 5,739,116 A | 4/1998 | Hamann et al. |
| 5,767,285 A | 6/1998 | Hamann et al. |
| 5,770,701 A | 6/1998 | McGahren et al. |
| 5,773,001 A | 6/1998 | Hamann et al. |
| 5,780,588 A | 7/1998 | Pettit et al. |
| 5,814,344 A | 9/1998 | Tice et al. |
| 5,820,883 A | 10/1998 | Tice et al. |
| 5,821,337 A | 10/1998 | Carter et al. |
| 5,837,234 A | 11/1998 | Gentile et al. |
| 5,840,523 A | 11/1998 | Simmons et al. |
| 5,849,716 A | 12/1998 | Akimoto |
| 5,853,763 A | 12/1998 | Tice et al. |
| 5,869,046 A | 2/1999 | Presta et al. |
| 5,877,296 A | 3/1999 | Hamann et al. |
| 5,893,397 A | 4/1999 | Peterson et al. |
| 5,993,412 A | 11/1999 | Deily et al. |
| 6,004,940 A | 12/1999 | Marasco et al. |
| 6,027,888 A | 2/2000 | Georgiou et al. |
| 6,083,715 A | 7/2000 | Georgiou et al. |
| 6,111,132 A | 8/2000 | Kim et al. |
| 6,143,724 A | 11/2000 | Ohira et al. |
| 6,210,670 B1 | 4/2001 | Berg |
| 6,265,150 B1 | 7/2001 | Terstappen et al. |
| 6,329,173 B1 | 12/2001 | Marasco et al. |
| 6,340,702 B1 | 1/2002 | Honda et al. |
| 6,399,071 B1 | 6/2002 | Duthaler |
| 6,455,571 B1 | 9/2002 | Maring et al. |
| 6,506,564 B1 | 1/2003 | Mirkin et al. |
| 6,528,286 B1 | 3/2003 | Ryll |
| 6,548,476 B1 | 4/2003 | Wu et al. |
| 6,680,054 B1 | 1/2004 | Reece et al. |
| 6,696,304 B1 | 2/2004 | Davies |
| 6,703,019 B1 | 3/2004 | Malfroy-Camine |
| 6,824,780 B1 | 11/2004 | Devaux et al. |
| 6,855,551 B2 | 2/2005 | Bawendi et al. |
| 6,873,914 B2 | 3/2005 | Winfield et al. |
| 6,984,630 B1 | 1/2006 | Descamps et al. |

(56) References Cited

U.S. PATENT DOCUMENTS

| | | |
|---|---|---|
| 6,994,966 B2 | 2/2006 | Dukler |
| 7,019,288 B2 | 3/2006 | Becker |
| 7,090,973 B1 | 8/2006 | Breton |
| 7,151,164 B2 | 12/2006 | Hansen et al. |
| 7,157,433 B2 | 1/2007 | Mercep et al. |
| 7,205,333 B2 | 4/2007 | Wu et al. |
| 7,488,491 B2 | 2/2009 | Tsjui et al. |
| 7,498,298 B2 | 3/2009 | Doronina et al. |
| 7,854,934 B2 | 12/2010 | Danishefsky |
| 7,888,337 B2 | 2/2011 | Wong et al. |
| 7,923,013 B2 | 4/2011 | Tsuji et al. |
| 7,928,077 B2 | 4/2011 | Wong et al. |
| 7,943,330 B2 | 5/2011 | Wong et al. |
| 7,960,139 B2 | 6/2011 | Sawa et al. |
| 7,977,097 B1 | 7/2011 | Gay et al. |
| 8,022,043 B2 | 9/2011 | Porcelli |
| 8,088,387 B2 | 1/2012 | Steeves et al. |
| 8,101,179 B2 | 1/2012 | Numazaki et al. |
| 8,268,969 B2 | 9/2012 | Wong et al. |
| 8,383,554 B2 | 2/2013 | Wong et al. |
| 8,507,660 B2 | 8/2013 | Wong et al. |
| 8,680,020 B2 | 3/2014 | Wong et al. |
| 8,815,941 B2 | 8/2014 | Withers |
| 8,906,832 B2 | 12/2014 | Wong et al. |
| 8,907,111 B2 | 12/2014 | Withers |
| 9,187,552 B2 | 11/2015 | Stadheim |
| 9,221,859 B2 | 12/2015 | Withers |
| 9,382,284 B2 | 7/2016 | Withers |
| 9,434,786 B2 | 9/2016 | Wang |
| 2002/0025313 A1 | 2/2002 | Micklus et al. |
| 2002/0038086 A1 | 3/2002 | Hynynen et al. |
| 2002/0065259 A1 | 5/2002 | Schatzberg et al. |
| 2003/0073713 A1 | 4/2003 | Schoenhard |
| 2003/0083299 A1 | 5/2003 | Ferguson |
| 2003/0104402 A1 | 6/2003 | Zauderer et al. |
| 2003/0118592 A1 | 6/2003 | Ledbetter et al. |
| 2003/0129186 A1 | 7/2003 | Beliveau et al. |
| 2003/0162695 A1 | 8/2003 | Schatzberg et al. |
| 2003/0175884 A1 | 9/2003 | Umana et al. |
| 2003/0219433 A1 | 11/2003 | Hansen et al. |
| 2004/0072290 A1 | 4/2004 | Umana et al. |
| 2004/0086423 A1 | 5/2004 | Wohlstadter |
| 2004/0131692 A1 | 7/2004 | Kreuter et al. |
| 2004/0137557 A1 | 7/2004 | DeFrees et al. |
| 2004/0204354 A1 | 10/2004 | Nelson et al. |
| 2004/0259142 A1 | 12/2004 | Chai et al. |
| 2005/0085413 A1 | 4/2005 | Jin et al. |
| 2005/0089473 A1 | 4/2005 | Black et al. |
| 2005/0106108 A1 | 5/2005 | Hansen et al. |
| 2005/0123546 A1 | 6/2005 | Umana et al. |
| 2005/0124533 A1 | 6/2005 | Schatzberg et al. |
| 2005/0221337 A1 | 10/2005 | Seeberger et al. |
| 2005/0255491 A1 | 11/2005 | Lee |
| 2006/0019256 A1 | 1/2006 | Clarke et al. |
| 2006/0073122 A1 | 4/2006 | Koezuka et al. |
| 2006/0073161 A1 | 4/2006 | Breton |
| 2006/0211856 A1 | 9/2006 | Tsuji et al. |
| 2006/0286140 A1 | 12/2006 | Wickstrom et al. |
| 2006/0286637 A1 | 12/2006 | Hamilton |
| 2007/0059769 A1 | 3/2007 | Blixt et al. |
| 2007/0065949 A1 | 3/2007 | Hutchens |
| 2007/0207090 A1* | 9/2007 | Giudice .............. A61K 39/095 424/45 |
| 2007/0213278 A1 | 9/2007 | Wong et al. |
| 2007/0219351 A1 | 9/2007 | Fiume et al. |
| 2007/0224189 A1 | 9/2007 | Lazar et al. |
| 2007/0238871 A1 | 10/2007 | Tsuji et al. |
| 2008/0070324 A1 | 3/2008 | Floyd |
| 2008/0220988 A1 | 9/2008 | Zhou |
| 2008/0260774 A1 | 10/2008 | Wong et al. |
| 2009/0035179 A1 | 2/2009 | Rakow et al. |
| 2009/0081255 A1 | 3/2009 | Bublot et al. |
| 2009/0123439 A1 | 5/2009 | Yun et al. |
| 2009/0285837 A1 | 11/2009 | Kao et al. |
| 2009/0298797 A1 | 12/2009 | Zheng et al. |
| 2009/0317837 A1 | 12/2009 | Wong et al. |
| 2010/0009339 A1 | 1/2010 | Bovin et al. |
| 2010/0022026 A1 | 1/2010 | Rump et al. |
| 2010/0047827 A1 | 2/2010 | Laine et al. |
| 2010/0047828 A1 | 2/2010 | Sorenson et al. |
| 2010/0068806 A1 | 3/2010 | Laine et al. |
| 2010/0112195 A1 | 5/2010 | Kodas et al. |
| 2010/0113397 A1 | 5/2010 | Wong et al. |
| 2010/0136009 A1 | 6/2010 | Papkoff et al. |
| 2010/0136042 A1 | 6/2010 | Wong et al. |
| 2010/0173323 A1 | 7/2010 | Strome |
| 2011/0086408 A1 | 4/2011 | Powers |
| 2011/0104188 A1 | 5/2011 | Tashiro et al. |
| 2011/0124116 A1 | 5/2011 | Wohlstadter et al. |
| 2011/0137570 A1 | 6/2011 | Lapadula et al. |
| 2011/0237459 A1 | 9/2011 | Nova et al. |
| 2011/0263828 A1 | 10/2011 | Wong et al. |
| 2012/0171201 A1 | 7/2012 | Sapra |
| 2012/0178705 A1 | 7/2012 | Liang et al. |
| 2012/0178802 A1 | 7/2012 | Withers et al. |
| 2012/0226024 A1 | 9/2012 | Wang et al. |
| 2012/0294859 A1 | 11/2012 | Goletz et al. |
| 2012/0328646 A1 | 12/2012 | Wong et al. |
| 2013/0189258 A1 | 7/2013 | Rother et al. |
| 2013/0196356 A1 | 8/2013 | Jackson et al. |
| 2013/0230886 A1 | 9/2013 | Votsmeier et al. |
| 2013/0295104 A1 | 11/2013 | Deckert et al. |
| 2013/0337018 A1 | 12/2013 | Fox |
| 2014/0051127 A1 | 2/2014 | Wong et al. |
| 2014/0086916 A1 | 3/2014 | Zha |
| 2014/0127241 A1 | 5/2014 | Leuschner et al. |
| 2014/0178365 A1 | 6/2014 | Ghaderi et al. |
| 2014/0302028 A1 | 10/2014 | Zha |
| 2015/0087814 A1 | 3/2015 | Wang |
| 2015/0160217 A1 | 6/2015 | Wong et al. |
| 2015/0309041 A1 | 10/2015 | Wong et al. |
| 2015/0344544 A1 | 12/2015 | Wong |
| 2015/0344551 A1 | 12/2015 | Wong et al. |
| 2015/0344559 A1 | 12/2015 | Wong et al. |
| 2015/0344585 A1 | 12/2015 | Wong et al. |
| 2015/0344587 A1 | 12/2015 | Wong et al. |
| 2016/0009803 A1 | 1/2016 | Rother et al. |
| 2016/0102151 A1 | 4/2016 | Wong et al. |
| 2016/0215061 A1 | 7/2016 | Shaeen |
| 2016/0274121 A1 | 9/2016 | Wong et al. |
| 2016/0280794 A1 | 9/2016 | Wong et al. |
| 2016/0289340 A1 | 10/2016 | Wong et al. |

FOREIGN PATENT DOCUMENTS

| | | | |
|---|---|---|---|
| EP | 0425235 B1 | 9/1996 | |
| EP | 1208909 A2 | 5/2002 | |
| EP | 1391213 A1 | 2/2004 | |
| EP | 2123271 | 11/2009 | |
| EP | 2187217 A1 | 5/2010 | |
| JP | 05-222085 | 8/1993 | |
| JP | H05-222085 | * 8/1993 | ............. C07H 15/04 |
| JP | 05-507068 | 10/1993 | |
| JP | 05-339283 A | 12/1993 | |
| JP | 11-343295 A | 12/1999 | |
| JP | 2005-06008 | 5/2000 | |
| WO | WO 87/00195 A1 | 1/1987 | |
| WO | WO 90/03430 A1 | 4/1990 | |
| WO | WO 91/00360 A1 | 1/1991 | |
| WO | WO 91/10741 A1 | 7/1991 | |
| WO | WO 92/00373 A1 | 1/1992 | |
| WO | WO 92/006691 | 4/1992 | |
| WO | WO 92/09690 A2 | 6/1992 | |
| WO | WO 93/01161 A1 | 1/1993 | |
| WO | WO 93/06213 A1 | 4/1993 | |
| WO | WO 93/07861 A1 | 4/1993 | |
| WO | WO 93/08829 A1 | 5/1993 | |
| WO | WO 93/09764 | 5/1993 | |
| WO | WO 93/16185 A2 | 8/1993 | |
| WO | WO 93/021232 A1 | 10/1993 | |
| WO | WO 94/04690 A1 | 3/1994 | |
| WO | WO 94/11026 | 5/1994 | |
| WO | WO 94/29351 | 12/1994 | |
| WO | WO 95/11010 A1 | 4/1995 | |

(56) References Cited

FOREIGN PATENT DOCUMENTS

| | | |
|---|---|---|
| WO | WO 96/07754 A1 | 3/1996 |
| WO | WO 96/16673 A1 | 6/1996 |
| WO | WO 96/33735 A1 | 10/1996 |
| WO | WO 96/34096 A1 | 10/1996 |
| WO | WO 97/05267 A2 | 2/1997 |
| WO | WO 97/013537 | 4/1997 |
| WO | WO 97/17852 A1 | 5/1997 |
| WO | WO 97/037705 | 10/1997 |
| WO | WO 98/00558 A1 | 1/1998 |
| WO | WO 98/02463 A1 | 1/1998 |
| WO | WO 98/24893 A2 | 6/1998 |
| WO | WO 99/034850 | 7/1999 |
| WO | WO 99/49019 A2 | 9/1999 |
| WO | WO 99/051642 | 10/1999 |
| WO | WO 99/057134 A1 | 11/1999 |
| WO | WO 01/42505 A2 | 6/2001 |
| WO | WO 01/86001 A1 | 11/2001 |
| WO | WO 02/088172 | 11/2002 |
| WO | WO 03/040104 A1 | 5/2003 |
| WO | WO 03/68821 A2 | 8/2003 |
| WO | WO 03/077945 A1 | 9/2003 |
| WO | WO 2004/035607 A2 | 4/2004 |
| WO | WO 2004/056312 A2 | 7/2004 |
| WO | WO 2004/063351 | 7/2004 |
| WO | WO 2004/103404 A1 | 12/2004 |
| WO | WO 2005/030258 A2 | 4/2005 |
| WO | WO 2005/044859 | 5/2005 |
| WO | WO 2005/088310 A2 | 9/2005 |
| WO | WO 2005/103081 A2 | 11/2005 |
| WO | WO 2006/055925 A2 | 5/2006 |
| WO | WO 2006/064983 A1 | 6/2006 |
| WO | WO 2006/106959 | 10/2006 |
| WO | WO 2006/126069 A2 | 11/2006 |
| WO | WO 2006/130458 A2 | 12/2006 |
| WO | WO 2007/078873 A1 | 7/2007 |
| WO | WO 2007/0133855 | 11/2007 |
| WO | WO 2007/146847 A2 | 12/2007 |
| WO | WO 2008/020596 A2 | 2/2008 |
| WO | WO 2008/087260 A1 | 7/2008 |
| WO | WO 2008/118013 | 10/2008 |
| WO | WO 2008/133801 A1 | 11/2008 |
| WO | WO 2008/133857 A1 | 11/2008 |
| WO | WO 2009/029888 A3 | 3/2009 |
| WO | WO 2010/006315 A2 | 1/2010 |
| WO | WO 2010/009271 A1 | 1/2010 |
| WO | WO 2010/011703 | 1/2010 |
| WO | WO 2011/005756 A1 | 1/2011 |
| WO | WO 2011/006237 A1 | 1/2011 |
| WO | WO 2011/031236 A1 | 3/2011 |
| WO | WO 2011/074621 A1 | 6/2011 |
| WO | WO 2011/089004 A1 | 7/2011 |
| WO | WO 2011/130332 | 10/2011 |
| WO | WO 2011/143262 A2 | 11/2011 |
| WO | WO 2011/145957 A1 | 11/2011 |
| WO | WO 2012/082635 A1 | 6/2012 |
| WO | WO 2012/094540 A2 | 7/2012 |
| WO | WO 2013/011347 A1 | 1/2013 |
| WO | WO 2013/012066 | 1/2013 |
| WO | WO 2013/024895 A1 | 2/2013 |
| WO | WO 2013/088395 A1 | 6/2013 |
| WO | WO 2013/120066 A1 | 8/2013 |
| WO | WO 2013/130603 A1 | 9/2013 |
| WO | WO 2013/152034 A1 | 10/2013 |
| WO | WO 2013/155375 A1 | 10/2013 |
| WO | WO 2013/181585 A2 | 12/2013 |
| WO | WO 2014/031498 | 2/2014 |
| WO | WO 2014/031762 A1 | 2/2014 |
| WO | WO 2014/078373 A1 | 5/2014 |
| WO | WO 2014/210397 A1 | 12/2014 |
| WO | WO 2014/210564 | 12/2014 |
| WO | WO 2015/026484 A1 | 2/2015 |
| WO | WO 2015/035337 A1 | 3/2015 |
| WO | WO 2015/038963 A1 | 3/2015 |
| WO | WO 2015/184008 | 12/2015 |
| WO | WO 2016/040369 A2 | 3/2016 |
| WO | WO 2016/118090 A1 | 7/2016 |

OTHER PUBLICATIONS

Wang et al., "Synthesis of Neisseria meningitidis Serogroup W135 Capsular Oligosaccharides for Immunogenicity Comparison and Vaccine Development" Angew Chem Int Ed (2013) vol. 52 pp. 9157-9161.*

English Machine Translation of H05-222085 above. Downloaded from wroldwide.espacenet.com. (Year: 1993).*

Abrahmsén et al, "Analysis of signals for secretion in the staphylococcal protein A gene," *EMBO J.*, Dec. 30, 1985, 4(13B):3901-3906.

Altschul SF et al., "Basic local alignment search tool", *J Mol Biol.* Oct. 5, 1990;215(3):403-10.

Altschul SF, et al., "Gapped BLAST and PSI-BLAST: a new generation of protein database search programs", *Nucleic Acids Res.* Sep. 1, 1997;25(17):3389-402.

Anderson et al., "Stimulation of Natural Killer T Cells by Glycolipids", *Molecules*, May 2013, 18(12), 15662-15688.

Arié et al., "Chaperone function of FkpA, a heat shock prolyl isomerase, in the periplasm of *Escherichia coli*," *Mol. Microbiol.*, Jan. 2001, 39(1):199-210.

Bachmann, *Cellular and Molecular Biology, vol. 2, Chapter 72: Derivations and Genotypes of Some Mutant Derivatives of Escherichia coli K-12*, Neidhardt et al., eds., 1987, pp. 1190-1219, American Society for Microbiology, Washington, D.C.

Baldwin et al., "Monoclonal antibodies in cancer treatment," *Lancet*, Mar. 15, 1986, 327(8481):603-605.

Barbas et al., "Assembly of combinatorial antibody libraries on phage surfaces: the gene III site," *Proc. Natl. Acad. Sci. U.S.A.*, Sep. 15, 1991, 88(18):7978-7982.

Barbas et al., "In vitro evolution of a neutralizing human antibody to human immunodeficiency virus type 1 to enhance affinity and broaden strain cross-reactivity," *Proc. Nat. Acad. Sci. U.S.A.*, Apr. 26, 1994, 91(9):3809-3813.

Barbas et al., "Semisynthetic combinatorial antibody libraries: a chemical solution to the diversity problem," *Proc. Natl. Acad. Sci. U.S.A.*, May 15, 1992, 89(10):4457-4461.

Barnes et al., "Methods for growth of cultured cells in serum-free medium," *Anal. Biochem.*, Mar. 1, 1980, 102(2):255-270.

Baselga J, et al., "Phase II study of weekly intravenous recombinant humanized anti-p185HER2 monoclonal antibody in patients with HER2/neu-overexpressing metastatic breast cancer", *J Clin Oncol.* Mar. 1996;14(3):737-44.

Bass et al., "Hormone phage: an enrichment method for variant proteins with altered binding properties," *Proteins*, 1990, 8(4):309-314.

Beck A., "Biosimilar, biobetter and next generation therapeutic antibodies" *MAbs*. Mar.-Apr. 2011;3(2):107-10. Epub Mar. 1, 2011.

Berra et al., "Correlation between ganglioside distribution and histological grading of human astrocytomas," *Int. J. Cancer*, Sep. 15, 1985, 36(3):363-366.

Birklé et al., "Role of tumor-associated gangliosides in cancer progression," *Biochimie*, Mar.-Apr. 2003, 85(3-4):455-463.

Bobo et al., "Convection-enhanced delivery of macromolecules in the brain," *Proc. Natl. Acad. Sci. U.S.A.*, Mar. 15, 1994, 91(6) 2076-2080.

Boerner et al., "Production of antigen-specific human monoclonal antibodies from in vitro-primed human splenocytes," *J. Immunol.*, Jul. 1, 1991, 147(1):86-95.

Bothmann et al., "The periplasmic *Escherichia coli* peptidylprolyl cis,trans-isomerase FkpA. I. Increased functional expression of antibody fragments with and without cis-prolines," *J. Biol. Chem.*, Jun. 2, 2000, 275(22):17100-17105.

Brennan et al., "Preparation of bispecific antibodies by chemical recombination of monoclonal immunoglobulin G$_1$ fragments," *Science*, Jul. 5, 1985, 229(4708):81-83.

(56) References Cited

OTHER PUBLICATIONS

Brimble et al., "The cell surface glycosphingolipids SSEA-3 and SSEA-4 are not essential for human ESC pluripotency," *Stem Cells*, Jan. 2007, 25(1):54-62.

Brodeur et al., *Monoclonal Antibody Production Techniques and Applications, Chapter 4: Mouse-Human Myeloma Partners for the Production of Heterohybridomas*, Schook, ed., 1987, pp. 51-63, Marcel Dekker, Inc., New York.

Brüggemann et al., "Designer mice: the production of human antibody repertoires in transgenic animals," *Year in Immunol.*, 1993, 7:33-40.

Capel PJ et al., "Heterogeneity of human IgG Fc receptors" *Immunomethods*. Feb. 1994;4(1):25-34.

Carter et al., "High level *Escherichia coli* expression and production of a bivalent humanized antibody fragment," *Nature Biotechnology*, Feb. 1992, 10(2):163-167.

Carter et al., "Humanization of an anti-p185$^{HER2}$ antibody for human cancer therapy," *Proc. Natl. Acad. Sci. U.S.A.*, May 15, 1992, 89(10):4285-4289.

Carter PJ. "Potent antibody therapeutics by design" *Nat Rev Immunol.* May 2006;6(5):343-357.

Chang et al., "Expression of Globo H and SSEA3 in breast cancer stem cells and the involvement of fucosyl transferases 1 and 2 in Globo H synthesis," *Proc. Natl. Acad. Sci. U.S.A.*, Aug. 19, 2008, 105(33):11667-11672.

Chen et al., "Chaperone activity of DsbC," *J. Bio. Chem.*, Jul. 9, 1999, 274(28):19601-19605.

Chen et al., "Selection and analysis of an optimized anti-VEGF antibody: crystal structure of an affinity-matured Fab in complex with antigen," *J. Mol. Biol.*, Nov. 5, 1999, 293(4):865-881.

Chen et al., "Selective killing of transformed cells by cyclin/cyclin-dependent kinase 2 antagonists," *Proc. Natl. Acad. Sci. U.S.A.*, Apr. 13, 1999, 96(8):4325-4329.

Chothia et al., "Canonical structures for the hypervariable regions of immunoglobulins," *J. Mol. Biol.*, Aug. 20, 1987, 196(4):901-917.

Clackson et al., "Making antibody fragments using phage display libraries," *Nature*, Aug. 15, 1991, 352(6336):624-628.

Clark EA et al., "Structure, function, and genetics of human B cell-associated surface molecules" *Adv Cancer Res.* 1989;52:81-149.

Clynes R, et al., "Fc receptors are required in passive and active immunity to melanoma" *Proc Natl Acad Sci USA*. Jan. 20, 1998;95(2):652-6.

Cunningham et al., "High-resolution epitope mapping of hGH-receptor interactions by alanine-scanning mutagenesis," *Science*, Jun. 2, 1989, 244(4908):1081-1085.

Daëron, "Fc receptor biology," *Annu. Rev. Immunol.*, 1997, 15:203-234.

De Haas et al., "Fcγ receptors of phagocytes," *J. Lab. Clin. Med.*, Oct. 1995, 126(4):330-341.

Durrant et al., "Immunology in the clinic review series; focus on cancer: glycolipids as targets for tumour immunotherapy," *Clin. Exp. Immunol.*, Feb. 2012, 167(2):206-215.

Embleton et al., "In-cell PCR from mRNA: amplifying and linking the rearranged immunoglobulin heavy and light chain V-genes within single cells," *Nucl. Acids Res.*, Aug. 11, 1992, 20(15):3831-3837.

Engels et al., "Gene synthesis [new synthetic methods (77)]," *Angew. Chem. Int. Ed. Engl.*, Jun. 1989, 28(6):716-734.

Fellouse et al., "Synthetic antibodies from a four-amino-acid code: a dominant role for tyrosine in antigen recognition," *Proc. Natl. Acad. Sci. U.S.A.*, Aug. 24, 2004, 101(34):12467-12472.

Fishwild et al., "High-avidity human IgGκ monoclonal antibodies from a novel strain of minilocus transgenic mice," *Nature Biotechnol.*, Jul. 1996, 14(7):845-851.

Fredman et al., "Expression of gangliosides GD3 and 3'-isoLM1 in autopsy brains from patients with malignant tumors," *J. Neurochem.*, Jan. 1993, 60(1):99-105.

Fredman et al., "Potential ganglioside antigens associated with human gliomas," *Neurol. Res.*, Jun. 1986, 8(2):123-126.

Fredman et al., "Sialyllactotetraosylceramide, a ganglioside marker for human malignant gliomas," *J. Neurochem.*, Mar. 1988, 50(3):912-919.

Fujita M et al., "A novel disaccharide substrate having 1,2-oxazoline moiety for detection of transglycosylating activity of endoglycosidases" *Biochim Biophys Acta.* Sep. 3, 2001;1528(1):9-14.

Galfrè et al., "Preparation of monoclonal antibodies: strategies and procedures," *Methods Enzymol.*, 1981, 73(Pt B):3-46.

Gazzano-Santoro et al., "A non-radioactive complement-dependent cytotoxicity assay for anti-CD20 nonclonal antibody," *J. Immunol. Methods*, Mar. 28, 1997, 202(2):163-171.

GenBank accession No. AAA24922.1, "endoglycosidase F [Elizabethkingia meningoseptica]," May 27, 2008.

GenBank accession No. AAA24923.1, "endoglycosidase, partial [Elizabethkingia meningoseptica]," Jun. 8, 1993.

GenBank accession No. AAA24924.1.1, "endoglycosidase, partial [Elizabethkingia meningoseptica]," Jun. 7, 1993.

GenBank accession No. AAA26738.1, "endo-beta-N-acetylglucosaminidase H [Streptomyces plicatus]," Apr. 26, 1993.

GenBank accession No. J05449.1, "F.meningosepticum peptide-N-4-(N-acetyl-beta-D-glucosaminyl) asparagine amidase (PNGase F) mRNA, complete cds," Jan. 16, 1996.

GenBank accession No. YP_212855.1, "Putative exported alpha-L-fucosidase protein [Bacteroides fragilis NCTC 9343]," Mar. 2, 2014.

Gill et al., "Direct brain infusion of glial cell line-derived neurotrophic factor in Parkinson disease," *Nature Med.*, May 2003, 9(5):589-595 and Addendum from Apr. 2006, 12(4):479.

Goding, *Monoclonal Antibodies: Principles and Practice 2$^{nd}$ ed., Chapter 3: Production of Monoclonal Antibodies*, 1986, pp. 59-103, Academic Press, London.

Goochee CF et al., "The oligosaccharides of glycoproteins: bioprocess factors affecting oligosaccharide structure and their effect on glycoprotein properties", *Biotechnology* (N Y). Dec. 1991;9(12):1347-55.

Gottschling et al., "Stage-specific embryonic antigen-4 is expressed in basaloid lung cancer and associated with poor prognosis," *Eur. Respir. J.*, Mar. 2013, 41(3):656-663.

Graham et al., "Characteristics of a human cell line transformed by DNA from human adenovirus type 5," *J. Gen. Virol.*, Jul. 1977, 36(1):59-72.

Gram et al., "In vitro selection and affinity maturation of antibodies from a naive combinatorial immunoglobulin library," *Proc. Natl. Acad. Sci. U.S.A.*, Apr. 15, 1992, 89(8):3576-3580.

Green, "Targeting targeted therapy," *N. Engl. J. Med.*, May 20, 2004, 350(21):2191-2193.

Griffiths et al., "Human anti-self antibodies with high specificity from phage display libraries," *EMBO J.*, Feb. 1993, 12(2):725-734.

Gruber et al., "Efficient tumor cell lysis mediated by a bispecific single chain antibody expressed in *Escherichia coli*," *J. Immunol.*, Jun. 1, 1994, 152(11):5368-5374.

Guss et al., "Structure of the IgG-binding regions of streptococcal protein G," *EMBO J.*, Jul. 1986, 5(7):1567-1575.

Guyer et al., "Immunoglobulin binding by mouse intestinal epithelial cell receptors," *J. Immunol.*, Aug. 1976, 117(2):587-593.

Hakomori et al., "Glycosphingolipid antigens and cancer therapy," *Chem. Biol.*, Feb. 1997, 4(2):97-104.

Hakomori, "Glycosylation defining cancer malignancy: new wine in an old bottle," *Proc. Natl. Acad. Sci. U.S.A.*, Aug. 6, 2002, 99(16):10231-10233.

Hara et al., "Overproduction of penicillin-binding protein 7 suppresses thermosensitive growth defect at low osmolarity due to an spr mutation of *Escherichia coli*," *Microbial Drug Resistance*, Spring 1996, 2(1):63-72.

Harris, "Production of humanized monoclonal antibodies for in vivo imaging and therapy," *Biochem. Soc. Transactions*, Nov. 1995, 23(4):1035-1038.

Hawkins et al., "Selection of phage antibodies by binding affinity. Mimicking affinity maturation," *J. Mol. Biol.*, 1992, 226(3):889-896.

Heyman, "Complement and Fc-receptors in regulation of the antibody response," *Immunol. Lett.*, Dec. 1996, 54(2-3):195-199.

(56) References Cited

OTHER PUBLICATIONS

Hinman et al., "Preparation and characterization of monoclonal antibody conjugates of the calicheamicins: a novel and potent family of antitumor antibiotics," *Cancer Res.*, Jul. 15, 1993, 53(14):3336-3342.
Hogrefe et al., "A bacteriophage lambda vector for the cloning and expression of immunoglobulin Fab fragments on the surface of filamentous phage," *Gene*, Jun. 15, 1993, 128(1):119-126.
Holliger et al., "'Diabodies': small bivalent and bispecific antibody fragments," *Proc. Natl. Acad. Sci. U.S.A.*, Jul. 15, 1993, 90(14):6444-6448.
Honegger et al., "Yet another numbering scheme for immunoglobulin variable domains: an automatic modeling and analysis tool," *J. Mol. Biol.*, Jun. 8, 2001, 309:657-670.
Hoogenboom et al., "By-passing immunisation: Human antibodies from synthetic repertoires of germline $V_H$ gene segments rearranged in vitro," *J. Mol. Biol.*, Sep. 20, 1992, 227(2):381-388.
Hoogenboom et al., "Multi-subunit proteins on the surface of filamentous phage: methodologies for displaying antibody (Fab) heavy and light chains," *Nucl. Acids Res.*, Aug. 11, 1991 19(15):4133-4137.
Huang et al., "Carbohydrate-based vaccines with a glycolipid adjuvant for breast cancer," *Proc. Natl. Acad. Sci. U.S.A.*, Feb. 12, 2013, 110(7):2517-2522.
Hung et al., "Investigation of SSEA-4 binding protein in breast cancer cells," *J. Am. Chem. Soc.*, Apr. 24, 2013, 135(16):5934-5937.
Hurle et al., "Protein engineering techniques for antibody humanization," *Curr. Opin. Biotechnol.*, Aug. 1994, 5(4):428-433.
Inouye et al., "Single-step purification of F(ab')$_{2\mu}$ fragments of mouse monoclonal antibodies (immunoglobulins M) by hydrophobic interaction high-performance liquid chromatography using TSKgel Ether-5PW," *J. Biochem. Biophys. Methods*, Feb. 1993, 26(1):27-39.
Jackson et al., "In vitro antibody maturation: Improvement of a high affinity, neutralizing antibody against IL-1β," *J. Immunol.*, Apr. 1, 1995, 154(7):3310-3319.
Jakobovits et al., "Analysis of homozygous mutant chimeric mice: deletion of the immunoglobulin heavy-chain joining region blocks B-cell development and antibody production," *Proc. Natl. Acad. Sci. U.S.A.*, Mar. 15, 1993, 90(6):2551-2555.
Jakobovits et al., "Germ-line transmission and expression of a human-derived yeast artificial chromosome," *Nature*, Mar. 18, 1993, 362(6417):255-258.
Jenkins N, Curling EM., "Glycosylation of recombinant proteins: problems and prospects", *Enzyme Microb Technol.* May 1994;16(5):354-64.
Jones et al., "Rapid PCR-cloning of full-length mouse immunoglobulin variable regions," *Nature Biotechnol.*, Jan. 1991, 9(1):88-89.
Jones et al., "Replacing the complementarity-determining regions in a human antibody with those from a mouse," *Nature*, May 29-Jun. 4, 1986, 321(6069):522-525.
Jones, "Analysis of polypeptides and proteins," *Adv. Drug Delivery Rev.*, Jan.-Apr. 1993, 10(1):29-90.
Kam et al., "Carbon nanotubes as multifunctional biological transporters and near-infrared agents for selective cancer cell destruction," *Proc. Natl. Acad. Sci. U.S.A.*, Aug. 16, 2005, 102(33):11600-11605.
Kaneko et al., "Anti-inflammatory activity of immunoglobulin G resulting from Fc sialylation," *Science*, Aug. 4, 2006, 313(5787):670-673.
Kannagi et al., "New globoseries glycosphingolipids in human teratocarcinoma reactive with the monoclonal antibody directed to a developmentally regulated antigen, stage-specific embryonic antigen 3," *J. Biol. Chem.*, Jul. 25, 1983, 258(14):8934-8942.
Kannagi et al., "Stage-specific embryonic antigens (SSEA-3 and -4) are epitopes of a unique globo-series ganglioside isolated from human teratocarcinoma cells," *EMBO J.*, 1983, 2(12):2355-2361.
Karlin S. et al., "Methods for assessing the statistical significance of molecular sequence features by using general scoring schemes", *Proc Natl Acad Sci U S A.* Mar. 1990;87(6):2264-8.
Kato et al., "GMab-1, a high-affinity anti-3'-isoLM1/3'6'-isoLD1 IgG monoclonal antibody, raised in lacto-series ganglioside-defective knockout mice," *Biochem. Biophys. Res. Commun.*, Jan. 1, 2010, 391(1):750-755.
Kim et al., "Localization of the site of the murine IgG1 molecule that is involved in binding to the murine intestinal Fc receptor," *Eur. J. Immunol.*, 1994, 24:2429-2434.
Köhler et al., "Continuous cultures of fused cells secreting antibody of predefined specificity," *Nature*, Aug. 7, 1975, 256(5517):495-497.
Kontermann, "Intrabodies as therapeutic agents," *Methods*, Oct. 2004, 34(2):163-170.
Kostelny et al., "Formation of a bispecific antibody by the use of leucine zippers," *J. Immunol.*, Mar. 1, 1992, 148(5):1547-1553.
Kozbor, "A human hybrid myeloma for production of human monoclonal antibodies," *J. Immunol.*, Dec. 1984, 133(6):3001-3005.
Kriegler M et al., "A novel form of NF/cachectin is a cell surface cytotoxic transmembrane protein: ramifications for the complex physiology of TNF" *Cell.* Apr. 8, 1988;53(1):45-53.
Kudo et al., "Up-regulation of a set of glycosyltransferase genes in human colorectal cancer," *Lab. Invest.*, Jul. 1998, 78(7):797-811.
Lau et al., "N-Glycans in cancer progression," *Glycobiology*, Oct. 2008, 18(10):750-760.
Lee et al., "Bivalent antibody phage display mimics natural immunoglobulin," *J. Immunol. Methods*, Jan. 2004, 284(1-2):119-132.
Lee et al., "High-affinity human antibodies from phage-displayed synthetic Fab libraries with a single framework scaffold," *J. Mol. Biol.*, Jul. 23, 2004, 340(5):1073-1093.
Lefranc et al., "IMGT, the international ImMunoGeneTics database," *Nucleic Acids Res.*, Jan. 1, 1999, 27(1):209-212.
Lehninger, *Biochemistry: The Molecular Basis of Cell Structure and Function*, $2^{nd}$ ed., 1975, pp. 73-75, Worth Publishers, New York.
Leung et al., "A method for random mutagenesis of a defined DNA segment using a modified polymerase chain reaction," *Technique—A Journal of Methods in Cell and Molecular Biology*, Aug. 1989, 1(1):11-15.
Lindmark et al., "Binding of immunoglobulins to protein A and immunoglobulin levels in mammalian sera," *J. Immunol. Meth.*, Aug. 12, 1983, 62(1):1-13.
Liu C, et al., "Expansion of spleen myeloid suppressor cells represses NK cell cytotoxicity in tumor-bearing host" *Blood.* May 15, 2007;109(10):4336-42. Epub Jan. 23, 2007.
Liu et al., "Eradication of large colon tumor xenografts by targeted delivery of maytansinoids," *Proc. Natl., Acad. Sci. U.S.A.*, Aug. 6, 1996, 93(16):8618-8623.
LoBuglio et al., "Mouse/human chimeric monoclonal antibody in man: kinetics and immune response," *Proc. Natl. Acad. Sci. U.S.A.*, Jun. 1989, 86(11):4220-4224.
Lode et al., "Targeted therapy with a novel enediyene antibiotic calicheamicin $\Theta^I_1$ effectively suppresses growth and dissemination of liver metastases in a syngeneic model of murine neuroblastoma," *Cancer Res.*, Jul. 15, 1998, 58(14):2925-2928.
Lonberg et al., "Antigen-specific human antibodies from mice comprising four distinct genetic modifications," *Nature*, Apr. 28, 1994, 368(6474):856-859.
Lonberg et al., "Human antibodies from transgenic mice," *Int. Rev. Immunol.*, 1995, 13(1):65-93.
Louis et al., "The 2007 WHO classification of tumours of the central nervous system," *Acta. Neuropathol.*, Aug. 2007, 114(2):97-109.
Lu et al., "Single chain anti-c-Met antibody conjugated nanoparticles for in vivo tumor-targeted imaging and drug delivery," *Biomaterials*, Apr. 2011, 32(12):3265-3274.
MacFarlane GT, et al., "Formation of glycoprotein degrading enzymes by Bacteroides fragilis" *FEMS Microbiol Lett.* Jan. 15, 1991;61(2-3):289-93.
Mandler et al., "Immunoconjugates of geldanamycin and anti-HER2 monoclonal antibodies: antiproliferative activity on human breast carcinoma cell lines," *J. Nat. Cancer Inst.*, Oct. 4, 2000, 92(19):1573-1581.

(56) References Cited

OTHER PUBLICATIONS

Mandler et al., "Modifications in synthesis strategy improve the yield and efficacy of geldanamycin-herceptin immunoconjugates," *Bioconjugate Chem.*, Jul.-Aug. 2002, 13(4):786-791.

Mandler et al., "Synthesis and evaluation of antiproliferative activity of a geldanamycin-Herceptin™ immunoconjugate," *Bioorganic & Med. Chem. Letters*, May 15, 2000, 10(10):1025-1028.

Månsson et al., "Characterization of new gangliosides of the lactotetraose series in murine xenografts of a human glioma cell line," *FEBS Lett.*, May 26, 1986, 201(1):109-113.

Marasco et al., "Design, intracellular expression, and activity of a human anti-human immunodeficiency virus type 1 gp120 single-chain antibody," *Proc. Natl. Acad. Sci. U.S.A.*, Aug. 15, 1993, 90(16):7889-7893.

Marasco, "Intrabodies: turning the humoral immune system outside in for intracellular immunization," *Gene Therapy*, Jan. 1997, 4(1):11-15.

Marks et al., "By-passing immunization. Human antibodies from V-gene libraries displayed on phage," *J. Mol. Biol.*, Dec. 5, 1991, 222(3):581-597.

Marks et al., "By-passing immunization: Building high affinity human antibodies by chain shuffling," *Nature Biotechnology*, Jul. 1992, 10(7):779-783.

Mather et al., "Culture of testicular cells in hormone-supplemented serum-free medium," *Annals N.Y. Acad. Sci.*, 1982, 383:44-68.

Mather, "Establishment and characterization of two distinct mouse testicular epithelial cell lines," *Biol. Reprod.*, Aug. 1980, 23(1):243-252.

Matsuda et al., "Structure and physical map of 64 variable segments in the 3' 0.8-megabase region of the human immunoglobulin heavy-chain locus," *Nature Genet.*, Jan. 1993, 3(1):88-94.

McCafferty et al., "Phage antibodies: Filamentous phage displaying antibody variable domains," *Nature*, Dec. 6, 1990, 348:552-554.

Meezan et al., "Comparative studies on the carbohydrate-containing membrane components of normal and virus-transformed mouse fibroblasts: II: Separation of glycoproteins and glycopeptides by Sephadex chromatography," *Biochemistry*, Jun. 1969, 8(6):2518-2524.

Meyer, "Malignant gliomas in adults," *N. Engl. J. Med.*, Oct. 23, 2008, 359(17):1850.

Mimura et al., "Role of oligosaccharide residues of IgG1-Fc in FcγRIIb binding," *J. Biol. Chem.*, Dec. 7, 2001, 276(49):45539-45547.

Mishima et al., "Growth suppression of intracranial xenografted glioblastomas overexpressing mutant epidermal growth factor receptors by systemic administration of monoclonal antibody (mAb) 806, a novel monoclonal antibody directed to the receptor," *Cancer Res.*, Jul. 15, 2001, 61(14):5349-5354.

Morelle, W. et al., "The Mass Spectrometric Analysis of Glycoproteins and their Glycan Sturctures", *Review in Current Analytical Chemistry*, vol. 1, No. 1 (2005), pp. 29-57.

Mori K, et al., "Non-fucosylated therapeutic antibodies: the next generation of therapeutic antibodies" *Cytotechnology.* Dec. 2007;55(2-3):109-14. Epub Oct. 31, 2007.

Morimoto et al., "Single-step purification of F(ab')$_2$ fragments of mouse monoclonal antibodies (immunoglobulins G1) by hydrophobic interaction high performance liquid chromatography using TSKgel Phenyl-5PW," *J. Biochem. Biophys. Meth.*, Mar. 1992, 24(1-2):107-117.

Morrison et al., "Chimeric human antibody molecules: mouse antigen-binding domains with human constant region domains," *Proc. Natl. Acad. Sci. U.S.A.*, Nov. 1984, 81(21):6851-6855.

Munson et al., "Ligand: a versatile computerized approach for characterization of ligand-binding systems," *Anal. Biochem.*, Sep. 1, 1980, 107(1):220-239.

Neuberger et al., "Recombinant antibodies possessing novel effector functions," *Nature*, Dec. 13-19, 1984, 312(5995):604-608.

Neuberger, "Generating high-avidity human Mabs in mice," *Nature Biotechnol.*, Jul. 1996, 14(7):826.

Nicolaou et al., "Calicheamicin $\Theta^I{}_1$: A rationally designed molecule with extremely potent and selective DNA cleaving properties and apoptosis inducing activity," *Angew. Chem. Intl. Ed. Engl.*, Feb. 1, 1994, 33(2):183-186.

Niculescu-Duvaz et al., "Antibody-directed enzyme prodrug therapy (ADEPT): A review," *Adv. Drg. Del. Rev.*, Jul. 7, 1997, 26(2-3):151-172.

Noto et al., "CD44 and SSEA-4 positive cells in an oral cancer cell line HSC-4 possess cancer stem-like cell characteristics," *Oral Oncol.*, Aug. 2013, 49(8):787-795.

Orlandi et al., "Cloning immunoglobulin variable domains for expression by the polymerase chain reaction," *Proc. Natl. Acad. Sci. U.S.A.*, May 1989, 86(10):3833-3837.

Ørum et al., "Efficient method for constructing comprehensive murine Fab antibody libraries displayed on phage." *Nucleic Acids Res.*, Sep. 25, 1993, 21(19):4491-4498.

Papanastassiou et al., "The potential for efficacy of the modified (ICP 34.5') herpes simplex virus HSV1716 following intratumoural injection into human malignant glioma: a proof of principle study," *Gene Therapy*, Mar. 2002, 9(6):398-406.

Pearlman et al., *Peptide and Protein Drug Delivery, Chapter 6: Analysis of Protein Drugs*, Lee, ed., 1991, pp. 247-301, Marcel Dekker Publishing, New York.

Peipp et al., "Antibody fucosylation differentially impacts cytotoxicity mediated by NK and PMN effector cells," *Blood*, 2008, 112(6):2390-2399.

Plückthun, "Mono- and bivalent antibody fragments produced in *Escherichia coli*: Engineering, folding and antigen binding," *Immunol. Rev.*, Dec. 1992, 130:151-188.

Plückthun, *Handbook of Experimental Pharmacology, vol. 113: The Pharacology of Monoclonal Antibodies, Chapter 11: Antibodies from Escherichia coli*, Rosenberg et al., eds., 1994, pp. 269-315, Springer-Verlag, Berlin.

Presta et al., "Humanization of an antibody directed against IgE," *J. Immunol.*, Sep. 1, 1993, 151(5):2623-2632.

Presta et al., "Humanization of an anti-vascular endothelial growth factor monoclonal antibody for the therapy of solid tumors and other disorders," *Cancer Res.*, Oct. 15, 1997, 57(20):4593-4599.

Presta, "Antibody engineering," *Curr. Opin. Biotechnol.*, Aug. 1992, 3(4):394-398.

Presta, "Antibody engineering," *Curr. Opin. Struct. Biol.*, Aug. 1992, 2(4):593-596.

Proba et al., "Functional antibody single-chain fragments from the cytoplasm of *Escherichia coli*: influence of thioredoxin reductase (TrxB)," *Gene*, Jul. 4, 1995, 159(2):203-207.

Puigbò P, Guzmán E, Romeu A, Garcia-Vallvé S. Optimizer: a web server for optimizing the codon usage of DNA sequences. *Nucleic Acids Res.* Jul. 2007;35(Web Server issue):W126-31. Epub Apr. 16, 2007.

Ramm et al., "The periplasmic *Escherichia coli* peptidylprolyl cis,trans-isomerase FkpA. II. Isomerase-independent chaperone activity in vitro," *J. Biol. Chem.*, Jun. 2, 2000, 275(22):17106-17113.

Ravetch et al., "Divergent roles for Fc receptors and complement in vivo," *Ann. Rev. Immunol.*, 1998, 16:421-432.

Ravetch et al., "Fc receptors," *Annu. Rev. Immunol.*, 1991, 9:457-492.

Reyes et al., "Expression of human β-interferon cDNA under the control of a thymidine kinase promoter from herpes simplex virus," *Nature*, Jun. 17, 1982, 297(5867):598-601.

Riechmann et al., "Reshaping human antibodies for therapy," *Nature*, Mar. 24, 1988, 332(6162):323-327.

Roguska et al., "Humanization of murine monoclonal antibodies through variable domain resurfacing," *Proc. Natl. Acad. Sci. U.S.A.*, Feb. 1, 1994, 91(3):969-973.

Roos et al., "Specific inhibition of the classical complement pathway by C1q-binding peptides," *J. Immunol.*, Dec. 15, 2001, 167(12):7052-7059.

Rowland et al, "Drug localisation and growth inhibition studies of vindesine-monoclonal anti-CEA conjugates in a human tumour xenograft," *Cancer Immunol. Immunother.*, 1986, 21(3):183-187.

Ruiz et al., "IMGT, the international ImMunoGeneTics database," *Nucl. Acids Res.*, Jan. 1, 2000, 28(1):219-221.

(56) References Cited

OTHER PUBLICATIONS

Saito et al., "Expression of globo-series gangliosides in human renal cell carcinoma," *Jpn. J. Cancer Res.*, Jul. 1997, 88(7):652-659.
Saito et al., "Human α2,3-sialyltransferase (ST3Gal II) is a stage-specific embryonic antigen-4 synthase," *J. Biol. Chem.*, Jul. 18, 2003, 278(29):26474-26479.
Sastry et al., "Cloning of the immunological repertoire in Escherichia coli for generation of monoclonal catalytic antibodies: construction of a heavy chain variable region-specific cDNA library," *Proc. Natl. Acad. Sci. U.S.A.*, Aug. 1989, 86(15):5728-5732.
Schenkel-Brunner, *Human Blood Groups, Chapter 8: P System*, 1995, pp. 211-234, Springer-Verlag, Vienna.
Schier et al., "Identification of functional and structural amino-acid residues by parsimonious mutagenesis," *Gene*, Mar. 9, 1996, 169(2):147-155.
Sell, "Cancer-associated carbohydrates identified by monoclonal antibodies," *Hum. Pathol.*, Oct. 1990, 21(10):1003-1019.
Shalaby et al., "Development of humanized bispecific antibodies reactive with cytotoxic lymphocytes and tumor cells overexpressing the HER2 protooncogene," *J. Exp. Med.*, Jan. 1, 1992, 175(1):217-225.
Shields et al., "High resolution mapping of the binding site on human IgG1 for FcγRI, FcγRII, FcγRIII, and FcRn and design of IgG1 variants with improved binding to the FcγR," *J. Biol. Chem.*, Mar. 2, 2001, 276(9):6591-6604.
Shields et al., "Lack of fucose on human IgG1 N-linked oligosaccharide improves binding to human FcγRIII antibody-dependent cellular toxicity," *J. Biol. Chem.*, Jul. 26, 2002, 277(30):26733-26740.
Shinkawa et al., "The absence of fucose but not the presence of galactose or bisecting N-acetylglucosamine of human IgG1 complex-type oligosaccharides shows the critical role of enhancing antibody-dependent cellular cytotoxicity," *J. Biol. Chem.*, Jan. 31, 2003, 278(5):3466-3473.
Sidhu et al., "Phage-displayed antibody libraries of synthetic heavy chain complementarity determining regions," *J. Mol. Biol.*, Apr. 23, 2004, 338(2):299-310.
Siebenlist et al., "*E. coli* RNA polymerase interacts homologously with two different promoters," *Cell*, Jun. 1980, 20(2):269-281.
Simmons et al., "Expression of full-length immunoglobulins in Escherichia coli: Rapid and efficient production of aglycosylated antibodies," *J. Immunol. Methods*, May 1, 2002, 263(1-2):133-147.
Sims et al., "A humanized CD18 antibody can block function without cell destruction," *J. Immunol.*, Aug. 15, 1993, 151(4):2296-2308.
Skerra, "Bacterial expression of immunoglobulin fragments," *Curr. Opinion in Immunol.*, Apr. 1993, 5(2):256-262.
Slamon DJ, et al., "Human breast cancer: correlation of relapse and survival with amplification of the HER-2/neu oncogene" *Science.* Jan. 9, 1987; 235(4785):177-82.
Smith RA et al., "The active form of tumor necrosis factor is a trimer" *J Biol Chem.* May 25, 1987;262(15):6951-4.
Smyth MJ, et al., "CD4+CD25+ T regulatory cells suppress NK cell-mediated immunotherapy of cancer" *J Immunol.* Feb. 1, 2006;176(3):1582-7.
Suresh et al., "Bispecific monoclonal antibodies from hybrid hybridomas," *Methods in Enzymology*, 1986, 121:210-228.
Suzuki E, et al., "A nonfucosylated anti-HER2 antibody augments antibody-dependent cellular cytotoxicity in breast cancer patients" *Clin Cancer Res.* Mar. 15, 2007;13(6):1875-82.
Svennerholm et al., "Human brain gangliosides: Developmental changes from early fetal stage to advanced age," *Biochim. Biophys. Acta*, Sep. 25, 1989, 1005(2):109-117.
Syrigos et al., "Antibody directed enzyme prodrug therapy (ADEPT): a review of the experimental and clinical considerations," *Anticancer Research*, Jan.-Feb. 1999, 19(1A):605-614.
Takeda et al., "Construction of chimaeric processed immunoglobulin genes containing mouse variable and human constant region sequences," *Nature*, Apr. 4-10, 1985, 314(6010):452-454.

Taylor-Papadimitriou et al., "Exploiting altered glycosylation patterns in cancer: Progress and challenges in diagnosis and therapy," *Trends Biotechnol.*, Jun. 1994, 12(6):227-233.
Thorpe, (1985) "Antibody Carriers of Cytotoxic Agents in Cancer Therapy: A Review," in *Monoclonal Antibodies '84: Biological and Clinical Applications*, A. Pinchera et al. (ed.s), pp. 475-506.
Tomlinson et al., "The repertoire of human germline $V_H$ sequences reveals about fifty groups of $V_H$ segments with different hypervariable loops," *J. Mol. Biol.*, Oct. 5, 1992, 227(3):776-798.
Traunecker et al., "Bispecific single chain molecules (Janusins) target cytotoxic lymphocytes on HIV infected cells," *EMBO J.*, Dec. 1991, 10(12):3655-3659.
Traylor et al., "Gangliosides of human cerebral astrocytomas," *J. Neurochem.*, Jan. 1980, 34(1):126-131.
Tsai Ti, et al., "Effective sugar nucleotide regeneration for the large-scale enzymatic synthesis of Globo H and SSEA4" *J Am Chem Soc.* Oct. 2, 2013;135(39):14831-9, Epub Sep. 17, 2013.
Tutt et al., "Trispecific F(ab')₃ derivatives that use cooperative signaling via the TCR/CD3 complex and CD2 to activate and redirect resting cytotoxic T cells," *J. Immunol.*, Jul. 1, 1991, 147(1):60-69.
Tyagarajan K et al., "Exoglycosidase purity and linkage specificity: assessment using oligosaccharide substrates and high-pH anion-exchange chromatography with pulsed amperometric detection" *Glycobiology.* Jan. 1996;6(1):83-93.
Urlaub et al., "Isolation of Chinese hamster cell mutants deficient in dihydrofolate reductase activity." *Proc. Natl. Acad. Sci. U.S.A.*, Jul. 1980, 77(7):4216-4220.
Valentine MA, et al., "Phosphorylation of the CD20 phosphoprotein in resting B lymphocytes. Regulation by protein kinase C" *J Biol Chem.* Jul. 5, 1989;264(19):11282-7.
van Beek et al., "Increased sialic acid density in surface glycoprotein of transformed and malignant cells—a general phenomenon?" *Cancer Res.*, Nov. 1973, 33(11):2913-2922.
Van Meir et al., "Exciting new advances in neuro-oncology: the avenue to a cure for malignant glioma," *CA Cancer J. Clin.*, May-Jun. 2010, 60(3):166-193.
Van Slambrouck et al., "Clustering of monosialyl-Gb5 initiates downstream signalling events leading to invasion of MCF-7 breast cancer cells," *Biochem. J.*, Feb. 1, 2007, 401(3):689-699.
Vaswani et al., "Humanized antibodies as potential therapeutic drugs," *Ann. Allergy, Asthma Immunol.*, Aug. 1998, 81(2):105-116, 119.
Verhoeyen et al., "Reshaping human antibodies: grafting an antilysozyme activity," *Science*, Mar. 25, 1988, 239(4847):1534-1536.
Vermeer AW et al., "The thermal stability of immunoglobulin: unfolding and aggregation of a multi-domain protein" *Biophys J.* Jan. 2000;78(1):394-404.
Wang et al., "Glycan microarray of Globo H and related structures for quantitative analysis of breast cancer," *Proc. Natl. Acad. Sci. U.S.A.*, Aug. 19, 2008, 105(33):11661-11666.
Ward et al., "Binding activities of a repertoire of single immunoglobulin variable domains secreted from *Escherichia coli*," *Nature*, Oct. 12, 1989, 341(6242):544-546.
Waterhouse et al., "Combinatorial infection and in vivo recombination: a strategy for making large phage antibody repertoires," *Nuc. Acids Res.*, May 11, 1993, 21(9):2265-2266.
Wikstrand et al., "Monoclonal antibody therapy of human gliomas: Current status and future approaches," *Cancer Metastasis Rev.*, 1999, 18(4):451-464.
Williams et al., "Cloning and sequencing of human immunoglobulin V lambda gene segments." *Eur. J. Immunol.*, Jul. 1993, 23(7):1456-1461.
Winter et al., "Making antibodies by phage display technology," *Annu. Rev. Immunol.*, 1994, 12:433-455.
Woof et al., "Human antibody-Fc receptor interactions illuminated by crystal structures," *Nat. Rev. Immunol.*, Feb. 2004, 4(2):89-99.
Yansura et al., "Nucleotide sequence selection for increased expression of heterologous genes in *Escherichia coli*," *Methods: A Companion to Methods in Enzymol.*, Aug. 1992, 4(2):151-158.

(56) References Cited

OTHER PUBLICATIONS

Ye et al., "Stage-specific embryonic antigen 4 expression in epithelial ovarian carcinoma," *Int. J. Gynecol. Cancer*, Aug. 2010, 20(6):958-964.
Yelton et al., "Affinity maturation of the BR96 anti-carcinoma antibody by codon-based mutagenesis." *J. Immunol.*, Aug. 15, 1995, 155(4):1994-2004.
Yu et al., "Anti-GD2 antibody with GM-CSF, interleukin-2, and isotretinoin for neuroblastoma," *N. Engl. J. Med.*, Sep. 30, 2010, 363(14):1324-1334.
Zapata et al., "Engineering linear F(ab')$_2$ fragments for efficient production in *Escherichia coli* and enhanced antiproliferative activity," *Protein Eng.*, Oct. 1995, 8(10):1057-1062.
Zarei et al., "Separation and identification of GM1b pathway Neu5Ac- and Neu5Gc gangliosides by on-line nanoHPLC-QToF MS and tandem MS: toward glycolipidomics screening of animal cell lines," *Glycobiology*, Jan. 2010, 20(1):118-126.
Zhang et al., "Selection of tumor antigens as targets for immune attack using immunohistochemistry: I. Focus on gangliosides," *Int. J. Cancer*, Sep. 26, 1997, 73(1):42-49.
International Search Report and Written Opinion issued for International application No. PCT/US2015/032738, dated Oct. 20, 2015, 15 pages.
International Search Report and Written Opinion issued for International application No. PCT/US2015/032744, dated Oct. 2, 2015, 12 pages.
International Search Report and Written Opinion issued for International application No. PCT/US2015/032740, dated Oct. 26, 2015, 13 pages.
International Search Report and Written Opinion issued for International application No. PCT/US2015/032737, dated Oct. 1, 2015, 13 pages.
International Search Report and Written Opinion issued for International application No. PCT/US2015/032745, dated Oct. 8, 2015, 13 pages.
International Search Report issued for International application No. PCT/US2015/049014, dated Dec. 14, 2015, 3 pages.
U.S. Appl. No. 15/005,930, dated Jan. 25, 2016, Wong et al.
U.S. Appl. No. 15/011,543, dated Jan. 30, 2016, Wong et al.
U.S. Appl. No. 15/011,544, dated Jan. 30, 2016, Wong et al.
U.S. Appl. No. 15/173,496, dated Jun. 3, 2016, Wong et al.
Abbas et al., "Functional diversity of helper T lymphocytes," *Nature*, Oct. 31, 1996, 383(6603):787-793.
Achtman, M., Epidemic Spread and Antigenic Variability of Neisseria Meningitidis, Trends Microbial 1995, 3, 186-192.
Adam et al., "Proteomic profiling of mechanistically distinct enzyme classes using a common chemotype," *Nat. Biotechnol.*, Aug. 2002, 20(8):805-809.
Agard, N. et al., A Strain-Promoted [3+2]Azide-Alkyne Cycloaddition for Covalent Modification of Biomolecules in Living Systems, J. Am. Chem. Soc. 2004, 126, 15046-15047.
Ahmadi, T. S. et al., Shape-Controlled Synthesis of Colloidal Platinum Nanoparticles, Science, 272, 1924 (1996).
Ahmed et al.,Structural Characterization of Anti-Inflammatory Immunoglobulin G Fc Proteins, K Mol Biol (2014) 426, 3166-3179.
Altevogt, Peter et al., Different Patterns of Lectin Binding and Cell Surface Sialylation Detected on Related High- and Low-Metastatic Tumor Lines, Cancer Res. 43, 5138-5144, 1983.
Amin, M. N. et al. Synthetic glycopeptides reveal the glycan specificity of HIV-neutralizing antibodies. Nat. Chem. Biol. 9, 521-526, (2013.
Andrews et al., Synthesis and influenza virus sialidase inhibitory activity of analogues of 4-Guanidino-Neu5Ac2en (Zanamivir modified in the glycerol side-chain. Eur J Med Chem Jul.-Aug. 1999;34(7-8):563-74.
Angata et al., "Chemical diversity in the sialic acids and related α-keto acids: an evolutionary perspective," *Chem. Rev.*, Feb. 2002, 102(2):439-469.

Anthony, Robert et al., Recapitulation of IVIG Anti-Inflammatory Activity with a Recombinant lgG Fc, Science Apr. 18, 2008. 320:373-376.
Arase et al., "NK1.1$^+$CD4$^+$CD8' thymocytes with specific lymphokine secretion," *Eur. J. Immunol.*, Jan. 1993, 23(1):307-310.
Aspeslagh et al., "Galactose-modified iNKT cell agonists stabilized by an induced fit of CD1d prevent tumour metastasis," *EMBO J.*, Jun. 1, 2011, 30(11):2294-2305.
Astronomo, R. D. & Burton, D.R. Carbohydrate vaccines: developing sweet solutions to sticky situations? Nat. Rev. Drug. Discov. 9, 308-324, (2010.
Bacilieri, Magdalena et al., Ligand-Based Drug Design Methodologies in Drug Discovery Process: An Overview, Current Drug Discovery Technologies, vol. 3 (3), Sep. 2006, p. 155-165.
Bacteroides Fragilis NCTC 9343, Complete Genome., Mar. 3, 2005, XP002775523, Database Accession No. CR626927, 2 Pages.
Bacteroides Thetaiotaomicron VPI-5482, Section 8 of 21 of the Complete Genome, XP002775522, Jan. 6, 2006, Database Accession No. AE016933, 2 Pages.
Bai, Dan et al., Exploring Forster Electronic Energy Transfer in a Decoupled Anthracenyl-based Borondipyrromethene (Bodipy) Dyad, Physical Chemistry Chemical Physics (2012), 14(13), 4447-4456.
Bailey, Ryan et al., Real-Time Multicolor DNA Detection with Chemoresponsive Diffraction Gratings and Nanoparticle Probes, J. Am Chem. Soc., 2003, 125, 13541-13547.
Banchereau et al., "Dendritic cells and the control of immunity," *Nature*, Mar. 19, 1998, 392(6673):245-252.
Bardotti, Angela et al., Size Determination of Bacterial Capsular Oligosaccharides Used to Prepare Conjugated Vaccines Against Neisseria Meningitidis Groups Y and W135, Vaccine 2005, 23, 1887-1899.
Barouch, D. H. Challenges in the development of an HIV-I vaccine. Nature 455, 613-619, (2008).
Barry, C.S. et al., 'Naked' and Hydrated Confirmers of the Conserved Core Pentasaccharide of N-Linked Glycoproteins and Its Building Blocks, Journal of the American Chemical Society, 2013, vol. 135(45), pp. 16895-16903.
Basak et al., In Vitro Elucidation of Substrate Specificity and Bioassay of Proprotein Convertase 4 Using Intramolecularly Quenched Fluorogenic Peptides, Biochem. J. Jun. 1, 2004, 380(pt 2): 505-514.
Baskin, J.M.; Amacher, S. L.; Bertozzi, C.R. "In vivo imaging of membraneassociated glycans in developing zebrafish." Science 2008, 320, 664-667.
Bassell, G.J. et al., Single mRNAs Visualized by Ultrastructural in Situ Hybridization are Principally Localized at Actin Filament Intersections in Fibroblasts, J. Cell Biol., 126, 863-876 (1994.
Baz et al., Emergence of oseltamivir-resistant pandemic H1N1 virus during prophylaxis. N Engl J Med. Dec. 3, 2009;361(23):2296-7. doi: 10.1056/NEJMc0910060. Epub Nov. 11, 2009.
Beckman et al., Antibody constructs in cancer therapy: protein engineering strategies to improve exposure in solid tumors, cancer, 109(2): 170-179 (2007).
Bendayan, Moise, Possibilities of False Immunocytochemical Results Generated by the Use of Momoclonal Antibodies: The Example of the Anti-Proinsulin Antibody, J. Histochem. Cytochem, 43: 881-886, (1995).
Bennett, Clay et al., Chemoenzymatic Approaches to Glycoprotein Synthesis, Chem. Soc. Rev. 2007, 36:1227-1238.
Berg, Jan-Olof et al., Purification of Glycoside Hydrolases From Bacteroides Fragilis, Applied and Environmental Microbiology, vol. 40, No. 1, Jul. 1980, p. 40-47.
Berge, Steven et al. J. Pharmaceutical Sciences (1977) 66: 1-19.
Best, M. D. " Click chemistry and bioorthogonal reactions: unprecedented selectivity in the labeling of biological molecules." Biochemistry 2009, 48, 6571-6584.
Bertozzi, CR et al., Glycans in Cancer and Inflammation—Potential for Therapeutics and Diagnostics, Nat Rev Drug Discovery, 2005, 4, 477-488.

(56) References Cited

OTHER PUBLICATIONS

Bigi et al., "Human sialidase NEU4 long and short are extrinsic proteins bound to outer mitochondrial membrane and the endoplasmic reticulum, respectively," *Glycobiology*, Feb. 2010, 20(2):148-157.
Blixt, O. et al. Printed covalent glycan array for ligand profiling of diverse glycan binding proteins. Proc. Natl. Acad. Sci. U.S.A. 101, 17033-17038, (2004.
Boens, N. et al., "Fluorescent indicators based on BODIPY." Chem. Soc. Rev. 2012, 41, 1130-1172.
Borg et al., "CD1d-lipid-antigen recognition by the semi-invariant NKT T-cell receptor," *Nature*, Jul. 5, 2007, 448(7149):44-49.
Bosmann et al., "Enzyme activity in invasive tumors of human breast and colon," *Proc. Natl. Acad. Sci. USA*, May 1974, 71(5):1833-1837.
Bost, Kenneth et al., Antibodies Against A Peptide Sequence Within the HIV Envelope Protein Crossreacts With Human Interleukin-2, Immunol. Invest., 17: 577-586 (1988).
Boyer, David et al., Photothermal Imaging of Nanometer-Sized Metal Particles Among Scatterers, Science, 2002, 297, 1160-1163.
Braun-Howland et al., Development of a Rapid Method for Detecting Bacterial Cell in Situ Using 16S rRNA-Targeted Probes, Biotechniques, 13, 928-931 (1992).
Bricard et al., "Enrichment of human CD4+ Vα24/Vβ11 invariant NKT cells in intrahepatic malignant tumors," *J. Immunol.*, Apr. 15, 2009, 182(2):5140-5151.
Bruchez, Marcel et al. Semiconductor Nanocrystals as Fluorescent Biological Labels, Science 281:2013-2016, 1998.
Buchini et al., "Towards a new generation of specific Trypanosoma cruzi trans-sialidase inhibitors," *Angew. Chem. Int. Ed. Engl.*, 2008, 47(14):2700-2703.
Burton, D.R., Mascola, J. R. Antibody responses to envelope glycoproteins in HIV-I infection. Nature Immunol. 16, 571-6, (2015).
Calarese, D. A. et al. Antibody domain exchange is an immunological solution to carbohydrate cluster recognition. Science 300, 2065-2071, (2003).
Cao, Y. C. et al., Nanoparticles with Raman Spectroscopic Fingerprints for DNA and RNA Detection, Science, 2002, 289, 1757-60.
Carlsson, Jan et al., Protein Thiolation and Reversible Protein-Protein Conjugation, Biochem J 173: 723-737 (1978).
Carter, A rationale for using steroids in the treatment of severe cases of H5N1 avian influenza. J Med Microbiol. Jul. 2007;56(Pt 7):875-83.
Centers for Disease Control and Prevention (CDC), "Influenza activity—United States and worldwide, 2007-08 season" *MMWR*, Jun. 27, 2008, 57(25):692-697.
Cespedes et al., Mouse models in oncogenesis and cancer therapy, Clin Transl Oncl., 8(5): 318-329 (2006).
Chan, Warren et al., Quantum Dot Bioconjugates for Ultrasenstive Nonisotopic Detection, Science 281:2016-2018 (1998).
Chandler et al., Synthesis of the potent influenza neuraminidase inhibitor 5-guanidino Neu5Ac2en. X-Ray molecular structure of 5-acetaminido-4amino-2,6-anahydro-3,4,5-tryoxy-D-erythoro-L-gluco-nononic acid. J Chem Soc Perkin Trans 1. 1995; 1173-1180.
Chang, S. H. et al. Glycan array on aluminum oxide-coated glass slides through phosphonate chemistry. J. Am. Chem. Soc. 132, 13371-13380, (2010).
Chang et al., "Potent immune-modulating and anticancer effects of NKT cell stimulatory glycolipids," *Proc. Natl. Acad. Sci. USA*, Jun. 19, 2007, 104(25):10299-10304.
Chao, W.; Fang, X.; Nisaraporn, S.; Jian, S.; Qian, W. "Tuning the optical properties of BODIPY dye through Cu(I) catalyzed azide-alkyne cycloaddition (CuAAC) reaction." Sci. China Chemistry 2012, 55, 125-130.
Chari, Ravi et al., Immunoconjuates Containing Novel Maytansinoids: Promising Anticancer Drugs Cancer Research 52: 127-131 (1992).

Chauhan, D. P.; Saha, T.; Lahiri, M.; Talukdar, P. "BODIPY based 'click on' fluorogenic dyes: application in live cell imaging." Tetrahedron Lett. 2014, 55, 244-247.
Cheng, Peter et al., Oseltamivir-and Amandtadine-resistant Influenza Viruses A (H1N1), Emerg. Infect. Dis., Jun. 2009, 15(6): 966-968.
Cheung et al., Stage-specific embryonic antigen-3 (SSEA-3) and beta3GalT5 are cancer specific and significant markers for breast cancer stem cells, PNAS, Jan. 26, 2016, vol. 113, No. 4, pp. 960-965.
Chiang et al., Ethyl caffeate suppresses NF-kappaB activation and its downstream inflammatory mediators, iNOS, COX-2, and PGE2 in vitro or in mouse skin. Br J Pharmacol. Oct. 2005; 146(3):352-63.
Chiari, M. et al., Advanced Polymers for Molecular Recognition and Sensing at the Interface. J Chromatography B, Apr. 15, 2008, 866(1-2):89-103.
Childs et al., Receptor-Binding Specificity of Pandemic Influenza A (H1N1) 2009 Virus Determined by Carbohydrate Microarray. Nat Biotechnol. 2009, 27(9): 797-799.
Cho, Se-Heon et al., Sialyl-Tn Antigen Expression Occurs Early During Human Mammary Carcinogenesis and Is Associated with High Nuclear Grade and Aneuploidy, Cancer Res. 54, 6302-6305, 1994.
Chong et al., Influenza Virus Sialidase: Effect of Calcium on Steady-State Kinetic Parameters, Biochim. Biophys. Acta, Mar. 8, 1991, 1077(1): 65-71.
Chothia et al., "Domain association in immunoglobulin molecules. The packing of variable domains," *J. Mol. Biol.*, Dec. 5, 1985, 186(3):651-663.
Chu, Kuo-Chinget al., Efficient and Stereoselective Synthesis of [alpha](2->9) Oligosialic Acids: From Monomers to Dodecamers, Angewandte Chemie International Edition, vol. 50, No. 40, Sep. 2011, 9391-9395.
Codelli, J. A. et al., Second-Generation Difluorinated Cycloctynes for Copper-Free Click Chemistry, J. Am. Chem. Soc. 2008, 130, 11486-11493.
Cohen-Daniel et al., Emergance of Oseltamivir-Resistant Influenza A/H3N2 Virus with Altered Hemagglutination Pattern in Hematopoietic Stem Cell Transplant Recipient, J Clin Virol., Feb. 2009, 44(2):138-140.
Coligan et al., Current Protocols in Immunology, sections 2.5.1-2. 6.7, 1991.
Collins et al., Crystal Structures of Oseltamivir-Resistant Influenza Virus Neuraminidase Mutants, Nature, Jun. 26, 2008, 453(7199):1258-1261.
Connor, Robert et al., Receptor Specifcity in Human, Avian, and Equine H2 and H3 Influenza Virus Isolates, Virology, 205: 17, 1994.
Cox et al., New Options for the Prevention of Influenza, N. Engl. J. Med. Oct. 28, 1999, 341(18): 1387-1388.
Cragg, M.S. et al., Complement-Mediated Lysis by Anti-CD20 mAb Correlates with Segregation into Lipid Rafts, Blood 101 (2003) 1045-1052.
Cragg, M.S. et al., Antibody Specificity Controls in Vivo Effector Mechanism of Anti-CD20 Reagents, Blood, 103 (2004) 2738-2743.
Craigo, J. K., Montelaro, R. C. Lessons in AIDS vaccine development learned from studies of equine infectious, anemia virus infection and immunity. Viruses 5, 2963-76, (2013).
Crispin et al., "Carbohydrate and domain architecture of an immature antibody glycoform exhibiting enhanced effector functions," J. Mol. Biol., Apr. 17, 2009, 387(5):1061-1066.
Cyranoski, Threat of Pandemic Brings Flu Drug Back to Life, Nat. Med. Sep. 2005, 11(9): 909.
Davies, JW et al., Streamlining Lead Discovery by Aligning in Silico and High-Throughput Screening, Curr Opin Chem Biol. Aug. 2006; 10(4):343-51.
Davodeau et al., "Close phenotypic and functional similarities between human and murine αβ T cells expressing invariant TCR alpha-chains," *J. Immunol.*, Jun. 15, 1997, 158(12):5603-5611.
De Almeida et al., "Thiacycloalkynes for copper-free click chemistry," *Angew. Chem. Int. Ed. Engl.*, Mar. 5, 2012, 51(10):2443-2447.
Debets, M. F. et al., Bioconjugation with Strained Alkenes and Alkynes, Acc. Chem. Res. 2011, 44, 805-815.

(56) References Cited

OTHER PUBLICATIONS

DeJong et al., Fatal outcome of human influenza A (H5N1) is associated with high viral load and hypercytokinemia. Nat Med Oct. 2006;12(10):1203-7. Epub Sep. 10, 2006.
DeLente, Jacqubs, Glycosylation Revisited, Trends in Biotechnology 3, letters to editor, No. 9 (1985).
Dellabona et al., "An invariant Vα24-JαQ/Vβ11 T cell receptor is expressed in all individuals by clonally expanded CD4⁻8⁻ T cells," *J. Exp. Med.*, Sep. 1, 1994, 180(3):1171-1176.
Demchenko, A.V., Ed., Hanbook of Chemical Glycosylation: Advances in Stereoselectivity and Therapeutic Relevance (2008) WILEY-VCH. Chapter 1. General Aspects of the Glycosidic Bond Formation, in 28 pages.
Dennis, Carina, Cancer: Off by a whisker, Nature 442: 739-741 (2006).
De Paz, J. L., Horlacher, T. & Seeberger, P.H. Oligosaccharide microarrays to map interactions of carbohydrates in biological systems. Methods Enzymol. 415, 269-292, (2006).
Dicker, Martina et al., Using Glyco-Engineering to Produce Therapeutic Proteins, Expert Opinion on Biological Therapy, vol. 15, Jan. 1, 2015, pp. 1501-1516.
Dhodapkar et al., "α-Galactosyl ceramide-loaded dendritic cells for expansion of natural killer T cells" CAPLUS 145:354715 (2006).
Dhodapkar et al., "A reversible defect in natural killer T cell function characterizes the progression of premalignant to malignant multiple myeloma," *J. Exp. Med.*, Jun. 16, 2003, 197(12):1667-1676.
Dohi, Taeko et al., Fucosyltransferase-Producing Sialyl Lea and Sialyl Lex Carbohydrate Antigen in Benign and Malignant Gastrointestinal Mucosa, Cancer 73, 1552, 1994.
Dohi, H. et al., Stereoselective Glycal Fluorophosphorlation: Synthesis of ADP-2-Fluoroheptose, an Inhibitor of the LPS Biosynthesis, Chem-Eur J 2008, 14, 9530-9539.
Dommerholt, Jan, Readily Accessible Bicyclononynes for Bioorthogonal Labeling and Three-Dimensional Imaging of Living Cells, Angew. Chem. Int. Ed. 2010, 49, 9422-9425.
Doores KJ, et al. A nonself sugar mimic of the HIV glycan shield shows enhanced antigenicity. Proc. Natl. Acad Sci. US.A. 107(40), 17107-17112, (2010).
Doores, K. J. & Burton, D.R. Variable Loop Glycan Dependency of the Broad and Potent HIV-I-Neutralizing Antibodies PG9 and PG16. J. Virol. 84, 10510-10521, (2010).
Doores, K. J. et al. Envelope glycans of immunodeficiency virions are almost entirely oligomannose antigens. Proc. Natl. Acad. Sci. U. S. A 107, 13800-13805, (2010).
Doronina, Svetlana et al., Development of Potent Monoclonal Antibody Auristatin Conjugates for Cancer Therapy, Nat Biotechnol 21(7): 778-784 (2003).
Dougan, Michael et al., Immune Therapy for Cancer, Annual Review of Immunology, 2009, 27, pp. 83-117.
Drugs of the future 25(7): 686 (2000).
Dubertret. Benoit et al., In Vivo Imaging of Quantum Dots Encapsulated in Phospholipid Micelles, Science 298:759-1762, 2002.
Duncan, AR; Winter, G, The binding Site for C1q on IgG, Nature 322:738-40 (1988).
Dunn et al., Zanamivir: A Review of Its Use in Influenza, Drugs, Oct. 1999, 58(4):761-784.
Eberl et al., "Selective bystander proliferation of memory CD4⁺and CD8⁺T cells upon NK T or T cell activation," *J. Immunol.*, Oct. 15, 2000, 165(8):4305-4311.
Eberl et al., "Selective induction of NK cell proliferation and cytotoxicity by activated NKT cells," *Eur. J. Immunol.*, Apr. 2000, 30(4):985-992.
Eggink, D. et al. Lack of complex N-glycans on HIV-I envelope glycoproteins preserves protein conformation and entry function. Virology 401, 236-247, (2010).
Eisen, Michael et al., Binding of the Influenza A Virus to Cell-Surface Receptors: Structures of Five Hemagglutinin-Sialyloligosaccharide Complexes Determined by X-Ray Crystallography, Virology, 232:19, 1997.

Ellis J., et al., Evaluation of Four Real-Time PCR Assays for Detection of Influenza A9H1N1)v Viruses, Euro Surveill. 2009; 14(22), p. 1-3.
European Search Report issued in connection with corresponding European Patent Application No. 15181446.4, dated Dec. 7, 2015, 10 pages.
Evans, Michael et al., "Mechanism-based profiling of enzyme families," Chem. Rev., Aug. 2006, 106(8):3279-3301.
Evans, "The rise of azide-alkyne 1,3-dipolar 'click' cycloaddition and its application to polymer science and surface modification," Australian J. Chem., Jun. 2007, 60(6):384-395.
Extended European Search Report dated Jan. 5, 2016 in European Patent Application No. 13830785.5, in 10 pages.
Extended European Search Report, App. No. 15799789.1, dated Nov. 28, 2017, 10 Pages.
Extended European Search Report, App. No. 158001917, dated Nov. 28, 2017, 12 Pages.
Extended European Search Report, App. No. 15799981.4, dated Nov. 29, 2017, 9 Pages.
Falkowska, E. et al. Broadly neutralizing HIV antibodies define a glycan-dependent epitope on the prelusion conformation of gp41 on cleaved envelope trimers. Immunity 40, 657-68, 2014.
Fan, Shu-Quan et al., Remarkable Transglycosylation Activity of Glycosynthase Mutants of Endo-D, an Endo-β-N-acetylglucosaminidase from Streptococcus Pneumoniae, JBC vol. 287, No. 14, pp. 11272-11281, Mar. 30, 2012.
Fazio, F. et al., Synthesis of sugar arrays in microtiter plate. J. Am. Chem. Soc. 124, 14397-14402, (2002).
FDA Guidance for Industry for Container Closure Systems for Packaging Human Drugs and Biologics, May 1999.
Fedson, Confronting the next influenza pandemic with anti-inflammatory and immunomodulatory agents: why they are needed and how they might work. Influenza Other Respi Virusts. Jul. 2009;3(4):129-42.
Feizi, Ten, Carbohydrate Differentiation Antigens: Probable Ligands for Cell Adhesion Molecules,Trends Biochem. Sci. 16, 84-86.
Fernandez-Tejada, Alberto et al., Designing synthetic vaccines for HIV. Expert Rev. Vaccines 14, 815-31, 2015.
Fernandez-Megia et al., A Click Approach to Unprotected Glycodendrimers. Macromolecules 2006, vol. 39, pp. 2113-2120.
Fessner et al., Enzymes in Organic Synthesis, Short Enzymatic Synthesis of L-Fucose Analogs. Eur. J. Org. Chem 2000, p. 125-132.
Fiehn, Oliver, Combining Genomics, Metabolome Analysis, and Biochemical Modelling to Understand Metabolic Networks, Comparative and Functional Genomics 2:155-168, 2001.
Fraker, PJ et al., Protein and Cell Membrane Iodinations with a Sparingly Soluble Chloroamide, 1,3,4,6-tetrachloro-3a,6a-diphrenylglycoluril, Biochem. Biophys. Res. Commun. 80: 49-57 (1978).
Frank, Natasha et al., The Therapeutic Promise of the Cancer Stem Cell Concept, Journal of Clinical Investigation, 120(1) 41-50, Jan. 2010.
Friscourt, F. et al., A Fluorogenic Probe for the Catalyst-Free Detection of Azide-Tagged Molecules, J. Am. Chem. Soc. 2012, 134, 18809-18815.
Friscourt et al., "Polar Dibenzocyclooctynes for Selective Labeling of Extracellular Glycoconjugates of Living Cells," *J. Am. Chem. Soc.*, Mar. 21, 2012, 134(11):5381-5389.
Fujimore, Kenji et al., A Modeling Analysis of Monoclonal Antibody Percolation Through Tumors: A Binding-Site Barrier, J Nuc Med. 31: 1191-1198 (1990).
Fujio, M. et al. "Structure-Based Discovery of Glycolipids for CD1d-Mediated NKT Cell Activation: Turning the Adjuvant versus Immunosuppression Activity." CAPLUS 145:240945 (2006).
Fujio, M. et al. "Structure-Based Discovery of Glycolipids for CD1d-Mediated NKT Cell Activation: Turning the Adjuvant versus Immunosuppression Activity." J. Am. Chem. Soc. (2006), vol. 128, pp. 9022-9023.
Fukui, S et al., Oligosaccharide microarrays for high-throughput detection and specificity assignments of carbohydrate- protein interactions. Nat. Biotechnol. 20, 1011-1017, (2002).

(56) References Cited

OTHER PUBLICATIONS

Gabius, HJ. Tumor Lectinology: at the intersection of carbohydrate chemistry, biochemistry, cell biology and oncology. Angew. Chem. Int. Ed. Engl. 27, 1267-1276.
Gamblin, SJ et al., The Structure and Receptor Binding Properties of the 1918 Influenza Hemagglutinin, Science, 303:1838, 2004.
Garces, F. et al. Structural evolution of glycan recognition by a family of potent HIV antibodies. Cell 159, 69-79, (2014).
Gaschen, B. et al. AIDS—Diversity Considerations in HIV-I vaccine selection. Science 296, 2354-2360, (2002).
Geiler et al., Comparison of pro-inflammatory cytokine expression and cellular signal transduction in human macrophages infected with different influenza A viruses. Med Microbiol Immunol. Feb. 2011;200(1):53-60.
GenBank accession No. WP_0080769537.1, published May 10, 2013.
GenBank accession No. WP_008767711.1, published May 10, 2013.
Geoghegan, Kieran et al., Site-Directed Conjugation of Nonpeptide Groups to Peptides and Proteins Via Periodate Oxidation of a 2-amino Alcohol. Applications to Modification at N-Terminal Serine, Bioconjugate chem. 3:138-146 (1992).
Gerson et al., "ESR. Spectra and Structures of Radical Anions in the Dibenzo[a, e]cyclooxtene Series," *Helvetica Chinica Acta*, Jan. 1, 1976, 59(6): 2038-2048.
Giaccone, Giuseppe et al., "A phase I study of the natural killer T-cell ligand α-galactosylceramide (KRN7000) in patients with solid tumors," *Clin. Cancer Res.*, Dec. 2002, 8(12):3702-3709.
Go, E. P. et al. Characterization of glycosylation profiles of HIV-I transmitted/founder envelopes by mass spectrometry. J. Virol. 85, 8270-8284, (2011).
Go, E. P. et al. Comparative Analysis of the Glycosylation Profiles of Membrane-Anchored HIV-I Envelope Glycoprotein Trimers and Soluble gp140. J. Virol. 89, 8245-57, (2015).
Godefroy, S. et al., Effect of Skin Barrier Disruption on Immune Responses to Topically Applied Cross-Reacting Material, CRM197 of Diphtheria Toxin, Infect. Immun. 2005, 73, 4803.
Goldenthal et al., "Safety Evaluation of Vaccine Adjuvants: National Cooperative Vaccine Development Working Group," *AIDS Res. Hum. Retroviruses*, 1993, 9(Supp.1):S47-S51.
Golkowski et al., "Strategy for catch and release of azide-tagged biomolecules utilizing a photolabile strained alkyne construct," *Organic and Biomolecular Chemistry*, Jan. 1, 2012, 10(23):4496.
Govorkova et al, Combination chemotherapy for influenza. Viruses. Aug. 2010;2(8):1510-29.
Gordon et al., "Reactivity of biarylazacyclooctynones in copper-free click chemistry," *J. Am. Chem. Soc.*, Jun. 6, 2012, 134(22): 9199-9208.
Graham, Duncan et al., Surface-Enhanced Resonance Raman Scattering as a Novel Method of DNA Discrimination, Angew. Chem., 2000, 112(6), 1103-1105.
Grandjean, C. et al., On the Preparation of Carbohydrate-Protein Conjugates Using the Traceless Staudinger Ligation, J Org Chem 2005, 70, 7123-7132.
Greenbaum et al., "Chemical approaches for functionally probing the proteome," *Mol. Cell. Proteomics*, 2002, 1:60-68.
Grubisha, D. S. et al., Femtomolar Detection of Prostate-Specific Antigen: An Immunoassay Based on Surface-Enhanced Raman Scattering and Immunogold labels, Anal. Chem. (2003), 75, 5936-5943.
Gulati et al., Deletions of Neuraminidase and Resistance to Oseltamivir May Be a Consequence of Restricted Receptor Specificity in Recent H3N2 Influenza Viruses. Virol. J. 2009, 6(22)L 1-15.
Gulland, Fire Cases of Spread of Oseltamivir Resistant Swine Flu Between Patients are Reported in Wales, BMJ, Nov. 23, 2009:339:b4975.
Ha, Ya et al., X-Ray Structures of H5 Avian and H9 Swine Influenza Virus Hemagglutinins Bound to Avian and Human Receptor Analogs, Proc Natl Acad Sci USA, 98:11181-11186, 2001.
Ha, Ya et al., X-Ray Structure of the Hemagglutinin of a Potential H3 Avian Progenitor of the 1968 Hong Kong Pandemic Influenza Virus, Virology, 309:209-218, 2003.
Hajishengallis, "Mucosal immunization with a bacterial protein antigen genetically coupled to cholera toxin A2/B subunits," *J. Immuol.*, May 1, 1995, 154(9):4322-4332.
Ham, Richard et al., Media and Growth Requirements, Meth. Enz 58, 44 (1979).
Hammerling et al., in: Monoclonal Antibodies and T-Cell Hybridomas 563-587, 1981.
Han, Junyan et al., 3- and 5-Functionalized BODIPYs via the Liebeskind-Srogl Reaction, Organic & Biomolecular Chemistry (2009), 7(1), 34-36.
Hanski, Christoph et al., Altered Glycosylation of the MUC-1 Protein Core Contributes to the Colon Carcinoma-Associated Increase of Mucin-Bound Sialyl-Lewis Expression, Cancer Res. 53, 4082-4088 (1993).
Hanski, C. et al., Characterization of the Major Sialyl-Lex-Poristive Mucins Present in Colon, Colon Carcinoma, and Sera of Patients with Colorectal Cancer, Cancer Res. 55, 928-933 (1995).
Hasegawa, Akira, et al., Synthesis of Sialyl Lewis X Ganglioside Analogues Containing Modified L-Fucose Residues, Carbohydr. Res. 1995, 274, 165-181.
Hata, K. et al., Limited Inhibitory Effects of Oseltamivir and Zanamivir on Human Sialidases, Antimicrobial Agents and Chemotherapy, vol. 52, No. 10, Oct. 2008, in 8 pages.
Healthy Living, "10 Simple and Natural Ways to Boost Your Immune System," Published Jan. 31, 2014, downloaded from online, http://www.everydayhealth.com/columns/white-seeber-grogan-the-remedy-chicks/ten-simple-natural-ways-to-b . . . on Aug. 19, 2016.
Henglein, A. et al., Absorption Spectrum and Some Chemical Reactions of Colloidal Platinum in Aqueous Solution, J. Phys. Chem., 99, 14129 (1995).
Herner, A et al., A new family of bioorthogonally applicable fluorogenic labelst, Org. Biomol. Chem. 2013, 11, 3297-3306.
Hey, Thomas et al., Artificial, non-antibody binding proteins for pharmaceutical and industrial application, Trends in Biotechnology 23(10) 514-522 (2005).
Hirabayashi, J. et al., Oligosaccharide Microarrays for Glycomics, Trends in Biotechnology 21 (4): 141-143, 2003.
Holmskov, Uffe et al., Collectins: Collagenous C-Type Lectins of the Innate Immune Defense System, 1994, Immunol. Today, 15: 67.
Honda et al., Synthesis and anti-influenza virus activity of 7-0-alkylated derivatives related to zanamivir. Bioorg Med Chem Lett. Aug. 5, 2002;12(15):1925-8.
Hotha, Srinivas et al., "Click Chemistry" Inspired Synthesis of Pseudo-Oligosaccharides and Amino Acid Glycoconjugates, J Org Chem 2006, 71, 364-367.
Horiya, S. et al., Recent strategies targeting HIV glycans in vaccine design. Nat. Chem. Biol. 10, 990-999, (2014).
Horn et al., Investigation into an Efficient Synthesis of 2,3-dehydro-N-acetyl Neuraminic Acid Leads to Three Decarboxylated Sialic Acid Dimers, Carbohdr. Res., Apr. 7, 2008, 343(5):936-940.
Howard et al., "Biological properties of interleukin 10," *Immunol. Today*, Jun. 1992, 13(6):198-200.
Hsu, Nien-Yeen et al., Desorption Ionization of Biomolecules on Metals, Anal. Chem., 80, 5203-5210, 2008.
Hsu et al., "Alkynyl sugar analogs for the labeling and visualization of glycoconjugates in cells," *Proc. Natl. Acad. Sci. USA*, Feb. 20, 2007, 104(8), 2614-2619.
Huang, Lijun et al., Iterative One-Pot Syntheses of Chitotetroses, Carbohydr. Res. 2006, 341, 1669-1679.
Huang et al., Recombinant immunotherpaeutics: current state and perspectives regarding the feasibility and market, Appl Microbiol Biotechnol, 87: 401-410. 2010.
Huang, Wei et al., Chemoenzymatic Glycoengineering of Intact IgG Antibodies for Gain of Functions, Journal American Chemical Socirty, vol. 134, No. 9, Jul. 25, 2012, pp. 12308-12318.
Immunogenicity, Wikipedia p. 1-3. Downloaded on Aug. 16, 2016 from https://en.wikipedia.org/wiki/Immunogenicity. (2016).

(56) References Cited

OTHER PUBLICATIONS

International Search Report and Written Opinion issued for International application No. PCT/US2015/011748, dated Aug. 21, 2015, 17 pages.
International Search Report dated Jan. 13, 2012, from corresponding International Patent Application No. PCT/US2011/035982, 17 pages.
International Search Report dated Nov. 13, 2014, from corresponding International Patent Application No. PCT/US2014/054617, 10 pages.
International Search Report issued for International application No. PCT/US15/22977, dated Jun. 22, 2015, 3 pages.
International Search Report issued for International application No. PCT/US15/40199, dated Mar. 2, 2016, 6 pages.
International Search Report issued for International application No. PCT/US2009/050754, dated Feb. 24, 2010, 10 pages.
International Search Report and Written Opinion in International Application No. PCT/US2017/021454, dated Jul. 31, 2017, 8 pages.
International Search Report and Written Opinion in International Application No. PCT/US2017/048074, dated Dec. 26, 2017, 17 pages.
Isshiki et al., Cloning, Expression, and Characterization of a Novel UDP-galactose:b-N-Acetylglucosamine b1,3-Galactosyltransferase (b3Gal-T5) Responsible for Synthesis of Type 1 Chain in Colorectal and Pancreatic Epithelia and Tumor Cells Derived Therefrom, The Journal of Biological Chemistry, Apr. 30, 1999, vol. 274, No. 18, pp. 12499-12507.
Ito, Akihero et al., A Novel Ganglioside Isolated From Renal Cell Carcinoma, Biol Chem 2001, 276, 16695.
Jacobs et al., "Metabolic labeling of glycoproteins with chemical tags through unnatural sialic acid biosynthesis," *Methods Enzymol.*, 2000, 327:260-275.
Japanese Office Action dated Apr. 21, 2015, from Related Japanese Patent Application No. 2013-510261, 6 Pages.
Jayasena, Sumedha, Aptamers: An Emerging Class of Molecules That Rival Antibodies in Diagnostics, Clin. Chem. (1999), 45, 1628-1650.
Jewett, J.C.; Bertozzi, C.R., Cu-Free Click Cycloaddition Reactions in Chemical Biology, Chem. Soc. Rev. 2010, 39, 1272-1279.
Jewett, J.C.; Sletten, E. M.; Bertozzi, C.R., Rapid Cu-Free Click Chemistry with Readily Synthesized Biarylazacyclooctynones, J. Am. Chem. Soc. 2010, 132, 3688-3690.
Jewett et al., "Synthesis of a fluorogenic cyclooctyne activate by Cu-free click chemistry," *Org. Lett.*, Nov. 18, 2011, 13(22):5937-5939.
Jin, R. C. et al., Photoinduced Conversion of Silver Nanospheres to Nanoprisms, Science (2001), 294, 1901-1903.
Jobling, Michael et al., Fusion Proteins Containing the A2 Domain of Cholera Toxin Assemble With B Polypeptides of Cholera Toxin to Form Immunoreactive and Functional Holotoxin-Like Chimeras, Infect Immun., 60: 4915-24, 1992.
John, F. & Hendrickson, T. L. Synthesis of Truncated Analogues for Studying the Process of Glycosyl Phosphatidylinositol Modification. Org. Lett. 12, 2080-2083, (2010).
Jonges, M. et al., Dynamics of Antiviral-Resistant Influenza Viruses in the Netherlands, 2005-2008, Antiviral Res., Sep. 2009, 83(3): 290-297.
Jorgensen, Trond et al., Up-Regulation of the Oligosaccharide Sialyl Lewisx: A New Prognostic Parameter in Metastatic Prostate Cancer, Cancer Res. 55, 1817-1819, 1995.
Jose, Jiney et al., Energy transfer dyads based on Nile Red, Tetrahedron Letters (2009), 50(47), 6442-6445.
Joshi, Shantaran et al., Cell Surface Properties Associated with Malignancy of Metastatic Large Cell Lymphoma Cells, (1987) Cancer Res. 47, 3551-3557.
Joyce, J. G. et al. An oligosaccharide-based HIV-I 2G12 mimotope vaccine induces carbohydrate-specific antibodies that fail to neutralize HIV-I virions. Proc. Natl. Acad. Sci. U. S. A 105, 15684-15689, (2008).

Kakeji, Y. et al., Correlation Between Sialyl Tn Antigen and Lymphatic Metastasis in Patients with Borrmann Type IV Gastric Carcinoma, Brit. J. Cancer 71, 191-195, 1995.
Kale et al., Detection of intact influenza viruses using biotinylated biantennary S-sialosides. J Am Chem Soc. Jul. 2, 2008;130(26):8169-71.
Kalesh et al., "Peptide-based activity-based probes (ABPs) for target-specific profiling of protein tyrosine phosphatases (PTPs)," *Chem. Commun.*, Jan. 28, 2010, 46(4):589-591.
Kamkaew, A. et al., "BODIPY dyes in photodynamic therapy." Chem. Soc. Rev. 2013, 42, 77-88.
Katagiri, Yohko et al Laminin Binding Protein, 34/67 Laminin Receptor, Carries Stage-Specific Embryonic Antigen-4 Epitope Defined By Monoclonal Antibody Raft.2, Biochemical and Biophysical Research Communcations, 332, 1004-1011, 2005.
Kawakami et al., "Critical role of V$\alpha$14+natural killer T cells in the innate phase of host protection against *Streptococcus pneumoniae* infection," *Eur. J. Immunol.*, Dec. 2003, 33(12):3322-3330.
Kawano et al., "CD1d-restricted and TCR-mediated activation of v$_\alpha$14 NKT cells by glycosylceramides," *Science*, Nov. 28, 1997, 278(5343):1626-1629.
Kanie, Osmau et al., Orthogonal glycosylation strategy in synthesis of extended blood group B determinant. Tetrahedron Lett. 37, 4551-4554 (1996).
Kannappan, Ramaswamy et al., "Photoaffinity labeling of sialidase with a biotin-conjugated phenylaminodizairine derivative of 2,3-didehydro-2-deoxy-N-acetylneuraminic acid," *Biol. Pharm. Bull.*, Mar. 2008, 31(3):352-356.
Karlin, Samuel et al., Applications and Statistics for Multiple High-Scoring Segments in Molecular Sequences, Proc. Natl. Acad Sci. USA 90:5873-77, 1993.
Karmakar, M. et al., Current Trends in Research and Application of Microbial Cellulases, Research Journal of Microbiology, (2001) 6(1): 41-53.
Kermani, Pouneh et al., Production of ScFv Antibody Fragments Following Immunization with a Phage-Displayed Fusion Protein and Analysis of Reactivity to Surface-Exposed Epitopes of the Protein F of Pseudomonas Aeruginosa by Cytofluorometry, Hybridoma, 14(4):323-328 (1995).
Kidd et al., "Profiling serine hydrolase activities in complex proteomes," *Biochemistry*, Apr. 3, 2001, 40(13):4005-4015.
Kiick, K.L. et al., Identificationof an Expanded Set of Translationally Active Methionine Analogues in *Escherichia coli*, tetrahedron 56:9487, 2001.
Kim et al., High-Throughput Screening of Glycan-Binding Proteins Using Miniature Pig Kidney N-Glycan-Immobilized Beads, Chemistry & biology 15.3, p. 215-223 (2008).
Kim, Gap-Sue et al., AB Initio Study of Excited Electronic States and Vibronic Spectra of Phenyl Radical, Chem Phys. Lett., 2002, 3 5 2, 421.
Kimura et al., Design and Synthesis of Immobilized Tamiflu Analog on Resin for Affinity Chromatography, Tetrahedron Lett., Jul. 1, 2009, 50(26):3205-3208.
King, M. et al., New Tetramethlthiepinium (TMTI) for Copper-Free Click Chemistry, Chem. Commun. 2012, 48, 9308-9309.
Kitamura et al., "$\alpha$-galactosylceramide induces early B-cell activation through IL-4 production by NKT cells," *Cell. Immunol.*, Jan. 10, 2000, 199(1):37-42.
Klein, J. et al., "Isomaltines and their N-acyl derivatives, their preparation, and use of some acyl derivatives as surfactants or for preparation of hydrophilic polymers," CAPLUS 110:95711 (1989).
Kolb et al., "Click chemistry: diverse chemical function from a few good reactions," *Angew. Chem. Int. Ed. Engl.*, Jun. 1, 2001, 40(11):2004-2021.
Kolb et al., "The growing impact of click chemistry on drug discovery," *Drug Discov. Today*, Dec. 15, 2003, 8(24):1128-1137.
Komba S, et al. Synthesis and Bioloical Activities of Three Sulfated Sialyl Lex Ganglioside Analogues for Clarifying the Real Carbohydrate Ligand Structure of L-Selectin, Bioorg. Med. Chem. 1996, 4, 1833-1847.
Komori, Tatsuya et al., Study on Systematizing the Synthesis of the A-Series Ganglioside Glycans GT1a, GD1a, and GM1 Using the

(56) References Cited

OTHER PUBLICATIONS

Newly Developed N-Troc-Protected GM3 and GaIN Intermediates, Carbohydr. Res. 2009, 344, 1453.
Kong, L. et al. Expression-system-dependent modulation of HIV-I envelope glycoprotein antigenicity and immunogenicity. J. Mol. Biol. 403, 131-147, (2010).
Kos, "Regulation of adaptive immunity by natural killer cells," Immunol. Res., 1998, 17(3):303-312.
Koshihara et al., 1984, Biochmica et biophysica acta, 792(1), pp. 92-97.
Kotteas et al., Immunotherapy for pancreatic cancer, J cancer Res Clin Oncol, 142(8): 1795-1805, 2016.
Krise, Jeffrey et al., Prodrugs of Phosphates, Phosphonates, and Phosphinates, Adv. Drug Deliv. Rev. 1996, 19(2), 287-310.
Kruis et al., Low dose balsalazide (1.5 g twice daily) and mesalazine (0.5 g three times daily) maintained remission of ulcerative colitis but high dose alsalazide (3.0 g twice daily) was superior in preventing relapses. Gut. Dec. 2001;49(6):783-9.
Kubin, R. F. et al., Fluorescence Quantum Yields of Some Rhodamine Dyes, Luminescence 1982, 27, 455-462.
Kubler-Kielb, J. et al., A New Method for Conjugation of Carbohydrates to Proteins Using an Aminooxy-Thiol Heterbifunctional Linker, J Org Chem 2005, 70, 6987-6990.
Kwong, Peter et al., Rational Design of Vaccines to Elicit Broadly Neutralizing Antibodies to HIV-I. Cold Spring Harb.Perspect. Med. 1, 2011, 1-16.
Lantz et al., "An invariant T cell receptor α chain is used by a unique subset of major histocompatibility complex class I-specific $CD4^+$ and $CD4^-8^-$ T cells in mice and humans," J. Exp. Med., Sep. 1, 1994, 180(3):1097-1106.
Lau, K. et al. Highly efficient chemoenzymatic synthesis of β1-4-linked galactosides with promiscuous bacterial β1-4-galactosyltransferases. Chem. Commun. 46, 6066-6068, (2010).
Le, Mai et al., Avian flu: Isolation of Drug-Resistant H5N1 Virus, Nature, Oct. 20, 2005, 437(7062):1108.
Lebens et al., Mucosal vaccines based on the use of cholera toxin B as immunogen and antigen carrier, Dev. Biol. Stand., 1994, 82:215-227.
Le Droumaguet, C. et al., Fluorogenic Click Reaction., Chem. Soc. Rev. 2010, 39, 1233-1239.
Lederman et al., A single amino acid substitution in a common African allele of the CD4 molecule ablates binding of the monoclonal antibody, OKT4, Molecular Immunology, 28, 1171-1181 (1991).
Lee et al., Analogs of Cell Surface Carbohydrates. Synthesis of D-Galactose Derivatives Having an Ethynyl, Vinyl or Epoxy Residue at c-5. Carbohydrate Research 1988, vol. 176, pp. 59-72.
Lee et al., A new Solvent System for Efficient Synthesis of 1,2,3-Triazoles, Tetrahedron Lett., Jul. 17, 2006, 47(29):5105-5109.
Lee et al., An Efficient and Practical Method for the Synthesis of Mono-N-Protected α,ω-diaminoalkanes, Tetrahedron Lett., Apr. 2, 2001, 42(14):2709-2711.
Lee, H.K. et al. Reactivity-based one-pot synthesis of oligomannoses: defining antigens recognized by 2G12, a broadly neutralizing anti-HIV-I antibody. Angew. Chem. Int. Ed. 43, 1000-1003, (2004.
Lee et al., Immunogenicity Study of Globo H Analogues with Modification at the Reducing or Nonreducing end of the tumor antigen, J Am Chem Soc, 136: 16844-16853 (2014).
Lemieux, R. U. et al., Halide ion catalyzed glycosidation reactions. Syntheses of a-linked disaccharides. J Am. Chem. Soc. 97(14), 4056-62, (1975).
Lei, Jianqing et al., Potential antitumor applications of a monoclonal antibody specifically targeting human papilloma virus 16 E749-57 peptide, Microbiology and Immunology, 2012, vol. 56, pp. 456-462.
Lew et al., Discovery and Development of GS 4104 (oseltamivir): an Orally Active Influenza Neuraminidase Inhibitor, Curr Med Chem, Jun. 2000, 7(6):663-672.
Li et al., β-endorphin omission analogs: Dissociation of Immunoreactivity from other biological activities, Proc Natl Avad Sci USA, 77:3211-3214 (1980).
Li, Y. L. et al., Crystallization and Melting Behaviors of PPC-BS/PVA Blends, 19, 1557-1566, 2003.
Li, Henghui et al., MALDI-MS Analysis of Sialylated N-Glycan Linkage Isomers Using Solid-Phase Two Step Derivatization Method, Analytica Chimica Acta 924 (2016) 77-85.
Li et al., "Design of a potent CD1d-binding NKT cell ligand as a vaccine adjuvant," Proc. Natl. Acad. Sci. USA, Jul. 20, 2010, 107:13010-13015.
Li, J.; Hu, M.; Yao, S. Q. "Rapid synthesis, screening, and identification of xanthone and xanthene-based fluorophores using click chemistry." Org. Lett. 2009, 11, 3008-3011.
Li, Lingling, et al., "Syntheses and spectral properties of functionalized, water-soluble BODIPY derivatives." J. Org. Chem. 2008, 73, 1963-1970.
Li, L. et al. Efficient chemoenzymatic synthesis of an N-glycan isomer library. Chem. Sci. 6, 5652-5661 (2015).
Liang et al., "Quantitative microarray analysis of intact glycolipid-CD1d interaction and correlation with cell-based cytokine production," J. Am. Chem. Soc., Sep. 17, 2008, 130(37):12348-12354.
Liang, Chi-Hui et al., Iron Oxide/Gold Core/Shell Nanoparticles for Ultrasensitive Detection of Carbohydrate-Protein Interactions, Anal. Chem. 2009; 81, 7750-7756.
Liang, P.H. et al., Quantitative Analysis of Carbohydrate-Protein Interactions Using Glycan Microarrays: Determination of Surface and Solution Dissociation Constants, J. Amer. Chem. Sci. 2007, 129, 11177-11184.
Liang, Yuh-Jin et al., Switching of the Core Structures of Glycosphingolipids From Blobo- and Lacto- to Ganglio-Series Upon Human Embryonic Stem Cell Differentiation, PNAS, 107(52), Dec. 2010, 22564-22569.
Liao, Shin-Fen et al., Immunization of Fucose-Containing Polysaccharides From Reishi Mushroom Induces Antibodies to Tumor-Associated Globo H-Series Epitopes, Proceedings National Academy of Sciences PNAS, vol. 110, No. 34, Aug. 1, 2013, pp. 13809-13814.
Lin et al., A common glycan structure on immunoglobulin G for enhancement of effector functions, PNAS, Aug. 25, 2015, vol. 112, No. 34, p. 10611-10616.
Liu et al., "Activity-based protein profiling: the serine hydrolases," Proc. Natl.Acad. Sci. USA, Dec. 21, 1999, 96(26):14694-14699.
Liu et al., Enhanced anti-influenza agents conjugated with anti-inflammatory activity. J Med Chem. Oct. 11, 2012;55(19):8493-501.
Liu et al., Intramolecular ion-pair prodrugs of znamivir nad guanidino-oseltamivir. Bioorganic & Medicinal Chemistry. Jun. 2011; 19(16):4796-4802.
Liu et al., Synthesis and anti-influenza activities of carboxyl alkoxyalkyl esters of 4-guanidino-Neu5Ac2en (zanamivir). Bioorg Med Chem Lett. Sep. 1, 2007;17(17):4851-4. Epub Jun. 20, 2007.
Lopes, J.F. et al., Simulataneous Chromatographic Separation of Enantiomers, Anomers and Structural Isomers of Some Biologically Relevant Monsaccharides. J. Chomatogr. A, (2008) 1188:34-42.
Lou, et al., Stage-specific embryonic antigent-4 as a potential therapeutic target in glioblastoma multiforms and other cancers. Proc Natl Acad Sci USA 2014, 111(7):2482-7.
Loudet, A.; Burgess, K. "BODIPY dyes and their derivatives: syntheses and spectroscopic properties." Chem. Rev. 2007, 107, 4891-4932.
Lu et al., "Design of a mechanism-based probe for neuraminidase to capture influenza viruses," Angew. Chem. Int. Ed. Engl., Oct. 28, 2005, 44(42):6888-6892.
Lu, Guokai et al., Reactivity-Based One-Pot Synthesis of Immunosuppressive Glycolipids From the Caribbean Sponge Plakortis Simplex, J. Chem. 2009, 27, 2217-2222.
MacBeath, G. and Schreiber, S. L., Printing Proteins as Microarrays for High-Throughput Function Determination, Science, 289, 1760-1763, 2000.
Makino et al., Predominant expression of invariant $V_\alpha 14^+$ TCR α chain in $NK1.1^+$ T cell populations, Int. Immunol., Jul. 1995, 7(7):1157-1161.

(56) References Cited

OTHER PUBLICATIONS

Mandal, M., Dudkin, V. Y., Geng, X. & Danishefsky, S. J. In pursuit of carbohydrate-based HIV vaccines, part I: The total synthesis of hybrid-type gp 120 fragments. Angew. Chem. Int. Ed. 43, 2557-2561, (2004).
Marcato et al., "Chapter 17: The Rocky Road from Cancer Stem Cell Discovery to Diagnostic Applicability," Cancer Stem Cells Theories and Practice, pp. 335-360, Mar. 22, 2011.
Massart, R., IEEE Transactions On Magnetics, 17, 1247 (1981).
Masuko, T. et al., Thiolation of Chitosan. Attachment of Proteins Via Thioether Formation, Biomacromolecules 2005, 6, 880-884.
Matrosovich M, et al., The Surface Glycoproteins of H5 Influenza Viruses Isolated From Humans, Chickens, and Wild Aquatic Birds Have Distinguishable Properties, J. Virol. 1999, 73, 1146-1155.
Matz et al., "Fluorescent proteins from nonbioluminescent Anthozoa species," *Nat. Biotechnol.*, Oct. 1999, 17(10):969-973.
McKimm-Breschkin et al., "Tethered neuraminidase inhibitors that bind an influenza virus: a first step towards a diagnostic method for influenza," Angew. Chem. Int. Ed Engl., Jul. 14, 2003, 42(27):3118-3121.
McKimm-Breschkin, "Resistance of influenza viruses to neuraminidase inhibitors—a review," Antiviral Res., Jul. 2000, 47(1): 1-17.
McKimm-Breschkin, J. et al., "Neuraminidase Sequence Analysis and Susceptibilities of Influenza Virus Clinical Isolates to Zanamivir and Oseltamivir,"Antimicrobial Agents and Chemotherapy, vol. 47, No. 7, Jul. 2003, in 10 pages.
Medelson et al., NKp46 O-glycan Sequences that are involved in the interaction with Hemagglutinin Type 1 of Influenza Virus. J. Virol. Feb. 10, 2010, 84(8):3789-3797.
McLellan, J. S. et al. Structure of HIV-I gp120 V1/V2 domain with broadly neutralizing antibody PG9. Nature 480, 336-343, 2011.
Merck, MAB4304, Anti-Stage-Specific Embryonic Antigen-4 Antibody, Clone MC-813-70, 4 Pages, 2017.
Milstein, C & Cuello, AC, Hybrid Hydridomas and their use in immunohistochemistry, Nature 305, 537-540, Oct. 1993.
Miyagi et al., "Mammalian sialidases: Physiological and pathological roles in cellular functions," *Glycobiology*, Jul. 2012, 22(7):880-896.
Miyagi et al., "Plasma membrane-associated sialidase as a crucial regulator of transmembrane signalling," *J. Biochenz*, Sep. 2008, 144(3):279-285.
Miyagi et al., "Sialidase and malignancy: a minireview," *Glycoconj. J.*, 2004, 20(3):189-198.
Miyagi, "Aberrant expression of sialidase and cancer progression," *Proc. Jpn. Acad. Ser. B. Phys. Biol. Sci.*, 2008(10), 84:407-418.
Miyaji, E. N. et al., Induction of Neutralizing Antibodies Against Diphtheria Toxin By Priming with Recombinant Mycobacterium Bovis BCG Expressing CRM197, a Mutant Diphtheria Toxin, Infect. Immun. 2001, 69, 869.
Miyamoto et al., "A synthetic glycolipid prevents autoimmune encephalomyelitis by inducing $T_H2$ bias of natural killer T cells," Nature, Oct. 4, 2001, 413(6855):531-534.
Moal, E. Le et al., Enhanced Fluorescence Cell Imaging with Metal-Coated Slides, Biophysical Journal, vol. 92, 2150-2161, Mar. 2007.
Monti et al., "Sialidases in vertebrates: a family of enzymes tailored for several cell functions," *Adv. Carbohydr. Chem. Biochem.*, 2010, 64:403-479.
Moody, M. D. et al., Array-based ELISAs for High-Throughput Analysis of Human Cytokines. Biotechniques (2001), 31, 186-194.
Morphy et al., Designed multiple ligands. An emerging drug discovery paradigm. J Med Chem. Oct. 20, 2005;48(21):6523-43.
Morphy et al., From magic bullets to designed multiple ligands. Drug Discov Today. Aug. 1, 2004;9(15):641-51.
Morrison, "Immunology. Success in specification," *Nature*, Apr. 28, 1994, 368(6474):812-813.
Moscona, "Global transmission of oseltamivir-resistant influenza," N Engl. J Med, Mar. 5, 2009, 360(10):953-956.
Moscona, Oseltamivir Resistance—Disabling Our Influenza Defenses, The New England Journal of Medicine, 2005, vol. 353, pp. 2633-2636.
Mosmann et al., "The expanding universe of T-cell subsets: Th1, Th2 and more," *Immunol. Today*, Mar. 1996, 17(3):138-146.
Mossong et al., "Emergence of oseltamivir-resistant influenza A H1N1 virus during the 2007-2008 winter season in Luxembourg: clinical characteristics and epidemiology," Antiviral Res., Oct. 2009, 84(1):91-94.
Mouquet, H. et al. Complex-type N-glycan recognition by potent broadly neutralizing HIV antibodies. Proc. Natl. Acad. Sci. U. S. A 109, E3268-E3277, (2012).
Murphy, C. I. et al. Enhanced expression, secretion, and large-scale purification of recombinant HIV-I gp 120 in insect cell using the baculovirus egt and p67 signal peptides. Protein Expres. Purif. 4, 349-357 (1993).
Muthana, S., Yu, H., Huang, S., and Chen, X. Chemoenzymatic synthesis of size-defined polysaccharides by sialyltransferase-catalyzed block transfer of oligosaccharides. J. Am. Chem. Soc. 129, 11918-11919, (2007).
Natarajan et al, Caffeic acid phenethyl ester is a potent and specific inhibitor of activation of nuclear transcription factor NF-kappa B. Proc Natl Acad Sci USA Aug. 20, 1996;93(17):9090-5.
Ni, Jing et al., Immunoassay Readout Method Using Extrinsic Raman Labels Adsorbed on Immunogold Colloids, Anal. Chem., 1999, 71(21), pp. 4903-4908.
Nieuwenhuis et al., "CD1d-dependent macrophage-mediated clearance of *Pseudomonas aeruginosa* from lung," *Nat. Med.*, Jun. 2002, 8(6):588-593.
Nielsen, U. B. et al., Multiplexed Sandwich Assays in Microarray Format, Journal Immunol. Meth. (2004), 290, 107-120.
Ning, X. et al., Visualizing Metabolically-Labeled Glycoconjugates of Living Cells by Copper-Free and Fast Huisgen Cycloadditions, J. Angew. Chem. Int. Ed. 2008, 47, 2253-2255.
Nowak, MW et al., Nicotinic Receptor Binding Site Probed With Unnatural Amino Acid Incorporation in Intact Cells, Science 268:439, 1995.
Novotný et al., "Structural invariants of antigen binding: comparison of immunoglobulin $V_L$-$V_H$ and $V_L$-$V_L$ domain dimers," *Proc. Natl. Acad. Sci. USA*, Jul. 1985, 82(14):4592-4596.
Oberli, Matthias et al., A Possible Oligosaccharide-Conjugate Vaccine Candidate for Clostridium Difficile is Antigenic and Immunogenic, Chemistry & Biology, vol. 18, No. 5, May 2011, 580-588.
Office Action dated Dec. 3, 2013, from corresponding Chinese Patent Application No. 201180034218.3, 15 total pages.
Office Action dated Oct. 22, 2014, from corresponding Chinese Patent Application No. 201180034218.3, 16 total pages.
O'Garra, "Cytokines induce the development of functionally heterogeneous T helper cell subsets," *Immunity*, Mar. 1998, 8(3):275-283.
Okada, Yoshio et al. Changes in the Expression of Sialyl-Lewisx, a Hepatic Necroinflammation-Associated Carbohydrate Neoantigen, in Human Depatocellular Carcinomas, (1994) Cancer 73, 1811-1816.
Okamura et al., "Interleukin-18: a novel cytokine that augments both innate and acquired immunity," *Adv. Immunol.*, 1998, 70:281-312.
Olden, Kenneth et al., Carbohydrate Moieties of Glycoproteins: A Re-Evaluation of Their Function, Biochem et Biophys Acta 650:209-232 (1982).
Otsubo N, et al., An Efficient and Straightforward Synthesis of Sialyl Lex Glycolipid as a Potent Selectin Blocker[[1]], Carbohydr. Res. 1998, 306, 517-530.
Ottolini et al., Combination anti-inflammatory and antiviral therapy of influenza in a cotton rat model. Pediatr. Pulmonol. 2003:36;290-4.
Oyelaran, 0. & Gildersleeve, J. C. Glycan arrays: recent advances and future challenges. Curr. Opin. Chem. Biol. 13, 406-413, (2009).
Pabst, M. et al., Glycan profiles of the 27 Nglycosylation sites of the HIV envelope protein CN54gp140. Biol. Chem. 393, 719-730, (2012).

(56) References Cited

OTHER PUBLICATIONS

Pacino, G. et al., Purification and Characterization of a Breast-Cancer-Associated Glycoprotein Not Expressed in Normal Breast and Identified by Monoclonal Antibody 83D4, Br. J. Cancer, 1991, 63, 390-398.
Pan, Yanbin et al., Synthesis and Immunological Properties of N-Modified GM3 Antigens as Therapeutic Cancer Vaccines, J. Med. Chem., 48(3), 875-883, 2005.
Pancera, M. et al. Crystal structure of PG16 and chimeric dissection with somatically related PG9: structure-function analysis of two quaternary-specific antibodies that effectively neutralize HIV-I. J. Virol. 84, 8098-8110, (2010).
Pancera, M. et al. Structural basis for diverse N-glycan recognition by HIV-I-neutralizing V1-V2-directed antibody PG16. Nat. Struct. Mol. Biol. 20, 804-813, (2013).
Parker, C. A.; Rees, W. T., Correction of Fluorescence Spectra and Measurement of Fluorescence Quantum Efficiency, Analyst 1960, 85, 587-600.
Parrish, M. L. et al., A Microarray Platform Comparison for Neuroscience Applications, J. Neurosci. Methods, 2004, 132, 57-68.
Patricelli et al., "Functional interrogation of the kinome using nucleotide acyl phosphates," Biochemistry, Jan. 16, 2007, 46(2):350-358.
Paulson, J. C., Blixt, 0. & Collins, B. E. Sweet spots in functional glycomics. Nat. Chem. Biol. 2, 238-248, (2006).
Peelle et al., "Characterization and use of green fluorescent proteins from Renilla mulleri and Ptilosarcus guemyi for the human cell display of functional peptides," J. Protein Chem., Aug. 2001, 20(6):507-519.
Peiris et al., Re-emergence of fatal human influenza A subtype H5N1disease. Lancet. Feb. 21, 2004 ;363(9409):617-9.
Pejchal, R. et al. A potent and broad neutralizing antibody recognizes and penetrates the HIV glycan shield. Science 334, 1097-1103, (2011).
Pellicci et al., "Differential recognition of CD1d-α-galactosyl ceramide by the Vβ8.2 and Vβ7 semi-invariant NKT T-cell receptors," Immunity, Jul. 17, 2009, 31(1):47-59.
Perlmutter, R.M. et al., Subclass Restriction of Murine Anti-Carbohydrate Antibodies, Journal of Immunology 1978, 121, 566-572.
Pettit, George et al., Antineoplastic Agents. Part 189. The Absolute Configuration and Synthesis of Natural (-)-Dolastatin 10, J Am Chem Soc. 111:5463-5465 (1989).
Pettit, George et al., Dolastatins 23: Stereospecific Synthesis of Dolaisoleuine, J Chem Soc Perkin Trans. 15:853-858 (1996).
Pettit, George et al., Antineoplastic Agents 365. Dolastatin 10 SAR Probes, Anti-Cancer Drug Design 13:243-277 (1998).
Pettit, Robin et al., Specific Activities of Dolastatin 10 and Peptide Derivatives Against Cryptococcus Neoformans, Antimicrob Agents Chemother. 42:2961-2965 (1998).
Pettit, George et al., The Dolastatins; 18: Stereospecific Synthesis of Dolaproine, Synthesis, 719-725 (1996).
Piizi, G. and Hardinger, S., Stereochemistry: an Introduction, UCLA Chemistry 30A Presentation, Fall 2002, in 40 pages.
Poloukhtine et al., "Selective labeling of living cells by a photo-triggered click reaction," J. Am. Chem. Soc., Nov. 4, 2009, 131(43):15769-15776.
Porcelli, S.A., "Preparation of α-galactosylceramide derivatives as modulators of immunity and autoimmunity," CAPLUS 147:440317 (2007).
Potier et al., "Fluorometric assay of neuraminidase with a sodium (4-methylumbelliferyl-alpha-D-N-acetylneuraminate) substrate," Anal. Biochem., Apr. 15, 1979, 94(2):287-296.
Pratt, M. R. & Bertozzi, C. R. Chemoselective ligation applied to the synthesis of a biantennary N-linked glycoform of CD52. J Am. Chem. Soc. 125, 6149-6159, (2003).
Prescher, J. A.; Bertozzi, C.R. "Chemistry in living systems." Nat. Chem. Biol. 2005, 1, 13-21.
Pritchard, L. K. et al. Structural Constraints Determine the Glycosylation of HIV-I Envelope Trimers. Cell Rep. 11, 1604-13, (2015).
Pritchard, Laura et al., Cell- and Protein- Directed Glycosylation of Native Cleaved HIV-I Envelope. J. Virol. 89, 8932-44, (2015).
Pshezhetsky, M. Potier, J. Biol. Chem. 1996, 271, 28359-28365. Association of N-acetylgalactosamine-6-sulfate sulfatase with the multienzyme lysosomal complex of betagalactosidase, cathepsin A, and neuraminidase. Possible implication for intralysosomal catabolism of keratan sulfate.
Qi, Jianjun et al., Developing visible fluorogenic 'clickon' dyes for cellular imaging, Bioconjugate Chem. 2011, 22, 1758-1762.
Rabbani, Said et al., Glycosyltransferases: An efficient tool for the enzymatic synthesis of oligosaccharides and derivatives as well as mimetics thereof Chimia 60, 23-27, (2006).
Raju et al., "Synthesis and evaluation of 3"-and 4"—deoxy and —fluoro analogs of the immunostimulatory glycolipid, KRN7000," Bioorg. Med. Chem. Lett., 2009, 19:4122-4125.
Rana, G. Kucukayan-Dogu, E. Bengu "Growth of vertically aligned carbon nanotubes over self-ordered nano-porous alumina films and their surface properties" Applied Surface Science, 2012, 258 7112-7117.
Raska, M. et al. Glycosylation patterns of HIV-I gp120 depend on the type of expressing cells and affect antibody recognition. J. Biol. Chem. 285, 20860-20869, (2010).
Rillahan, C. D. & Paulson, J. C. Glycan microarrays for decoding the glycome. Annu. Rev. Biochem. 80, 797-823, (2011).
Ritamo, Ilja al., Comparison of the Glycosylation of in Vitro Generated Polyclonal Human lgG and Therapeutic Immunoglins, Mol Immunol. Feb. 2014; 57(2): 255-62.
Rogers, GN et al., Single Amino Acid Substitutions in Influenza Haemagglutinin Change Receptor Binding Specificity. Nature, 304:76, 1983.
Rogers, GN et al., Receptor Determinants of Human and Animal Influenza Virus Isolates: Differences in Receptor Specificity of the H3 Hemagglutinin Based on Species of Origin. Virology, 127:361, 1983.
Romagnani, "Induction of $T_H1$ and $T_H2$ responses: a key role for the 'natural' immune response?" Immunol. Today, Oct. 1992, 13(10):379-381.
Rosenstein, N. E. et al, Meningococcal Disease, N Engl J Med 2001, 344, 1378-1388.
Rostovtsev et al., "A stepwise Huisgen cycloaddition process catalyzed by copper(I) regioselective ligation of azides and terminal alkynes," Angew. Chem. Int. Ed. Engl., Jul. 15, 2002, 41(41):2596-2599.
Roth, Jurgen et al., Reexpression of Poly(sialic Acid) Units of the Neural Cell Adhesion Molecule in Wilms Tumor, Proc. Natl. Acad. Sci. 85, 2999-3000, 1988.
Rudnick et al., Affinity and Avidity in Antibody-Based Tumor Targeting, Can Biotherp & Radoipharm, 24, 155-162 (2009).
Russell et al., "The structure of H5N1 avian influenza neuraminidase suggests new opportunities for drug design," Nature, Sep. 7, 2006, 443(7107):45-49.
Saito, Seiichi et al., Haptoglobin-β Chain Defined by Monoclonal Antibody RM2 as a Novel Serum Marker for Prostate Cancer, Int. J Cancer, 2008, 123(3), 633-640.
Saitoh, Osamu et al., Differential Glycosylation and Cell Surface Expression of Lysosomal Membrane Glycoproteins in Sublines of a Human Colon Cancer Exhibiting Distinct Metastatic Potentials*, J. Biol. Chem. 267, 5700-5711, 1992.
Sakurama, Haruko et al., Differences in the Substrate Specificities and Active-Site Structures of Two α-L-Fucosidases (Glycoside Hydrolase Family 29) From Bacteroides Thetaiotaomicron, Bioscience Biotechnology Biochemistry, vol. 76, No. 5, May 23, 2012, pp. 1022-1024.
Salisbury et al., "Activity-based probes for proteomic profiling of histone deacetylase complexes," Proc. Natl. Acad. Sci. USA, Jan. 23, 2007, 104(4):1171-1176.
Salomon et al., Inhibition of the cytokine response does not protect against lethal H5N1 nfluenza infection. Proc Natl Acad Sci U S A Jul. 24, 2007;104(30): 12479-81.
Sanna, Peitro et al., Directed Selection of Recombinant Human Monoclonal Antibodies to Herpes Simplex Virus Glycoproteins From Phage Display Libraries, Proc. Natl. Acad. Sci., 92:6439 (1995).

(56) References Cited

OTHER PUBLICATIONS

Sarkar et al., "Disaccharide uptake and priming in animal cells: inhibition of sialyl Lewis X by acetylated Galβ1→4G1cNAcβ-O-naphthalenemethanol," Proc. Natl. Acad. Sci. USA, Apr. 11, 1995, 92(8):3323-3327.
Sauter, NK et al., Binding of Influenza Virus Hemagglutinin to Analogs of Its Cell-Surface Receptor, Sialic Acid: Analysis by Proton Nuclear Magnetic Resonance Spectroscopy and X-Ray Crystallography. Biochemistry, 31 :9609, 1992.
Sawa, M.; Hsu, T.-L.; Itoh,T.; Sugiyama, M. ; Hanson, S. R. ; Vogt, P. K.; Wong, C.-H. "Glycoproteomic probes for fluorescent imaging of fucosylated glycans in vivo." Proc. Nat. Acad. Sci. US.A., 2006, 103, 12371-12376.
Sawada, Tetsuji et al., E-Selectin Binding by Pancreatic Tumor Cells is Inhibited by Cancer Sera, Int. J. Cancer 57, 901-907, 1994.
Sawada, Ritsuko et al., Differential E-Selectin-Dependent Adhesion Efficiency in Sublines of a Human Colon Cancer Exhibiting Distinct Metastatic Potentials, J. Biol. Chem. 269, 1425-1431, 1994.
Scanlan, C. N. et al., Exploiting the defensive sugars of HIV-I for drug and vaccine design. Nature 446, 1038-1045, (2007).
Schena, M. et al., Quantitative Monitoring of Gene Expression Patterns with a Complementary DNA Microarray, Science, 1995, 270:467-70.
Schengrund et al., "Localization of sialidase in the plasma membrane of rat liver cells," J. Biol. Chem., May 10, 1972, 247(9):2742-2746.
Schmitz, U. et al., Phage Display: A Molecular Tool for the Generation of Antibodies-A Review, Placenta, 21 Suppl. A:S 106 (2000).
Schneider, M.C. et al., Interactions Between Neisseria Meningitidis and the Complement System, Trends Microbial 2007, 15, 233-240.
Schroder et al., The Peptides, vol. 1, p. 76-136, 1965.
Schug, Kevin et al., "Noncovalent binding between guanidinium and anionic groups: focus on biological- and synthetic-based arginine/guanidinium interactions with phosph[on]ate and sulf[on]ate residues," Chem. Rev., Jan. 2005, 105(1):67-113.
Schweitzer, Barry et al., Multiplexed Protein Profiling on Microarrays by Rolling-Circle Amplification, Nat. Biotechnol. (2002), 20, 359-365.
Scurr, D. J. et al. Surface characterization of carbohydrate microarrays. Langmuir 26, 17143-17155, (2010).
Serna, S. et al., Construction of N-Glycan Microarrays by Using Modular Synthesis and On-Chip Nanoscale Enzymatic Glycosylation. Chem. Eur. J 16, 13163-13175, (2010).
Severi et al., "Sialic acid utilization by bacterial pathogens," Microbiology, Sep. 2007, 153(Pt 9):2817-2822.
Seyrantepe et al., "Neu4, a novel human lysosomal lumen sialidase, confers normal phenotype to sialidosis and galactosialidosis cells," J. Biol. Chem., Aug. 27, 2004, 279(35):37021-37029.
Sheu et al., "Surveillance for neuraminidase inhibitor resistance among human influenza A and B viruses circulating worldwide from 2004 to 2008," Antimicrob. Agents Chemother., Sep. 2008, 52(9):3284-3292.
Shevinsky, LH et al., Monoclonal Antibody to Murine Embryos Defines a Stage-Specific Embryonic Antigen Expressed on Mouse Embryos and Human Teratocarinoma Cells., CELL vol. 30, Issue 3, Oct. 1982, pp. 697-705.
Shie, Jiun-Jie et al., "A concise and flexible synthesis of the potent anti-influenza agents tamiflu and tamiphosphor," Angew. Chem. Int. Ed Engl., 2008, 47(31):5788-5791.
Shie, Jiun-Jie et al., an Azido-BODIPY Probe for Glycosylation: Initiation of Strong Fluorescence Upon Triazole Formation, J. Am. Chem. Soc. 2014, 136, 9953-9961.
Shieh, Peyton et at, Fluorogenic Azidofluoresceins for Biological Imaging, J. Am. Chem. Soc. 2012, 134, 17428-17431.
Shivatare, S. S. et al. Efficient convergent synthesis of bi-, tri-, and tetra-antennary complex type N-glycans and their HIV-1 antigenicity. J. Am. Chem. Soc. 135, 15382-15391, (2013).
Shivatare, S. S. et al., Modular Synthesis of N-Glycans and Arrays for the Hetero-Ligand Binding Analysis of HIV Antibodies, Nature Chemistry, Mar. 7, 2016, vol. 8(4), p. 338-346.
Shriver, Zachary et al., Glycomics: a Pathway to a Class of New and Improved Therapeutics, Nat Rev Drug Disc, 2004, 3, 863-873.
Sieber et al., "Proteomic profiling of metalloprotease activities with cocktails of active-site probes," Nat. Chem. Biol., May 2006, 2(5):274-281.
Sivakumar, Krishnamoorthy et al., "A fluorogenic 1,3-dipolar cycloaddition reaction of 3-azidocoumarins and acetylenes." Org. Lett. 2004,24, 4603-4606.
Skehel, John et at, Receptor Binding and Membrane Fusion in Virus Entry: The Influenza Hemagglutinin, Ann. Rev Biochem, 69:531, 2000.
Sletten et al., "Bioorthogonal Chemistry: Fishing for Selectivity in a Sea of Functionality," Angew. Che. Int. Ed. Engl., Aug. 27, 2009, 48(38):6974-6998.
Sok, Devin et al., SnapShot: Broadly Neutralizing Antibodies. Cell 155, 728-728, (2013).
Solomons, G. and Fryhle, C., Chapter 5 Titled, Stereochemistry: Chiral Molecules, p. 184-228, in "Organic Chemistry," 7th Edition, Wiley, Jun. 18, 2001.
Soriano del Amo, David et al. Chemoenzymatic synthesis of the sialyl Lewis X glycan and its derivatives. Carbohydr. Res. 345, 1107-13, (2010).
Spinosa, Maria Rita et al., The Neisseria Meningitidis Capsule is Important for Intracellular Survival in Huamn Cells, Infect Immun 2001, 75, 3594-3603.
Srinivasan, Quantitative et al., Biochemical Rationale for Differences in Transmissibility of 1918 Pandemic Influenza A Viruses, Proc. Natl. Acad. Sci., 105, 2800-2805, 2008.
Stein, K.E. et al., The Immune Response to an Isomaltohexosyl-Protein Conjugate, a Thymus-Dependent Analogue of Alpha(1 Replaced By 6) Dextran., J Immunol 1982, 128, 1350-1354.
Stein, K.E., Thymus-Independent and Thymus-Dependent Responses to Polysaccharide Antigens, J Infect Dis 1992, 165 Suppl 1, S49-52.
Stephens, David, Conquering the Meningococcus, FEALS Microbial Rev 2007, 31, 3-14.
Stephens, D.S. et al., Epidemic Meningitis, Meningococcaemia, and Neisseria Meningitidis, Lancet 2007, 369, 2196-2210.
Stephenson et al., "Neuraminidase inhibitor resistance after oseltamivir treatment of acute influenza A and B in children," Clin. Infect. Dis., Feb. 15, 2009, 48(4):389-396.
Stevanovic, Stefan, Identification of Tumour-Associated T-Cell Epitopes for Vaccine Development, Nat. Rev. Cancer, 2002, 2, 514-520.
Stevens, James et al., Structure of the Uncleaved Human H1 Hemagglutinin From the Extinct 1918 Influenza Virus, Science, 303:1866, 2004.
Stevens, James et al., Structure and Receptor Specificity of the Hemagglutinin From an H5N1 Influenza Virus, Science, 312:404, 2006.
Stevens et al., Glycan Microarry Analysis of the Hemagglutinins From Modern and Pandemic Influenza Viruses Reveals Different Receptor Specificities. Journal of Molecular Biology 355.5 (2006): 1143-1155.
Stickings, P. et al., nfect. Immun. 2008, 76, 1766.
Stockmann, H. et al., Development and Evaluation of New Cyclootynes for Cell Surface Glycan Imaging in Cancer Cells, J. Chem. Sci. 2011, 2, 932-936.
Streicher et al., "Building a successful structural motif into sialylmimetics-cyclohexenephosphonate monoesters as pseudo-sialosides with promising inhibitory properties," Bioorg. Med Chem., Feb. 15, 2006, 14(4):1047-1057.
Stubbs et al., "Synthesis and use of mechanism-based protein-profiling probes for retaining β-D-glucosaminidases facilitate identification of Pseudomonas aeruginosa NagZ," J. Am. Chem. Soc., Jan. 9, 2008, 130(1):327-335.
Su, G. Hahner, W. Zhou "Investigation of the pore formation in anodic aluminum oxide" J Mater. Chem. 2008, 18 5787-5795.

(56) References Cited

OTHER PUBLICATIONS

Sun, B., Srinibasan, B., Huang, X., Pre-activation-based one-pot synthesis of an alpha-(2,3)-sialylated core-fucosylated complex type bi-antennary N-glycan dodecasaccharide. Chem. Eur. J 14 (23), 7072-81, (2008).
Supplementary European Search Report in European Application No. EP 13775664.9, dated Oct. 27, 2015, in 7 pages.
Sutton, VR et al., Bc1-2 Prevents Apoptosis Induced by Perforin and Granzyme B, But Not That Mediated by Whole Cytotoxic Lymphocytes, J of Immunology 1997, 158(12), 5783.
Tahir et al., "Loss of IFN-γ production by invariant NKT cells in advanced cancer," *J. Immunol.*, Oct. 1, 2001, 167(7):4046-4050.
Takakura, Yoshimitsu et al., Molecular cloning, expression and properties of an alpha/beta-Galactoside alpha 2,3-sialyltransferase from Vibrio sp. JT-FAJ-16. J. Biochem. 142, 403-412, (2007).
Takano, Ryo et al., Sialylation and Malignant Potential in Tumour Cell Glycosylation Mutants, Glycobiology 4, 665-674 (1994).
Taki, Takao et al., Glycolipids of Metastatic Tissue in Liver From Colon Cancer: Appearance of Sialylated Lex and Lex Lipids, J. Biochem. 103, 998-1003, 1998.
Talmadge et al., Murine models to evaluate novel and conventional therapeutic strategies for cancer, Am. J. Pathol, 170(3): 793-804 (2007).
Tanaka, Hiroshi et al., An Efficient Convergent Synthesis of GP1c Ganglioside Epitope, J Am Chem Soc. 2008, 130, 17244.
Tanaka, Katsunori et al., Synthesis of a Sialic Acid Containing Complex-Type N-Glycan on a Solid Support, Chemistry-an Asian Journal, 2009, vol. 4 (4), p. 574-580.
Taton, T. Andrew et al., Scanometric DNA Array Detection with Nanoparticle Probes, Science 289 (2000) 1757-1760.
Taton, T. Andrew et al., Two-Color Labeling of Oligonucleotide Arrays Via Size-Selective Scattering of Nanoparticle Probes, J. Am. Chem. Soc. (2001), 123, 5164-5165.
Telford et al., "The Aspergillus Fumigatus Sialidase is a 3'-Deoxy-D-galacto-2-nonulosonic Acid Hydrolase (KDNase)," The Journal of Biological Chemistry, 286(12), 10783-10792 (Mar. 25, 2011).
"The Human Protein Atlas", B3GALT5 URL:http://www.proteinatlas.org/ENSG00000183778-B3GALT5/cancer, Sep. 9, 2015.
Thurber, Greg et al., Antibody Tumor Penetration: Transport Opposed by Systemic and Antigen-Mediated Clearance, Adv Drug Deliv Rev, 60: 1421-1434, 2008.
Toba, et al., "Synthesis and biological evaluation of truncated α-glaactosylceramide derivatives focusing on cytokine induction profile," Bioorganic & Medicinal Chemistry 20(2012): 2850-2859.
Toshima, K. Glycosyl fluorides in glycosidations. Carbohydr. Res. 327, 15-26 (2000).
Trinchieri, "Interleukin-12: a proinflammatory cytokine with immunoregulatory functions that bridge innate resistance and antigen-specific adaptive immunity," *Annu. Rev. Immunol.*, 1995, 13:251-276.
Tsai et al., "Design and synthesis of activity probes for glycosidases," *Org. Lett.*, Oct. 17, 2002, 4(21):3607-3610.
Tsai, Charng-sheng et al., Development of Trifunctional Probes for Glycoproteomic Analysis, Chem. Commun. 2010, 46, 5575-5577.
Tsai, Tsung-I et al., An Effective Bacterial Ducosidase for Glycoprotein Remodeling, ACS Chemical Biology, vol. 12, No. 1, Jan. 20, 2017, pp. 63-72.
Tseng, Susan Y. et al., Glycan Arrays on Aluminum Coated Glass Slides. Chem. Asian J, 2008, 3, 1395-1405.
Tsuji, et al., "Preparation of glycolipids and analogs as antigens for NKT cells for use in vaccines and immunotherapy," CAPLUS 149:492050 (2008).
Tsukamoto, Hiroshi et al., Photobacterium sp. JT-ISH-224 produces two sialyltransferases, alpha-/beta-galactoside alpha2,3-sialyltransferase and betagalactoside alpha2,6-sialyltransferase. J. Biochem. 143, 187-197, 2008.
Tumpey, Terrence et al., Characterization of the Reconstructed 1918 Spanish Influenza Pandemic Virus, Science, 310:77, 2005.

Tzeng, Y. L. et al, Epidemiology and Pathogenesis of Neisseria Meningitidis, Microbes Infect 2000, 2, 687-700.
Uchida, Tsuyoshi et al., Diphtheria Toxin and Related Proteins, J Biol. Chem. 218; 3838-3844 (1973).
Udommaneethanakit et al., "Dynamic behavior of avain influenza A virus neuraminidase subtype H5N1 in complex with oseltamivir, zanamivir, peramivir, and their phosphonate analogues," J Chem. Inf Model, Oct. 2009, 49(10):2323-2332.
Ulevitch, RJ et al., Receptor-Dependent Mechanisms of Cell Stimulation by Bacterial Endotoxin, 1995, Annu. Rev. Immunol., 13: 437.
Ulrich, G.; Ziessel, R.; Harriman, A. "The chemistry of fluorescent bodipy dyes: Versatility unsurpassed." Angew. Chem. Int. Ed. 2008, 47, 1184-1201.
van der Horst et al., "Photoaffinity labeling of a bacterial sialidase with an aryl azide derivative of sialic acid," *J. Biol. Chem.*, Jul. 5, 1990, 265(19), 10801-10804.
Van Hest, Jan C.M. et al., Efficient Introduction of Alkene Functionality Into Proteins in Vivo (1998) FEES Lett. 428:68.
Vaki, Ajit et al., Symbols Nomenclatures for Glycan Representation, Proteomics. Dec. 2009, 9(24): 5398-5399.
Varghese et al., Three-dimensional structure of the complex of 4-guanidino-Neu5Ac2en and nfluenza virus neuraminidase. Protein Sci. Jun. 1995;4(6):1081-7.
Varki, "Glycan-based interactions involving vertebrate sialic-acid-recognizing proteins," *Nature*, Apr. 26, 2007, 446(7139):1023-1029.
Vasella et al., "Synthesis of a phosphonic acid analogue of N-Acetyl-2,3-didehydro-2-deoxyneuraniinic acid, an inhibitor of Vibrio cholerae sialidase," Helv. Chim. Acta, Mar. 13, 1991, 74(2):451-463.
Vavricka, Christopher et al., Influenza Neuraminidase Operates Via a Nucleophilic Mechanism and Can Be Targeted by Covalent Inhibitors, Nature Communcations, 4:1491 (2013).
Vinogradova et al., "Molecular mechanism of lysosomal sialidase deficiency in galactosialidosis involves its rapid degradation," *Biochem. J.*, Mar. 1, 1998, 330(Pt 2.):641-650.
Vippagunta, Sudha et al., Crystalline Solids, Advanced Drug Delivery Reviews 48, 3-26 (2001).
Virji, Mumtaz et al., Pathogenic Neisseriae: Surface Modulation, Pathogenesis and Infection Control, Nat Rev, Microbial 2009, 7, 274-286.
Vitetta, ES et al., Redesigning Nature's Poisons to Create Anti-Tumor Reagents, Science 23(8): 1098 (1987).
Vocadlo et al., "A strategy for functional proteomic analysis of glycosidase activity from cell lysates," *Angew. Chem. Int. Ed. Engl.*, Oct. 11, 2004, 43(40):5338-5342.
Von Itzstein et al., "Rational design of potent sialidase-based inhibitors of influenza virus replication," Nature, Jun. 3, 1993, 363(6428):418-423.
Voskoglou-Nomikos, Clinical predictive value of the in vitro cell line, human xenograft, and mouse allograft preclinical cancer models, Clin Can Res, 9: 4227-4239 (2003).
Wada et al., "A crucial role of plasma membrane-associated sialidase in the survival of human cancer cells," *Oncogene*, Apr. 12, 2007, 26(17):2483-2490.
Wagner, R et al., "Functional balance between haemagglutinin and neuraminidase in influenza virus infections," Rev. Med Viral., May-Jun. 2002, 12(3): 159-166.
Walls et al., "Activity-based protein profiling of protein tyrosine phosphatases," *Methods Mol. Biol.*, 2009, 519:417-429.
Walker, L. M. et al. Broad neutralization coverage of HIV by multiple highly potent antibodies. Nature 477, 466-470, (2011).
Wang, Chao et al., Tuning the Optical Properties of BODIPY Dye Through Cu(I) Catalyzed Azide-Alkyne Cycloaddition (CuAAC) Reaction, Sci. China Chemistry 2012, 55, 125-130.
Wang, Zhen et al., Multi-Component One-Pot Synthesis of the Tumor-Associated Carbohydrate Antigen Globo-H Based on Preactivation of Thioglycosyl Donors, J Org. Chem. 2007, 72, 6409.
Wang et al., "A continuous colorimetric assay for rhinovirus-14 3C protease using peptide p-nitroanilides as substrates," Anal. Biochem., Oct. 15, 1997, 252(2):238-245.

(56) References Cited

OTHER PUBLICATIONS

Wang, Michael et al., "Mechanism by which mutations at his274 alter sensitivity of influenza A virus NI neuraminidase to oseltamivir carboxylate and zanamivir," Antimicrob. Agents Chemother., Dec. 2002, 46(12):3809-3816.
Wang, D., Liu, S., Trummer, B. J., Deng, C. & Wang, A. Carbohydrate microarrays for the recognition of cross-reactive molecular markers of microbes and host cells. Nat. Biotechnol . 20, 275-281, (2002).
Wang et al., Computational Studies of H5N1 Influenza Virus Resistance to Oseltamivir. Protein Sci. 2009, 18(4): 707-715; p. 713.
Wang, C. C. et al. Glycans on Influenza Hemagglutinin Affect Receptor Binding and Immune Response, Proc. Natl. Acad. Sci. 2009, 106, 18137-18142.
Wang, L. X. Carbohydrate-based vaccines against HIV/AIDS. Acs Sym. Ser. 932, 133-160 (2006).
Wang, L. X. Synthetic carbohydrate antigens for HIV vaccine design. Curr. Opin. Chem. Biol. 17, 997-1005, (2013).
Wang, W. et al. A systematic study of the N-glycosylation sites of HIV-I envelope protein on infectivity and antibody-mediated neutralization. Retrovirology, 10, 14, (2014).
Wang, Zhen et al. A general strategy for the chemoenzymatic synthesis of asymmetrically branched N-glycans. Science 341, 379-383, (2013).
Watts et al., "The Synthesis of Some Mechanistic Probes for Sialic Acid Processing Enzymes and the Labeling of a Sialidase from Trypanosoma Rangeli," Canadian Journal of Chemistry, 82(11), 1581-1588 (2004).
Watts et al., "*Trypanosoma cruzi* trans-sialidase operates through a covalent sialyl-enzyme intermediate: tyrosine is the catalytic nucleophile," *J. Am. Chem. Soc.*, Jun. 25, 2003, 125(25):7532-7533.
Weibel, Robert et al., Tumor-Associated Membrane Sialoglycoprotein on Human Small Cell Lung Carcinoma Identified by the lgG2a Monoclonal Antibody SWA20, (1988) Cancer Res. 48, 4318-4323.
Wen, Wen Hsien et al., "Synergistic effect of zanamavir-porphyrin conjugates on inhibition of neuraminidase and inactivation of influenza virus," J Med Chem., Aug. 13, 2009, 52(15):4903-4910.
White, Clinton et al., "A sialic acid-derived phosphonate analog inhibits different strains of influenza virus neuraminidase with different efficiencies," J Mol. Biol., Feb. 3, 1995, 245(5):623-634.
Wilen et al., "Strategies in optical resolutions," Tetrahedron, 1977, 33(21):2725-2736.
Wiltshire, S. et al. Proc. Natl. Acad. Sci. (2000) 97, 10113-10119.
Wiseman, GA et al., Phase I/II 90Y-Zevalin (yttrium-90 Ibritumomab Tiuxetan, IDEC-Y2B8) Radioimmunotherapy Dosimetry Results in Relapsed or Refractory Non-Hodgkin's Lymphoma, Eur Jour Nucl Med 27(7): 766-77 (2000).
Wiseman, Gregory et al., Ibritumomab Tiuxetan Radioimmunotherapy for Patients with Relapsed or Refractory Non-Hodgkin Lymphoma and Mild Thrombocytopenia: a Phase II Multicenter Trial, Blood 99(12): 4336-42 (2002).
Witte et al., "Ultrasensitive in situ visualization of active glucocerebrosidase molecules," *Nat. Chem. Biol.*, Dec. 2010, 6(12):907-913.
Witzig, Thomas et al., Randomized Controlled Trial of Yttrium-90-Labeled Ibritumomab Tiuxetan Radioimmunotherpay Versus Rituximab Immunotherapy for Patients with Relapsed or Refractory Low-Grade, Follicular, or Transformed B-Cell Non-Hodgkin's Lymphoma, J Clin Oncol 20(10):2453-63 (2002).
Witzig, Thomas et al., Treatment with Ibritumomab Tiuxetan Radioimmunotherapy in Patients with Rituximab-Refractory Follicular Non-Hodgkin's Lymphoma, J Clin Oncol 20(15):3262-69 (2002).
Wong et al., α-Galactosyl Ceramide Analogs and Their use as Therapeutic, 2010:50988, 2 Pages.
Woo et al. Cytokine profiles induced by the novel swine-origin influenza A/HINI virus: mplications for treatment strategies. J Infect Dis. Feb. 1, 2010;201(3):346-53.

Woyke, Tanja et al., Effect of Auristatin PHE on Microtubule Integrity and Nuclear Localization in Cryptococcus Neoformans, Antimicrob. Agents and Chemother. 45(12): 3580-3584 (2001).
Wright et al. Antibody variable region glycosylation: biochemical and clinical effects, Springer Semin Immunopathology, 15:259-273 (1993).
Wu et al., "Avidity of CD1d-ligand-receptor ternary complex contributes to T-helper 1 (Thl) polarization and anticancer efficacy," *Proc. Natl. Acad. Sci. USA*, Oct. 18, 2011, 108(42):17275-17280.
Wu, Xueling et al. Rational design of envelope identifies broadly neutralizing human monoclonal antibodies to HIV-I. Science 329, 856-861, (2010).
Wu, Liangxing et al., Fluorescent Cassettes for Monitoring Three-Component Interactions in Vitro and in Living Cells, Journal of the American Chemical Society (2009), 131(26), 9156-9157.
Wu et al., "Catalytic azide-alkyne cycloaddition: reactivity and applications," Aldrichimica Acta, 2007, 40(1):7-17.
Xie, F.; Sivakumar, K.; Zeng, Q. B.; Bruckman, M. A.; Hodges, B.; Wang, Q. "A fluorogenic 'click' reaction of azidoanthracene derivatives." Tetrahedron 2008, 64, 2906-2914.
Yamaguchi, Kazunori et al., "Evidence for mitochondrial localization of a novel human sialidase (NEU4)," *Biochem. J.*, Aug. 15, 2005, 390(Pt 1):85-93.
Yamane-Ohnuki, Naoko et al., Production of Therapeutic Antibodies with Controlled Fucosylation, mAbs 2009, 1;3:230-236.
Yamashita et al., CS-8958, a prodrug of the new neuraminidase inhibitor R-125489, shows ong-acting anti-influenza virus activity. Antimicrob Agents Chemother. Jan. 2009;53(1): 186-92.
Yamashita, Yoshito et al., Alterations in Gastric Mucin with Malignant Transformation: Novel Pathway for Mucin Synthesis, (1995) J. Natl. Cancer Inst. 87, 441-446.
Yang, JM et al., Alterations of )-Glycan Biosynthesis in Human Colon Cancer Tissues, (1994) Glycobiology 4, 873-884.
Yaniv, Nature 297: 17-18, 1982.
Yates AJ et al., Brain Tumors in Childhood. Childs Brain 5(1), 31-39 (1979).
Yguerabide, Juan et al., Light-Scattering Submicroscopic Particles as Highly Fluorescent Analogs and Their Use as Tracer Labels in Clinical and Biological Applications: IL Experimental Characterization, Anal. Biochem. (1998), 262, 157-176.
Ying et al., One-bead-one-inhibitor-one-substrate screening of neuraminidase activity. Chembiochem. Oct. 2005;6(10):1857-65.
Yoshida M, et al. Glycoconjugate J. 1993, 10, 324.
Yoshimoto et al., "CD4$^{pos}$, NK1.1$^{pos}$ T cells promptly produce interleukin 4 in response to in vivo challenge with anti-CD3," *J. Exp. Med.*, Apr. 1, 1994, 179(4):1285-1295.
Yuen et al., Human infection by avian influenza A H5N1. Hong Kong Med J. Jun. 2005;1 1(3):189-99.
Zhang et al., "New cerebrosides from Acanthopanax gracilistylus," CAPLUS 156:225776 (2011).
Zhang, Hai-Long et al., A Novel Combined Conjugate Vaccine: Enhanced Immunogenicity of bFGF with CRM197 as a Carrier Protein, Molecular Medicine Reports, 4, 857-863, 2011.
Zheng et al., Delayed antiviral plus immunomodular treatment still reduces mortality in mice infected by high inoculum of influenza A/H5N1 virus. Proc Natl Acad Sci U S A. Jun. 10, 2008;105(23):8091-6.
Zhou et al., A fluorogenic probe for the copper(I)-catalyzed azide-alkyne ligation reaction: modulation of the fluorescence emission via $^3(n,\pi)$-$^1(\pi,\pi^*)$ inversion, J. Am. Chem. Soc., Jul. 28, 2004, 126(29):8862-8863.
Zhu, X et al., Mass spectrometric characterization of the glycosylation pattern of HIV-gp120 expressed in CHO cells. Biochemistry 39, 11194-11204 (2000).
Zou, et al., Chemoenzymatic synthesis and Fc gamma receptor binding of homogenous glycoforms of antibody Fc to FcIIIa receptor. J Am Chem Soc. 2011, 133(46):18975-91.
Zimmermann et al., Multi-target therapeutics: when the whole is greater than the sum of the parts. Drug Discov Today. Jan. 2007;12(1-2):34-42. Epub Nov. 28, 2006.

\* cited by examiner

Synthesis of disaccharide to decasaccharide. Reagents and conditions: a) NaOMe, MeOH, r.t. 65~75%; b) NIS, TfOH, CH$_2$Cl$_2$, -40 °C, 64% for 14, 52% for 17, 46% for 20, 35% for 23; c) BF$_3$ · OEt$_2$, acetonitrile, 0 °C; NaOH, MeOH/H$_2$O; Pd(OH)$_2$/H$_2$, MeOH/H$_2$O, 35~50%, over three steps.

Oligosaccharide conjugating to carrier protein. Reagent and conditions: a) DTSSP, pH 7.4 PBS buffer, r.t.; DTT, 40 °C, 70~75%; b) sulfo-EMCS, pH 8.0 PBS buffer, r.t. ; c) pH 7.4 PBS, r.t.

| Conjugates | Average incorporation |
|---|---|
| DT-2 | 5.7 |
| DT-4 | 4.9 |
| DT-6 | 2.9 |
| DT-8 | 2.8 |
| DT-10 | 3.1 |

Figure 5

GLYCAN CONJUGATES AND USE THEREOF

CROSS-REFERENCE TO RELATED APPLICATION

This application is a U.S. national stage application under 35 U.S.C. 371(e) of PCT application No. PCT/US14/44740, filed Jun. 27, 2014, which claims priority of U.S. Provisional Patent Application Ser. No. 61/840,324, filed Jun. 27, 2013 and titled "GLYCAN CONJUGATES AND USE THEREOF," the contents of which are incorporated herein in their entirety by reference.

FIELD OF INVENTION

The invention relates to meningococcal antigens and immunogenic compositions comprising such. In particular, the application relates to glycan conjugates comprising oligosaccharide antigens derived from Neisseria meningitidis and their application in therapy.

BACKGROUND OF THE INVENTION

Neisseria meningitidis (meningococcus) is a Gram negative human pathogen that causes meningococcal disease, including meningitis and bacterial septicemia induced shock that affect children and young adults ((a) Y. L. Tzeng, D. S. Stephens, Microbes Infect 2000, 2, 687-700; b) M. Virji, Nat Rev Microbiol 2009, 7, 274-286). Vaccines for protecting against meningococcal disease include polysaccharide based vaccines, protein vaccines, and meningococcal outer membrane vesicle (OMV) vaccines.

Based on the surface capsular oligosaccharides of the organism, 13 serogroups of N. meningitidis have been identified, among which A, B, C, Y, and W135 are the major pathogenic strains (N. E. Rosenstein, B. A. Perkins, D. S. Stephens, T. Popovic, J. M. Hughes, N Engl J Med 2001, 344, 1378-1388; b) D. S. Stephens, FEMS Microbiol Rev 2007, 31, 3-14). Group A is the pathogen most often implicated in seasonal epidemic disease in developing countries of Asia and sub-Saharan Africa (M. Achtman, Trends Microbiol 1995, 3, 186-192). Serogroups B and C cause majority of the cases in industrial countries, such as United States of America and other developed countries (D. S. Stephens, B. Greenwood, P. Brandtzaeg, Lancet 2007, 369, 2196-2210). Serogroups W135 and Y are responsible for the remaining cases in the developed countries.

The capsular polysaccharide plays an important role in the bacterial pathogenesis; its antiphagocytic properties help the bacteria to escape from antibody and complement deposition (a) M. R. Spinosa, C. Progida, A. Tala, L. Cogli, P. Alifano, C. Bucci, Infect Immun 2007, 75, 3594-3603; b) M. C. Schneider, R. M. Exley, S. Ram, R. B. Sim, C. M. Tang, Trends Microbiol 2007, 15, 233-240). On the other hand, the unique structures of the capsular polysaccharide also make a good target for vaccine design. Currently, the major source of polysaccharide for vaccine preparation is from acidic lysis of bacteria and column chromatography purification (A. Bardotti, G. Averani, F. Berti, S. Berti, C. Galli, S. Giannini, B. Fabbri, D. Proietti, N. Ravenscroft, S. Ricci, Vaccine 2005, 23, 1887-1899). Due to the limit of purification, the obtained polysaccharide is heterogeneous; therefore, the vaccine quality is inconsistent. Therefore, there remains a need for developing capsular polysaccharides for homogeneous vaccines.

SUMMARY OF THE INVENTION

Neisseria meningitidis (meningococcus) has serogroups: A, B, C, Y and W135, according to the nature of the capsule polysaccharides. Because many bacterial polysaccharides are poor immunogens, development of vaccines based on bacterial capsule polysaccharides is often challenging.

The present invention is based on the unexpected discoveries that glycan conjugates comprising an oligosaccharide antigen derived from N. meningitidis and a carrier such as a toxin protein, successfully elicited immune responses specific to the oligosaccharide antigens.

Accordingly, the present invention provides synthetic glycan conjugates, immmunogenic compositions comprising such, and kits thereof. The present invention further provides methods of using the synthetic glycan conjugates and immunogenic compositions thereof to treat or reduce the risk for infectious diseases (e.g., bacterial infections), such as infections caused by Neisseria meningitides (e.g., Neisseria meningitides serogroups W135).

In one aspect, the present invention provides a compound of Formula (F-1)

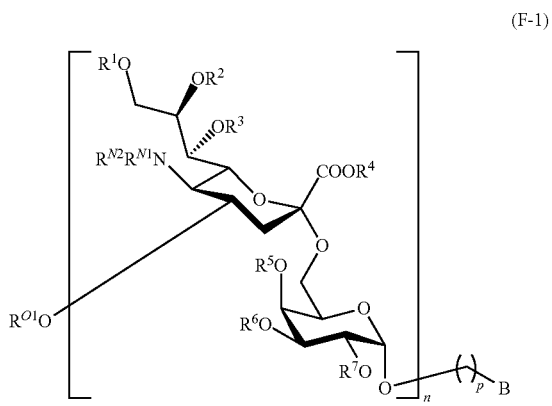

(F-1)

or a salt thereof, wherein each instance of $R^1$, $R^2$, $R^3$, $R^4$, $R^5$, $R^6$, and $R^7$ is independently hydrogen, optionally substituted $C_{1-6}$ alkyl, or an oxygen protecting group; or optionally $R^1$ and $R^2$ are taken with the intervening atoms to form a heterocyclic ring; or optionally $R^2$ and $R^3$ are taken with the intervening atoms to form a heterocyclic ring; or optionally $R^5$ and $R^6$ are taken with the intervening atoms to form a heterocyclic ring; or $R^{N1}$ and $R^{O1}$ are taken together with the intervening atoms to form a heterocyclic ring; each instance of $R^{N1}$ and $R^{N2}$ is independently hydrogen, optionally substituted $C_{1-6}$ alkyl, optionally substituted acyl, or a nitrogen protecting group; each instance of $R^{O1}$ is independently hydrogen, optionally substituted $C_{1-6}$ alkyl, or an oxygen protecting group; B is $-N_3$ or $N(R^{BN})_2$; each instance of $R^{BN}$ is independently hydrogen, optionally substituted $C_{1-6}$ alkyl, optionally substituted acyl, or a nitrogen protecting group; n is an integer of 1 to 100, inclusive; and p is an integer of 1 to 10, inclusive.

In one aspect, the present invention provides a compound of Formula (F-2)

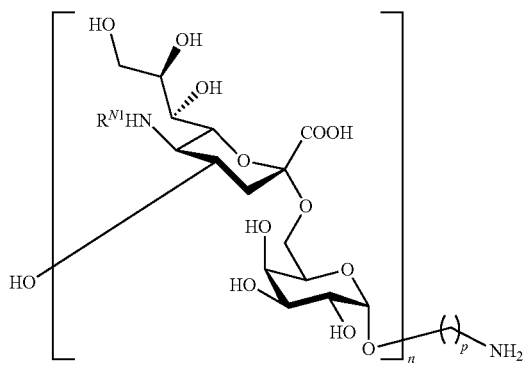

(F-2)

or a salt thereof.

In one aspect, the present invention provides a glycan conjugate or a pharmaceutically acceptable salt thereof, comprising a carrier and a glycan moiety of Formula (I)

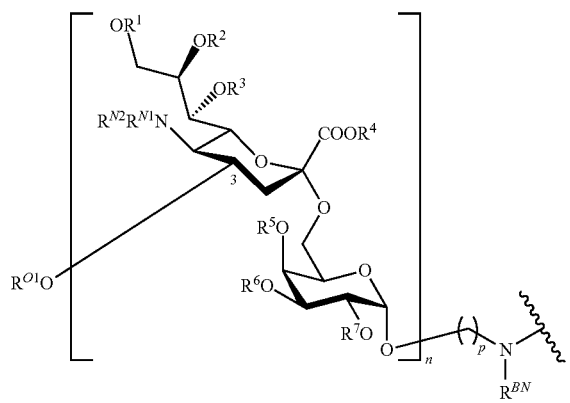

(I)

wherein: the glycan moiety is covalently linked to the carrier through a linker -L-; each instance of $R^1$, $R^2$, $R^3$, $R^4$, $R^5$, $R^6$, and $R^7$ is independently hydrogen, optionally substituted $C_{1-6}$ alkyl, or an oxygen protecting group; or optionally $R^1$ and $R^2$ are taken with the intervening atoms to form a heterocyclic ring; or optionally $R^2$ and $R^3$ are taken with the intervening atoms to form a heterocyclic ring; or optionally $R^5$ and $R^6$ are taken with the intervening atoms to form a heterocyclic ring; or optionally $R^6$ and $R^7$ are taken with the intervening atoms to form a heterocyclic ring; or $R^{N1}$ and $R^{O1}$ are taken together with the intervening atoms to form a heterocyclic ring; each instance of $R^{N1}$, $R^{N2}$, and $R^{BN}$ is independently hydrogen, optionally substituted $C_{1-6}$ alkyl, optionally substituted acyl, or a nitrogen protecting group; each instance of $R^{O1}$ is independently hydrogen, optionally substituted $C_{1-6}$ alkyl, or an oxygen protecting group; each instance of L is a bond, —C(=O)—, —C(=O)NR$^{La}$—, —C(=O)S—, —C(=O)O—, —C(=S)NR$^{La}$—, trans-CR$^{Lb}$=CR$^{Lb}$—, cis-CR$^{Lb}$=CR$^{Lb}$—, —C≡C—, —C(R$^{Lb}$)$_2$O—, —C(R$^{Lb}$)$_2$NR$^{La}$—, —C(R$^{Lb}$)$_2$S—, —S(=O)$_2$O—, —S(=O)$_2$NR$^{La}$—, or an optionally substituted $C_{1-30}$ hydrocarbon chain, optionally wherein one or more carbon units of the hydrocarbon chain is replaced with —O—, —S—, —NR$^{La}$—, —C(=O)—, —NR$^{La}$C(=O)—, —NR$^{La}$C(=O)O—, —C(=O)NR$^{La}$—, —OC(=O)NR$^{La}$—, —SC(=O)—, —C(=O)S—, —OC(=O)—, —C(=O)O—, —NR$^{La}$C(=S)—, —C(=S)NR$^{La}$—, trans-CR$^{Lb}$=CR$^{Lb}$—, cis-CR$^{Lb}$=CR$^{Lb}$—, —C≡C—, —S(=O)$_2$O—, —OS(=O)$_2$—, —S(=O)$_2$NR$^{La}$—, or —NR$^{La}$S(=O)$_2$—, wherein $R^{La}$ is hydrogen, optionally substituted $C_{1-15}$ alkyl, or a nitrogen protecting group, or $R^{La}$ is joined with the adjacent carbon atom to form an optionally substituted heterocyclic ring, and wherein each occurrence of $R^{Lb}$ is independently selected from the group consisting of hydrogen, halogen, optionally substituted $C_{1-15}$ alkyl, optionally substituted alkenyl, optionally substituted alkynyl, optionally substituted carbocyclyl, optionally substituted heterocyclyl, optionally substituted aryl, and optionally substituted heteroaryl, or $R^{Lb}$ is joined with the adjacent carbon or nitrogen or oxygen atom to form an optionally substituted carbocyclic or heterocyclic ring, or two $R^{Lb}$ groups are joined to form an optionally substituted carbocyclic or optionally substituted heterocyclic ring; p is an integer of 1 to 10, inclusive; and n is an integer of 1 to 100, inclusive.

In certain embodiments, the glycan conjugate is of Formula (I-a)

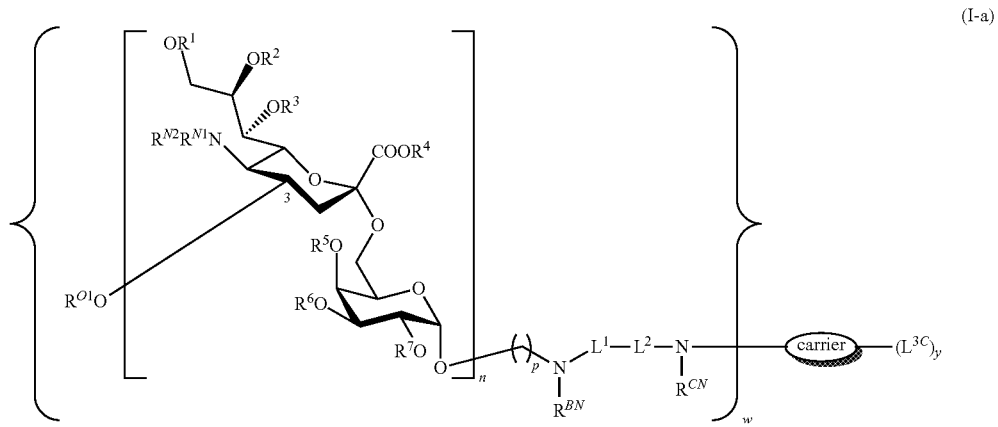

(I-a)

wherein each instance of $L^1$ is a bond, —O—, —S—, —NR$^{L1a}$—, —C(=O)—, —NR$^{L1a}$C(=O)—, —NR$^{L1a}$C(=O)O—, —C(=O)NR$^{L1a}$—, —OC(=O)NR$^{L1a}$—, —SC(=O)—, —C(=O)S—, —OC(=O)—, —C(=O)O—, —NR$^{L1a}$C(=S)—, —C(=S)NR$^{L1a}$—, trans- $CR^{L1b}=CR^{L1b}$—, cis-$CR^{L1b}=CR^{L1b}$—, —C≡C—, —OC$(R^{L1b})_2$—, —C$(R^{L1b})_2$O—, —$NR^{L1a}C(R^{L1b})_2$—, —C$(R^{L1b})_2$—, —C$(R^{L1b})_2$S—, —S(=O)$_2$O—, —OS(=O)$_2$—, —S(=O)$_2$$NR^{L1a}$—, —$NR^{L1a}$S(=O)$_2$—, or an optionally substituted $C_{1-20}$ hydrocarbon chain, optionally wherein one or more carbon units of the hydrocarbon chain is replaced with —O—, —S—, —$NR^{L1a}$—, —C(=O)—, —$NR^{L1a}$C(=O)—, —$NR^{L1a}$C(=O)O—, —C(=O)$NR^{L1a}$—, —OC(=O)$NR^{L1a}$—, —SC(=O)—, —C(=O)S—, —OC(=O)—, —C(=O)O—, —$NR^{L1a}$C(=S)—, —C(=S)$NR^{L1a}$—, trans-$CR^{L1b}=CR^{L1b}$—, cis-$CR^{L1b}=CR^{L1b}$—, —C≡C—, —S(=O)$_2$O—, —OS(=O)$_2$—, —S(=O)$_2$$NR^{L1a}$—, or —$NR^{L1a}$S(=O)$_2$—, wherein $R^{L1a}$ is hydrogen, optionally substituted $C_{1-6}$ alkyl, or a nitrogen protecting group, or $R^{L1a}$ is joined with the adjacent carbon atom to form an optionally substituted heterocyclic ring, and wherein each occurrence of $R^{L1b}$ is independently selected from the group consisting of hydrogen, halogen, optionally substituted $C_{1-10}$ alkyl, optionally substituted alkenyl, optionally substituted alkynyl, optionally substituted carbocyclyl, optionally substituted heterocyclyl, optionally substituted aryl, and optionally substituted heteroaryl, or $R^{L1b}$ is joined with the adjacent carbon or nitrogen or oxygen atom to form an optionally substituted carbocyclic or heterocyclic ring, or two $R^{L1b}$ groups are joined to form an optionally substituted carbocyclic or optionally substituted heterocyclic ring; each instance of $L^2$ is a moiety derived from a crosslinking reagent capable of crosslinking the carrier and $L^1$; each instance of $L^{3C}$ is a crosslinking reagent capable of crosslinking the carrier and $L^1$; each instance of $R^{CN}$ is independently hydrogen, optionally substituted $C_{1-6}$ alkyl, optionally substituted acyl, or a nitrogen protecting group; w is a integer of 1 to 100, inclusive; and y is 0 or an integer of 1 to 100, inclusive.

In certain embodiments, the invention provides a glycan conjugate of Formula (I-b):

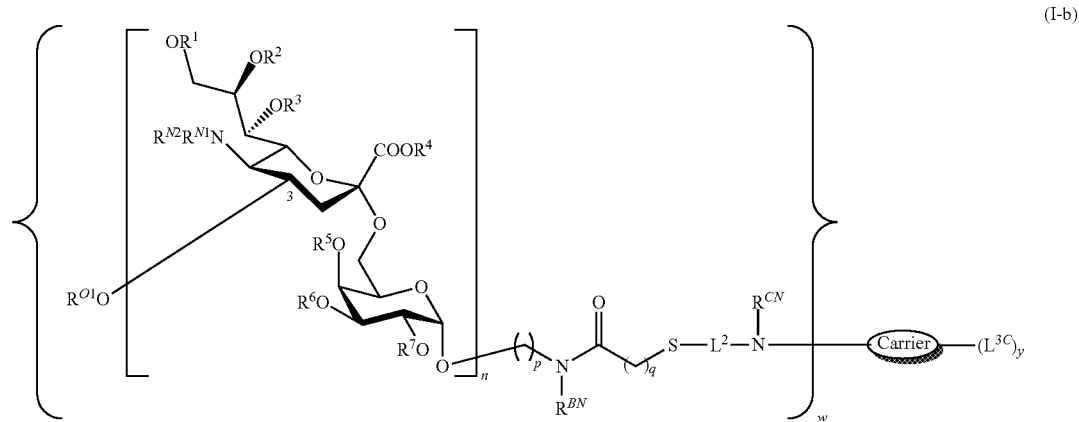

(I-b)

or a pharmaceutically acceptable salt thereof, wherein: each instance of p is an integer of 1 to 8, inclusive; and each instance of q is an integer of 1 to 8, inclusive.

In certain embodiments, the invention provides a glycan conjugate of Formula (I-c)

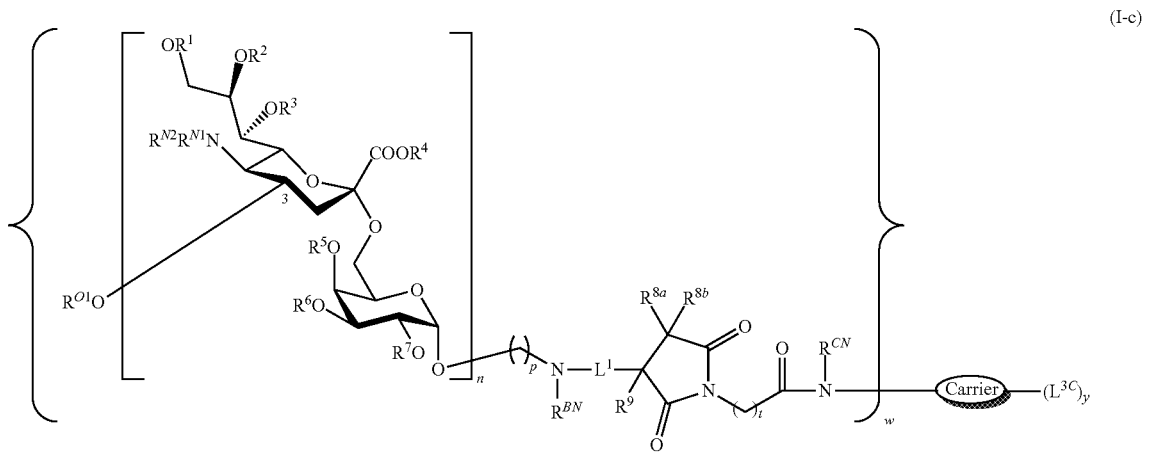

(I-c)

wherein each instance of $R^{8a}$, $R^{8b}$, and $R^9$ is independently hydrogen, halogen, or optionally substituted $C_{1-6}$ alkyl; and t is an integer of 1 to 8, inclusive.

In certain embodiments, the invention provides a glycan conjugate of Formula (I-d)

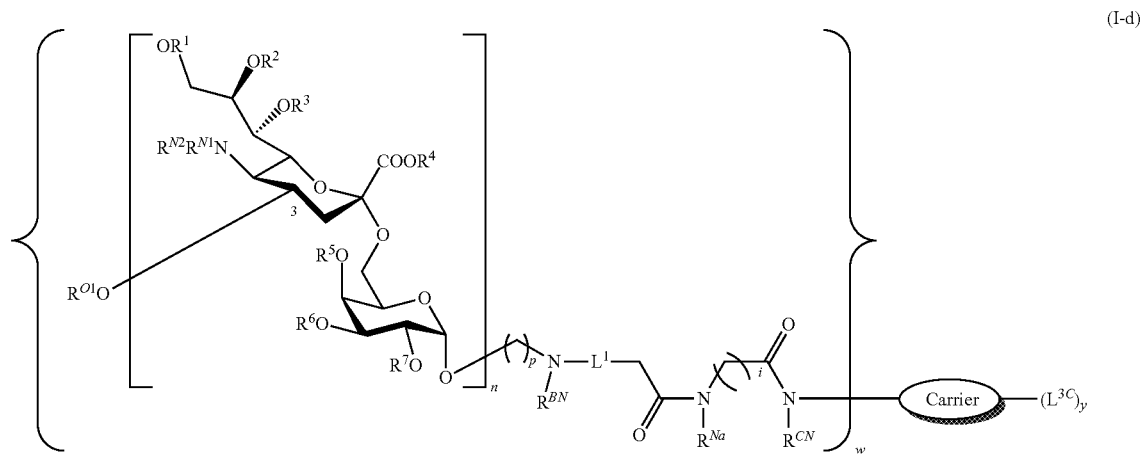

(I-d)

wherein each instance of $R^{Na}$ is independently hydrogen, optionally substituted $C_{1-6}$ alkyl, optionally substituted acyl, or a nitrogen protecting group; and i is an integer of 1 to 8, inclusive.

In certain embodiments, the invention provides a glycan conjugate of Formula (I-e)

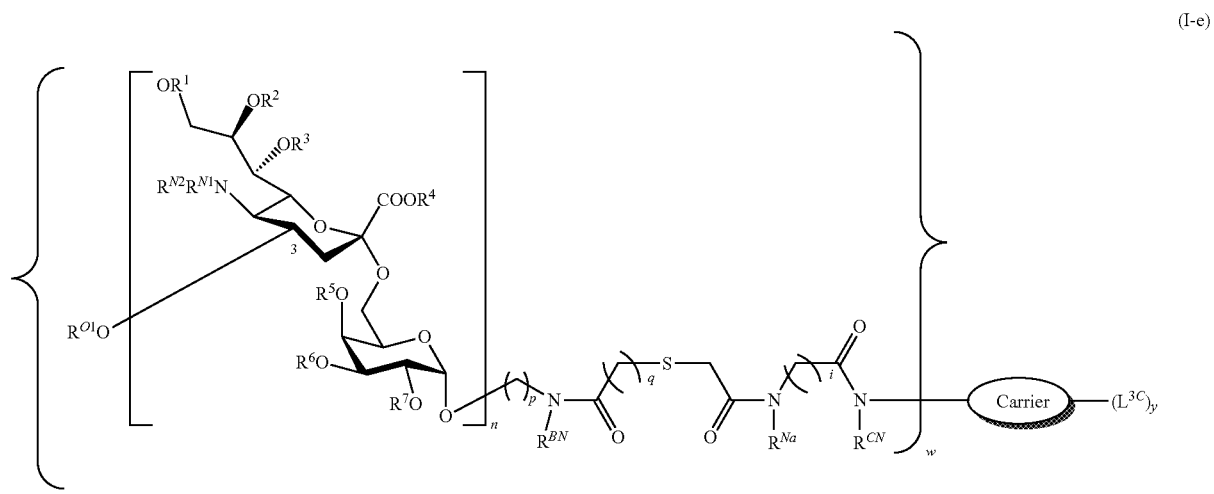

(I-e)

wherein each instance of $R^{Na}$ is independently hydrogen, optionally substituted $C_{1-6}$ alkyl, optionally substituted acyl, or a nitrogen protecting group; each instance of q is an integer of 1 to 8, inclusive; and i is an integer of 1 to 8, inclusive.

In certain embodiments, the invention provides a glycan conjugate of Formula (I-f)

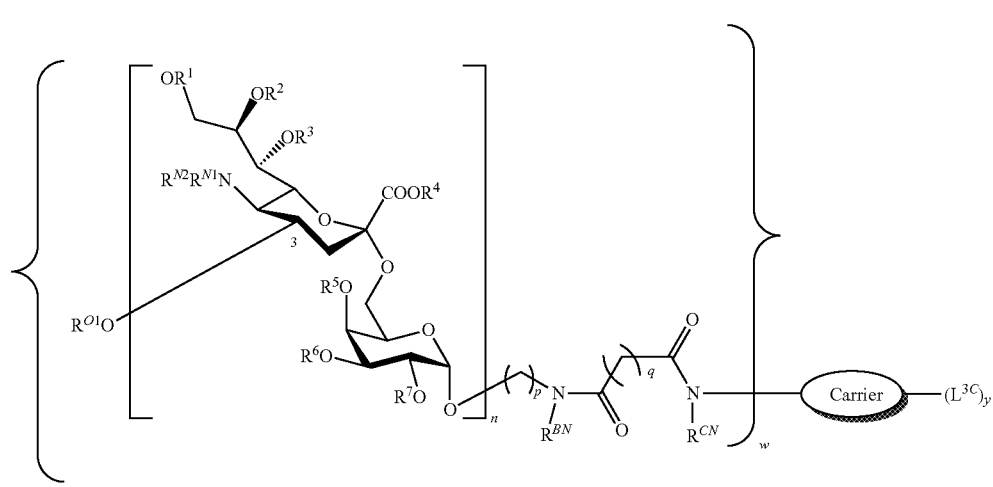

(I-f)

wherein each instance of q is an integer of 1 to 8, inclusive.

As generally defined herein, n is an integer of 1 to 100, inclusive. In certain embodiments, n is an integer of 1 to 80, inclusive. In certain embodiments, n is an integer of 1 to 60, inclusive. In certain embodiments, n is an integer of 1 to 40, inclusive. In certain embodiments, n is an integer of 1 to 20, inclusive. In certain embodiments, n is an integer of 1 to 10, inclusive. In certain embodiments, n is an integer of 1 to 8, inclusive. As generally defined herein, n is an integer of 1 to 8 inclusive. In certain embodiments, n is 1. In certain embodiments, n is 2. In certain embodiments, n is 3. In certain embodiments, n is 4. In certain embodiments, n is 5. In certain embodiments, n is 6. In certain embodiments, n is 7. In certain embodiments, n is 8.

In certain embodiments, w is an integer of 1 to 10, inclusive.

In certain embodiments, y is 0 or an integer of 1 to 10, inclusive.

In certain embodiments, p is 5.

In certain embodiments, $R^1$, $R^2$, $R^4$, $R^5$, $R^6$, and $R^7$ are hydrogen.

In certain embodiments, $R^{N1}$ is acetyl.

In certain embodiments, $R^{N2}$ is hydrogen.

In certain embodiments, $R^{BN}$ is hydrogen.

In certain embodiments, $R^{CN}$ is hydrogen.

In certain embodiments, the carrier is a protein, a lipid, a lipolized protein, a virus, a peptide comprising a T cell epitope, or a dendrimer of glycopeptides. In certain embodiments, the carrier is a toxin protein selected from the group consisting of diphtheria toxin cross-reacting material 197 (DT-CRM197), diphtheria toxoid, tetanus toxoid, and outer-membrane protein (OMP). In certain embodiments, the toxin protein is DT-CRM197.

In certain embodiments, the glycan conjugate is of the formula

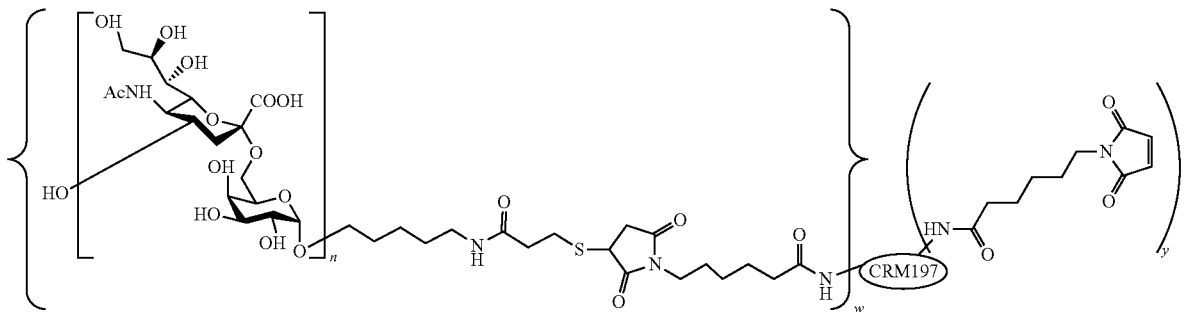

In another aspect, the present invention provides a glycan conjugate mixture comprising at least two of the glycan conjugates as described herein. In certain embodiments, the average value of w in the glycan mixture is from about 1.0 to about 100.0. In certain embodiments, the average value of w in the glycan mixture is from about 1.0 to 10.0. In certain embodiments, the average value of w in the glycan mixture is about 5.7, 4.9, 2.9, 2.8, or 3.1. In certain embodiments, the average value of w in the glycan mixture is about 4.9, 2.9, 2.8, or 3.1.

In another aspect, the present invention provides methods of synthesizing the glycan conjugates as described herein.

In another aspect, the present invention provides immmunogenic compositions comprising a glycan conjugate or a glycan conjugate mixture as provided herein and a pharmaceutically acceptable excipient. In certain embodiments, the immmunogenic compositions further comprise an adjuvant. In certain embodiments, the adjuvant is C34, 7DW8-5, C17, C23, C30, α-galactoceramide, Aluminum salt, Squalene, MF59, or QS-21. In certain embodiments, the immmunogenic compositions described herein include an immmunogenically effective amount of an inventive glycan conjugate. In certain embodiments, the immmunogenic compositions described herein include an pharmaceutically effective amount of an inventive glycan conjugate. The invetive glycan conjugates described herein are useful for inducing an immune response against an infectious disease in a subject. In certain embodiments, the infectious disease is a bacterial infection. In certain embodiments, the infectious disease is caused by Gram-positive bacteria. In certain embodiments, the infectious disease is caused by Gram-negative bacteria. In certain embodiments, the infectious disease is caused by *N. meningitidis*. In certain embodiments, the immmunogenic compositions provided herein induce IgG and IgM antibodies and provided an immunogenicity against the bacteria. In certain embodiments, the immmunogenic compositions provided herein induce more IgG antibodies and IgM antibodies. In certain embodiments, the immmunogenic compositions provided herein mainly induce IgG1 and IgG3.

In another aspect, the present invention provides kits comprising the inventive glycan conjugates, or glycan conjugate mixture thereof, or immmunogenic compositions thereof. The kits of the invention may include a single dose or multiple doses of the inventive glycan conjugates, a glycan conjugate mixture thereof, or immmunogenic compositions thereof. The provided kits may be useful for treating or reducing the risk of infectious diseases such bacterial infections. The kits may also include packaging information describing the use or prescribing information for the subject or a health care professional. Such information may be required by a regulatory agency such as the U.S. Food and Drug Administration (FDA). The kit may also optionally include a device for administration of the compound or composition, for example, a syringe for parenteral administration.

In another aspect, the present invention provides methods for treating and/or reducing the risk for infectious diseases in a subject comprising administering to the subject therapeutically effective amount of a glycan conjugate, or a glycan conjugate thereof, or an immunogenic composition as described herein.

In another aspect, the present invention provides methods for inhibiting bacterial growth in a subject comprising administering to a subject a therapeutically effective amount of a glycan conjugate, or a glycan conjugate mixture, or an immunogenic composition as described herein. In another aspect, the present invention provides methods for inhibiting bacterial infections comprising administering to a subject a therapeutically effective amount of a glycan conjugate, or a glycan conjugate mixture, or an immunogenic composition as described herein.

In certain embodiments, the bacterial infection is an infection with a Gram-positive bacterium. In certain embodiments, the bacterium is selected from the group consisting of *Staphylococcus, Streptococcus, Micrococcus, Peptococcus, Peptostreptococcus, Enterococcus, Bacillus, Clostridium, Lactobacillus, Listeria, Erysipelothrix, Propionibacterium, Eubacterium*, and *Corynebacterium*. In certain embodiments, the bacterial infection is an infection with a Gram-negative bacterium. In certain embodiments, the Gram-negative bacterium is selected from the group consisting of *Escherchia coli, Caulobacter crescentus, Pseudomonas aeruginosa, Agrobacterium tumefaciens, Branhamella catarrhalis, Citrobacter diversus, Enterobacter aerogenes, Klebsiella pneumoniae, Proteus mirabilis, Salmonella typhimurium, Neisseria meningitidis, Serratia marcescens, Shigella sonnei, Neisseria gonorrhoeae, Acinetobacter baumannii, Salmonella enteriditis, Fusobacterium nucleatum, Veillonella parvula, Bacteroides forsythus, Acti-* *nobacillus actinomycetemcomitans, Aggregatibacter actinomycetemcomitans, Porphyromonas gingivalis, Helicobacter pylori, Francisella tularensis, Yersinia pestis, Morganella morganii, Edwardsiella tarda, Acinetobacter baumannii* and *Haemophilus influenzae*. In certain embodiments, the bacterium is *N. meningitides*. In certain embodiments, the bacterium is *N. meningitides* serogroups W135.

In another aspect, the present invention provides methods for inhibiting bacterial cell growth comprising contacting the bacterial cell with a glycan conjugate, or a glycan conjugate mixture thereof, or an immunogenic composition thereof. In certain embodiments, the contacting step is performed in in vitro. In certain embodiments, the contacting step is performed by administering the glycan conjugate, the glycan conjugate mixture, or the immunogenic composition as described herein, to a subject in need thereof.

Also described herein are pharmaceutical compositions for use in eliciting immune responses against bacterial antigens and/or in treating bacterial infections, wherein the pharmaceutical compositions comprising a glycan-conjugate or a glycan conjugate mixture as described herein and a pharmaceutically acceptable expicient. In certain embodiments, the provided pharmaceutical compositions further comprise an adjuvant. In certain embodiments, provided herein is a pharmaceutical compositions for use in manufacturing medicant for use in bacterial immunotherapy.

In another aspect, the present invention provides methods of preparing the inventive glycan conjugates, the glycan conjugate mixtures thereof, or immunogenic compositions thereof.

In certain embodiments, the invention provides a method of preparing a glycan conjugate as described herein, comprising coupling a compound of Formula (C-1)

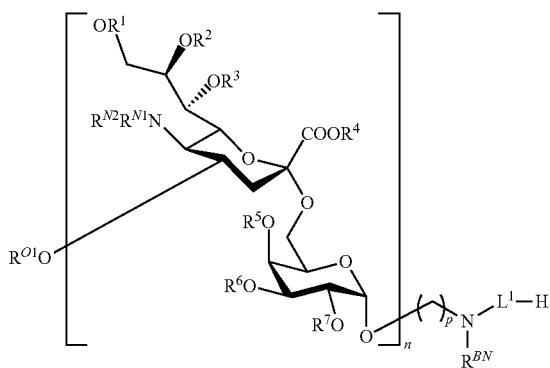

or a salt thereof, with a compound of the Formula (C-2)

wherein $L^{2C}$ is a crosslinking reagent capable of crosslinking an amino group and $L^1$-H.

In certain embodiments, $L^{2C}$ is a crosslinking reagent capable of crosslinking an amine group and —SH. In certain embodiments, $L^{2C}$ is of one of the following formulae:

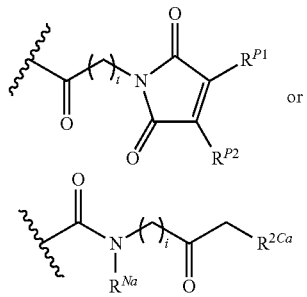

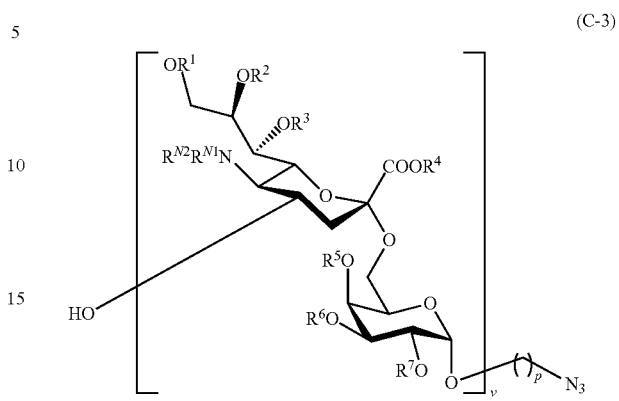

or a salt thereof,
wherein each instance of $R^{P1}$ and $R^{P2}$ are each independently hydrogen, halogen, or optionally substituted $C_{1-6}$ alkyl; each instance of $R^{Na}$ is independently hydrogen, optionally substituted $C_{1-6}$ alkyl, optionally substituted acyl, or a nitrogen protecting group; each instance of $R^{2Ca}$ is a leaving group selected from selected from —Br, —Cl, —I, —OS(=O)$_2$R$^{2CO}$, or —OS(=O)R$^{2CO}$, wherein R$^{2CO}$ is selected from the group consisting of optionally substituted alkyl, optionally substituted alkenyl, optionally substituted alkynyl, optionally substituted carbocyclyl, optionally substituted heterocyclyl, optionally substituted aryl, and optionally substituted heteroaryl; and each oft and i is independently an integer of 1 to 8, inclusive.

In certain embodiments, the molar ratio of the compound of Formula (C-1) to the compound of Formula (C-2) is from about 1 to about 100. In certain embodiments, the molar ratio of the compound of Formula (C-1) to the compound of Formula (C-2) is from about 1 to about 80. In certain embodiments, the molar ratio of the compound of Formula (C-1) to the compound of Formula (C-2) is from about 1 to about 60. In certain embodiments, the molar ratio of the compound of Formula (C-1) to the compound of Formula (C-2) is from about 1 to about 40. In certain embodiments, the molar ratio of the compound of Formula (C-1) to the compound of Formula (C-2) is from about 1 to about 20. In certain embodiments, the molar ratio of the compound of Formula (C-1) to the compound of Formula (C-2) is from about 1 to about 10. In certain embodiments, the coupling is carried out in the presence of phosphate buffered saline (PBS).

In certain embodiments, the method further comprises glycosylating a compound of Formula (C-3)

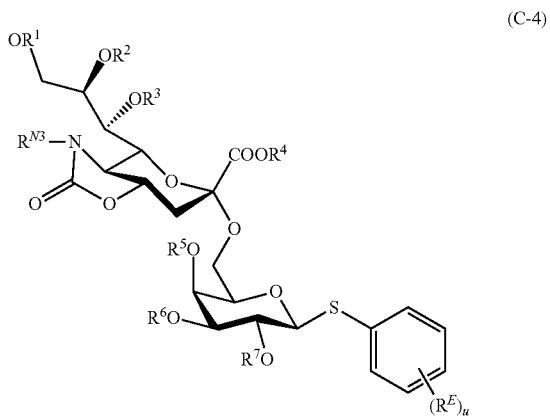

with a compound of Formula (C-4)

to give a compound of Formula (C-5)

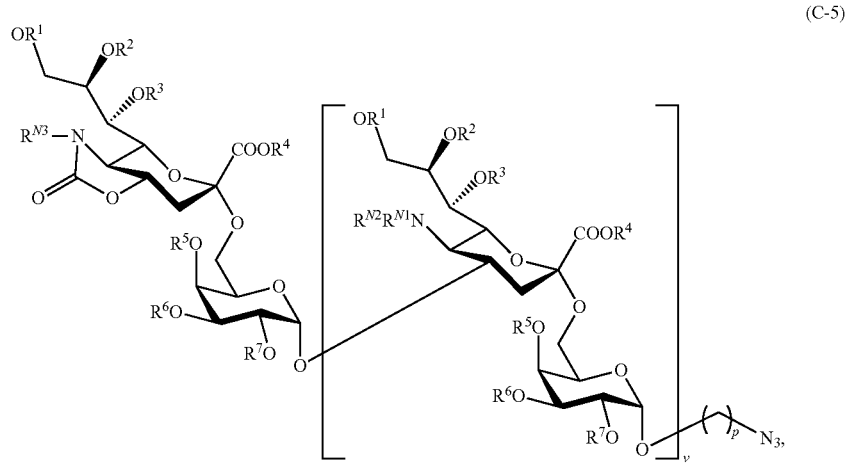

wherein v is an integer of 1 to 99, inclusive; u is 0, 1, 2, 3, 4, or 5; each occurrence of $R^E$ is independently halogen, —CN, —NO$_2$, —N$_3$, optionally substituted alkyl, optionally substituted alkenyl, optionally substituted alkynyl, optionally substituted carbocyclyl, optionally substituted phenyl, optionally substituted heterocyclyl, optionally substituted heteroaryl, —OR$^{CE}$, —N(R$^{CE}$)$_2$, —SR$^{CE}$, —C(=O)R$^{CE}$, —C(=O)OR$^{CE}$, or —C(=O)N(R$^{CE}$)$_2$, wherein each R$^{CE}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl; or an oxygen protecting group when attached to an oxygen, or a nitrogen protecting group when attached to nitrogen, or a sulfur protecting group when attached to sulfur; and R$^{N3}$ is independently hydrogen, optionally substituted alkyl, or a nitrogen protecting group.

In certain embodiments, the method further comprises reacting the compound of Formula (C-5) in the presence of a base to give a compound of Formula (C-6)

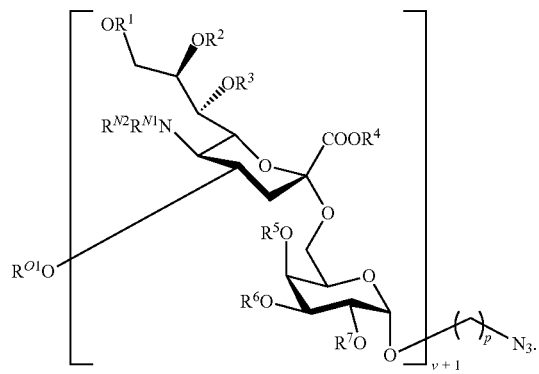

(C-6)

In certain embodiments, the base is NaOCH$_3$.

In certain embodiments, the method further comprises reacting the compound of Formula (C-6) with a reducing agent to give a compound of Formula (C-7)

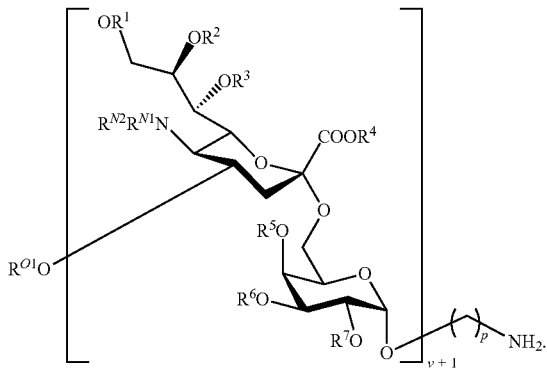

(C-7)

In certain embodiments, the method further comprises: (a) activating a compound of Formula (C-7) to give a compound of Formula (C-1); and (b) activating a carrier to give a compound of Formula (C-2).

The details of certain embodiments of the invention are set forth herein. Other features, objects, and advantages of the invention will be apparent from the Detailed Description, the Figures, the Examples, and the Claims.

BRIEF DESCRIPTION OF THE DRAWINGS

FIG. 5 shows oligosaccharide conjugated to the carrier.

DETAILED DESCRIPTION OF THE INVENTION

Chemical Definitions

Figure 1:
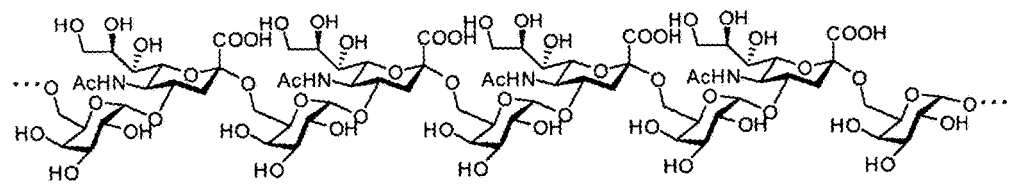
FIG. 1 shows structure of *N. meningitidis* serogroup W135 capsular oligosaccharide. The oligosaccahride is composed of a repeating unit of →6)-α-D-Galp-(1→4)-α-D-Neup5Ac(9OAc)-(2→.

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, Organic Chemistry, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

"Alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents. In certain embodiments, the alkyl group is unsubstituted $C_{1-10}$ alkyl (e.g., —$CH_3$). In certain embodiments, the alkyl group is substituted $C_{1-10}$ alkyl.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_2$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_2$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), 17ydroxy[2.2.1]heptanyl ($C_7$), 17ydroxy[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused to one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_6$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In certain embodiments, the heteroatom is independently selected from nitrogen, sulfur, and oxygen. In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, and thiorenyl. Exemplary 4-membered heterocyclyl groups containing one heteroatom include, without limitation, azetidinyl, oxetanyl, and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl, and thiepanyl. Exemplary 8-membered heterocyclyl groups containing one heteroatom include, without limitation, azocanyl, oxecanyl, and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Arylalkyl" is a subset of alkyl and aryl, as defined herein, and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen, and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl, as defined herein, and refers to an optionally substituted alkyl group substituted by an optionally substituted heteroaryl group.

"Partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., it contains all single bonds.

Alkyl, alkenyl, alkynyl, carbocyclyl, heterocyclyl, aryl, and heteroaryl groups, as defined herein, which are divalent bridging groups are further referred to using the suffix -ene, e.g., alkylene, alkenylene, alkynylene, carbocyclylene, heterocyclylene, arylene, and heteroarylene.

As used herein, the term "optionally substituted" refers to a substituted or unsubstituted moiety.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, -Osi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; or two hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$; each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups; each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups; each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups; each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, -Osi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two R$^{dd}$ substituents can be joined to form =O or =S; each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups; each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl), —N(C$_{1-6}$ alkyl), —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl), —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl), —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl), —OC(NH)NH(C$_{1-6}$ alkyl), —OC(NH)NH$_2$, —NHC(NH)N(C$_{1-6}$ alkyl), —NHC(=NH)NH$_2$, —NHSO$_2$(C$_{1-6}$ alkyl), —SO$_2$N(C$_{1-6}$ alkyl), —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, -Osi(C$_{1-6}$ alkyl)$_3$-C(=S)N(C$_{1-6}$ alkyl), C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl), C$_{1-6}$ alkyl, C$_{1-6}$ perhaloalkyl, C$_{2-6}$ alkenyl, C$_{2-6}$ alkynyl, $C_{3-10}$ carbocyclyl, $C_{6-10}$ aryl, 3-10 membered heterocyclyl, 5-10 membered heteroaryl; or two $R^{gg}$ substituents can be joined to form =O or =S; wherein $X^-$ is a counterion.

"Halo" or "halogen" refers to fluorine (fluoro, —F), chlorine (chloro, —Cl), bromine (bromo, —Br), or iodine (iodo, —I).

"Acyl" as used herein refers to a moiety selected from the group consisting of —C(=O)$R^{aa}$, —CHO, —CO$_2R^{aa}$, —C(=O)N($R^{bb}$)$_2$, —C(=N$R^{bb}$)$R^{aa}$, —C(=N$R^{bb}$)O$R^{aa}$, —C(=N$R^{bb}$)N($R^{bb}$)$_2$, —C(=O)N$R^{bb}$SO$_2R^{aa}$, —C(=S)N($R^{bb}$)$_2$, —C(=O)S$R^{aa}$, and —C(=S)S$R^{aa}$, wherein $R^{aa}$ and $R^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —O$R^{aa}$, —N($R^{cc}$)$_2$, —CN, —C(=O)$R^{aa}$, —C(=O)N($R^{cc}$)$_2$, —CO$_2R^{aa}$, —SO$_2R^{aa}$, —C(=N$R^{bb}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)$_2R^{aa}$, —P(=O)($R^{aa}$)$_2$, —P(=O)$_2$N($R^{cc}$)$_2$, —P(=O)(N$R^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined above.

In certain embodiments, the substituent present on a nitrogen atom is a nitrogen protecting group (also referred to as an amino protecting group). Nitrogen protecting groups include, but are not limited to, —OH, —O$R^{aa}$, —N($R^{cc}$)$_2$, —C(=O)$R^{aa}$, —C(=O)N($R^{cc}$)$_2$, —CO$_2R^{aa}$, —SO$_2R^{aa}$, —C(=N$R^{cc}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzyloxymethyl)benzamide.

Nitrogen protecting groups such as carbamate groups (e.g., —C(=O)O$R^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-Adamantyl)-1-methylethyl (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Nitrogen protecting groups such as sulfonamide groups (e.g., —S(=O)$_2R^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-hydroxyl, N-methylamine, N-allylamine, N-[2-(trimethylsily)ethoxy]methylamine (SEM), N-3-acetoxypropylamine, N-(1-isopropyl-4-nitro-2-oxo-3-pyroolin-3-yDamine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3$, $-P(=O)_2R^{aa}$, $-P(=O)(R^{aa})_2$, $-P(=O)(OR^{cc})_2$, $-P(=O)_2N(R^{bb})_2$, and $-P(=O)(NR^{bb})_2$, wherein $R^{aa}$, $R^{bb}$, and $R^{cc}$ are as defined herein. Oxygen protecting groups are well known in the art and include those described in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl(CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napthyl carbonate, methyl dithiocarbonate, 2-iodobenzoate, 4-azidobutyrate, 4-nitro 1 methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is an sulfur protecting group (also referred to as a thiol protecting group). Sulfur protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3$, $-P(=O)_2R^{aa}$, $-P(=O)(R^{aa})_2$, $-P(=O)(OR^{cc})_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Sulfur protecting groups are well known in the art and include those described in *Protecting Groups in Organic Synthesis*, T. W. Greene and P. G. M. Wuts, 3$^{rd}$ edition, John Wiley & Sons, 1999, incorporated herein by reference.

As used herein, the term "leaving group" is given its ordinary meaning in the art of synthetic organic chemistry and refers to an atom or a group capable of being displaced by a nucleophile. Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, -OTs), methanesulfonate (mesylate, -OMs), p-bromobenzenesulfonyloxy (brosylate, -OBs), or trifluoromethanesulfonate (triflate, -OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties.

General Definitions

The following definitions are more general terms used throughout the present application:

As used herein, a "carbohydrate group" or a "carbohydrate" refers to a monosaccharide or a polysaccharide (e.g., a disaccharide or oligosaccharide). Exemplary monosaccharides include, but are not limited to, natural sugars, such as allose, altrose, glucose, mannose, gulose, idose, galactose, talose, ribose, arabinose, xylose, and lyxose. Disaccharides are two joined monosaccharides. Exemplary disaccharides include, but are not limited to, sucrose, maltose, cellobiose, and lactose. Typically, an oligosaccharide includes between three and ten monosaccharide units (e.g., raffinose, stachyose). The carbohydrate group may be a natural sugar or a modified sugar. Exemplary modified sugars include, but are not limited to, sugars where the hydroxyl group is replaced with an amino group and/or alkyl group (e.g., such as desosamine), 2'-deoxyribose wherein a hydroxyl group is removed, 2'-fluororibose wherein a hydroxyl group is replace with a fluorine, or N-acetylglucosamine, or a nitrogen-containing form of glucose (e.g., 2'-fluororibose, deoxyribose, and hexose), and the like. Various carbohydrates are further described below and herein. Carbohydrates may exist in many different forms, for example, conformers, cyclic forms, acyclic forms, stereoisomers, tautomers, anomers, and isomers.

As used herein, the term "conjugated" or "conjugation" refers to an association of two molecules, for example, a glycan moiety and a protein carrier, with one another in a way that they are linked by a direct or indirect covalent or non-covalent interaction. In certain embodiments, the association is covalent, and the entities are said to be "conjugated" to one another.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyl-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$ alkyl)$_4$ salts. Representative alkali or alkaline earth metal salts include sodium, lithium, potassium, calcium, magnesium, and the like. Further pharmaceutically acceptable salts include, when appropriate, non-toxic ammonium, quaternary ammonium, and amine cations formed using counterions such as halide, hydroxide, carboxylate, sulfate, phosphate, nitrate, lower alkyl sulfonate, and aryl sulfonate.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female and at any stage of development. A non-human animal may be a transgenic animal.

The terms "administer," "administering," or "administration," as used herein refers to implanting, absorbing, ingesting, injecting, inhaling, or otherwise introducing an inventive compound, or a pharmaceutical composition thereof.

As used herein, the terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments, treatment may be administered after one or more signs or symptoms have developed or have been observed. In other embodiments, treatment may be administered in the absence of signs or symptoms of the disease or condition. For example, treatment may be administered to a susceptible individual (e.g., an individual at risk for the disease) prior to the onset of symptoms (e.g., in light of a history of symptoms and/or in light of genetic or other susceptibility factors). Treatment may also be continued after symptoms have resolved, for example, to delay or prevent recurrence.

As used herein, the terms "condition," "disease," and "disorder" are used interchangeably.

An "effective amount" of a compound refers to an amount sufficient to elicit a desired biological response, i.e., treating the condition. As will be appreciated by those of ordinary skill in this art, the effective amount of a compound may vary depending on such factors as the desired biological endpoint, the pharmacokinetics of the compound, the condition being treated, the mode of administration, and the age and health of the subject. An effective amount encompasses therapeutic and prophylactic treatment. In certain embodiments, the effective amount encompasses an amount effective in eliciting an immune responses specific to a bacterial infectious disease. In certain embodiments, the effective amount encompasses an amount effective in eliciting an immune responses specific to an infectious disease caused by a gram-negative bacterium. In certain embodiments, the effective amount encompasses an amount effective in eliciting an immune responses specific to an infectious disease caused by *Neisseria meningitides*. In certain embodiments, the effective amount encompasses an amount effective in eliciting an immune responses specific to an infectious disease caused by *Neisseria meningitides* serogroup W135.

A "therapeutically effective amount" of a compound is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" of a compound is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

In certain embodiments, a compound of the present invention is provided as a salt. Salts are well known in the art. For example, Berge et al., describe pharmaceutically acceptable salts in detail in *J. Pharmaceutical Sciences*, 1977, 66, 1-19, incorporated herein by reference. Salts of the compounds of this invention include those derived from suitable inorganic and organic acids and bases. Examples include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further salts include, when appropriate, ammonium, quaternary ammonium, and amine cations formed using counterions such as halide, hydroxide, carboxylate, sulfate, phosphate, nitrate, lower alkyl sulfonate and aryl sulfonate.

As used herein "inhibition," "inhibiting," and "inhibit", refer to the ability of a compound to reduce, slow, halt or prevent activity of a particular biological process relative to a control vehicle or absence of the compound (e.g., by at least 20%, 50%, 80%, 90%, 95%, or 100%). In certain embodiments, the biological process is in vitro (e.g., cellular assay). In certain embodiments, the biological process is in vivo. In certain embodiments, a probe compound of the present invention inhibits a glycosyltransferase protein.

The term "independently" is used herein to indicate that the groups can be identical or different.

As used herein, the term "antigen" is defined as any substance capable of eliciting an immune response: e.g., a B-cell response or a T-cell response.

As used herein, the term "immunogenicity" refers to the ability of an immunogen, antigen, or vaccine to stimulate an immune response.

As used herein, the term "immunotherapy" refers to an array of treatment strategies based upon the concept of modulating the immune system to achieve a prophylactic and/or therapeutic goal.

As used herein, the term "epitope" is defined as the parts of an antigen molecule which contact the antigen binding site of an antibody or a T cell receptor.

As used herein, the term "immunogenic composition" refers to a preparation that contains an antigen, such as proteins, peptides, lipid, polysaccharides, or whole disease-causing organisms (killed or weakened), and capable of elicit an immune response specific to the antigen. An immunogenic composition (e.g., a vaccine) may be used to confer immunity against a disease associated with the antigen, e.g., against an infection caused by an microorganism from which the antigen is derived. An immunogenic composition or the antigen contained therein can be natural, synthetic, or prepared by recombinant DNA technology.

As used herein, the term "adjuvant" refers to a substance capable of modifying (e.g., enhancing) the immune response to an immunogen when it is used in conjunction with the immunogen. An adjuvant may not elicit immune responses specific to itself. In some examples, the α-GalCer analogs described herein (e.g., C34) are used as adjuvants to modify or augment the effects of an immunogen by stimulating the immune system of a patient who is administered the immunogen to respond to the immunogen more vigorously. In other examples, the adjuvant can be an aluminum salt.

As used herein, the term "antigen specific" or "immunogen specific" refers to a property of a cell population such that supply of a particular antigen or immunogen, or a fragment thereof, results in specific cell proliferation.

The present invention provides synthetic glycan conjugates comprising oligosaccharide antigens derived from *Neisseria meningitidis* (e.g., serogroup W135), immmunogenic compositions thereof, and kits thereof, as well as methods of synthesizing the oligosaccharide antigens and glycan conjugates and methods of using such for eliciting immune responses specific to the oligosaccharide antigens and treating or reducing the risk for infectious diseases (e.g., bacterial infections such as those caused by *Neisseria meningitidis*).

Compounds

The present invention provides carbohydrate compounds of Formula (F-1):

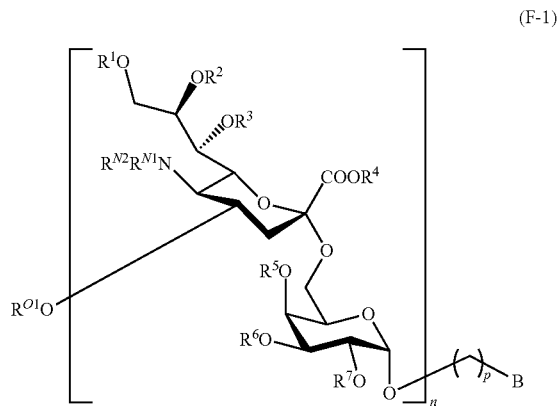

(F-1)

or a salt thereof,
wherein each instance of $R^1$, $R^2$, $R^3$, $R^4$, $R^5$, $R^6$, and $R^7$ is independently hydrogen, optionally substituted $C_{1-6}$ alkyl, or an oxygen protecting group; or optionally $R^1$ and $R^2$ are taken with the intervening atoms to form a heterocyclic ring; or optionally $R^2$ and $R^3$ are taken with the intervening atoms to form a heterocyclic ring; or optionally $R^5$ and $R^6$ are taken with the intervening atoms to form a heterocyclic ring; or $R^{N1}$ and $R^{O1}$ are taken together with the intervening atoms to form a heterocyclic ring; each instance of $R^{N1}$ and $R^{N2}$ is independently hydrogen, optionally substituted $C_{1-6}$ alkyl, optionally substituted acyl, or a nitrogen protecting group; each instance of $R^{O1}$ is independently hydrogen, optionally substituted $C_{1-6}$ alkyl, or an oxygen protecting group; B is $-N_3$ or $N(R^{BN})_2$; each instance of $R^{BN}$ is independently hydrogen, optionally substituted $C_{1-6}$ alkyl, optionally substituted acyl, or a nitrogen protecting group; n is an integer of 1 to 100, inclusive; and p is an integer of 1 to 10, inclusive.

As generally defined herein, B is $-N_3$ or $N(R^{BN})_2$, wherein each instance of $R^{BN}$ is independently hydrogen, optionally substituted $C_{1-6}$ alkyl, or a nitrogen protecting group. In some embodiments, B is $-N_3$. In some embodiments, B is $NH_2$. In some embodiments, B is $NHR^{BN}$, wherein $R^{BN}$ is optionally substituted $C_{1-6}$ alkyl. In some embodiments, B is $NHR^{BN}$, wherein $R^{BN}$ is methyl, ethyl, or propyl. In some embodiments, B is $NHR^{BN}$, wherein $R^{BN}$ is a nitrogen protecting group. In some embodiments, B is $NHR^{BN}$, wherein $R^{BN}$ is Ac, Bn, BOC, Cbz, Troc, Fmoc, trifluoroacetyl, triphenylmethyl, or Ts. In some embodiments, B is $N(R^{BN})_2$, wherein $R^{BN}$ are the same. In some embodiments, B is $N(R^{BN})_2$, wherein $R^{BN}$ are different. In some embodiments, B is $N(R^{BN})_2$, wherein each instance of $R^{BN}$ is Ac, Bn, BOC, Cbz, Troc, Fmoc, trifluoroacetyl, triphenylmethyl, or Ts. In some embodiments, B is $NBnR^{BN}$, wherein $R^{BN}$ is Ac, Bn, BOC, Cbz, Troc, Fmoc, trifluoroacetyl, triphenylmethyl, or Ts. In some embodiments, B is NBnCbz.

As generally defined herein, p is an integer of 1 to 10, inclusive. In certain embodiments, p is 1. In certain embodiments, p is 2. In certain embodiments, p is 3. In certain embodiments, p is 4. In certain embodiments, p is 5. In certain embodiments, p is 6. In certain embodiments, p is 7. In certain embodiments, p is 8. In certain embodiments, p is 9. In certain embodiments, p is 10.

As used herein, $R^1$, $R^2$, $R^3$, $R^4$, $R^5$, $R^6$, and $R^7$ are as defined herein.

In certain embodiments, the carbohydrate compounds provided herein are of Formula (F-2):

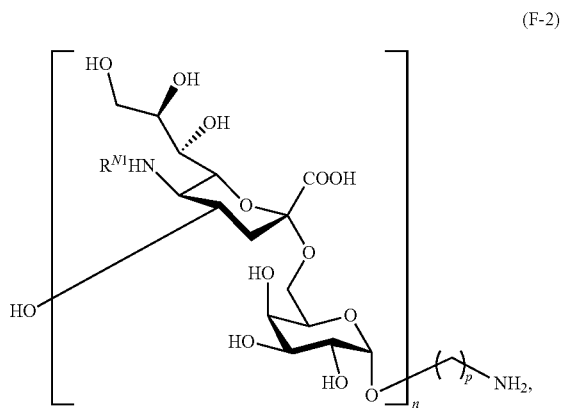

(F-2)

or a salt thereof.

In other embodiments, the carbohydrate compounds provided herein are of Formula (F-3):

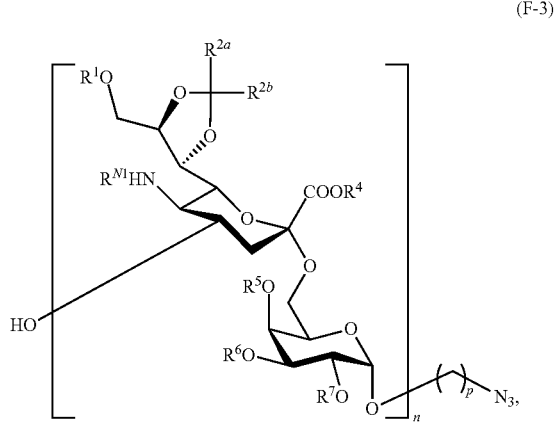

(F-3)

or a salt thereof, wherein each instance of $R^{2a}$ and $R^{2b}$ is independently optionally substituted $C_{1-6}$ alkyl. In certain embodiments, $R^{2a}$ is unsubstituted $C_{1-6}$ alkyl. In certain embodiments, $R^{2a}$ is methyl, ethyl, or propyl. In certain embodiments, $R^{2b}$ is unsubstituted $C_{1-6}$ alkyl. In certain embodiments, $R^{2b}$ is methyl, ethyl, or propyl.

Alternatively, the carbohydrate compounds described herein can have the structure of Formula (F-4):

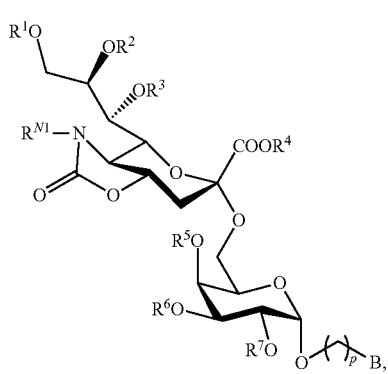

(F-4)

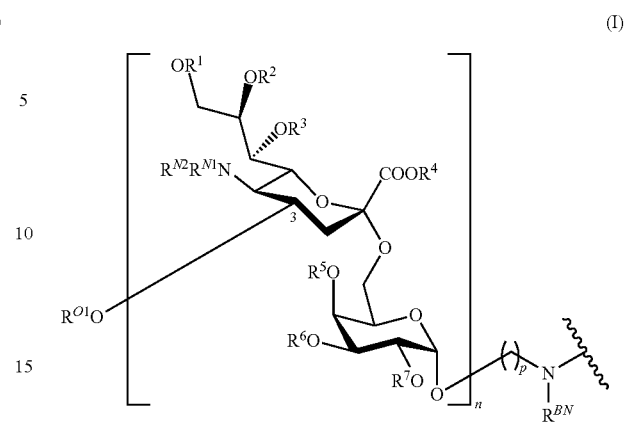

(I)

or a salt thereof.

As used herein, n is an integer of 1 to 100, inclusive. In certain embodiments, n is an integer of 1 to 80, inclusive. In certain embodiments, n is an integer of 1 to 60, inclusive. In certain embodiments, n is an integer of 1 to 40, inclusive. In certain embodiments, n is an integer of 1 to 20, inclusive. In certain embodiments, n is an integer of 1 to 10, inclusive. In certain embodiments, n is an integer of 1 to 8, inclusive. In certain embodiments, n is 1. In certain embodiments, n is 2. In certain embodiments, n is 3. In certain embodiments, n is 4. In certain embodiments, n is 5. In certain embodiments, n is 6. In certain embodiments, n is 7. In certain embodiments, n is 8.

Alternatively, the carbohydrate compounds described herein can have the structure of Formula (F-5):

wherein: the glycan moiety is covalently linked to the carrier through a linker -L-; each instance of $R^1$, $R^2$, $R^3$, $R^4$, $R^5$, $R^6$, and $R^7$ is independently hydrogen, optionally substituted $C_{1-6}$ alkyl, or an oxygen protecting group; or optionally $R^1$ and $R^2$ are taken with the intervening atoms to form a heterocyclic ring; or optionally $R^2$ and $R^3$ are taken with the intervening atoms to form a heterocyclic ring; or optionally $R^5$ and $R^6$ are taken with the intervening atoms to form a heterocyclic ring; or optionally $R^6$ and $R^7$ are taken with the intervening atoms to form a heterocyclic ring; or $R^{N1}$ and $R^{O1}$ are taken together with the intervening atoms to form a heterocyclic ring; each instance of $R^{N1}$, $R^{N2}$, and $R^{BN}$ is independently hydrogen, optionally substituted $C_{1-6}$ alkyl,

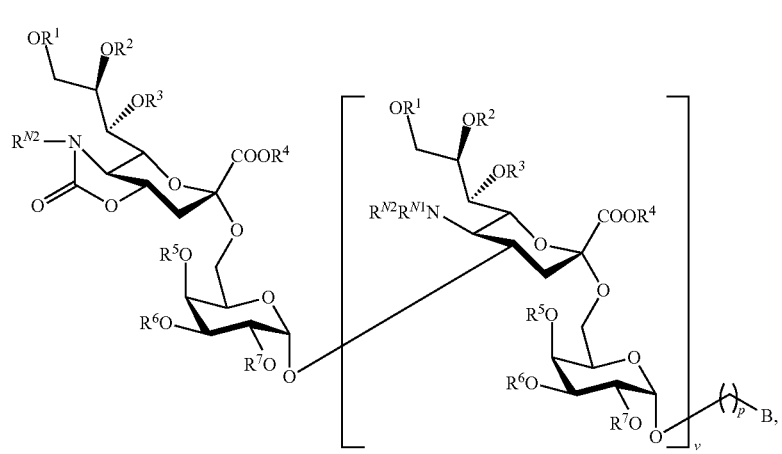

(F-5)

or a salt thereof, wherein v is an integer from 1 to 99, inclusive.

Glycan Conjugates

The present invention provides a glycan conjugate or a pharmaceutically acceptable salt thereof, comprising a carrier and a glycan moiety of Formula (I):

optionally substituted acyl, or a nitrogen protecting group; each instance of $R^{O1}$ is independently hydrogen, optionally substituted $C_{1-6}$ alkyl, or an oxygen protecting group; each instance of L is independently a bond, —C(=O)—, —C(=O)NR$^{La}$—, —C(=O)S—, —C(=O)O—, —C(=S) NR$^{La}$—, trans-CR$^{Lb}$=CR$^{Lb}$—, cis-CR$^{Lb}$=CR$^{Lb}$—, —C≡C—, —C(R$^{Lb}$)$_2$O—, —C(R$^{Lb}$)$_2$NR$^{La}$—, —C(R$^{Lb}$)$_2$S—, —S(=O)$_2$O, —S(=O)$_2$NR$^{La}$, or an optionally substituted $C_{1-30}$ hydrocarbon chain, optionally wherein one or more carbon units of the hydrocarbon chain is replaced with —O—, —S—, —NR$^{La}$—, —C(=O)—, —NR$^{La}$C(=O)—, —NR$^{La}$C(=O)O—, —C(=O)NR$^{La}$—, —OC(=O)NR$^{La}$—, —SC(=O)—, —C(=O)S—, —OC(=O)—, —C(=O)O—, —NR$^{La}$C(=S)—, —C(=S)NR$^{La}$—, trans-CR$^{Lb}$=CR$^{Lb}$—, cis-CR$^{Lb}$=CR$^{Lb}$, —C≡C—, —S(=O)$_2$O—, —OS(=O)$_2$—, —S(=O)$_2$NR$^{La}$—, or —NR$^{La}$S(=O)$_2$—, wherein each instance of R$^{La}$ is hydrogen, optionally substituted $C_{1-15}$ alkyl, or a nitrogen protecting group, or R$^{La}$ is joined with the adjacent carbon atom to form an optionally substituted heterocyclic ring, and wherein each occurrence of R$^{Lb}$ is independently selected from the group consisting of hydrogen, halogen, optionally substituted $C_{1-15}$ alkyl, optionally substituted alkenyl, optionally substituted alkynyl, optionally substituted carbocyclyl, optionally substituted heterocyclyl, optionally substituted aryl, and optionally substituted heteroaryl, or R$^{Lb}$ is joined with the adjacent carbon or nitrogen or oxygen atom to form an optionally substituted carbocyclic or heterocyclic ring, or two R$^{Lb}$ groups are joined to form an optionally substituted carbocyclic or optionally substituted heterocyclic ring; p is an integer of 1 to 10, inclusive; and n is an integer of 1 to 100, inclusive.

In certain embodiments, the glycan conjugate is of Formula (I-a):

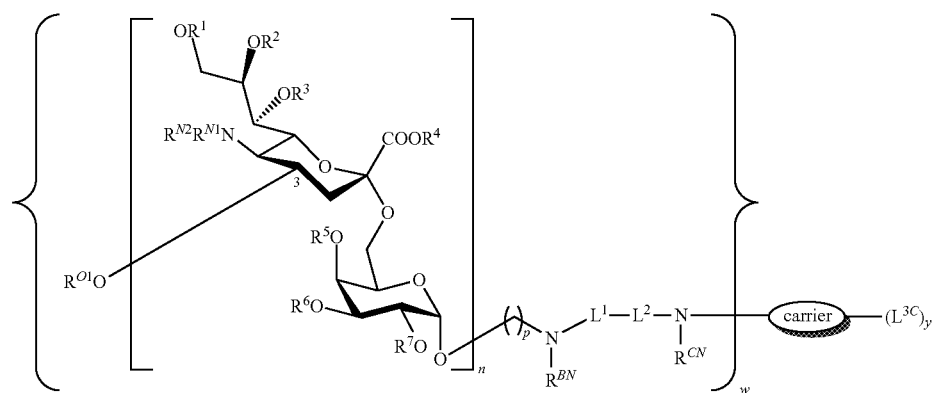

(I-a)

wherein each instance of L$^1$ is independently a bond, —O—, —S—, —NR$^{L1a}$—, —C(=O)—, —NR$^{L1a}$C(=O)—, —NR$^{L1a}$C(=O)O—, —C(=O)NR$^{L1a}$—, —OC(=O)NR$^{L1a}$—, —SC(=O)—, —C(=O)S—, —OC(=O)—, —C(=O)O—, —NR$^{L1a}$C(=S)—, —C(=S)NR$^{L1a}$—, trans-CR$^{L1b}$=CR$^{L1b}$—, cis-CR$^{L1b}$=CR$^{L1b}$—, —C≡C—, —OC(R$^{L1b}$)$_2$—, —C(R$^{L1b}$)$_2$O—, —NR$^{L1a}$C(R$^{L1b}$)$_2$—, —C(R$^{L1b}$)$_2$NR$^{L1a}$—, —SC(R$^{L1b}$)$_2$—, —C(R$^{L1b}$)$_2$S—, —S(=O)$_2$O—, —OS(=O)$_2$—, —S(=O)$_2$NR$^{L1a}$—, —NR$^{L1a}$S(=O)$_2$—, or an optionally substituted $C_{1-20}$ hydrocarbon chain, optionally wherein one or more carbon units of the hydrocarbon chain is replaced with —O—, —S—, —NR$^{L1a}$—, —C(=O)—, —NR$^{L1a}$C(=O)—, —NR$^{L1a}$—C(=O)O—, —C(=O)NR$^{L1a}$—, —OC(=O)NR$^{L1a}$—, —SC(=O)—, —C(=O)S—, —OC(=O)—, —C(=O)O—, —NR$^{L1a}$C(=S)—, —C(=S)NR$^{L1a}$—, trans-CR$^{L1b}$=cR$^{L1b}$—, cis-CR$^{L1b}$=CR$^{L1b}$—, —C≡C—, —S(=O)$_2$O—, —OS(=O)$_2$—, —S(=O)$_2$NR$^{L1a}$—, or —NR$^{L1a}$S(=O)$_2$—, wherein each instance of R$^{L1a}$ is hydrogen, optionally substituted $C_{1-6}$ alkyl, or a nitrogen protecting group, or R$^{L1a}$ is joined with the adjacent carbon atom to form an optionally substituted heterocyclic ring, and wherein each occurrence of R$^{L1b}$ is independently selected from the group consisting of hydrogen, halogen, optionally substituted $C_{1-10}$ alkyl, optionally substituted alkenyl, optionally substituted alkynyl, optionally substituted carbocyclyl, optionally substituted heterocyclyl, optionally substituted aryl, and optionally substituted heteroaryl, or R$^{L1b}$ is joined with the adjacent carbon or nitrogen or oxygen atom to form an optionally substituted carbocyclic or heterocyclic ring, or two R$^{L1b}$ groups are joined to form an optionally substituted carbocyclic or optionally substituted heterocyclic ring; each instance of L$^2$ is independently a moiety derived from a crosslinking reagent capable of crosslinking the carrier and L$^1$-H; each instance of L$^{3C}$ is independently a crosslinking reagent capable of crosslinking the carrier and L$^1$-H; each instance of R$^{CN}$ is independently hydrogen, optionally substituted $C_{1-6}$ alkyl, optionally substituted acyl, or a nitrogen protecting group; w is a integer of 1 to 100, inclusive; and y is 0 or an integer of 1 to 100, inclusive.

In some embodiments, R$^{O1}$ may be hydrogen, one of R$^{N1}$ and R$^{N2}$ may be hydrogen, and/or one or more of R$^1$, R$^2$, R$^3$, R$^5$, and R$^6$ are hydrogen. In some examples, R$^{N1}$ and R$^{N2}$ may be hydrogen and acetyl, respectively, or vise versa. In other examples, R$^7$ is hydrogen. Examples of the glycan conjugates described herein include, but are not limited to Formula (II) and Formula (III) described herein, or pharmaceutically acceptable salts thereof.

As generally defined herein, R$^1$ is independently hydrogen, optionally substituted $C_{1-6}$ alkyl, optionally substituted carbohydrate, or an oxygen protecting group. In certain embodiments, R$^1$ is hydrogen. In certain embodiments, R$^1$ is optionally substituted $C_{1-6}$ alkyl, optionally substituted carbohydrate, or an oxygen protecting group. In certain embodiments, R$^1$ is optionally substituted $C_{1-6}$ alkyl. In certain embodiments, R$^1$ is unsubstituted $C_{1-6}$ alkyl. In certain embodiments, R$^1$ is methyl, ethyl, or propyl. In certain embodiments, R$^1$ is optionally substituted carbohydrate as defined herein. In certain embodiments, R$^1$ is an oxygen protecting group. In certain embodiments, R$^1$ is acyl. In certain embodiments, R$^1$ is acetyl or Bz. In certain embodiments, R$^1$ is Bn, PMB. In certain embodiments, R$^1$ is substituted silyl. In certain embodiments, R$^1$ is TBDPS.

As generally defined herein, R$^2$ is independently hydrogen, optionally substituted $C_{1-6}$ alkyl, optionally substituted carbohydrate, or an oxygen protecting group. In certain embodiments, R$^2$ is hydrogen. In certain embodiments, R$^2$ is optionally substituted $C_{1-6}$ alkyl, optionally substituted carbohydrate, or an oxygen protecting group. In certain embodiments, $R^2$ is optionally substituted $C_{1-6}$ alkyl. In certain embodiments, $R^2$ is unsubstituted $C_{1-6}$ alkyl. In certain embodiments, $R^2$ is methyl, ethyl, or propyl. In certain embodiments, $R^2$ is optionally substituted carbohydrate as defined herein. In certain embodiments, $R^2$ is an oxygen protecting group. In certain embodiments, $R^2$ is acyl. In certain embodiments, $R^2$ is acetyl or Bz. In certain embodiments, $R^2$ is Bn, PMB. In certain embodiments, $R^2$ is substituted silyl. In certain embodiments, $R^2$ is TBDPS.

As generally defined herein, $R^3$ is independently hydrogen, optionally substituted $C_{1-6}$ alkyl, optionally substituted carbohydrate, or an oxygen protecting group. In certain embodiments, $R^3$ is hydrogen. In certain embodiments, $R^3$ is optionally substituted $C_{1-6}$ alkyl, optionally substituted carbohydrate, or an oxygen protecting group. In certain embodiments, $R^3$ is optionally substituted $C_{1-6}$ alkyl. In certain embodiments, $R^3$ is unsubstituted $C_{1-6}$ alkyl. In certain embodiments, $R^3$ is methyl, ethyl, or propyl. In certain embodiments, $R^3$ is optionally substituted carbohydrate as defined herein. In certain embodiments, $R^3$ is an oxygen protecting group. In certain embodiments, $R^3$ is acyl. In certain embodiments, $R^3$ is acetyl or Bz. In certain embodiments, $R^3$ is Bn, PMB. In certain embodiments, $R^3$ is substituted silyl. In certain embodiments, $R^3$ is TBDPS.

As generally defined herein, $R^4$ is independently hydrogen, optionally substituted $C_{1-6}$ alkyl, optionally substituted carbohydrate, or an oxygen protecting group. In certain embodiments, $R^4$ is hydrogen. In certain embodiments, $R^4$ is optionally substituted $C_{1-6}$ alkyl, optionally substituted carbohydrate, or an oxygen protecting group. In certain embodiments, $R^4$ is optionally substituted $C_{1-6}$ alkyl. In certain embodiments, $R^4$ is unsubstituted $C_{1-6}$ alkyl. In certain embodiments, $R^4$ is methyl, ethyl, or propyl. In certain embodiments, $R^4$ is optionally substituted carbohydrate as defined herein. In certain embodiments, $R^4$ is an oxygen protecting group. In certain embodiments, $R^4$ is acyl. In certain embodiments, $R^4$ is acetyl or Bz. In certain embodiments, $R^4$ is Bn, PMB. In certain embodiments, $R^4$ is substituted silyl. In certain embodiments, $R^4$ is TBDPS.

As generally defined herein, $R^5$ is independently hydrogen, optionally substituted $C_{1-6}$ alkyl, optionally substituted carbohydrate, or an oxygen protecting group. In certain embodiments, $R^5$ is hydrogen. In certain embodiments, $R^5$ is optionally substituted $C_{1-6}$ alkyl, optionally substituted carbohydrate, or an oxygen protecting group. In certain embodiments, $R^5$ is optionally substituted $C_{1-6}$ alkyl. In certain embodiments, $R^5$ is unsubstituted $C_{1-6}$ alkyl. In certain embodiments, $R^5$ is methyl, ethyl, or propyl. In certain embodiments, $R^5$ is optionally substituted carbohydrate as defined herein. In certain embodiments, $R^5$ is an oxygen protecting group. In certain embodiments, $R^5$ is acyl. In certain embodiments, $R^5$ is acetyl or Bz. In certain embodiments, $R^5$ is Bn, PMB. In certain embodiments, $R^5$ is substituted silyl. In certain embodiments, $R^5$ is TBDPS.

As generally defined herein, $R^6$ is independently hydrogen, optionally substituted $C_{1-6}$ alkyl, optionally substituted carbohydrate, or an oxygen protecting group. In certain embodiments, $R^6$ is hydrogen. In certain embodiments, $R^6$ is optionally substituted $C_{1-6}$ alkyl, optionally substituted carbohydrate, or an oxygen protecting group. In certain embodiments, $R^6$ is optionally substituted $C_{1-6}$ alkyl. In certain embodiments, $R^6$ is unsubstituted $C_{1-6}$ alkyl. In certain embodiments, $R^6$ is methyl, ethyl, or propyl. In certain embodiments, $R^6$ is optionally substituted carbohydrate as defined herein. In certain embodiments, $R^6$ is an oxygen protecting group. In certain embodiments, $R^6$ is acyl. In certain embodiments, $R^6$ is acetyl or Bz. In certain embodiments, $R^6$ is Bn, PMB. In certain embodiments, $R^6$ is substituted silyl. In certain embodiments, $R^6$ is TBDPS.

As generally defined herein, $R^7$ is independently hydrogen, optionally substituted $C_{1-6}$ alkyl, optionally substituted carbohydrate, or an oxygen protecting group. In certain embodiments, $R^7$ is hydrogen. In certain embodiments, $R^7$ is optionally substituted $C_{1-6}$ alkyl, optionally substituted carbohydrate, or an oxygen protecting group. In certain embodiments, $R^7$ is optionally substituted $C_{1-6}$ alkyl. In certain embodiments, $R^7$ is unsubstituted $C_{1-6}$ alkyl. In certain embodiments, $R^7$ is methyl, ethyl, or propyl. In certain embodiments, $R^7$ is optionally substituted carbohydrate as defined herein. In certain embodiments, $R^7$ is an oxygen protecting group. In certain embodiments, $R^7$ is acyl. In certain embodiments, $R^7$ is acetyl or Bz. In certain embodiments, $R^7$ is Bn, PMB. In certain embodiments, $R^7$ is substituted silyl. In certain embodiments, $R^7$ is TBDPS.

As generally defined herein, $R^{O1}$ is independently hydrogen, optionally substituted $C_{1-6}$ alkyl, optionally substituted carbohydrate, or an oxygen protecting group. In certain embodiments, $R^{O1}$ is hydrogen. In certain embodiments, $R^{O1}$ is optionally substituted $C_{1-6}$ alkyl, optionally substituted carbohydrate, or an oxygen protecting group. In certain embodiments, $R^{O1}$ is optionally substituted $C_{1-6}$ alkyl. In certain embodiments, $R^{O1}$ is unsubstituted $C_{1-6}$ alkyl. In certain embodiments, $R^{O1}$ is methyl, ethyl, or propyl. In certain embodiments, $R^{O1}$ is optionally substituted carbohydrate as defined herein. In certain embodiments, $R^{O1}$ is an oxygen protecting group. In certain embodiments, $R^{O1}$ is acyl. In certain embodiments, $R^{O1}$ is acetyl or Bz. In certain embodiments, $R^{O1}$ is Bn, PMB. In certain embodiments, $R^{O1}$ is substituted silyl. In certain embodiments, $R^{O1}$ is TBDPS.

In certain embodiments, $R^1$ and $R^2$ are taken with the intervening atoms to form an optionally substituted heterocyclic ring. In certain embodiments, $R^1$ and $R^2$ are taken with the intervening atoms to form an optionally substituted 5-membered heterocyclic ring. In certain embodiments, $R^1$ and $R^2$ are taken with the intervening atoms to form an optionally substituted 5-membered heterocyclic ring with two oxygen. In certain embodiments, $R^1$ and $R^2$ are taken with the intervening atoms to form a di-methylated 5-membered heterocyclic ring with two oxygen. In certain embodiments, $R^1$ and $R^2$ are taken with the intervening atoms to form a 5-membered heterocyclic ring of the formula wherein $R^{ra}$ and $R^{rb}$ are each independently optionally substituted $C_{1-6}$ alkyl. In certain embodiments, $R^1$ and $R^2$ are taken with the intervening atoms to form a 5-membered heterocyclic ring of the formula

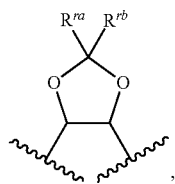

wherein $R^{ra}$ and $R^{rb}$ are each independently unsubstituted $C_{1-6}$ alkyl. In certain embodiments, $R^1$ and $R^2$ are taken with the intervening atoms to form a 5-membered heterocyclic ring of the formula

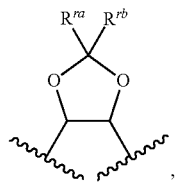

wherein $R^{ra}$ and $R^{rb}$ are each independently methyl, ethyl, or propyl.

In certain embodiments, $R^2$ and $R^3$ are taken with the intervening atoms to form an optionally substituted heterocyclic ring. In certain embodiments, $R^2$ and $R^3$ are taken with the intervening atoms to form an optionally substituted 5-membered heterocyclic ring. In certain embodiments, $R^2$ and $R^3$ are taken with the intervening atoms to form an optionally substituted 5-membered heterocyclic ring with two oxygen. In certain embodiments, $R^2$ and $R^3$ are taken with the intervening atoms to form a di-methylated 5-membered heterocyclic ring with two oxygen. In certain embodiments, $R^3$ and $R^4$ are taken with the intervening atoms to form a 5-membered heterocyclic ring of the formula

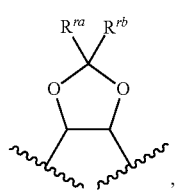

wherein $R^{ra}$ and $R^{rb}$ are each independently optionally substituted $C_{1-6}$ alkyl. In certain embodiments, $R^2$ and $R^3$ are taken with the intervening atoms to form a 5-membered heterocyclic ring of the formula

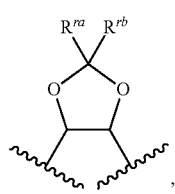

wherein $R^{ra}$ and $R^{rb}$ are each independently unsubstituted $C_{1-6}$ alkyl. In certain embodiments, $R^2$ and $R^3$ are taken with the intervening atoms to form a 5-membered heterocyclic ring of the formula

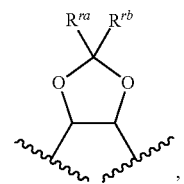

wherein $R^{ra}$ and $R^{rb}$ are each independently methyl, ethyl, or propyl.

In certain embodiments, $R^5$ and $R^6$ are taken with the intervening atoms to form an optionally substituted heterocyclic ring. In certain embodiments, $R^5$ and $R^6$ are taken with the intervening atoms to form an optionally substituted 5-membered heterocyclic ring. In certain embodiments, $R^5$ and $R^6$ are taken with the intervening atoms to form an optionally substituted 5-membered heterocyclic ring with two oxygen. In certain embodiments, $R^5$ and $R^6$ are taken with the intervening atoms to form a di-methylated 5-membered heterocyclic ring with two oxygen. In certain embodiments, $R^5$ and $R^6$ are taken with the intervening atoms to form a 5-membered heterocyclic ring of the formula

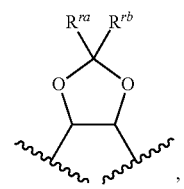

wherein $R^{ra}$ and $R^{rb}$ are each independently optionally substituted $C_{1-6}$ alkyl. In certain embodiments, $R^5$ and $R^6$ are taken with the intervening atoms to form a 5-membered heterocyclic ring of the formula

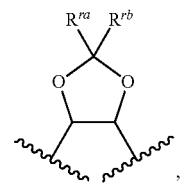

wherein $R^{ra}$ and $R^{rb}$ are each independently unsubstituted $C_{1-6}$ alkyl. In certain embodiments, $R^5$ and $R^6$ are taken with the intervening atoms to form a 5-membered heterocyclic ring of the formula

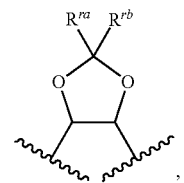

wherein $R^{ra}$ and $R^{rb}$ are each independently methyl, ethyl, or propyl.

In certain embodiments, $R^6$ and $R^7$ are taken with the intervening atoms to form an optionally substituted heterocyclic ring. In certain embodiments, $R^6$ and $R^7$ are taken with the intervening atoms to form an optionally substituted 5-membered heterocyclic ring. In certain embodiments, $R^6$ and $R^7$ are taken with the intervening atoms to form an optionally substituted 5-membered heterocyclic ring with two oxygen. In certain embodiments, $R^6$ and $R^7$ are taken with the intervening atoms to form a di-methylated 5-membered heterocyclic ring with two oxygen. In certain embodiments, $R^6$ and $R^7$ are taken with the intervening atoms to form a 5-membered heterocyclic ring of the formula

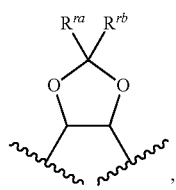

, wherein $R^{ra}$ and $R^{rb}$ are each independently optionally substituted $C_{1-6}$ alkyl. In certain embodiments, $R^6$ and $R^7$ are taken with the intervening atoms to form a 5-membered heterocyclic ring of the formula

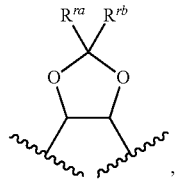

, wherein $R^{ra}$ and $R^{rb}$ are each independently unsubstituted $C_{1-6}$ alkyl. In certain embodiments, $R^6$ and $R^7$ are taken with the intervening atoms to form a 5-membered heterocyclic ring of the formula

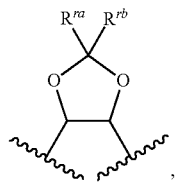

, wherein $R^{ra}$ and $R^{rb}$ are each independently methyl, ethyl, or propyl.

As generally defined herein, $R^{N1}$ is hydrogen, optionally substituted $C_{1-6}$ alkyl, or a nitrogen protecting group. In some embodiments, $R^{N1}$ is hydrogen. In some embodiments, $R^{N1}$ is optionally substituted $C_{1-6}$ alkyl. In certain embodiments, $R^{N1}$ is methyl. In certain embodiments, $R^{N1}$ is ethyl. In certain embodiments, $R^{N1}$ is propyl. In certain embodiments, $R^{N1}$ is a nitrogen protecting group. In certain embodiments, $R^{N1}$ is acyl. In certain embodiments, $R^{N1}$ is acetyl. In certain embodiments, $R^{N1}$ is Bn, BOC, Cbz, Troc, Fmoc, trifluoroacetyl, triphenylmethyl, or Ts.

As generally defined herein, $R^{N2}$ is hydrogen, optionally substituted $C_{1-6}$ alkyl, or a nitrogen protecting group. In some embodiments, $R^{N2}$ is hydrogen. In some embodiments, $R^{N2}$ is optionally substituted $C_{1-6}$ alkyl. In certain embodiments, $R^{N2}$ is methyl. In certain embodiments, $R^{N2}$ is ethyl. In certain embodiments, $R^{N2}$ is propyl. In certain embodiments, $R^{N2}$ is a nitrogen protecting group. In certain embodiments, $R^{N2}$ is acyl. In certain embodiments, $R^{N2}$ is acetyl. In certain embodiments, $R^{N2}$ is Bn, BOC, Cbz, Troc, Fmoc, trifluoroacetyl, triphenylmethyl, or Ts.

In certain embodiments, $R^{N1}$ and $R^{O1}$ are taken with the intervening atoms to form an optionally substituted heterocyclic ring. In certain embodiments, $R^{N1}$ and $R^{O1}$ are taken with the intervening atoms to form an optionally substituted 5-membered heterocyclic ring. In certain embodiments, $R^{N1}$ and $R^{O1}$ are taken with the intervening atoms to form an optionally substituted 5-membered heterocyclic ring of the formula

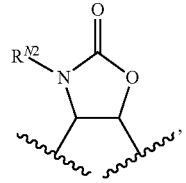

, wherein $R^{N2}$ is defined herein. In certain embodiments, $R^{N1}$ and $R^{O1}$ are taken with the intervening atoms to form an optionally substituted 5-membered heterocyclic ring of the formula

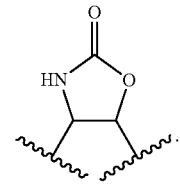 [SMILES: *C1NC(=O)OC1*]

.

As generally defined herein, p is an integer of 1 to 8 inclusive. In certain embodiments, p is 1. In certain embodiments, p is 2. In certain embodiments, p is 3. In certain embodiments, p is 4. In certain embodiments, p is 5. In certain embodiments, p is 6. In certain embodiments, p is 7. In certain embodiments, p is 8.

In certain embodiments, the glycan conjugate is of Formula (I-b):

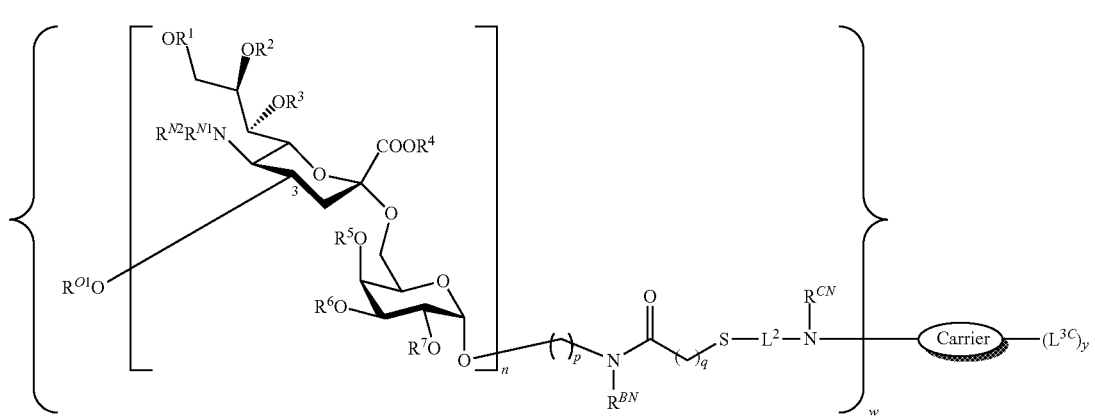

(I-b)

or a pharmaceutically acceptable salt thereof, wherein: each instance of q is an integer of 1 to 8, inclusive.

In certain embodiments, the glycan conjugate is of Formula (I-c)

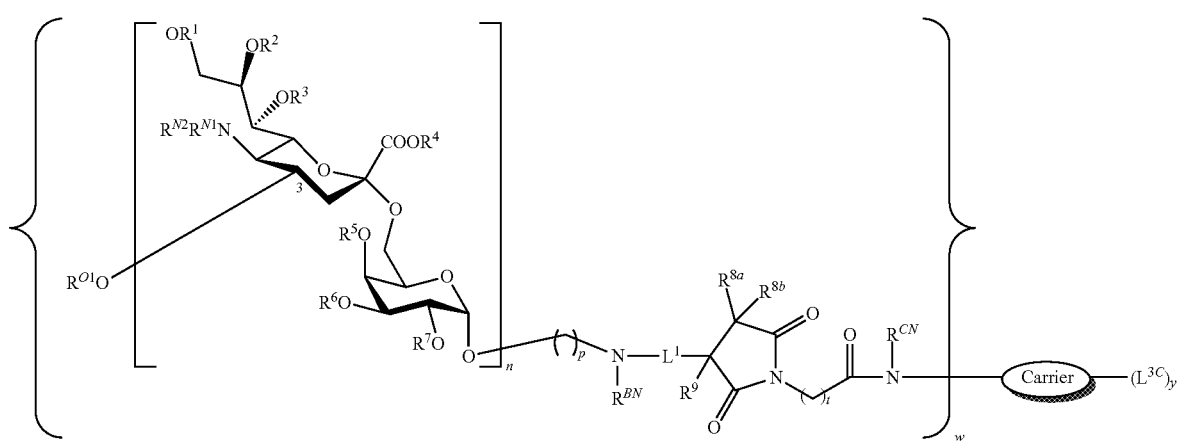

(I-c)

wherein each instance of $R^{8a}$, $R^{8b}$, and $R^9$ is independently hydrogen, halogen, or optionally substituted $C_{1-6}$ alkyl; and t is an integer of 1 to 8, inclusive.

In certain embodiments, the glycan conjugate is of Formula (I-d)

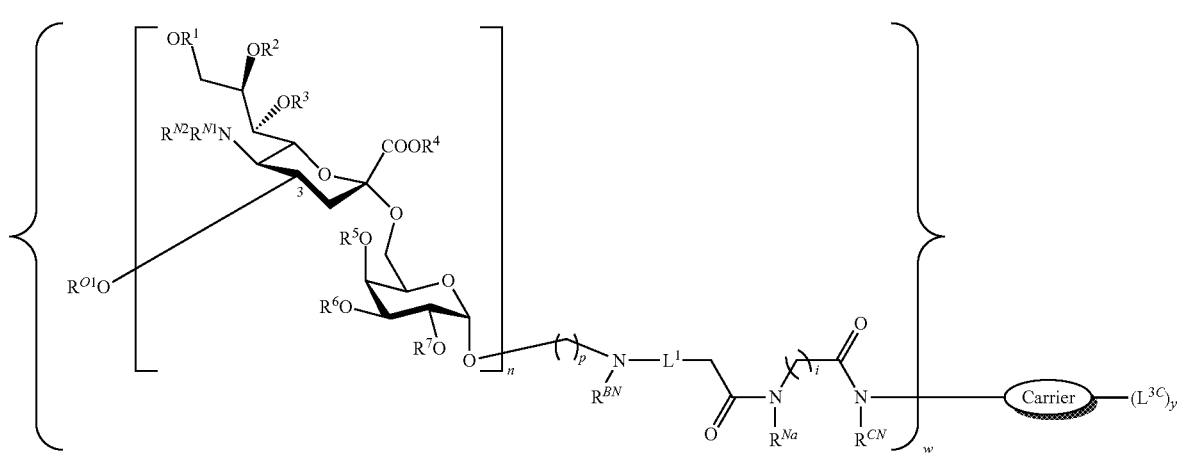

(I-d)

wherein each instance of $R^Na$ is independently hydrogen, optionally substituted $C_{1-6}$ alkyl, optionally substituted acyl, or a nitrogen protecting group; and i is an integer of 1 to 8, inclusive.

In certain embodiments, the glycan conjugate is of Formula (I-e)

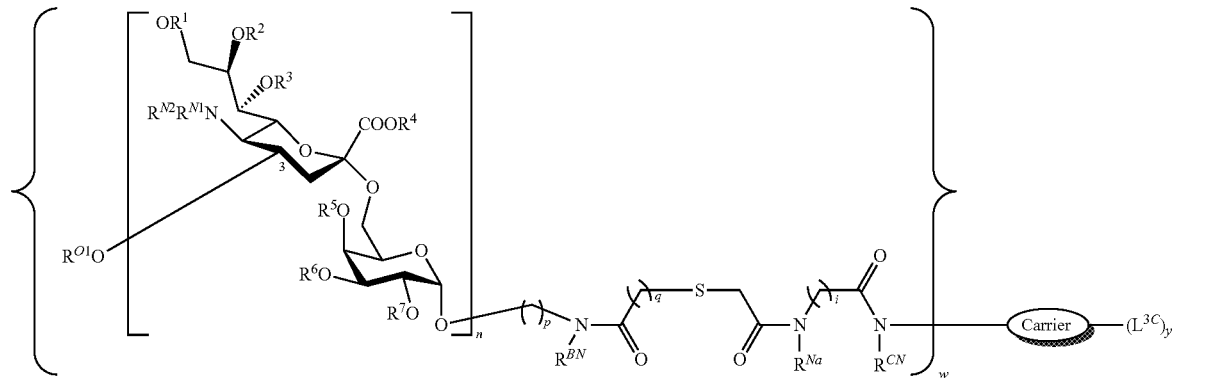

(I-e)

wherein each instance of $R^{Na}$ is independently hydrogen, optionally substituted $C_{1-6}$ alkyl, optionally substituted acyl, or a nitrogen protecting group; each instance of q is an integer of 1 to 8, inclusive; and i is an integer of 1 to 8, inclusive.

In certain embodiments, the glycan conjugate is of Formula (I-f)

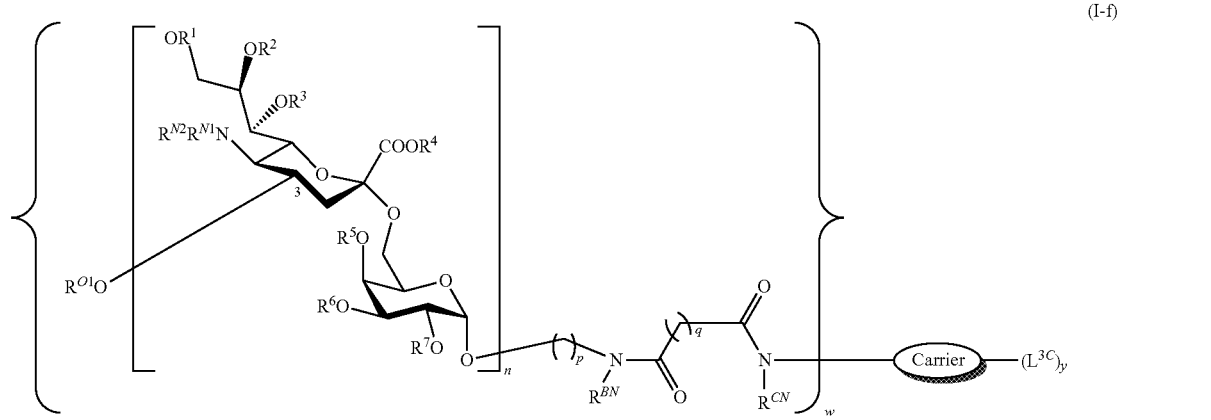

(I-f)

wherein each instance of q is an integer of 1 to 8, inclusive.

As generally defined herein, $R^{8a}$ is independently hydrogen, halogen, or optionally substituted $C_{1-6}$ alkyl. In certain embodiments, $R^{8a}$ is hydrogen. In certain embodiments, $R^{8a}$ is halogen. In certain embodiments, $R^{8a}$ is F. In certain embodiments, $R^{8a}$ is Cl. In certain embodiments, $R^{8a}$ is Br. In certain embodiments, $R^{8a}$ is I. In certain embodiments, $R^{8a}$ is optionally substituted $C_{1-6}$ alkyl. In certain embodiments, $R^{8a}$ is optionally substituted $C_{1-6}$ alkyl. In certain embodiments, $R^{8a}$ is unsubstituted $C_{1-6}$ alkyl. In certain embodiments, $R^{8a}$ is methyl, ethyl, or propyl.

As generally defined herein, $R^{8b}$ is independently hydrogen, halogen, or optionally substituted $C_{1-6}$ alkyl. In certain embodiments, $R^{8b}$ is hydrogen. In certain embodiments, $R^{8b}$ is halogen. In certain embodiments, $R^{8b}$ is F. In certain embodiments, $R^{8b}$ is Cl. In certain embodiments, $R^{8b}$ is Br. In certain embodiments, $R^{8b}$ is I. In certain embodiments, $R^{8b}$ is optionally substituted $C_{1-6}$ alkyl. In certain embodiments, $R^{8b}$ is optionally substituted $C_{1-6}$ alkyl. In certain embodiments, $R^{8b}$ is unsubstituted $C_{1-6}$ alkyl. In certain embodiments, $R^{8b}$ is methyl, ethyl, or propyl.

As generally defined herein, $R^9$ is independently hydrogen, halogen, or optionally substituted $C_{1-6}$ alkyl. In certain embodiments, $R^9$ is hydrogen. In certain embodiments, $R^9$ is halogen. In certain embodiments, $R^9$ is F. In certain embodiments, $R^9$ is Cl. In certain embodiments, $R^9$ is Br. In certain embodiments, $R^9$ is I. In certain embodiments, $R^9$ is optionally substituted $C_{1-6}$ alkyl. In certain embodiments, $R^9$ is optionally substituted $C_{1-6}$ alkyl. In certain embodiments, $R^9$ is unsubstituted $C_{1-6}$ alkyl. In certain embodiments, $R^9$ is methyl, ethyl, or propyl.

As generally defined herein, q is an integer of 1 to 8 inclusive. In certain embodiments, q is 1. In certain embodiments, q is 2. In certain embodiments, q is 3. In certain embodiments, q is 4. In certain embodiments, q is 5. In certain embodiments, q is 6. In certain embodiments, q is 7. In certain embodiments, q is 8.

As generally defined herein, t is an integer of 1 to 8 inclusive. In certain embodiments, t is 1. In certain embodiments, t is 2. In certain embodiments, t is 3. In certain embodiments, t is 4. In certain embodiments, t is 5. In certain embodiments, t is 6. In certain embodiments, t is 7. In certain embodiments, t is 8.

In some embodiments, p is 1, q is an integer of 1 to 8 inclusive, and t is an integer of 1 to 8 inclusive. In some embodiments, p is 2, q is an integer of 1 to 8 inclusive, and t is an integer of 1 to 8 inclusive. In some embodiments, p is 3, q is an integer of 1 to 8 inclusive, and t is an integer of 1 to 8 inclusive. In some embodiments, p is 4, q is an integer of 1 to 8 inclusive, and t is an integer of 1 to 8 inclusive. In some embodiments, p is 5, q is an integer of 1 to 8 inclusive, and t is an integer of 1 to 8 inclusive. In some embodiments, p is 6, q is an integer of 1 to 8 inclusive, and t is an integer of 1 to 8 inclusive. In some embodiments, p is 7, q is an integer of 1 to 8 inclusive, and t is an integer of 1 to 8 inclusive. In some embodiments, p is 8, q is an integer of 1 to 8 inclusive, and t is an integer of 1 to 8 inclusive. In some embodiments, p is 4, q is 1, and t is an integer of 1 to 8 inclusive. In some embodiments, p is 4, q is 2, and t is an integer of 1 to 8 inclusive. In some embodiments, p is 4, q is 3, and t is an integer of 1 to 8 inclusive. In some embodiments, p is 4, q is 4, and t is an integer of 1 to 8 inclusive. In some embodiments, p is 4, q is 5, and t is an integer of 1 to 8 inclusive. In some embodiments, p is 4, q is 6, and t is an integer of 1 to 8 inclusive. In some embodiments, p is 4, q is 7, and t is an integer of 1 to 8 inclusive. In some embodiments, p is 4, q is 8, and t is an integer of 1 to 8 inclusive. In some embodiments, p is 4, q is 2, and t is an integer of 1 to 8 inclusive. In some embodiments, p is 4, q is 2, and t is 1. In some embodiments, p is 4, q is 2, and t is 3. In some embodiments, p is 4, q is 2, and t is 4. In some embodiments, p is 4, q is 2, and t is 5. In some embodiments, p is 4, q is 2, and t is 6. In some embodiments, p is 4, q is 2, and t is 7. In some embodiments, p is 4, q is 2, and t is 8.

As generally defined herein, w is an integer from 1 to 100. In certain embodiments, w is an integer from 1 to 90. In certain embodiments, w is an integer from 1 to 80. In certain embodiments, w is an integer from 1 to 70. In certain embodiments, w is an integer from 1 to 60. In certain embodiments, w is an integer from 1 to 50. In certain embodiments, w is an integer from 1 to 40. In certain embodiments, w is an integer from 1 to 30. In certain embodiments, w is an integer from 1 to 20. In certain embodiments, w is an integer from 1 to 10. In certain embodiments, w is an integer from 1 to 5. In certain embodiments, w is an integer from 10 to 100. In certain embodiments, w is an integer from 10 to 20. In certain embodiments, w is an integer from 10 to 30. In certain embodiments, w is an integer from 20 to 30. In certain embodiments, w is an integer from 20 to 40. In certain embodiments, w is an integer from 30 to 50. In certain embodiments, w is an integer from 40 to 60. In certain embodiments, w is an integer from 50 to 70. In certain embodiments, w is an integer from 60 to 80. In certain embodiments, w is an integer from 70 to 90. In certain embodiments, w is an integer from 80 to 100.

As generally defined herein, y is 0 or an integer from 1 to 100. In certain embodiments, y is 0. In certain embodiments, y is an integer from 1 to 100. In certain embodiments, y is an integer from 1 to 90. In certain embodiments, y is an integer from 1 to 80. In certain embodiments, y is an integer from 1 to 70. In certain embodiments, y is an integer from 1 to 60. In certain embodiments, y is an integer from 1 to 50. In certain embodiments, y is an integer from 1 to 40. In certain embodiments, y is an integer from 1 to 30. In certain embodiments, y is an integer from 1 to 20. In certain embodiments, y is an integer from 1 to 10. In certain embodiments, y is an integer from 10 to 100. In certain embodiments, y is an integer from 10 to 20. In certain embodiments, y is an integer from 10 to 30. In certain embodiments, y is an integer from 20 to 30. In certain embodiments, y is an integer from 20 to 40. In certain embodiments, y is an integer from 30 to 50. In certain embodiments, y is an integer from 40 to 60. In certain embodiments, y is an integer from 50 to 70. In certain embodiments, y is an integer from 60 to 80. In certain embodiments, y is an integer from 70 to 90. In certain embodiments, y is an integer from 80 to 100.

In certain embodiments, n is an integer of 1 to 100, inclusive. In certain embodiments, n is an integer of 1 to 80, inclusive. In certain embodiments, n is an integer of 1 to 60, inclusive. In certain embodiments, n is an integer of 1 to 40, inclusive. In certain embodiments, n is an integer of 1 to 20, inclusive. In certain embodiments, n is an integer of 1 to 10, inclusive. In certain embodiments, n is an integer of 1 to 8, inclusive. As generally defined herein, n is an integer of 1 to 8 inclusive. In certain embodiments, n is 1. In certain embodiments, n is 2. In certain embodiments, n is 3. In certain embodiments, n is 4. In certain embodiments, n is 5. In certain embodiments, n is 6. In certain embodiments, n is 7. In certain embodiments, n is 8.

In certain embodiments, each of $R^1$, $R^2$, $R^3$, $R^4$, $R^5$, $R^6$, and $R^7$ is independently a carbohydrate of Formula (s-1):

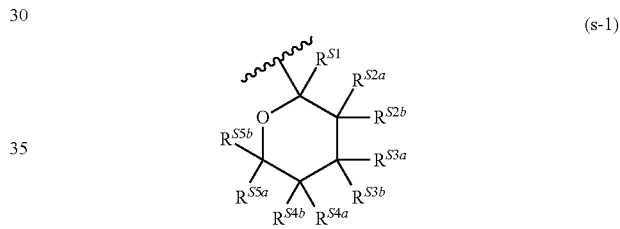

wherein: each of $R^{S1}$, $R^{S2a}$, $R^{S2b}$, $R^{S3a}$, $R^{S3b}$, $R^{S4a}$, $R^{S4b}$, $R^{S5a}$, and $R^{S5b}$ is independently hydrogen, optionally substituted alkyl, $-OR^{SO}$, or $-N(R^{SN})_2$; each instance of $R^{SO}$ is independently hydrogen, optionally substituted alkyl, optionally substituted heterocyclyl, or an oxygen protecting group; and each instance of $R^{SN}$ is independently hydrogen, optionally substituted alkyl, or a nitrogen protecting group; or optionally two $R^{SN}$ are taken with the intervening atoms to form a heterocyclic ring.

As generally defined herein, each instance of $R^{S1}$ is independently hydrogen, optionally substituted alkyl, $-OR^{SO}$, or $-N(R^{SN})_2$. In certain embodiments, $R^{S1}$ is hydrogen. In certain embodiments, $R^{S1}$ is optionally substituted alkyl. In certain embodiments, $R^{S1}$ is substituted $C_{1-6}$ alkyl. In certain embodiments, $R^{S1}$ is unsubstituted $C_{1-6}$ alkyl. In certain embodiments, $R^{S1}$ is methyl, ethyl, propyl, butyl, pentyl, or hexyl.

In certain embodiments, $R^{S1}$ is $-OR^{SO}$, wherein $R^{SO}$ is independently hydrogen, optionally substituted alkyl, optionally substituted alkyl, optionally substituted heterocyclyl, or an oxygen protecting group. In certain embodiments, $R^{S1}$ is $-OH$. In certain embodiments, $R^{S1}$ is $-OR^{SO}$, wherein $R^{SO}$ is optionally substituted alkyl. In certain embodiments, $R^{S1}$ is $-O$-methyl, $-O$-ethyl, or $-O$-propyl. In certain embodiments, $R^{S1}$ is optionally substituted $-O$-alkyl-aryl. In certain embodiments, $R^{S1}$ is $-O-Bn$. In certain embodiments, $R^{S1}$ is $-OR^{SO}$, wherein $R^{SO}$ is an oxygen protecting group. In certain embodiments, $R^{S1}$ is —OR$^{SO}$, wherein R$^{SO}$ is acyl. In certain embodiments, R$^{S1}$ is —O-acetyl or —O—Bz. In certain embodiments, R$^{S1}$ is —OR$^{SO}$, wherein R$^{SO}$ is optionally substituted heterocyclyl. In certain embodiments, R$^{S1}$ is —OR$^{SO}$, wherein R$^{SO}$ is an oxygen protecting group. In certain embodiments, R$^{S1}$ is —OR$^{SO}$, wherein R$^{SO}$ is PMB, Bn, TBS, or TMS.

In certain embodiments, R$^{S1}$ is —N(R$^{SN}$)$_2$. In some embodiments, R$^{S1}$ is —N(R$^{SN}$)$_2$, wherein each R$^{SN}$ is the same. In some embodiments, R$^{S1}$ is —N(R$^{SN}$)$_2$, wherein each R$^{SN}$ is different. In certain embodiments, R$^{S1}$ is —NH$_2$. In certain embodiments, R$^{S1}$ is —NHR$^{SN}$. In certain embodiments, R$^{S1}$ is —NHR$^{SN}$, wherein R$^{SN}$ is optionally substituted C$_{1-6}$ alkyl. In certain embodiments, R$^{S1}$ is —NHR$^{SN}$, wherein R$^{SN}$ is unsubstituted C$_{1-6}$ alkyl. In certain embodiment, R$^{S1}$ is —NHR$^{SN}$, wherein R$^{SN}$ is substituted C$_{1-6}$ alkyl. In certain embodiments, R$^{S1}$ is —NH—benzyl. In certain embodiment, R$^{S1}$ is —NHR$^{SN}$, wherein R$^{SN}$ is a nitrogen protecting group. In certain embodiment, R$^{S1}$ is —NHAc, —NHBoc, Troc, Bn, or Cbz. In certain embodiments, R$^{S1}$ is —N(R$^{SN}$)$_2$, wherein each R$^{SN}$ is independently optionally substituted C$_{1-6}$ alkyl. In certain embodiments, R$^{S1}$ is —N(R$^{SN}$)$_2$, wherein each R$^{SN}$ is independently unsubstituted C$_1$ alkyl. In certain embodiments, R$^{S1}$ is —N(CH$_3$)R$^{SN}$, wherein each R$^{SN}$ is independently optionally substituted C$_{1-6}$ alkyl. In certain embodiments, R$^{S1}$ is —N(CH$_3$)R$^{SN}$, wherein each R$^{SN}$ is independently unsubstituted C$_{1-6}$ alkyl. In certain embodiments, R$^{S1}$ is —N(CH$_2$CH$_3$)R$^{SN}$, wherein each R$^{SN}$ is independently optionally substituted C$_{1-6}$ alkyl. In certain embodiments, R$^{S1}$ is —N(CH$_2$CH$_3$)R$^{SN}$, wherein each R$^{SN}$ is independently unsubstituted C$_{1-6}$ alkyl. In certain embodiments, R$^{S1}$ is —N(R$^{SN}$)$_2$, wherein each R$^{SN}$ is independently selected from the group consisting of methyl, ethyl, isopropyl, isobutyl, isoamyl, and benzyl. In some embodiments, R$^{S1}$ is —N(R$^{SN}$)$_2$, wherein two R$^{SN}$ groups are taken together with the intervening atoms to form an optionally substituted heterocyclic ring. For example, in certain embodiments, R$^{S1}$ is of the formula:

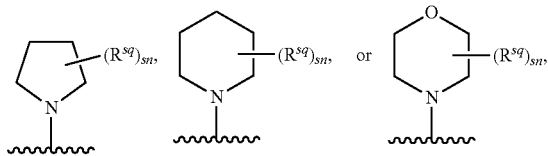

wherein R$^{sq}$ is as defined herein, and sn is 0, 1, 2, or 3.

As generally defined above, each instance of R$^{S2a}$ and R$^{S2b}$ is independently hydrogen, optionally substituted alkyl, —OR$^{SO}$, or —N(R$^{SN}$)$_2$. In certain embodiments, at least one instance of R$^{S2a}$ and R$^{S2b}$ is hydrogen. In certain embodiments, at least one instance of R$^{S2a}$ and R$^{S2b}$ is optionally substituted alkyl. In certain embodiments, at least one instance of R$^{S2a}$ and R$^{S2b}$ is substituted C$_{1-6}$ alkyl. In certain embodiments, at least one instance of R$^{S2a}$ and R$^{S2b}$ is unsubstituted C$_{1-6}$ alkyl. In certain embodiments, at least one instance of R$^{S2a}$ and R$^{S2b}$ is methyl, ethyl, propyl, butyl, pentyl, or hexyl. In certain embodiments, at least one instance of R$^{S2a}$ and R$^{S2b}$ is isopropyl, isobutyl, or isoamyl. In certain embodiments, at least one instance of R$^{S2a}$ and R$^{S2b}$ is isobutyl. In certain embodiments, at least one instance of R$^{S2a}$ and R$^{S2b}$ is tert-butyl. In certain embodiments, at least one instance of R$^{S2a}$ and R$^{S2b}$ is —OR$^{SO}$, wherein R$^{SO}$ is independently hydrogen, optionally substituted alkyl, optionally substituted alkyl, optionally substituted heterocyclyl, or an oxygen protecting group. In certain embodiments, at least one instance of R$^{S2a}$ and R$^{S2b}$ is —OH. In certain embodiments, at least one instance of R$^{S2a}$ and R$^{S2b}$ is —OR$^{SO}$, wherein R$^{SO}$ is optionally substituted alkyl. In certain embodiments, at least one instance of R$^{S2a}$ and R$^{S2b}$ is —O-methyl, —O-ethyl, or —O-propyl. In certain embodiments, at least one instance of R$^{S2a}$ and R$^{S2b}$ is optionally substituted —O-alkyl-aryl. In certain embodiments, at least one instance of R$^{S2a}$ and R$^{S2b}$ is —O-Bz. In certain embodiments, at least one instance of R$^{S2a}$ and R$^{S2b}$ is —OR$^{SO}$, wherein R$^{SO}$ is an oxygen protecting group. In certain embodiments, at least one instance of R$^{S2a}$ and R$^{S2b}$ is —OR$^{SO}$, wherein R$^{SO}$ is carbonyl. In certain embodiments, at least one instance of R$^{S2a}$ and R$^{S2b}$ is —OR$^{SO}$, wherein R$^{SO}$ is acetyl. In certain embodiments, at least one instance of R$^{S2a}$ and R$^{S2b}$ is —OR$^{SO}$, wherein R$^{SO}$ is optionally substituted heterocyclyl.

In certain embodiments, at least one instance of R$^{S2a}$ and R$^{S2b}$ is —N(R$^{SN}$)$_2$. In some embodiments, at least one instance of R$^{S2a}$ and R$^{S2b}$ is —N(R$^{SN}$)$_2$, wherein each R$^{SN}$ is the same. In some embodiments, at least one instance of R$^{S2a}$ and R$^{S2b}$ is —N(R$^{SN}$)$_2$, wherein each R$^{SN}$ is different. In certain embodiments, at least one instance of R$^{S2a}$ and R$^{S2b}$ is —NH$_2$. In certain embodiments, at least one instance of R$^{S2a}$ and R$^{S2b}$ is —NHR$^{SN}$. In certain embodiments, at least one instance of R$^{S2a}$ and R$^{S2b}$ is —NHR$^{SN}$, wherein R$^{SN}$ is optionally substituted C$_{1-6}$ alkyl. In certain embodiments, at least one instance of R$^{S2a}$ and R$^{S2b}$ is —NHR$^{SN}$, wherein R$^{SN}$ is unsubstituted C$_{1-6}$ alkyl. In certain embodiment, at least one instance of R$^{S2a}$ and R$^{S2b}$ is —NHR$^{SN}$, wherein R$^{SN}$ is substituted C$_{1-6}$ alkyl. In certain embodiments, at least one instance of R$^{S2a}$ and R$^{S2b}$ is —NH-benzyl. In certain embodiment, at least one instance of R$^{S2a}$ and R$^{S2b}$ is —NHR$^{SN}$, wherein R$^{SN}$ is a nitrogen protecting group. In certain embodiment, at least one instance of R$^{S2a}$ and R$^{S2b}$ is —NHFmoc. In certain embodiment, at least one instance of R$^{S2a}$ and R$^{S2b}$ is —NHBoc. In certain embodiments, at least one instance of R$^{S2a}$ and R$^{S2b}$ is —N(R$^{SN}$)$_2$, wherein each R$^{SN}$ is independently optionally substituted C$_{1-6}$ alkyl. In certain embodiments, at least one instance of R$^{S2a}$ and R$^{S2b}$ is —N(R$^{SN}$)$_2$, wherein each R$^{SN}$ is independently unsubstituted C$_{1-6}$ alkyl. In certain embodiments, at least one instance of R$^{S2a}$ and R$^{S2b}$ is —N(CH$_3$)R$^{SN}$, wherein each R$^{SN}$ is independently optionally substituted C$_{1-6}$ alkyl. In certain embodiments, at least one instance of R$^{S2a}$ and R$^{S2b}$ is —N(CH$_3$)R$^{SN}$, wherein each R$^{SN}$ is independently unsubstituted C$_{1-6}$ alkyl. In certain embodiments, at least one instance of R$^{S2a}$ and R$^{S2b}$ is —N(CH$_2$CH$_3$)R$^{SN}$, wherein each R$^{SN}$ is independently optionally substituted C$_{1-6}$ alkyl. In certain embodiments, at least one instance of R$^{S2a}$ and R$^{S2b}$ is —N(CH$_2$CH$_3$)R$^{SN}$, wherein each R$^{SN}$ is independently unsubstituted C$_{1-6}$ alkyl. In certain embodiments, at least one instance of R$^{S2a}$ and R$^{S2b}$ is —N(R$^{SN}$)$_2$, wherein each R$^{SN}$ is independently selected from the group consisting of methyl, ethyl, isopropyl, isobutyl, isoamyl, and benzyl. In some embodiments, at least one instance of R$^{S2a}$ and R$^{S2b}$ is —N(R$^{SN}$)$_2$, wherein two R$^{SN}$ groups are taken together with the intervening atoms to form an optionally substituted heterocyclic ring. For example, in certain embodiments, at least one instance of R$^{S2a}$ and R$^{S2b}$ is of the formula:

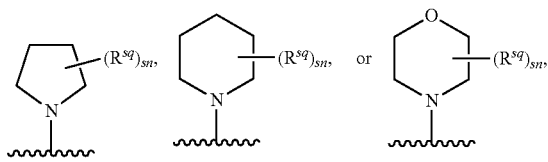

wherein $R^q$ is as defined herein, and sn is 0, 1, 2, or 3.

As generally defined above, each instance of RS3a and RS3b is independently hydrogen, optionally substituted alkyl, —$OR^{SO}$, or —N(RSN)2. In certain embodiments, at least one instance of RS3a and RS3b is hydrogen. In certain embodiments, at least one instance of RS3a and RS3b is optionally substituted alkyl. In certain embodiments, at least one instance of RS3a and RS3b is substituted C1-6 alkyl. In certain embodiments, at least one instance of RS3a and RS3b is unsubstituted C1-6 alkyl. In certain embodiments, at least one instance of RS3a and RS3b is methyl, ethyl, propyl, butyl, pentyl, or hexyl. In certain embodiments, at least one instance of RS3a and RS3b is isopropyl, isobutyl, or isoamyl. In certain embodiments, at least one instance of RS3a and RS3b is isobutyl. In certain embodiments, at least one instance of RS3a and RS3b is tert-butyl. In certain embodiments, at least one instance of RS3a and RS3b is —$OR^{SO}$, wherein RSO is independently hydrogen, optionally substituted alkyl, optionally substituted alkyl, optionally substituted heterocyclyl, or an oxygen protecting group. In certain embodiments, at least one instance of RS3a and RS3b is —OH. In certain embodiments, at least one instance of RS3a and RS3b is —ORSO, wherein RSO is optionally substituted alkyl. In certain embodiments, at least one instance of RS3a and RS3b is —O-methyl, —O-ethyl, or —O— propyl. In certain embodiments, at least one instance of RS3a and RS3b is optionally substituted —O-alkyl-aryl. In certain embodiments, at least one instance of RS3a and RS3b —O-Bz. In certain embodiments, at least one instance of RS3a and RS3b is —ORSO, wherein RSO is an oxygen protecting group. In certain embodiments, at least one instance of RS3a and RS3b is —ORSO, wherein RSO is carbonyl. In certain embodiments, at least one instance of RS3a and RS3b is —ORSO, wherein RSO is acetyl. In certain embodiments, at least one instance of RS3a and RS3b is —ORSO, wherein RSO is optionally substituted heterocyclyl. In certain embodiments, at least one instance of RS3a and RS3b is —N(RSN)2. In some embodiments, at least one instance of RS3a and RS3b is —N(RSN)2, wherein each RSN is the same. In some embodiments, at least one instance of RS3a and RS3b is —N(RSN)2, wherein each RSN is different. In certain embodiments, at least one instance of RS3a and RS3b is —NH2. In certain embodiments, at least one instance of RS3a and RS3b is —NHRSN. In certain embodiments, at least one instance of RS3a and RS3b is —NHRSN, wherein RSN is optionally substituted C1-6 alkyl. In certain embodiments, at least one instance of RS3a and RS3b is —NHRSN, wherein RSN is unsubstituted C1-6 alkyl. In certain embodiment, at least one instance of RS3a and RS3b is —NHRSN, wherein RSN is substituted C1-6 alkyl. In certain embodiments, at least one instance of RS3a and RS3b is —NH-benzyl. In certain embodiment, at least one instance of RS3a and RS3b is —NHRSN, wherein RSN is a nitrogen protecting group. In certain embodiment, at least one instance of RS3a and RS3b is —NHFmoc. In certain embodiment, at least one instance of RS3a and RS3b is —NHBoc. In certain embodiments, at least one instance of RS3a and RS3b is —N(RSN)2, wherein each RSN is independently optionally substituted C1-6 alkyl. In certain embodiments, at least one instance of RS3a and RS3b is —N(RSN)2, wherein each RSN is independently unsubstituted C1-6 alkyl. In certain embodiments, at least one instance of RS4a and RS4b is —N(CH3)RSN, wherein each RSN is independently optionally substituted C1-6 alkyl. In certain embodiments, at least one instance of RS3a and RS3b is —N(CH3)RSN, wherein each RSN is independently unsubstituted C1-6 alkyl. In certain embodiments, at least one instance of RS3a and RS3b is —N(CH2CH3)RSN, wherein each RSN is independently optionally substituted C1-6 alkyl. In certain embodiments, at least one instance of RS3a and RS3b is —N(CH2CH3)RSN, wherein each RSN is independently unsubstituted C1-6 alkyl. In certain embodiments, at least one instance of RS3a and RS3b is —N(RSN)2, wherein each RSN is independently selected from the group consisting of methyl, ethyl, isopropyl, isobutyl, isoamyl, and benzyl. In some embodiments, at least one instance of RS3a and RS3b is —N(RSN)2, wherein two RSN groups are taken together with the intervening atoms to form an optionally substituted heterocyclic ring. For example, in certain embodiments, at least one instance of $R^{S3a}$ and $R^{S3b}$ is of the formula:

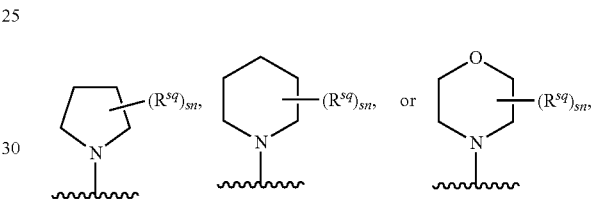

wherein $R^{sq}$ is as defined herein, and sn is 0, 1, 2, or 3.

As generally defined above, each instance of $R^{S4a}$ and $R^{S4b}$ is independently hydrogen, optionally substituted alkyl, —$OR^{SO}$, or —$N(R^{SN})_2$. In certain embodiments, at least one instance of $R^{S4a}$ and $R^{S4b}$ is hydrogen. In certain embodiments, at least one instance of $R^{S4a}$ and $R^{S4b}$ is optionally substituted alkyl. In certain embodiments, at least one instance of $R^{S4a}$ and $R^{S4b}$ is substituted $C_{1-6}$ alkyl. In certain embodiments, at least one instance of $R^{S4a}$ and $R^{S4b}$ is unsubstituted $C_{1-6}$ alkyl. In certain embodiments, at least one instance of $R^{S4a}$ and $R^{S4b}$ is methyl, ethyl, propyl, butyl, pentyl, or hexyl. In certain embodiments, at least one instance of $R^{S4a}$ and $R^{S4b}$ is isopropyl, isobutyl, or isoamyl. In certain embodiments, at least one instance of $R^{S4a}$ and $R^{S4b}$ is isobutyl. In certain embodiments, at least one instance of $R^{S4a}$ and $R^{S4b}$ is tert-butyl.

In certain embodiments, at least one instance of $R^{S4a}$ and $R^{S4b}$ is —$OR^{SO}$, wherein $R^{SO}$ is independently hydrogen, optionally substituted alkyl, optionally substituted alkyl, optionally substituted heterocyclyl, or an oxygen protecting group. In certain embodiments, at least one instance of $R^{S4a}$ and $R^{S4b}$ is —OH. In certain embodiments, at least one instance of $R^{S4a}$ and $R^{S4b}$ is —$OR^{SO}$, wherein $R^{SO}$ is optionally substituted alkyl. In certain embodiments, at least one instance of $R^{S4a}$ and $R^{S4b}$ is —O-methyl, —O-ethyl, or —O-propyl. In certain embodiments, at least one instance of $R^{S4a}$ and $R^{S4b}$ is optionally substituted —O-alkyl-aryl. In certain embodiments, at least one instance of $R^{S4a}$ and $R^{S4b}$ is —O-Bz. In certain embodiments, at least one instance of $R^{S4a}$ and $R^{S4b}$ is —$OR^{SO}$, wherein $R^{SO}$ is an oxygen protecting group. In certain embodiments, at least one instance of $R^{S4a}$ and $R^{S4b}$ is —$OR^{SO}$, wherein $R^{SO}$ is carbonyl. In certain embodiments, at least one instance of $R^{S4a}$ and $R^{S4b}$ is —$OR^{SO}$, wherein $R^{SO}$ is acetyl. In certain embodiments, at least one instance of $R^{S4a}$ and $R^{S4b}$ is —$OR^{SO}$, wherein $R^{SO}$ is optionally substituted heterocyclyl.

In certain embodiments, at least one instance of $R^{S4a}$ and $R^{S4b}$ is —$N(R^{SN})_2$. In some embodiments, at least one instance of $R^{S4a}$ and $R^{S4b}$ is —$N(R^{SN})_2$, wherein each $R^{SN}$ is the same. In some embodiments, at least one instance of $R^{S4a}$ and $R^{S4b}$ is —$N(R^{SN})_2$, wherein each $R^{SN}$ is different. In certain embodiments, at least one instance of $R^{S4a}$ and $R^{S4b}$ is —$NH_2$. In certain embodiments, at least one instance of $R^{S4a}$ and $R^{S4b}$ is —$NHR^{SN}$. In certain embodiments, at least one instance of $R^{S4a}$ and $R^{S4b}$ is —$NHR^{SN}$, wherein $R^{SN}$ is optionally substituted $C_{1-6}$ alkyl. In certain embodiments, at least one instance of $R^{S4a}$ and $R^{S4b}$ is —$NHR^{SN}$, wherein $R^{SN}$ is unsubstituted $C_{1-6}$ alkyl. In certain embodiment, at least one instance of $R^{S4a}$ and $R^{S4b}$ is —$NHR^{SN}$, wherein $R^{SN}$ is substituted $C_{1-6}$ alkyl. In certain embodiments, at least one instance of $R^{S4}$a and $R^{S4b}$ is —NH-benzyl. In certain embodiment, at least one instance of $R^{S4a}$ and $R^{S4b}$ is —$NHR^{SN}$, wherein $R^{SN}$ is a nitrogen protecting group. In certain embodiment, at least one instance of $R^{S4a}$ and $R^{S4b}$ is —NHFmoc. In certain embodiment, at least one instance of $R^{S4a}$ and $R^{S4b}$ is —NHBoc. In certain embodiments, at least one instance of $R^{S4a}$ and $R^{S4b}$ is —$N(R^{SN})_2$, wherein each $R^{SN}$ is independently optionally substituted $C_{1-6}$ alkyl. In certain embodiments, at least one instance of $R^{S4a}$ and $R^{S4b}$ is —$N(R^{SN})_2$, wherein each $R^{SN}$ is independently unsubstituted $C_{1-6}$ alkyl. In certain embodiments, at least one instance of $R^{S4a}$ and $R^{S4b}$ is —$N(CH_3)R^{SN}$, wherein each $R^{SN}$ is independently optionally substituted $C_{1-6}$ alkyl. In certain embodiments, at least one instance of $R^{S4a}$ and $R^{S4b}$ is —$N(CH_3)R^{SN}$, wherein each $R^{SN}$ is independently unsubstituted $C_{1-6}$ alkyl. In certain embodiments, at least one instance of $R^{S4a}$ and $R^{S4b}$ is —$N(CH_2CH_3)R^{SN}$, wherein each $R^{SN}$ is independently optionally substituted $C_{1-6}$ alkyl. In certain embodiments, at least one instance of $R^{S4a}$ and $R^{S4b}$ is —$N(CH_2CH_3)R^{SN}$, wherein each $R^{SN}$ is independently unsubstituted $C_{1-6}$ alkyl. In certain embodiments, at least one instance of $R^{S4a}$ and $R^{S4b}$ is —$N(R^{SN})_2$, wherein each $R^{SN}$ is independently selected from the group consisting of methyl, ethyl, isopropyl, isobutyl, isoamyl, and benzyl.

In some embodiments, at least one instance of $R^{S4a}$ and $R^{S4b}$ is —$N(R^{SN})_2$, wherein two $R^{SN}$ groups are taken together with the intervening atoms to form an optionally substituted heterocyclic ring. For example, in certain embodiments, at least one instance of $R^{S4a}$ and $R^{S4b}$ is of the formula:

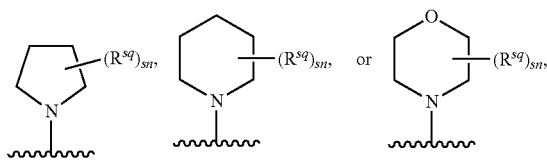

wherein $R^q$ is as defined herein, and sn is 0, 1, 2, or 3.

As generally defined above, each instance of $R^{S5a}$ and $R^{S5b}$ is independently hydrogen, optionally substituted alkyl, —$OR^{SO}$, or —$N(R^{SN})_2$. In certain embodiments, at least one instance of $R^{S5a}$ and $R^{S5b}$ is hydrogen. In certain embodiments, at least one instance of $R^{S5a}$ and $R^{S5b}$ is optionally substituted alkyl. In certain embodiments, at least one instance of $R^{S5a}$ and $RS5^b$ is substituted $C_{1-6}$ alkyl. In certain embodiments, at least one instance of $R^{S5a}$ and $R^{S5b}$ is unsubstituted $C_{1-6}$ alkyl. In certain embodiments, at least one instance of $R^{S5a}$ and $R^{S5b}$ is methyl, ethyl, propyl, butyl, pentyl, or hexyl. In certain embodiments, at least one instance of $R^{S5a}$ and $R^{S5b}$ is isopropyl, isobutyl, or isoamyl. In certain embodiments, at least one instance of $R^{S5a}$ and $R^{S5b}$ is isobutyl. In certain embodiments, at least one instance of $R^{S5a}$ and $R^{S5b}$ is tert-butyl.

In certain embodiments, at least one instance of $R^{S5a}$ and $R^{S5b}$ is —$OR^{SO}$, wherein $R^{SO}$ is independently hydrogen, optionally substituted alkyl, optionally substituted alkyl, optionally substituted heterocyclyl, or an oxygen protecting group. In certain embodiments, at least one instance of $R^{S5a}$ and $R^{S5b}$ is —OH. In certain embodiments, at least one instance of $R^{S4a}$ and $R^{S4b}$ is —$OR^{SO}$, wherein $R^{SO}$ is optionally substituted alkyl. In certain embodiments, at least one instance of $R^{S5a}$ and $R^{S5b}$ is —O-methyl, —O-ethyl, or —O-propyl. In certain embodiments, at least one instance of $R^{S5a}$ and $R^{S5b}$ is optionally substituted —O-alkyl-aryl. In certain embodiments, at least one instance of $R^{S5a}$ and $R^{S5b}$ is —O-Bz. In certain embodiments, at least one instance of $R^{S5a}$ and $R^{S5b}$ is —$OR^{SO}$, wherein $R^{SO}$ is an oxygen protecting group. In certain embodiments, at least one instance of $R^{S5a}$ and $R^{S5b}$ is —$OR^{SO}$, wherein $R^{SO}$ is carbonyl. In certain embodiments, at least one instance of $R^{S5a}$ and $R^{S5b}$ is —$OR^{SO}$, wherein $R^{SO}$ is acetyl. In certain embodiments, at least one instance of $R^{S5a}$ and $R^{S5b}$ is —$OR^{SO}$, wherein $R^{SO}$ is optionally substituted heterocyclyl.

In certain embodiments, at least one instance of $R^{S5a}$ and $R^{S5b}$ is —$N(R^{SN})_2$. In some embodiments, at least one instance of $R^{S5a}$ and $R^{S5b}$ is —$N(R^{SN})_2$, wherein each $R^{SN}$ is the same. In some embodiments, at least one instance of $R^{S5a}$ and $R^{S5b}$ is —$N(R^{SN})_2$, wherein each $R^{SN}$ is different. In certain embodiments, at least one instance of $R^{S5a}$ and $R^{S5b}$ is —$NH_2$. In certain embodiments, at least one instance of $R^{S5a}$ and $R^{S5b}$ is —$NHR^{SN}$. In certain embodiments, at least one instance of $R^{S5a}$ and $R^{S5b}$ is —$NHR^{SN}$, wherein $R^{SN}$ is optionally substituted $C_{1-6}$ alkyl. In certain embodiments, at least one instance of $R^{S5a}$ and $R^{S5b}$ is —$NHR^{SN}$, wherein $R^{SN}$ is unsubstituted $C_{1-6}$ alkyl. In certain embodiment, at least one instance $R^{S5a}$ and $R^{S5b}$ is —$NHR^{SN}$, wherein $R^{SN}$ is substituted $C_{1-6}$ alkyl. In certain embodiments, at least one instance of $R^{S5a}$ and $R^{S5b}$ is —NH-benzyl. In certain embodiment, at least one instance of $R^{S5a}$ and $R^{S5b}$ is —$NHR^{SN}$ wherein $R^{SN}$ is a nitrogen protecting group. In certain embodiment, at least one instance of $R^{S4a}$ and $R^{S4b}$ is —NHFmoc. In certain embodiment, at least one instance of $R^{S5a}$ and $R^{S5b}$ is —NHBoc.

In certain embodiments, at least one instance of $R^{S5a}$ and $R^{S5b}$ is —$N(R^{SN})_2$, wherein each $R^{SN}$ is independently optionally substituted $C_{1-6}$ alkyl. In certain embodiments, at least one instance of $R^{S5a}$ and $R^{S5b}$ is —$N(R^N)_2$, wherein each $R^{SN}$ is independently unsubstituted $C_{1-6}$ alkyl. In certain embodiments, at least one instance of $R^{S5a}$ and $R^{S5b}$ is —$N(CH_3)R^{SN}$, wherein each $R^{SN}$ is independently optionally substituted $C_{1-6}$ alkyl. In certain embodiments, at least one instance of $R^{S5a}$ and $R^{S5b}$ is —$N(CH_3)R^{SN}$, wherein each $R^{SN}$ is independently unsubstituted $C_{1-6}$ alkyl. In certain embodiments, at least one instance of $R^{S5a}$ and $R^{S5b}$ is —$N(CH_2CH_3)R^{SN}$, wherein each $R^{SN}$ is independently optionally substituted $C_{1-6}$ alkyl. In certain embodiments, at least one instance of $R^{S5a}$ and $R^{S5b}$ is —$N(CH_2CH_3)R^{SN}$, wherein each $R^{SN}$ is independently unsubstituted $C_{1-6}$ alkyl. In certain embodiments, at least one instance of $R^{S5a}$ and $R^{S5b}$ is —$N(R^{SN})_2$, wherein each $R^{SN}$ is independently selected from the group consisting of methyl, ethyl, isopropyl, isobutyl, isoamyl, and benzyl.

In some embodiments, at least one instance of $R^{S5a}$ and $R^{S5b}$ is —$N(R^N)_2$, wherein two $R^{SN}$ groups are taken together with the intervening atoms to form an optionally substituted heterocyclic ring. For example, in certain embodiments, at least one instance of $R^{S5a}$ and $R^{S5b}$ is of the formula:

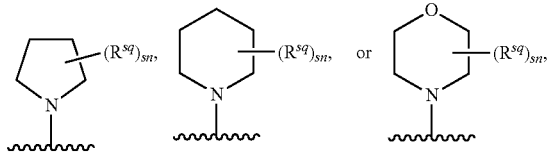

wherein $R^{sq}$ is as defined herein, and sn is 0, 1, 2, or 3.

As used herein, each instance $R^{sq}$ is independently halogen, optionally substituted alkyl, —$OR^{SO1}$, or —$N(R^{SN1})_2$, wherein $R^{SO1}$ is independently hydrogen, optionally substituted alkyl, or an oxygen protecting group; and $R^{SN1}$ is independently hydrogen, optionally substituted alkyl, or a nitrogen protecting group; or optionally two $R^{SN1}$ are taken together with the intervening atoms to form an optionally substituted heterocyclic ring.

As generally defined herein, each instance of $R^{SO}$ is independently hydrogen, optionally substituted alkyl, carbonyl, optionally substituted heterocyclyl, or an oxygen protecting group.

In certain embodiments, $R^{SO}$ is hydrogen. In certain embodiments, $R^{SO}$ is optionally substituted alkyl. In certain embodiments, $R^{SO}$ is optionally substituted $C_{1-6}$ alkyl. In certain embodiments, $R^{SO}$ is methyl, ethyl, or propyl. In certain embodiments, $R^{SO}$ is optionally substituted aralkyl, e.g., optionally substituted benzyl (Bn). In certain embodiments, $R^{SO}$ is optionally substituted heterocyclyl. In certain embodiments, $R^{SO}$ is carbonyl. In certain embodiments, $R^{SO}$ is —$C(=O)CH_3$ (acetyl, Ac). In certain embodiments, $R^{SO}$ is —$C(=O)Ph$ (benzoyl, Bz). In certain embodiments, $R^{SO}$ is an oxygen protecting group.

As generally defined herein, each instance of $R^{SN}$ is independently hydrogen, optionally substituted alkyl, optionally substituted heterocyclyl, or a nitrogen protecting group; or optionally two $R^{SN}$ are taken together with the intervening atoms to form an optionally substituted heterocyclic ring. In certain embodiments, $R^{SN}$ is hydrogen. In certain embodiments, $R^{SN}$ is optionally substituted alkyl. In certain embodiments, $R^{SN}$ is optionally substituted $C_{1-6}$ alkyl. In certain embodiments, $R^{SN}$ is methyl, ethyl, or propyl. In certain embodiments, $R^{SN}$ is substituted aralkyl, e.g., optionally substituted benzyl (Bn). In certain embodiments, $R^{SN}$ is optionally substituted heterocyclyl. In certain embodiments, $R^{SN}$ is carbonyl. In certain embodiments, $R^{SN}$ is carbonyl. In certain embodiments, $R^{SN}$ is —$C(=O)CH_3$ (acetyl, Ac). In certain embodiments, $R^{SN}$ is —$C(=O)Ph$ (benzoyl, Bz). In certain embodiments, $R^{SN}$ is a nitrogen protecting group.

As generally defined herein, each instance of $L^1$ is independently a bond, —O—, —S—, —$NR^{L1a}$—, —$C(=O)$—, —$NR^{L1a}C(=O)$—, —$NR^{L1a}C(=O)O$—, —$C(=O)NR^{L1a}$—, —$OC(=O)NR^{L1a}$—, —$SC(=O)$—, —$C(=O)S$—, —$OC(=O)$—, —$C(=O)O$—, —$NR^{L1a}C(=S)$—, —$C(=S)NR^{L1a}$—, trans-$CR^{L1b}=CR^{L1b}$—, cis-$CR^{L1b}=CR^{L1b}$—, —$C\equiv C$—, —$OC(R^{L1b})_2$—, —$C(R^{L1b})_2O$—, —$NR^{L1a}C(R^{L1b})_2$—, —$C(R^{L1b})_2NR^{L1a}$—, —$SC(R^{L1b})_2$—, —$C(R^{L1b})_2S$—, —$S(=O)_2O$—, —$OS(=O)_2$—, —$S(=O)_2NR^{L1a}$—, —$NR^{L1a}S(=O)_2$—, or an optionally substituted $C_{1-20}$ hydrocarbon chain, optionally wherein one or more carbon units of the hydrocarbon chain is replaced with —O—, —S—, —$NR^{L1a}$—, —$C(=O)$—, —$NR^{L1a}C(=O)$—, —$NR^{L1a}C(=O)O$—, —$C(=O)NR^{L1a}$—, —$OC(=O)NR^{L1a}$—, —$SC(=O)$—, —$C(=O)S$—, —$OC(=O)$—, —$C(=O)O$—, —$NR^{L1a}C(=S)$—, —$C(=S)NR^{L1a}$—, trans-$CR^{L1b}=CR^{L1b}$—, cis-$CR^{L1b}=CR^{L1b}$—, —$C\equiv C$—, —$S(=O)_2O$—, —$OS(=O)_2$—, —$S(=O)_2NR^{L1a}$—, or —$NR^{L1a}S(=O)_2$—, wherein $R^{L1a}$ is hydrogen, optionally substituted $C_{1-6}$ alkyl, or a nitrogen protecting group, or $R^{L1a}$ is joined with the adjacent carbon atom to form an optionally substituted heterocyclic ring, and wherein each occurrence of $R^{L1b}$ is independently selected from the group consisting of hydrogen, halogen, optionally substituted $C_{1-10}$ alkyl, optionally substituted alkenyl, optionally substituted alkynyl, optionally substituted carbocyclyl, optionally substituted heterocyclyl, optionally substituted aryl, and optionally substituted heteroaryl, or $R^{L1b}$ is joined with the adjacent carbon or nitrogen or oxygen atom to form an optionally substituted carbocyclic or heterocyclic ring, or two $R^{L1b}$ groups are joined to form an optionally substituted carbocyclic or optionally substituted heterocyclic ring. In certain embodiments, $L^1$ is a bond. In certain embodiments, $L^1$ is an optionally substituted $C_{1-20}$ hydrocarbon chain, optionally wherein one or more carbon units of the hydrocarbon chain is replaced with —O—, —S—, —$NR^{L1a}$—, —$C(=O)$—, —$NR^{L1a}C(=O)$—, —$NR^{L1a}C(=O)O$—, —$C(=O)NR^{L1a}$—, —$OC(=O)NR^{L1a}$—, —$SC(=O)$—, —$C(=O)S$—, —$OC(=O)$—, —$C(=O)O$—, —$NR^{L1a}C(=S)$—, —$C(=S)NR^{L1a}$—, trans-$CR^{L1b}=CR^{L1b}$—, cis-$CR^{L1b}=CR^{L1b}$—, —$C\equiv C$—, —$S(=O)_2O$—, —$OS(=O)_2$—, —$S(=O)_2NR^{L1a}$—, or —$NR^{L1a}S(=O)_2$—. In certain embodiments, $L^1$ is of the formula —$C(=O)$—$(CH_2)_q$—S— or —$C(=O)$—$(CH_2)_q$—$C(=O)$—, wherein q is an integer of 1 to 8, inclusive.

In certain embodiments, q is 1. In certain embodiments, q is 2. In certain embodiments, q is 3. In certain embodiments, q is 4. In certain embodiments, q is 5. In certain embodiments, q is 6. In certain embodiments, q is 7. In certain embodiments, q is 8.

In certain embodiments, $R^{L1a}$ is hydrogen or optionally substituted $C_{1-6}$ alkyl. In certain embodiments, $R^{L1a}$ is hydrogen. In certain embodiments, $R^{L1a}$ is methyl, ethyl, or propyl.

In certain embodiments, $R^{L1b}$ is hydrogen or optionally substituted $C_{1-6}$ alkyl. In certain embodiments, $R^{L1b}$ is hydrogen. In certain embodiments, $R^{L1b}$ is methyl, ethyl, or propyl.

As generally defined herein, each instance of $L^2$ is a moiety derived from a crosslinking reagent capable of crosslinking the carrier and $L^1$-H. Crosslinking reagents suited to the invention are widely known in the art (see, for example, 1994 Pierce Technical Handbook: cross-linking available at http://www.piercenet.com/resources/browse.cfm?fldID=184), including bromoacetic NHS ester, 6-(iodoacetamido)caproic acid NHS ester, maleimidoacetic acid NHS ester, maleimidobenzoic acide NHS ester, etc. In certain embodiments, each instance of $L^2$ is a moiety derived from a crosslinking reagent capable of crosslinking the amino group on the surface of the carrier and $L^1$-H. In certain embodiments, $L^2$ is of the formula

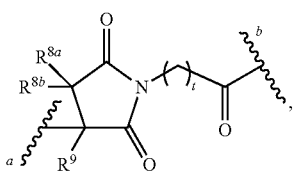

-continued

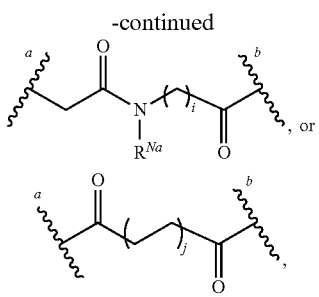, or wherein $R^{8a}$, $R^{8b}$ and $R^9$ are each independently hydrogen, halogen, or optionally substituted $C_{1-6}$ alkyl; $R^{Na}$ is independently hydrogen, optionally substituted $C_{1-6}$ alkyl, optionally substituted acyl, or a nitrogen protecting group; i is an integer from 1 to 8, inclusive; and j is an integer from 1 to 8, inclusive, end a is linked to $L^1$-H; and end b is linked to the amino group on the surface of the carrier. In certain embodiments, $L^2$ is of the formula

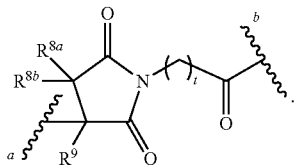

In certain embodiments, $L^2$ is of the formula

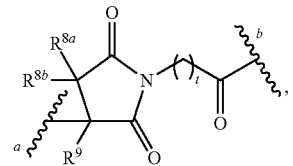

wherein $R^{8a}$, $R^{8b}$ and $R^9$ are hydrogen. In certain embodiments, $L^2$ is of the formula

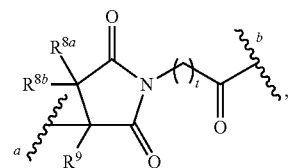

wherein $R^{8a}$, $R^{8b}$ and $R^9$ are hydrogen and t is 5.

As generally defined herein, each instance of $R^{CN}$ is independently hydrogen, optionally substituted $C_{1-6}$ alkyl, optionally substituted acyl, or a nitrogen protecting group. In some embodiments, $R^{CN}$ is hydrogen. In some embodiments, $R^{CN}$ is optionally substituted $C_{1-6}$ alkyl. In certain embodiments, $R^{CN}$ is methyl. In certain embodiments, $R^{CN}$ is ethyl. In certain embodiments, $R^{CN}$ is propyl. In certain embodiments, $R^{CN}$ is optionally substituted acyl. In certain embodiments, $R^{CN}$ is acetyl. In certain embodiments, $R^{CN}$ is a nitrogen protecting group. In certain embodiments, $R^{N2}$ is Bn, BOC, Cbz, Troc, Fmoc, trifluoroacetyl, triphenylmethyl, or Ts.

As generally defined herein, each instance of $R^{BN}$ is independently hydrogen, optionally substituted $C_{1-6}$ alkyl, optionally substituted acyl, or a nitrogen protecting group. In some embodiments, $R^{BN}$ is hydrogen. In some embodiments, $R^{BN}$ is optionally substituted $C_{1-6}$ alkyl. In certain embodiments, $R^{BN}$ is methyl. In certain embodiments, $R^{BN}$ is ethyl. In certain embodiments, $R^{BN}$ is propyl. In certain embodiments, $R^{BN}$ is optionally substituted acyl. In certain embodiments, $R^{BN}$ is acetyl. In certain embodiments, $R^{BN}$ is a nitrogen protecting group. In certain embodiments, $R^{N2}$ is Bn, BOC, Cbz, Troc, Fmoc, trifluoroacetyl, triphenylmethyl, or Ts.

As generally defined herein, $L^{3C}$ is independently a cross-linking reagent or a crosslining reagent moiety wherein the crosslinking reagent is capable of crosslinking the carrier and $L^1$-H. In certain embodiments, $L^{3C}$ is one of the following formulae:

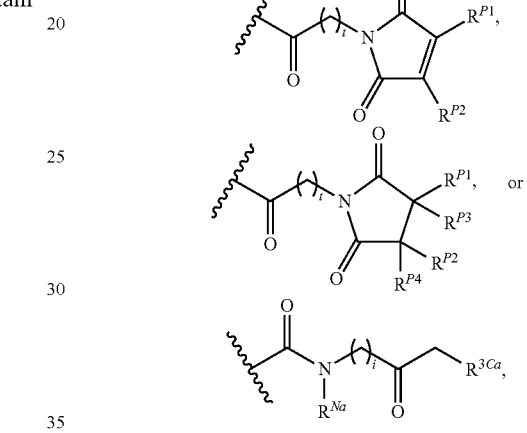

wherein $R^{P1}$, $R^{P2}$, and $R^{3Ca}$ are each independently hydrogen, halogen, or optionally substitute $C_{1-6}$ alkyl; each of $R^{P3}$ and $R^{P4}$ independently optionally substituted alkyl, optionally substituted alkenyl, optionally substituted alkynyl, optionally substituted carbocyclyl, optionally substituted 3- to 6-membered heterocyclyl, optionally substituted aryl, optionally substituted heteroaryl, —$OR^{3CO}$, —$SR^{3CS}$, or —$N(R^{3CN})_2$; $R^{3CO}$ is independently hydrogen, substituted alkyl, optionally substituted alkenyl, optionally substituted alkynyl, optionally substituted carbocyclyl, optionally substituted 3- to 6-membered heterocyclyl, optionally substituted aryl, optionally substituted heteroaryl, or an oxygen protecting group; $R^{2CS}$ is independently hydrogen, substituted alkyl, optionally substituted alkenyl, optionally substituted alkynyl, optionally substituted carbocyclyl, optionally substituted 3- to 6-membered heterocyclyl, optionally substituted aryl, optionally substituted heteroaryl, or a sulfur protecting group; each instance of $R^{3CN}$ is independently hydrogen, substituted alkyl, optionally substituted alkenyl, optionally substituted alkynyl, optionally substituted carbocyclyl, optionally substituted 3- to 6-membered heterocyclyl, optionally substituted aryl, optionally substituted heteroaryl, or a nitrogen protecting group.

In certain embodiments, $R^{P1}$ is hydrogen. In certain embodiments, $R^{P1}$ is halogen. In certain embodiments, $R^{P1}$ is optionally substituted $C_{1-6}$ alkyl. In certain embodiments, $R^{P1}$ is methyl, ethyl, or propyl.

In certain embodiments, $R^{P2}$ is hydrogen. In certain embodiments, $R^{P2}$ is halogen. In certain embodiments, $R^{P2}$ is optionally substituted $C_{1-6}$ alkyl. In certain embodiments, $R^{P2}$ is methyl, ethyl, or propyl.

In certain embodiments, $R^{P3}$ is hydrogen. In certain embodiments, $R^{P3}$ is halogen. In certain embodiments, $R^{P3}$ is optionally substituted $C_{1-6}$ alkyl. In certain embodiments, $R^{P3}$ is methyl, ethyl, or propyl. In certain embodiments, $R^{P3}$ is —$SR^{3CS}$, wherein $R^{3CS}$ is optionally substituted alkyl.

In certain embodiments, $R^{P4}$ is hydrogen. In certain embodiments, $R^{P4}$ is halogen. In certain embodiments, $R^{P4}$ is optionally substituted $C_{1-6}$ alkyl. In certain embodiments, $R^{P4}$ is methyl, ethyl, or propyl. In certain embodiments, $R^{P4}$ is —$SR^{3CS}$, wherein $R^{3CS}$ is optionally substituted alkyl.

In certain embodiments, $R^{3Ca}$ is hydrogen. In certain embodiments, $R^{3Ca}$ is halogen. In certain embodiments, $R^{3Ca}$ is optionally substituted $C_{1-6}$ alkyl. In certain embodiments, $R^{3Ca}$ is methyl, ethyl, or propyl.

In certain embodiments, $L^{3C}$ is one of the following formulae:

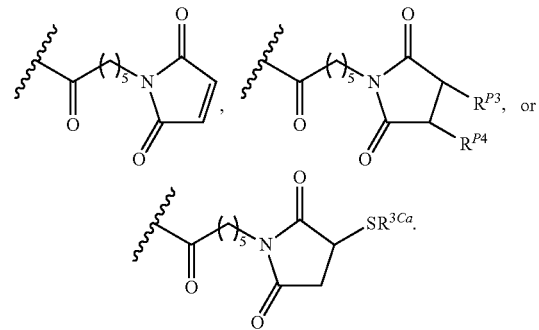

In certain embodiments, $L^{3C}$ is a crosslinking reagent of the formula

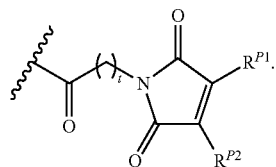

In certain embodiments, $L^{3C}$ is a crosslinking reagent moiety of the formula

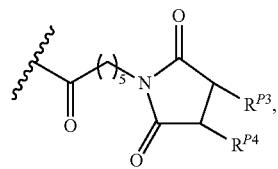

prepared from a nucleophilic reaction with the crosslinking reagent of the formula

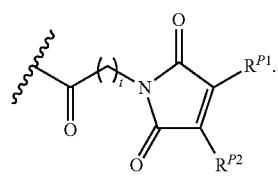

In certain embodiments, $L^{3C}$ is a crosslinking reagent moiety of the formula

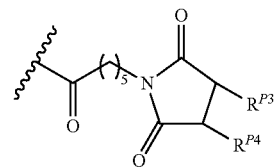

wherein $R^{P3}$ is hydrogen and $R^{P4}$ is —$SR^{3CS}$; or $R^{P3}$ is —$SR^{3CS}$ and $R^{P4}$ is hydrogen.

In some embodiments, the glycan moiety is of Formula (II)

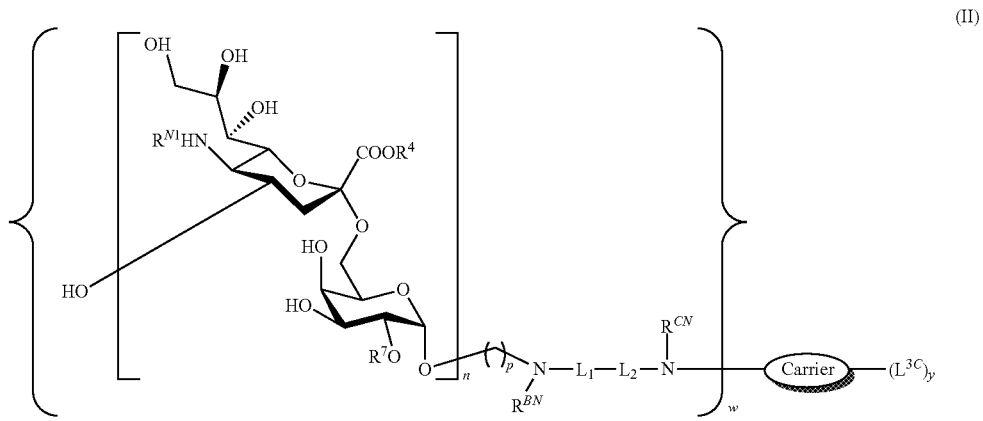

or a pharmaceutically acceptable salt thereof.

In some embodiments, the glycan conjugate is of Formula (III)

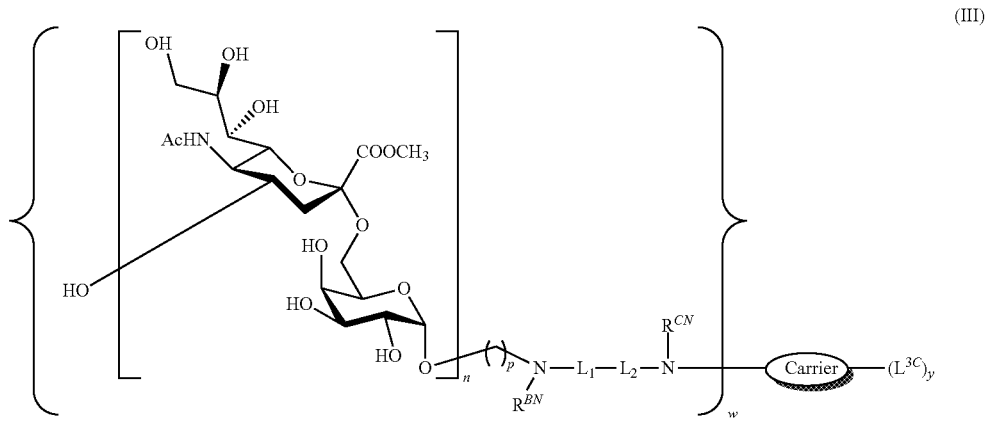

or a pharmaceutically acceptable salt thereof.

In certain embodiments, $R^1$ and $R^2$ are hydrogen. In certain embodiments, $R^1$, $R^2$, and $R^6$ are all hydrogen. In certain embodiments, $R^1$, $R^2$, and $R^3$ are all hydrogen. In certain embodiments, $R^1$ and $R^2$ are acetyl. In certain embodiments, $R^1$, $R^2$, and $R^3$ are acetyl. In certain embodiments, $R^1$, $R^2$, and $R^6$ are acetyl. In certain embodiments, $R^1$ and $R^2$ are Bn. In certain embodiments, $R^1$ is TBDPS and $R^2$ and $R^3$ are taken with the intervening atoms to form a 5-membered heterocyclic ring of the formula

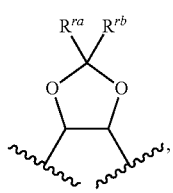

wherein $R^{ra}$ and $R^{rb}$ are each independently methyl, ethyl, or propyl.

In certain embodiments, $R^5$ and $R^6$ are hydrogen. In certain embodiments, $R^5$, $R^6$ and $R^7$ are hydrogen. In certain embodiments, $R^5$, $R^6$ and $R^7$ are acetyl. In certain embodiments, $R^5$, $R^6$ and $R^7$ are acetyl. In certain embodiments, $R^5$, $R^6$ and $R^7$ are Bn.

In certain embodiments, $R^{N1}$ is acetyl and $R^{N2}$ is hydrogen. In certain embodiments, $R^{N1}$ and $R^{N2}$ are hydrogen.

Any of the glycan moieties described herein may be conjugated with a carrier to enhance the immunogenicity of the glycan moieties. Such carriers include, but are not limited to, a protein, a lipid, a lipolized protein, a virus, a peptide comprising a T cell epitope, or a dendrimer of glycopeptides. In some embodiments, the carrier is a toxin protein selected from the group consisting of diphtheria toxin cross-reacting material 197 (DT-CRM197), diphtheria toxoid, tetanus toxoid, and outer-membrane protein (OMP). In other examples, the carrier is the toxin protein is DT-CRM197.

In certain embodiments, the glycan conjugate described herein is of the formula:

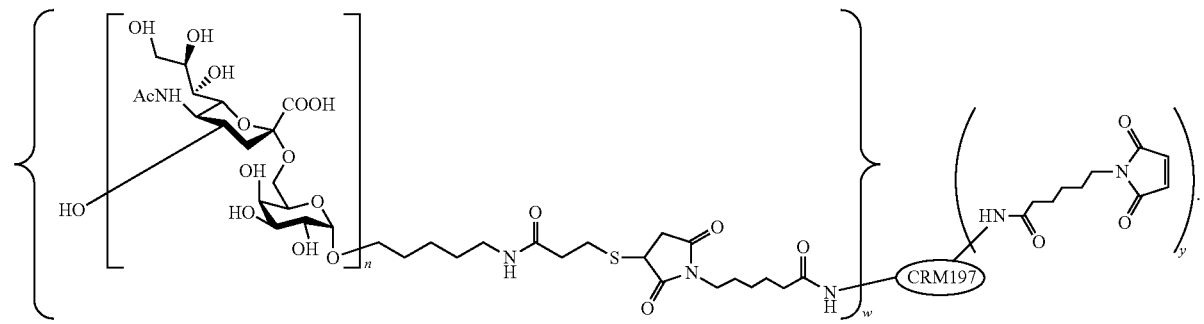

In another aspect, the present invention provides a glycan conjugate mixture comprising at least two of the glycan conjugates described herein. In some embodiments, the average value of w (average molar ratio of the glycan moiety to the carrier) in the glycan conjugate mixture provided herein is from about 1.0 to about 100.0, e.g., about 1.0 to about 90.0; about 1.0 to about 80.0; about 1.0 to about 70.0; about 1.0 to about 60.0; about 1.0 to about 50.0; about 1.0 to about 40.0; about 1.0 to about 30; about 1.0 to about 20.0; or about 1.0 to about 5.0. In certain embodiments, the glycan conjugate mixture has an average value of w of 5.7, 4.9, 2.9, 2.8, or 3.1. In certain embodiments, the glycan conjugate mixture has an average value of w of 4.9, 2.9, 2.8, or 3.1.

In some embodiments, for all the compounds and glycan conjugates described herein, all the variants in each unit of the n bracket can be the same, completely different, or partially different. In some embodiments, all the variants in each unit of the n bracket are the same. In some embodiments, all the variants in each unit of the n bracket are completely different. In some embodiments, some of the variants in each unit of the n bracket are partially different. For example, when n is 3, the compound of Formula (F-1) is of the formula

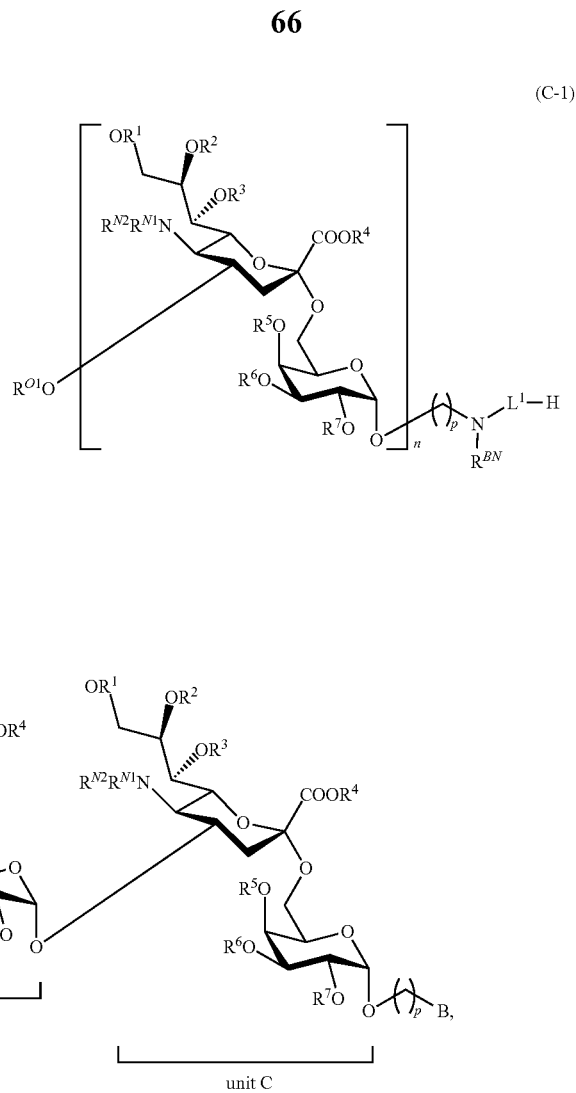

wherein unit A, unit B, unit C can be the same, completely different, or partially different (i.e. $R^1$, $R^2$, $R^3$, $R^4$, $R^5$, $R^6$, $R^7$, $R^{N1}$, and $R^{N2}$ can be the same, completely different, or partially different in unit A, unit B, or unit C).

Figure 10:
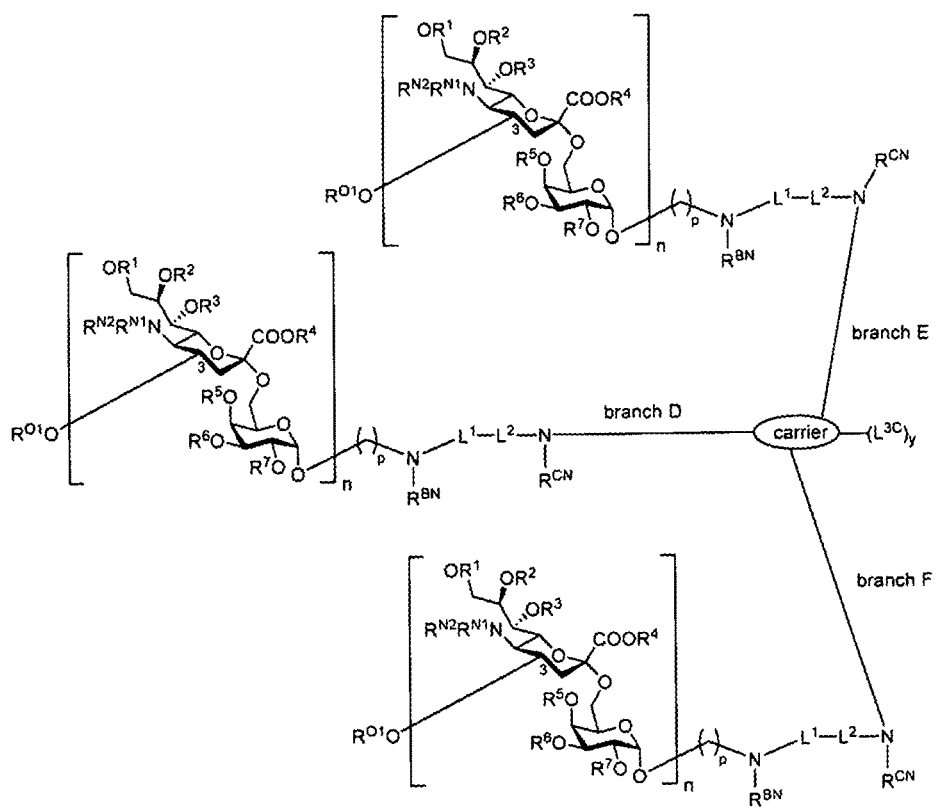
FIG. 10 shows an exemplified hybrid glycan conjugate.

In some embodiments, the glycan conjugates described herein encompass hybrid conjugates to the carrier. In some embodiments, for all glycan conjugates described herein, all the variants in each unit of the w bracket can be the same, completely different, or partially different. In some embodiments, all the variants in each unit of the w bracket are the same. In some embodiments, all the variants in each unit of the w bracket are different. In some embodiments, some of the variants in each unit of the w bracket are partially different. For example, when w is 3, the compound of Formula (I-a) is of the structure in FIG. 10, wherein branch D, branch E, and branch F can be the same, completely different, or partially different (i.e. $R^1$, $R^2$, $R^3$, $R^4$, $R^5$, $R^6$, $R^7$, $R^{N1}$, $R^{N2}$, n, p, $R^{BN}$, $R^{CN}$, $L^1$, and $L^2$ can be the same, completely different, or partially different in branch D, branch E, branch F).

Method of Synthesizing Glycan Moieties and Glycan Conjugates

The present invention provides methods of preparing glycan moiety of Formula (I-a). The method of preparing the glycan conjugates may comprise coupling a compound of Formula (C-1)

or a salt thereof,
with a compound of the Formula (C-2)

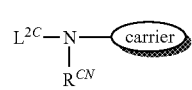

wherein $L^{2C}$ is a crosslinking reagent capable of crosslinking an amino group and $L^1$-H.

As generally defined herein, $L^{2C}$ is independently a crosslinking reagent capable of crosslinking the carrier and $L^1$-H. In certain embodiments, $L^{2C}$ is a crosslinking reagent capable of crosslinking an amine group and —SH. In certain embodiments, $L^{2C}$ is one of the following formulae:

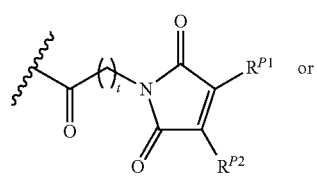

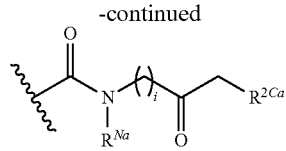

or a salt thereof,
wherein each instance of $R^{P1}$ and $R^{P2}$ are each independently hydrogen, halogen, or optionally substituted C1-6 alkyl; each instance of $R^{2Ca}$ is a leaving group selected from selected from —Br, —Cl, —I, —OS(=O)$_2R^{2CO}$, or —OS(=O)$R^{2CO}$, wherein $R^{2CO}$ is selected from the group consisting of optionally substituted alkyl, optionally substituted alkenyl, optionally substituted alkynyl, optionally substituted carbocyclyl, optionally substituted heterocyclyl, optionally substituted aryl, and optionally substituted heteroaryl; and each of t and i is independently an integer of 1 to 8, inclusive.

As generally used herein, $R^{P1}$ and $R^{P2}$ are each independently hydrogen or optionally substituted $C_{1-6}$alkyl. In certain embodiments, $R^{P1}$ is hydrogen. In certain embodiments, $R^{P1}$ is optionally substituted $C_{1-6}$alkyl. In certain embodiments, $R^{P1}$ is unsubstituted $C_{1-6}$ alkyl. In certain embodiments, $R^{P1}$ is methyl, ethyl, or propyl. In certain embodiments, $R^{P2}$ is hydrogen. In certain embodiments, $R^{P2}$ is optionally substituted $C_{1-6}$ alkyl. In certain embodiments, $R^{P2}$ is unsubstituted $C_{1-6}$ alkyl. In certain embodiments, $R^{P2}$ is methyl, ethyl, or propyl. In certain embodiments, both $R^{P1}$ and $R^{P2}$ are hydrogen. In certain embodiments, $R^{P1}$ and $R^{P2}$ are each independently optionally substituted $C_{1-6}$ alkyl.

As generally used herein, $R^{2Ca}$ is a leaving group. In certain embodiments, $R^{2Ca}$ is a leaving group selected from selected from the group consisting of —Br, —Cl, —I, —OS(=O)$_2R^{2CO}$, or —OS(=O)$R^{2CO}$, wherein $R^{2CO}$ is selected from the group consisting of optionally substituted alkyl, optionally substituted alkenyl, optionally substituted alkynyl, optionally substituted carbocyclyl, optionally substituted heterocyclyl, optionally substituted aryl, and optionally substituted heteroaryl. In certain embodiments, $R^{2Ca}$ is —Br, —Cl, or —I. In certain embodiments, $R^{2Ca}$ is —OS(=O)$_2R^{2CO}$, or —OS(=O)$R^{2CO}$, wherein $R^{2CO}$ is optionally substituted alkyl such as methyl, ethyl, or propyl.

In certain embodiments, the molar ratio of the compound of Formula (C-1) to the compound of Formula (C-2) is from about 1 to about 100.

In certain embodiments, the coupling is carried out in the presence of phosphate buffered saline (PBS).

The synthesis of the glycan moiety of Formula (I) generally involves coupling a compound of Formula (C-1) with a compound of Formula (C-2). In certain embodiments, the coupling reaction is carried out in the presence of a buffer. In certain embodiments, the coupling reaction is carried out in pH from about 6.0 to 9.0. In certain embodiments, the coupling reaction is carried out under pH from about 6.0 to 8.0. In certain embodiments, the coupling reaction is carried out under pH from about 7.0 to 9.0. In certain embodiments, the coupling reaction is carried out under pH from about 7.5 to 8.0. In certain embodiments, the coupling reaction is carried out under pH from about 7.0 to 7.5. In certain embodiments, the coupling reaction is carried out in the presence of phosphate buffered saline (PBS).

In certain embodiments, the molar ratio of the compound of Formula (C-1) to the compound of Formula (C-2) is from about 1 to about 100. In certain embodiments, the molar ratio of the compound of Formula (C-1) to the compound of Formula (C-2) is from about 1 to about 20. In certain embodiments, the molar ratio of the compound of Formula (C-1) to the compound of Formula (C-2) is from about 10 to about 30. In certain embodiments, the molar ratio of the compound of Formula (C-1) to the compound of Formula (C-2) is from about 20 to about 40. In certain embodiments, the molar ratio of the compound of Formula (C-1) to the compound of Formula (C-2) is from about 30 to about 50. In certain embodiments, the molar ratio of the compound of Formula (C-1) to the compound of Formula (C-2) is from about 40 to about 60. In certain embodiments, the molar ratio of the compound of Formula (C-1) to the compound of Formula (C-2) is from about 50 to about 70. In certain embodiments, the molar ratio of the compound of Formula (C-1) to the compound of Formula (C-2) is from about 60 to about 80. In certain embodiments, the molar ratio of the compound of Formula (C-1) to the compound of Formula (C-2) is from about 70 to about 90. In certain embodiments, the molar ratio of the compound of Formula (C-1) to the compound of Formula (C-2) is from about 80 to about 100.

In certain embodiments, the method of preparing a glycan conjugate as described herein further comprising glycosylating a compound of Formula (C-3)

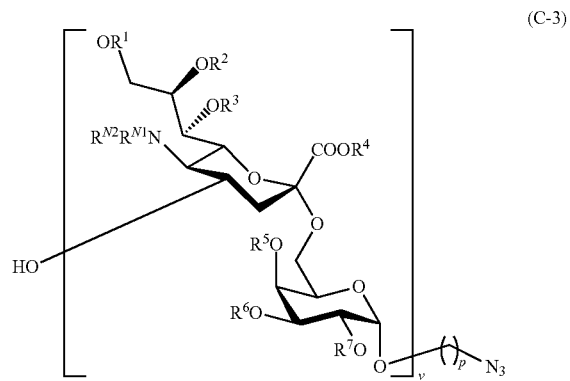

with a compound of Formula (C-4)

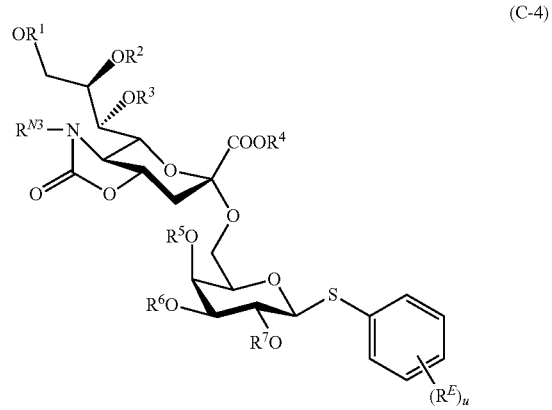

to give a compound of Formula (C-5)

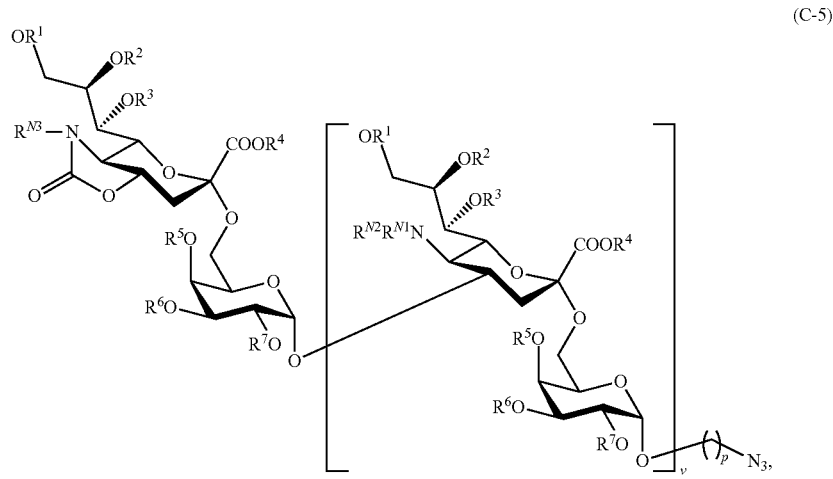

(C-5)

wherein v is an integer of 1 to 99 inclusive; u is 0, 1, 2, 3, 4, or 5; each occurrence of $R^E$ is independently halogen, —CN, —NO$_2$, —N$_3$, optionally substituted alkyl, optionally substituted alkenyl, optionally substituted alkynyl, optionally substituted carbocyclyl, optionally substituted phenyl, optionally substituted heterocyclyl, optionally substituted heteroaryl, —OR$^{CE}$, —N(R$^{CE}$)$_2$, —SR$^{CE}$, —C(=O)R$^{CE}$, —C(=O)OR$^{CE}$, or —C(=O)N(R$^{CE}$)$_2$, wherein each $R^{CE}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl; or an oxygen protecting group when attached to an oxygen, or a nitrogen protecting group when attached to nitrogen, or a sulfur protecting group when attached to sulfur; and $R^{N3}$ is independently hydrogen, optionally substituted alkyl, or a nitrogen protecting group.

As generally defined herein, v is an integer from 1 to 99 inclusive. In certain embodiments, v is an integer from 1 to 90. In certain embodiments, v is an integer from 1 to 80. In certain embodiments, v is an integer from 1 to 70. In certain embodiments, v is an integer from 1 to 60. In certain embodiments, v is an integer from 1 to 50. In certain embodiments, v is an integer from 1 to 40. In certain embodiments, v is an integer from 1 to 30. In certain embodiments, v is an integer from 1 to 20. In certain embodiments, v is an integer from 1 to 10. In certain embodiments, v is an integer from 10 to 99. In certain embodiments, v is an integer from 10 to 20. In certain embodiments, v is an integer from 10 to 30. In certain embodiments, v is an integer from 20 to 30. In certain embodiments, v is an integer from 20 to 40. In certain embodiments, v is an integer from 30 to 50. In certain embodiments, v is an integer from 40 to 60. In certain embodiments, v is an integer from 50 to 70. In certain embodiments, v is an integer from 60 to 80. In certain embodiments, v is an integer from 70 to 90. In certain embodiments, v is an integer from 80 to 99.

As generally defined herein, u is 0, 1, 2, 3, 4, or 5. In certain embodiments, u is 0. In certain embodiments, u is 1. In certain embodiments, u is 2. In certain embodiments, u is 3. In certain embodiments, u is 4. In certain embodiments, u is 5.

As generally defined herein, each occurrence of $R^E$ is independently halogen, —CN, —NO$_2$, —N$_3$, optionally substituted alkyl, optionally substituted alkenyl, optionally substituted alkynyl, optionally substituted carbocyclyl, optionally substituted phenyl, optionally substituted heterocyclyl, optionally substituted heteroaryl, —OR$^{CE}$, —N(R$^{CE}$)$_2$, —SR$^{CE}$, —C(=O)R$^{CE}$, —C(=O)OR$^{CE}$, or —C(=O)N(R$^{CE}$)$_2$, wherein each $R^{CE}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl; or an oxygen protecting group when attached to an oxygen, or a nitrogen protecting group when attached to nitrogen, or a sulfur protecting group when attached to sulfur. In certain embodiments, $R^E$ is halogen. In certain embodiments, $R^E$ is F. In certain embodiments, $R^E$ is Cl. In certain embodiments, $R^E$ is Br. In certain embodiments, $R^E$ is I. In certain embodiments, $R^E$ is an optionally substituted alkyl. In certain embodiments, $R^E$ is an optionally substituted $C_{1-6}$ alkyl. In certain embodiments, $R^E$ is an unsubstituted $C_{1-6}$ alkyl. In certain embodiments, $R^E$ is methyl, ethyl, or propyl.

In certain embodiments, u is 1 and $R^E$ is an optionally substituted $C_{1-6}$ alkyl. In certain embodiments, u is 1 and $R^E$ is unsubstituted $C_{1-6}$ alkyl. In certain embodiments, u is 1 and $R^E$ is methyl, ethyl, or propyl.

As generally defined herein, $R^{N3}$ is independently hydrogen, optionally substituted alkyl, acyl, or a nitrogen protecting group. In some embodiments, $R^{N3}$ is hydrogen. In some embodiments, $R^{N3}$ is optionally substituted $C_{1-6}$ alkyl. In certain embodiments, $R^{N3}$ is methyl. In certain embodiments, $R^{N3}$ is ethyl. In certain embodiments, $R^{N3}$ is propyl. In certain embodiments, $R^{N3}$ is acetyl. In certain embodiments, $R^{N3}$ is a nitrogen protecting group. In certain embodiments, $R^{N3}$ is acyl. In certain embodiments, $R^{N3}$ is Bn, BOC, Cbz, Troc, Fmoc, trifluoroacetyl, triphenylmethyl, or Ts.

The glycosylation reaction is carried out in the present of NIS/TfOH, NIS/AgOTf, NIS/TMSOTf, or NIS/BF$_3$—OEt$_2$. In certain embodiments, the glycosylation reaction is carried out in the present of NIS/TfOH.

In certain embodiments, the method of preparing a glycan conjugate described herein further comprises reacting the compound of Formula (C-5) in the presence of a base to give a compound of Formula (C-6)

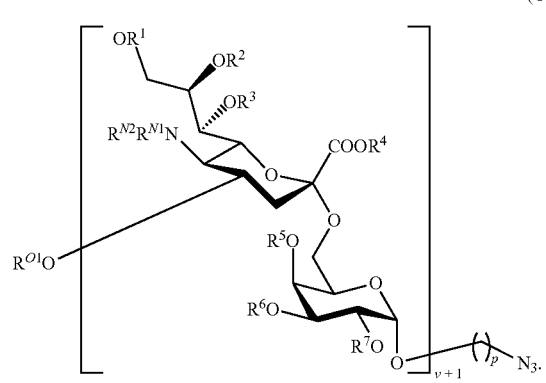
(C-6)

In some embodiments, the base used in the reaction may be an inorganic base such as sodium hydroxide, potassium hydroxide, sodium carbonate, sodium hydrogencarbonate, potassium carbonate, potassium hydrogencarbonate and the like. In some embodiments, the base is NaOMe. In certain embodiments, the Zemplen condition is adopted including NaOMe in the presence of MeOH. It is to be understood the condition can be modified to other suitable base and organic solvent.

In certain embodiments, the method of preparing a glycan conjugate described herein further comprises reacting the compound of Formula (C-6) with a reducing agent to give a compound of Formula (C-7)

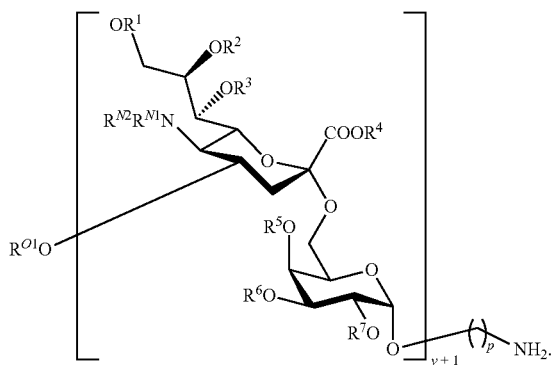
(C-7)

In certain embodiments, the reducing agent is any agent providing hydrogen to the compound in the reaction. In certain embodiments, the reducing agent is $BF_3 \cdot OEt_2$, $H_2$, organo silane with Si—H bond (e.g. $(TMS)_3SiH$ or $Et_3SiH$). In certain embodiments, the reducing agent is $BF_3 \cdot OEt_2$.

A method of preparing a glycan conjugate described herein may comprise reacting (a) activating a compound of Formula (C-7) to give a compound of Formula (C-1); and (b) activating a carrier to give a compound of Formula (C-2).

In certain embodiments, the activating agent for the compound of Formula (C-7) is a compound of Formula (C-8)

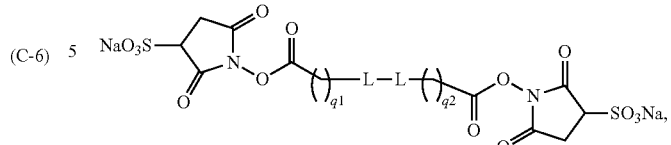
(C-8)

wherein each of q1 and q2 is independently an integer of 1 to 5, inclusive; and L is —S—. In certain embodiments, q1 and q2 are 1. In certain embodiments, q1 and q2 are 2. In certain embodiments, the activating reaction is carried out under pH from about 6.0 to 9.0. In certain embodiments, the activating reaction is carried out under pH from about 6.0 to 8.0. In certain embodiments, the activating reaction is carried out under pH from about 7.0 to 9.0. In certain embodiments, the activating reaction is carried out under pH from about 7.5 to 8.0. In certain embodiments, the activating reaction is carried out under pH from about 7.0 to 7.5. In certain embodiments, the activating reaction is carried out in the presence of a buffer. In certain embodiments, the activating reaction is carried out in the presence of phosphate buffered saline (PBS).

In certain embodiments, the activating agent for the carrier is a compound of Formula (C-9)

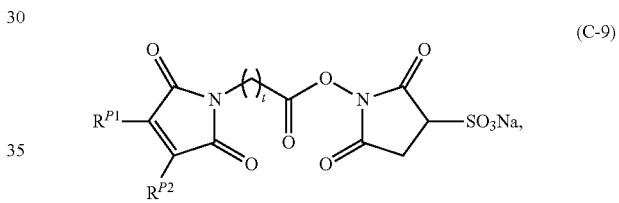
(C-9)

wherein t is as defined herein. In certain embodiments, t is 3. In certain embodiments, t is 4. In certain embodiments, t is 5. In certain embodiments, t is 6. In certain embodiments, t is 7. In certain embodiments, the activating reaction is carried out under pH from about 6.0 to 9.0. In certain embodiments, the activating reaction is carried out under pH from about 6.0 to 8.0. In certain embodiments, the activating reaction is carried out under pH from about 7.0 to 9.0. In certain embodiments, the activating reaction is carried out under pH from about 7.5 to 8.0. In certain embodiments, the activating reaction is carried out under pH from about 7.0 to 7.5. In certain embodiments, the activating reaction is carried out in the presence of a buffer. In certain embodiments, the activating reaction is carried out in the presence of phosphate buffered saline (PBS).

As used herein, an activating reagent denotes a reagent which can react with one of the starting materials of a chemical reaction to form one or more active intermediate which subsequently facilitates the completion of the reaction. The active intermediate may not be stable enough to be separated and characterized. Examples of the activating reagent include, but are not limited to the coupling reagents used in amide/peptide synthesis, such as carbodiimide compound (EDC, DCC, DIC, and the like) and benzotriazole compounds (such as HOBt and HOAt); certain oxides and chloride (such as $P_2O_5$ and $POCl_3$); a reagent which react with a molecule to form a leaving group (such as MsCl, $Tf_2O$, and reagents for Mitsunobu reaction); and etc. In certain embodiments, the activating reagent is 3,3'-Dithiobis (sulfosuccinimidyl propionate) (DTSSP) and/or N-[ε-maleimidocaproyloxy]sulfosuccinimide ester) (sulfo-EMCS).

It is to be understood that a compound of Formula (F-1) can also be prepared following the general procedure of preparing a compound of Formulae (C-5), (C-6), and (C-3) as described above.

Immunogenic Compositions

The present invention provides immunogenic compositions comprising a glycan conjugate described herein and a pharmaceutically acceptable excipient. In certain embodiments, the provided immunogenic composition further comprise an adjuvant. Such immunogenic compositions can be used to elicit desired immune responses, such as immune responses specific to the glycan conjugate, particularly the glycan moiety in the conjugate. In certain embodiments, a provided composition comprises two or more glycan conjugates described herein.

The immunogenic compositions described herein can be prepared by any method known in the art of pharmacology, for example, as described in U.S. Pat. Nos. 4,601,903; 4,599,231; 4,599,230; and 4,596,792, all of which are incorporated by reference herein. In general, such preparatory methods include the steps of bringing an the glycan conjugate described herein into association with an adjuvant and/or a pharmaceutically acceptable excipient and/or one or more other accessory ingredients, and then, if necessary and/or desirable, shaping and/or packaging the product into a desired single- or multi-dose unit.

The immunogenic compositions disclosed herein can be included in a pharmaceutical or nutraceutical composition together with additional active agents, carriers, vehicles, excipients, or auxiliary agents identifiable by a person skilled in the art upon reading of the present disclosure.

The immunogenic compositions described herein may further comprise an adjuvant. An adjuvant is an agent that modifies the immunogenicity of the glycan conjugate in the composition. Adjuvant typically does not elicit immune responses specific to itself but modulates (e.g., enhances) immune responses specific to a given immunogenic agent (an antigen). Adjuvant can be inorganic or organic chemical, macromolecule or whole cells of certain killed bacteria which enhance the immune response to a given antigen.

The immunogenic compositions described herein may further comprises an adjuvant. An adjuvant is an agent that modifies the immunogenicity of the glycan conjugate in the composition. Adjuvant typically does not elicit immune responses specific to it but enhances immune responses specific to a given immunogenic agent (an antigen). Adjuvant can be inorganic or organic chemical, macromolecule or whole cells of certain killed bacteria which enhance the immune response to a given antigen. In certain embodiments, the adjuvant is a mineral salt/gel, e.g., aluminium hydroxide and aluminium or calcium phosphate gels. In certain embodiments, the adjuvant is an oil-in water and water-in-oil emulsion, amphiphilic molecule and surfactant based formulation, e.g., MF59 (microfluidised detergent stabilised oil-in-water emulsion), QS-21 (purified saponin, which is plant-derived), AS03 (consisting of an oil-in-water emulsion plus alpha-tocopherol), Montanide ISA-51, and Montanide ISA-720. In certain embodiments, the adjuvant is liposome, virosome (unilamellar liposomal vehicles incorporating influenza haemagglutinin), ISCOMS (structured complex of saponins and lipids), and polylactide co-glycolide (PLG), PLG-Dimethylaminoethane-carbamoyl-Cholesterol (PLGA/DC-cholesterol) particles, and Iscomatrix. In certain embodiments, the adjuvant is aicrobial derivative (natural and synthetic), e.g., monophosphoryl lipid A (MPL), Detox (MPL+M. Phlei cell wall skeleton), AGP [RC-529] (synthetic acylated monosaccharide), DC_Chol (lipoidal immunostimulators able to self-organise into liposomes), OM-174 (lipid A derivative), CpG motifs (synthetic oligodeoxynucleotides containing immunostimulatory CpG motifs), modified heat labile enterotoxin (LT) and cholera toxin (CT) (genetically modified bacterial toxins that have been genetically modified to provide non-toxic adjuvant effects); synthetic dsRNA, Poly IC:LC (Hiltonol) and Poly I: Poly C12U (Ampligen®). In certain embodiments, the adjuvant is an endogenous human immunostimulator, e.g., hGM-CSF or hIL-12 (cytokines that can be administered either as protein or plasmid encoded), Immudaptin (C3d tandem array). In certain embodiments, the adjuvant is an inert vehicles, e.g., gold particle. In certain embodiments, the adjuvant is an inert polysaccharides, e.g., Advax (delta-inulin), derived from plants (dahlias). In certain embodiments, combination adjuvants or adjuvant systems can used in the immunogenic compositions described herein, for example, combinations of vaccine delivery systems and immunostimulatory agents. Combination adjuvants or adjuvant systems may result in more effective delivery of the immunostimulatory adjuvant as well as the antigen, e.g., AS01 consisting of liposomes, MPL, and QS-21; AS02 consisting of an oil-in-water emulsion plus MPL and QS-21; AS03 consisting of an oil-in-water emulsion plus alpha-tocopherol; AS04 consisting of MPL and aluminum hydroxide; AS15 consisting of liposomes, MPL, QS-21 and a CpG oligodeoxynucleotide; and GLA-SE consisting of a synthetic acylated monosaccharide in a stable oil in-water emulsion.

In some embodiments, the adjuvant used in the immunogenic compositions described herein is C34, 7DW8-5, C17, C23, C30, α-galactoceramide, Aluminum salt, Squalene, MF59, or QS-21 (see U.S. Pat. No. 8,268,969 and U.S. Publication No. 2008-0260774, both of which are incorporated into reference in the present application).

Pharmaceutically acceptable excipients include any and all solvents, diluents, or other liquid vehicles, dispersions, suspension aids, surface active agents, isotonic agents, thickening or emulsifying agents, preservatives, solid binders, lubricants, and the like, as suited to the particular dosage form desired. General considerations in formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21st Edition (Lippincott Williams & Wilkins, 2005).

In certain embodiments, the immunogenic compositions described herein can be prepared, packaged, and/or sold in bulk, as a single unit dose, and/or as a plurality of single unit doses. As used herein, a "unit dose" is discrete amount of the immunogenic compositions described herein comprising a predetermined amount of the glycan conjugate described herein.

Relative amounts of the glycan conjugate, the pharmaceutically acceptable excipient, and/or any additional ingredients in a immunogenic compositions described herein will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided immunogenic compositions described herein include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60], sorbitan tristearate (Span 65), glyceryl monooleate, sorbitan monooleate (Span 80)), polyoxyethylene esters (e.g., polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g., Cremophor™), polyoxyethylene ethers, (e.g., polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F68, Poloxamer 188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the glycan conjugates of the invention are mixed with solubilizing agents such as Cremophor™, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Compositions for rectal or vaginal administration are typically suppositories which can be prepared by mixing the glycan conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The glycan conjugates can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets, and pills, the dosage forms may comprise buffering agents. They may optionally comprise opacifying agents and can be of a composition that they release the glycan conjugates only, or preferentially, in a certain part of the intestinal tract, optionally, in a delayed manner. Examples of embedding compositions which can be used include polymeric substances and waxes.

Dosage forms for topical and/or transdermal administration of immunogenic compositions described herein may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as can be required.

Suitable devices for use in delivering intradermal immunogenic compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599, 302; 5,334,144; 5,993,412; 5,649,912; 5,569,189; 5,704, 911; 5,383,851; 5,893,397; 5,466,220; 5,339,163; 5,312, 335; 5,503,627; 5,064,413; 5,520,639; 4,596,556; 4,790, 824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) of the glycan conjugates described herein, although the concentration of the glycan conjugates can be as high as the solubility limit of the active ingredient in the solvent. Formulations for topical administration may further comprise one or more of the additional ingredients described herein.

Immunogenic compositions described herein of the invention can be prepared, packaged, and/or sold in a formulation suitable for pulmonary administration via the buccal cavity. Such a formulation may comprise dry particles which comprise the glycan conjugates and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the glycan conjugates may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Immunogenic compositions described herein of the invention formulated for pulmonary delivery may provide the glycan conjugates in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Immunogenic compositions described herein can be useful for pulmonary delivery are useful for intranasal delivery of a immunogenic compositions described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) and as much as 100% (w/w) of the glycan conjugates provided herein, and may comprise one or more of the additional ingredients described herein. An immunogenic compositions described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

An immunogenic compositions described herein can be prepared, packaged, and/or sold in a formulation for ophthalmic administration. Such formulations may, for example, be in the form of eye drops including, for example, a 0.1/1.0% (w/w) solution and/or suspension of the glycan conjugate in an aqueous or oily liquid carrier. Such drops may further comprise buffering agents, salts, and/or one or more other of the additional ingredients described herein.

Although the descriptions of immunogenic compositions described herein are principally suitable for administration to humans, it will be understood by the skilled artisan that such compositions are generally suitable for administration to animals of all sorts. Modification of immunogenic compositions described herein suitable for administration to humans in order to render the compositions suitable for administration to various animals is well understood, and the ordinarily skilled veterinary pharmacologist can design and/or perform such modification with ordinary experimentation.

Immunogenic compositions described herein provided herein are typically formulated in dosage unit form for ease of administration and uniformity of dosage. It will be understood, however, that the total daily usage of the immunogenic compositions described herein will be decided by the attending physician within the scope of sound medical judgment. The quantity to be administered also depends on the subject to be treated, including, for example, the capacity of the individual's immune system to synthesize antibodies, and if needed, to produce a cell-mediated immune response. Suitable regimes for initial administration and booster doses are also variable, but may include an initial administration followed by subsequent administrations. The specific therapeutically effective dose level for any particular subject or organism will depend upon a variety of factors including the disease, disorder, or condition being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), and/or the condition of the subject (e.g., whether the subject is able to tolerate oral administration).

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

Also encompassed by the invention are kits (e.g., pharmaceutical packs) to treat or reduce the risk of bacterial infections. The kits provided may comprise an inventive pharmaceutical composition or compound and a container (e.g., a vial, ampule, bottle, syringe, and/or dispenser package, or other suitable container). The kits provided may comprise an additional therapeutically active agents include, but are not limited to, antibiotics, anti-viral agents, anesthetics, anti-coagulants, inhibitors of an enzyme, steroidal agents, steroidal or non-steroidal anti-inflammatory agents, antihistamine, immunosuppressant agents, antigens, vaccines, antibodies, decongestant, sedatives, opioids, pain-relieving agents, analgesics, anti-pyretics, hormones, and prostaglandins, etc. In some embodiments, provided kits may optionally further include a second container comprising a pharmaceutical excipient for dilution or suspension of an inventive pharmaceutical composition or compound. In some embodiments, the inventive pharmaceutical composition or compound provided in the container and the second container are combined to form one unit dosage form.

Uses of Glycan Conjugates Described Herein

The present invention provides glycan conjugates and immunogenic compositions comprising such for use in treating or reducing the risk of an infectious disease such as bacterial infection in a subject. In certain embodiments, a glycan conjugate population as described herein, either homogenous or heterogenous, is provided in an effective amount in the immunogenic composition. In certain embodiments, the effective amount is a therapeutically effective amount. In certain embodiments, the effective amount is a prophylactically effective amount. The glycan conjugates or immunogenic compositions described herein may be effective in treating the infection, delaying onset of the infection, or reducing the risk for the infection. In certain embodiments, the effective amount is an amount effective in eliciting immune responses specific to a bacterium, e.g., a bacterium from which the oligosaccharide antigen in the immunogenic composition is derived. In certain embodiments, the effective amount is therapeutically effective amount, for example, the amount is sufficient for inhibiting bacterial growth or alleviating a condition caused by the infection. In certain embodiments, the bacterium which is the causative agent of the infection is a Gram-negative bacterium. In certain embodiments, the bacterium is a Gram-positive bacterium. In certain embodiments, the bacterium is *N. meningitides*. In certain embodiments, the bacterium is *N. meningitides* serogroup W135.

The immunogenic compositions described herein can also be used to generate antibodies in human or animals for production of antibodies, which can be used in both treatment and diagnosis of the infectious disease. In some embodiments, the immunogenic compositions described herein can also be used to generate antibodies for production of *N. meningitidis* antibodies. In some embodiments, the immunogenic compositions described herein can also be used to generate antibodies for production of *N. meningitidis* serogroup W135 antibodies. Methods of making monoclonal and polyclonal antibodies and fragments thereof in human and/or animals (e.g., mouse, rabbit, goat, sheep, or horse) are well known in the art. See, for example, Harlow and Lane, (1988) Antibodies: A Laboratory Manual, Cold Spring Harbor Laboratory, New York. The term "antibody" includes intact immunoglobulin molecules as well as fragments thereof, such as Fab, F(ab').sub.2, Fv, scFv (single chain antibody), and dAb (domain antibody; Ward, et. al. (1989) Nature, 341, 544).

In some embodiments, the provided glycan conjugates, immunogenic compositions are useful in treating and/or reducing the risk of an infectious disease. In some embodiments, the provided glycan conjugates, immunogenic compositions thereof are useful to delay the onset of, slow the progression of, or ameliorate the symptoms of the infectious disease. In some embodiments, the provided glycan conjugates, immunogenic compositions are administered in combination with other compounds, drugs, or therapeutics to treat or reduce the risk of the infectious disease.

In yet another aspect, provided here is a method of treating or reducing the risk of a bacterial infection caused by bacteria that are resistant to other treatments. In certain embodiments, provided is a method of treating or reducing the risk of a bacterial infection caused by bacteria that are multi-drug tolerant. In certain embodiments, provided is a method of treating or preducing the risk of a bacterial infection caused by bacteria that are multi-drug resistant. In certain embodiments, provided is a method of treating or preducing the risk of a bacterial infection caused by bacteria that neither grow nor die in the presence other treatments. In certain embodiments, provided is a method of treating or preducing the risk of a bacterial infection caused by bacteria that neither grow nor die as a result of other treatments. In certain embodiments, provided methods can be conducted in vivo (i.e., by administration to a subject). For example, in certain embodiments, provided is a method of treating and/or reducing the risk of a bacterial infection. The method may comprise administering an effective amount of a glycan conjugate, immunogenic composition thereof as described herein to a subject with a bacterial infection or at risk of developing a bacterial infection.

In another aspect, the present invention provides a method of killing bacteria in a subject comprising administering an effective amount of glycan conjugate, immunogenic composition as described herein.

In certain embodiments, the bacterial infection being treated is an infection with a Gram positive bacterium. In certain embodiments, the Gram positive bacterium is a bacterium of the phylum Firmicutes. In certain embodiments, the bacteria is a member of the phylum Firmicutes and the genus *Enterococcus*, i.e., the bacterial infection is an *Enterococcus* infection. Exemplary Enterococci bacteria include, but are not limited to, *E. avium, E. durans, E. faecalis, E. faecium, E. gallinarum, E. solitarius, E. casseliflavus*, and *E. raffinosus*. In certain embodiments, the *Enterococcus* infection is an *E. faecalis* infection. In certain embodiments, the *Enterococcus* infection is an *E. faecium* infection.

In certain embodiments, the bacterial infection being treated is an infection with a Gram negative bacterium. In certain embodiments, the Gram negative bacteria species is selected from the group consisting of *Staphylococcus* sp., *Enterococcus* sp., *Escherichia coli, Bacillus* sp., *Salmonella* sp., *Mycobacterium* sp., and meningococcus. In certain embodiments, the Gram negative bacteria species is *N. meningitides*. In certain embodiments, the Gram negative bacteria species is *N. meningitides* serogroup W135.

In certain embodiments, the bacterial infection is resistant to other antibiotic therapy. For example, in certain embodiments, the bacterial infection is vancomycin resistant (VR). In certain embodiments, the bacterial infection is a vancomycin-resistant *E. faecalis* infection. In certain embodiments, the bacterial infection is a vancomycin-resistant *E. faecium* infection. In certain embodiments, the bacterial infection is vancomycin-resistant *Staphylococcus aureus* (VRSA). In certain embodiments, the bacterial infection is vancomycin-resistant Enterococci (VRE). In certain embodiments, the bacterial infection is a methicillin-resistant (MR). In certain embodiments, the bacterial infection is a methicillin-resistant *S. aureus* (MRSA) infection. In certain embodiments, the bacterial infection is methicillin-resistant *Staphylococcus epidermidis* (MRSE). In certain embodiments, the bacterial infection is penicillin-resistant *Streptococcus pneumonia*. In certain embodiments, the bacterial infection is quinolone-resistant *Staphylococcus aureus* (QRSA). In certain embodiments, the bacterial infection is multi-drug resistant *Mycobacterium tuberculosishas*.

To perform the treatment methods described herein, an effective amount of any of the glycan conjugates or immunogenic compositions described herein may be administered to a subject in need of the treatment via a suitable route, as described above. The subject, such as a human subject, can be a patient having an infectious disease (e.g., bacterial infection), suspected of having an infectious disease, or susceptible to an infectious disease. The amount of the glycan conjugate or immunogenic composition administered to the subject may be effective in eliciting immune responses specific to the glycan moiety in the conjugate or composition. In some embodiments, the amount of the glycan conjugate or immunogenic composition is sufficient to elicit immune responses leading to the inhibition of bacterial growth and/or reduction of bacteria population. In other embodiments, the amount of the glycan conjugate or immunogenic composition may be effective in delaying the onset of the infectious disease or reducing the risk for developing an infectious disease.

The exact amount of the provided glycan conjugates, immunogenic compositions required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount, protective amount, or immunogenic amount, of the provided glycan conjugates, immunogenic compositions for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the provided glycan conjugates, immunogenic compositions may be administered orally or parenterally at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of the provided glycan conjugates, immunogenic compositions to an adult. The amount to be administered to, for example, a child or an adolescent can be determined by a medical practitioner or person skilled in the art and can be lower or the same as that administered to an adult.

It will be also appreciated that the provided glycan conjugates, immunogenic compositions can be administered in combination with one or more additional therapeutically active agents. The provided glycan conjugates, immunogenic compositions can be administered in combination with additional therapeutically active agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The provided glycan conjugates, immunogenic compositions can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the inventive compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

In certain embodiments, the provided glycan conjugate or immunogenic composition is administered in combination with one or more additional therapeutically active agents described herein.

Exemplary additional therapeutically active agents include, but are not limited to, antibiotics, anti-viral agents, anesthetics, anti-coagulants, inhibitors of an enzyme, steroidal agents, steroidal or non-steroidal anti-inflammatory agents, antihistamine, immunosuppressant agents, antigens, vaccines, antibodies, decongestant, sedatives, opioids, pain-relieving agents, analgesics, anti-pyretics, hormones, and prostaglandins, etc. Therapeutically active agents include small organic molecules such as drug compounds (e.g., compounds approved by the US Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins and cells.

In certain embodiments, the additional therapeutically agent is an antibiotic. Exemplary antibiotics include, but are not limited to, penicillins (e.g., penicillin, amoxicillin), cephalosporins (e.g., cephalexin), macrolides (e.g., erythromycin, clarithormycin, azithromycin, troleandomycin), fluoroquinolones (e.g., ciprofloxacin, levofloxacin, ofloxacin), sulfonamides (e.g., co-trimoxazole, trimethoprim), tetracyclines (e.g., tetracycline, chlortetracycline, oxytetracycline, demeclocycline, methacycline, sancycline, doxycline, aureomycin, terramycin, minocycline, 6-deoxytetracycline, lymecycline, meclocycline, methacycline, rolitetracycline, and glycylcycline antibiotics (e.g., tigecycline)), aminoglycosides (e.g., gentamicin, tobramycin, paromomycin), aminocyclitol (e.g., spectinomycin), chloramphenicol, sparsomycin, quinupristin/dalfoprisin (Syndercid™). In certain embodiments, the additional additional therapeutically agent is third-generation cephalosporin antibiotics (i.e. cefotaxime, ceftriaxone) or rifampicin.

In certain embodiments, the subject being treated is a mammal. In certain embodiments, the subject is a human. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent, dog, or non-human primate. In certain embodiments, the subject is a non-human transgenic animal such as a transgenic mouse or transgenic pig.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

In order that the invention described herein may be more fully understood, the following examples are set forth. It should be understood that these examples are for illustrative purposes only and are not to be construed as limiting this invention in any manner.

All chemicals were from commercial sources in reagent grade and used without further purification. Ethyl acetate and hexane were purified by distillation, and water was Mill-Q-purified. Anhydrous dichloromethane ($CH_2Cl_2$) was also used without purification or distillation. All reactions were performed under argon atmosphere. Pulverized molecular sieves MS-4Å (Aldrich) for glycosylation was activated by heating at 350° C. for 3~6 hours. Reactions were monitored by thin-layer chromatography (TLC) analysis, which was performed on glass plates pre-coated with silica gel 60 F254 (0.25 mm, Merck). The TLC was detected by UV light (254 nm), p-anisaldehyde A, or ceric ammonium molybdate. The products were purified by flash chromatography with silica gel (Merck, 40-63 m size). $^1$H NMR and $^{13}$C NMR sprecta were recorded on Bruker AVANCE 600 (600 MHz) spectrometer at 25° C. Chemical shift on $^1$H NMR was assigned according to TMS ($\delta$=0 ppm, in $CDCl_3$), $CD_3OD$ ($\delta$=3.3 ppm), and $D_2O$ ($\delta$=4.8 ppm). Chemical shifts measurements are reported in delta ($\delta$) units, and splitting patterns are described as singlet (s), doublet (d), triplet (t), quartet (q), or multiplet (m). Coupling constants (J) are reported in Hertz (Hz). High resolution ESI mass spectra were recorded on a Bruker Daltonics or Brucker Bio-TOF III spectrameter. MALDI specta were recorded on Bruker Ultraflex II sepctrameter. To fabricating the microarray, amine-contained oligosaccharide were prepared by dissolving in the printing buffer (300 mM phosphate buffer, 0.005% Tween 20, pH 8.5) in 10 mM concentration. Microarrays were printed (BioDot; Cartesian Technologies) by robotic pin (SMP3; TeleChem International) deposition of ~0.6 nL of various solutions from 96-well plate onto NHS-coated glass slide (NexterionHslide; SCHOTTNorthAmerica). Alexa Fluor 647-conjugated goat anti-mouse IgG antibody, DyLight 649-conjugated goat anti-mouse IgM antibody, Alexa Fluor 488-conjugated goat anti-mouse IgG1 antibody, Alexa Flour 594-conjugated goat anti-mouse IgG2a antibody, Cy3-conjugated goat anti-mouse IgG2b antibody, Alexa Flour 488-conjugated anti-mouse IgG2c antibody, and Alexa Fluor 647-conjugated goat anti-mouse IgG3 antibody were purchased from Jackson ImmunoResearch. The micoarray slides were scanned at 635 nm, 594 nm, 532 nm, or 488 nm wavelength with a microarray fluorescence chip reader (ArrayWorx microarray reader). The fluorescence data were analyzed by GenePix Pro software (Axon Instruments).

Synthesis of Glycan Conjugates and Related Compounds
Synthesis of Sialic Acid Building Block.
The N-acetylated thioglycoside compound 2 was synthesized by the reported three steps method using the known thio sialoside compound 1 as a starting material. In order to increase α-stereoselectivity and yield of the following sialylation reaction, dibutyl phosphate group was introduced to replace thiophenyl group in the anomeric center of thioglycoside 2 at 0° C. under N-iodosuccinimide (NIS) and trifluoromethanesulfonic acid (TfOH) activation ovenight. Both α- and β-phosphate sialoside isomers were obtained in a 1/2 mixture in 82% yield (Scheme 1). The configuration of α and β sialyl phosphate (compound 3 and 4) was determined by NMR spectometer examination. $^3J(C_1—H_{3ax})$=5.7 Hz of compound 3 for α isomer, while $^3J(C_1—H_{3ax})$ coupling constant of the β phosphate sialoside (compound 4) was too small to be detected.

microarray, a 5-azido-pentanol linker was installed on the galactose anomeric position with α linkage by adopting thiol galactoside 6, which was reported to direct high α-selectivity as the result of steric effect by the 4,6-di-tert-butylsilylene (DTBS) protection group. Glycosylaion of compound 6 and 5-azido-1-pentanol under NIS/TfOH activation at −40° C. in $CH_2Cl_2$ for 1 hour gave galactoside 7 in 86% yield and only α form. The DTBS group was removed in the presence of TBAF in THF overnight to obtain compound 8 in 81% yield. Compound 9 was synthesized by sequentially 4,6-benzylidene protection and selective ring opening by borane.THF/TMSOTf in 72% yield after two steps (Scheme 2).

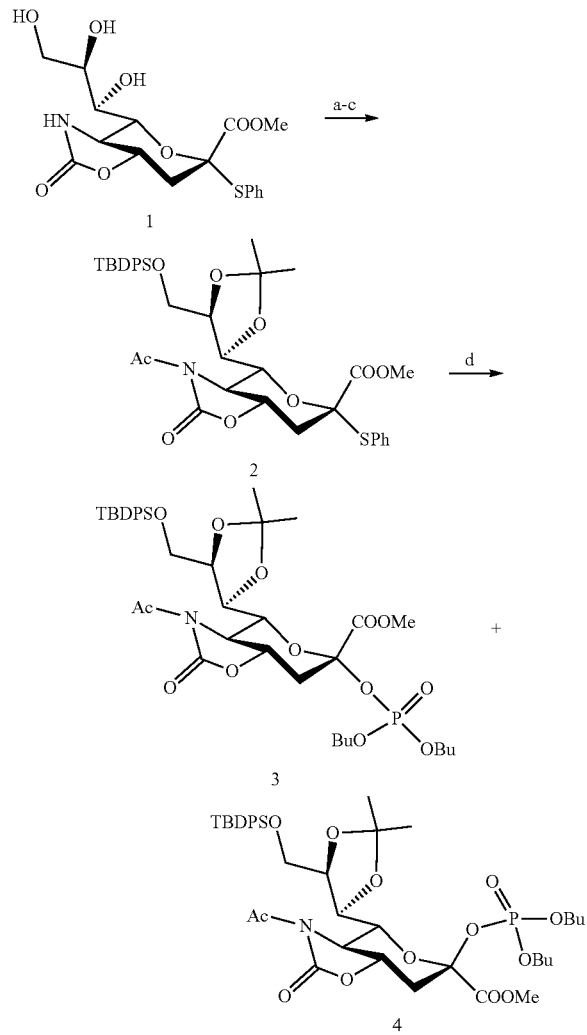

Scheme 1. Synthesis of sialic acid building block 3 and 4.

Reagent and conditions: a) TBDPSCl, Imidazole, DMF, r.t.; (b) DMP, CSA, $CH_2Cl_2$, r.t., 92%, two steps; (c) AcCl, DMAP, $CH_2Cl_2$, 0° C., 85%; (d) dibutyl phosphate, NIS, TfOH, $CH_2Cl_2$, 0° C., 82%, α:β = 1:2.

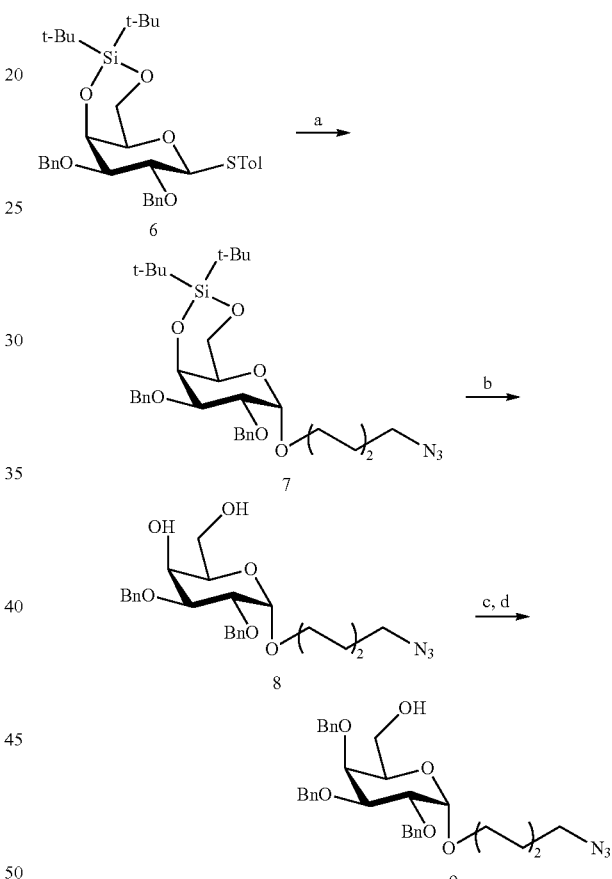

Scheme 2. Synthesis of galactose building block 9.

Reagent and conditions: a) 5-azidopentan-1-ol, NIS, TfOH, $CH_2Cl_2$, -40° C., 86%; b) TBAF, THF, r.t., 81%; c) BDA, CSA, DMF, r.t., quant.; d) $BF_3$·THF, TMSOTf, $CH_2Cl_2$, 0° C., 72%.

Synthesis of Galactose Building Block.

The 2,3,4-O-tribenzyl thiol galactoside compound 5 was synthesized by the reported method with a minor modification (H. Dohi, R. Perion, M. Durka, M. Bosco, Y. Roue, F. Moreau, S. Grizot, A. Ducruix, S. Escaich, S. P. Vincent, Chem-Eur J 2008, 14, 9530-9539). For the purpose of conjugation with carrier protein and immobilization on the Synthesis of Disaccharide Building Block.

The reactive condition of α- and β-phosphate sialoside with galactoside was explored. The α-phosphate sialoside (compound 3) reacted with compound 5 under the activation of TMSOTf in $CH_2Cl_2$ at −78° C. for 10 minutes to give a Neu5Ac-α-(2→6)-Gal disaccharide 10 as a single isomer in 92% yield (Scheme 3). The configuration of the disaccharide was examined by NMR spectrometer, and the new formed α-glycosidic bond was confirmed by $^3J(C_1—H_{3ax})$=5.7 Hz coupling constant. Although a previous report indicated that β-phosphate sialoside was less reactive than α-phosphate sialoside and required higher temperature for activation (C.

H. Hsu, K. C. Chu, Y. S. Lin, J. L. Han, Y. S. Peng, C. T. Ren, C. Y. Wu, C. H. Wong, Chem-Eur J 2008, 16, 1754-1760), it was found that using galactoside 5 as an acceptor, the β-phosphate sialoside 4 was fully activated even with temperature as low as −70° C. The α-isomer was also obtained as product 11 in 86% yield by using 3 as a donor and 9 as an acceptor (Scheme 3).

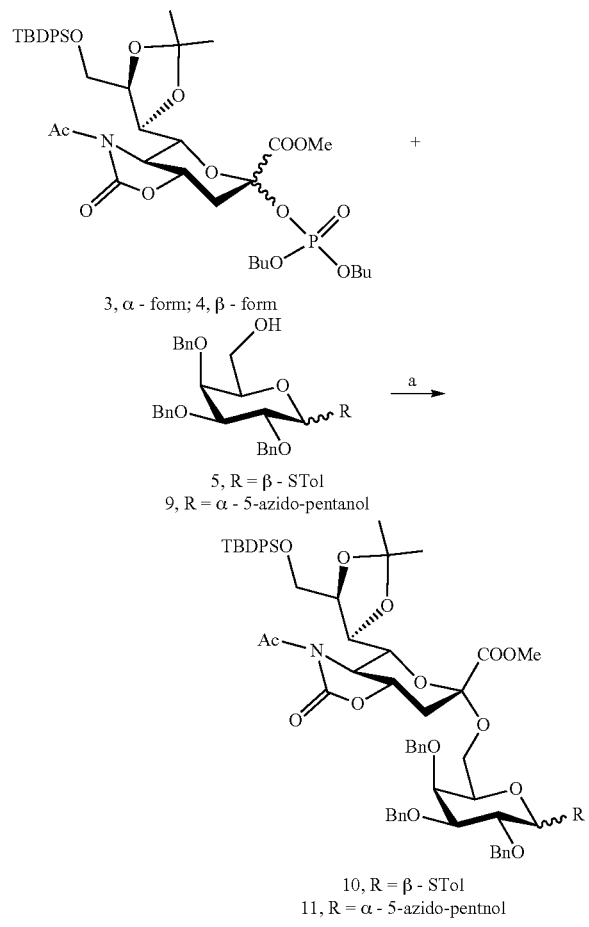

Scheme 3. Synthesis of disaccharide building block 10 and 11.

3, α - form; 4, β - form

5, R = β - STol
9, R = α - 5-azido-pentanol

10, R = β - STol
11, R = α - 5-azido-pentnol

Reagent and conditions: a) TMSOTf, CH₂Cl₂, -70° C., about 90%.

Oligosaccharide Elongation.

Figure 4:
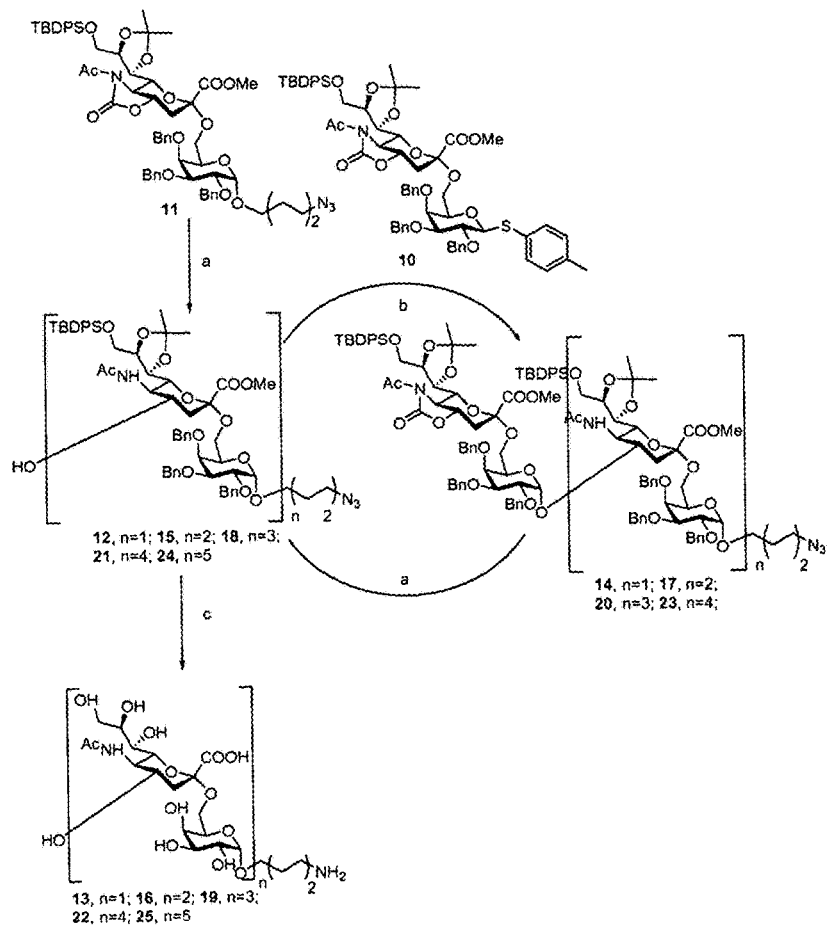
FIG. 4 shows synthesis of disaccharide to decasaccharide.

The oligosaccharide elongation was done via an iterative glycosylation and deprotectoin strategy by using the synthesize disaccharide 10 as a common donor for [2+n] glycosylation reaction to construct oligosaccharides up to decasaccharide. Compound 11 was used as a reducing end building block and selectively removed its oxazolidione ring under the Zemplén condition to obtain product 12 in 78% yield. Glycosylation of the disaccharide donor 10 and alcohol acceptor 12 in the presence of NIS/TfOH activation in CH₂Cl₂ at −40° C. for 1 hour gave fully protected tetrasaccharide 14 in 64% yield. Compound 14 was further undergone the Zemplén condition to open the oxazolidinoe ring to give tetrasaccharide acceptor 15 in 75% yield. The fully protected hexasaccharide 17 was synthesized by the [2+4] glycosylation using 10 and 15 with 52% yield and single stereoisomer. Repeating the oxazolidione ring opening and the same [2+n] glycosylation strategy, octasaccharide 20 and decasaccharide 23 were synthesized. But with the increasing length of the oligosaccharide, the yields decreased to 46% and 35%, respectively. These products are also obtained in single α isomer. The alcohol product of hexasaccharide 18, octasaccharide 21, and decasacchride 24 were obtained from the fully protected oligosacchride under the Zemplén condition in 70~80% yield (FIG. 4).

Finally, the total deprotected compounds can be obtained by global deprotection methods from the alcohol compounds of 12, 15, 18, 21 and 24. First, the TBDPS group and isopropylidene group of the alcohol compounds were removed in the presence of excess BF₃. OEt₂ at 0° C. for 3 hours owing to the fluoride and acidic property of BF₃. Then, the methyl ester group was removed under strong base NaOH in MeOH. Finally, all benzyl groups were removed through hydrogenation reaction under catalyst Pd(OH)₂ and H₂ in MeOH/H₂O. The final deprotected products 13, 16, 19, 22, and 25 can be obtained in 45%~60% yield over three steps (Scheme 4). Notably, the estimated coupling constant value of galactose anomeric proton was about 3~4 Hz. The small coupling constant confirmed that α-linked Gal-(1→4)-Neu5Ac oligosaccharide was obtained.

Carbohydrate-Protein Conjugation.

Many chemical approaches have been developed to cross-link carbohydrate and protein: (1) the Staudinger ligation employees a substituted phosphite to react with the azide-modified protein to form the carbohydrate-protein conjugation via the amide bond formation (C. Grandjean, A. Boutonnier, C. Guerreiro, J. M. Fournier, L. A. Mulard, J Org Chem 2005, 70, 7123-7132); (2) oxime conjugation introduces an aminooxy group on the protein to react with oligosaccharide containing aldehyde or keto group (J. Kubler-Kielb, V. Pozsgay, J Org Chem 2005, 70, 6987-6990); (3) frequently used Michael addition often uses thiol group addition to maleimide to form a stable thioester linkage (T. Masuko, A. Minami, N. Iwasaki, T. Majima, S. Nishimura, Y. C. Lee, Biomacromolecules 2005, 6, 880-884); and (4) recently, the method of copper (I)-catalyzed cycloaddition of azide to alkyens (click chemistry) provides efficient glycoconjugation (a) H. C. Kolb, M. G. Finn, K. B. Sharpless, Angew Chem Int Ed Engl 2001, 40, 2004-2021; b) S. Hotha, S. Kashyap, J Org Chem 2006, 71, 364-367). However, the triazole ring produces undesired immunogenicity. Thus, the thiol-maleimide coupling method was adopted for carbohydrate-protein conjugation for its high efficiency in sialic acid-rich compounds. 3,3-dithiobis sulfosuccinimidylpropionate (DTSSP) was allowed to react with the deprotected amino compounds 13, 16, 19, 22, and 25 in pH 7.4 PBS buffer overnight. The disulfide bond was cleaved in the present of dithiothreitol (DTT) at 40° C. for 1 hour to obtain the free thio products 32, 33, 34, 35, and 36 as Michael donors in 70~75% yield. To generate maleimide reactive group on the protein, CRM197 was reacted with sulfo-EMCS in pH 8.0 PBS buffer for 1 hour. The number of maleimide-linker on the protein was determined by MALDI-TOF mass spectrometer. In average, 20 maleimide linkers were coupled on diphtheria toxin mutant CRM197. Oligosaccharides were incorporated into carrier protein CRM197 by conjugating thiol modified oligosaccharide products 32, 33, 34, 35, and 36 and maleimide modified CRM197 in pH 7.4 PBS buffer for 1 hour (FIG. 5) to obtain the disaccharide- to decasaccharide-glycoconjugates DT-2, DT-4, DT-6, DT-8, and DT-10 with various carbohydrate epitope on DT. Again, the number of oligosaccharides conjugating to protein DT was determined by MALDI-TOF mass spectrometer (Table 1).

TABLE 1

The number of oligosaccharide conjugating to protein

| Conjugates | Average incorporation (n) |
|---|---|
| DT-2 | 5.7 |
| DT-4 | 4.9 |
| DT-6 | 2.9 |
| DT-8 | 2.8 |
| DT-10 | 3.1 |

Mean number of oligosaccharide coupled onto the carrier protein. The longer oligosaccharides have lower coupling number due to the structure effect.

Synthetic Procedures

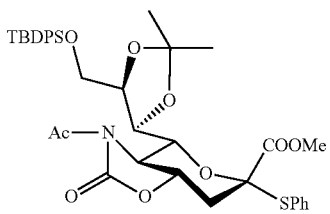

Methyl-(5-acetamino-9-O-tert-butyldiphenylsilyl-7,
8-O-isopropylidene-5-N,4-O-carbonyl-3,5-dideoxy-
2-thio-D-glycero-α-D-galacto-non-2-ulopyranoside)
onate (2)

A mixture of imidazole (1.36 g, 20.03 mmol) and compound 1 (4 g, 10.01 mmol) was dissolved in dry DMF (40 mL). The solution was cooled to 0° C., followed by adding tert-butylchlorodiphenylsilane (3.3 mL, 12.01 mmol). The reaction was stirred overnight at room temperature. After reaction, the solvent was removed under reduced pressure. The residue was diluted with EtOAc and washed with 1N $HCl_{(aq)}$, saturated $NaHCO_{3(aq)}$, and brine. The organic layer was dried over $MgSO_4$ and concentrated. Then, camphorsulfonic acid (2.32 g, 10.01 mmol) and 2,3-dimethoxypropane (40 mL) was added to the residue. The reaction was stirred at room temperature for 3 hours. After reaction, the solution was quenched with $Et_3N$ (2 mL, 15 mmol), and the solvent was removed under reduced pressure. The residue was purified by silica gel column chromatography (EtOAc/hexane=1/3). Purified compound (5 g, 7.37 mmol) was dissolved in $CH_2Cl_2$ (50 ml) and cooled to 0° C. N,N-Diisopropylethylamine (12.18 mL, 73.7 mmol) and acetyl chloride (4.21 mL, 59 mmol) was added sequentially and slowly at 0° C. Overnight, the reaction was stirred from 0° C. to room temperature. After reaction, the solution was washed with saturated $NaHCO_{3(aq)}$, and brine. The organic layer was dried over $MgSO_4$ and concentrated. The residue was purified by silica gel column chromatography (EtOAc/hexane=1/5) to give compound 2 (4.51 g, 85%): $^1$H NMR (600 MHz, $CDCl_3$) δ 7.69 (dd, J=8.2, 1.2 Hz, 2H), 7.62-7.55 (m, 4H), 7.43-7.36 (m, 2H), 7.35-7.27 (m, 5H), 7.27-7.21 (m, 2H), 4.98 (d, J=7.1 Hz, 1H), 4.36 (dd, J=12.9, 6.9 Hz, 1H), 4.18 (dd, J=10.8, 7.2 Hz, 1H), 4.10-3.96 (m, 3H), 3.83 (ddd, J=12.7, 11.2, 3.4 Hz, 1H), 3.27 (s, 3H), 3.16 (dd, J=11.8, 3.4 Hz, 1H), 2.49 (s, 3H), 2.14 (t, 1H), 1.77 (s, 3H), 1.43 (s, 3H), 1.00 (s, 9H). $^{13}$C NMR (150 MHz, $CDCl_3$) δ 172.43, 167.94, 153.85, 136.82, 135.59, 133.82, 133.76, 130.14, 129.65, 129.52, 128.68, 128.61, 127.63, 127.55, 109.76, 88.76, 78.32, 77.77, 76.93, 75.50, 61.96, 59.84, 52.44, 36.68, 26.78, 26.50, 25.86, 25.21, 19.18. HRMS (ESI-TOF) calcd. for $C_{38}H_{45}NO_9SSiNa$ $[M+Na]^+$: 742.2477, found: 742.2476.

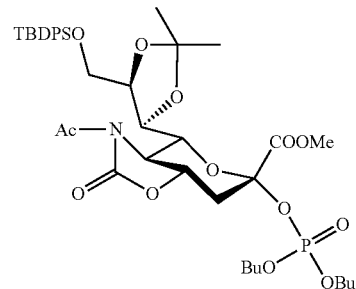

Methyl-(5-acetamino-9-O-tert-butyldiphenylsilyl-7,
8-O-isopropylidene-5-N,4-O-carbonyl-2-dibutyl-
phosphoryl-3,5-dideoxy-D-glycero-α-D-galacto-
non-2-ulopyranoside)onate (3, α form)

A mixture of compound 2 (3 g, 4.17 mmol), dibutyl phosphate (2.63 g, 12.5 mmol), and activated pulverized MS-4Å in dry $CH_2Cl_2$ (30 mL) was stirred at room temperature for 3 hours. The solution was cooled to 0° C. and sequentially added N-iodosuccinimide (1.8 g, 8.32 mmol) and 0.5M trifluoromethanesulfonic acid in ether (1.67 mL, 0.834 mmol). The reaction was stirred at 0° C. overnight. After reaction, the solution was filtered through celite. The filtrate was then quenched with 20% $Na_2S_2O_{3(aq)}$ and wash with saturated $NaHCO_{3(aq)}$ and brine. The organic layer was dried over $MgSO_4$ and concentrated. The residue was purified by silica gel column chromatography (EtOAc/hexane=1/5 to 1/3) to give compound 3 and 4 (2.80 g, 82%, α/β=1/2).

$^1$H NMR (600 MHz, $CDCl_3$) δ 7.76-7.62 (m, 4H), 7.48-7.30 (m, 6H), 4.93 (dd, J=7.1, 1.3 Hz, 1H), 4.42 (dd, J=9.2, 1.4 Hz, 1H), 4.32 (q, J=6.4 Hz, 1H), 4.18 (dd, J=10.9, 6.4 Hz, 1H), 4.16-4.09 (m, 2H), 4.09-3.96 (m, 5H), 3.64 (s, 3H), 3.10 (dd, J=11.9, 3.5 Hz, 1H), 2.49 (s, 3H), 2.35-2.26 (m, 1H), 1.68-1.58 (m, 4H), 1.50 (s, 3H), 1.42-1.32 (m, 7H), 1.04 (s, 9H), 0.91 (dt, J=15.9, 7.4 Hz, 6H). $^{13}$C NMR (150 MHz, $CDCl_3$) δ 172.49, 167.44, 154.00, 135.65, 135.62, 133.76, 133.61, 129.73, 129.66, 127.72, 127.68, 109.25, 98.63, 98.60, 77.58, 77.56, 76.39, 74.23, 68.35, 68.31, 67.94, 67.90, 62.57, 59.54, 53.13, 36.86, 32.07, 32.04, 26.85, 26.27, 25.48, 25.10, 19.23, 18.61, 18.58, 13.56. HRMS (ESI-TOF) calcd. for $C_{40}H_{58}NO_{13}PSiNa$ $[M+Na]^+$: 842.3307, found: 842.3351.

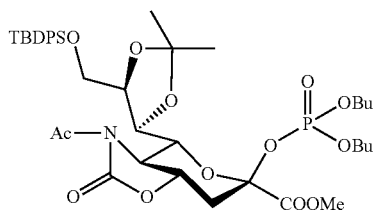

Methyl-(5-acetamino-9-O-tert-butyldiphenylsilyl-7,8-O-isopropylidene-5-N,4-O-carbonyl-2-dibutyl-phosphoryl-3,5-dideoxy-D-glycero-β-D-galacto-non-2-ulopyranoside)onate (4, β form)

$^1$H NMR (600 MHz, CDCl$_3$) δ 7.73-7.59 (m, 4H), 7.47-7.34 (m, 6H), 4.96 (d, J=7.6 Hz, 1H), 4.48 (ddd, J=12.9, 11.4, 3.6 Hz, 1H), 4.36 (d, J=9.4 Hz, 1H), 4.29 (dd, J=12.9, 6.9 Hz, 1H), 4.14-4.08 (m, 2H), 4.08-3.98 (m, 3H), 3.96-3.87 (m, 2H), 3.75 (s, 3H), 3.01 (dd, J=13.2, 3.6 Hz, 1H), 2.59 (t, J=13.1 Hz, 1H), 2.53 (s, 3H), 1.65-1.58 (m, 2H), 1.57-1.50 (m, 2H), 1.40-1.29 (m, 10H), 1.05 (d, J=5.6 Hz, 9H), 0.90 (dt, J=17.9, 7.4 Hz, 6H). $^{13}$C NMR (150 MHz, CDCl$_3$) δ 172.57, 165.38, 153.93, 135.54, 135.50, 133.57, 133.53, 129.80, 129.73, 127.78, 127.75, 109.48, 99.97, 99.95, 77.32, 76.38, 76.20, 74.52, 68.30, 68.26, 68.14, 68.10, 62.44, 59.49, 53.24, 35.02, 32.17, 32.12, 32.07, 26.86, 25.91, 25.66, 25.02, 19.27, 18.61, 18.58, 13.57, 13.52. HRMS (ESI-TOF) calcd. for C$_{40}$H$_{58}$NO$_{13}$PSiNa [M+Na]$^+$: 842.3307, found: 842.3351.

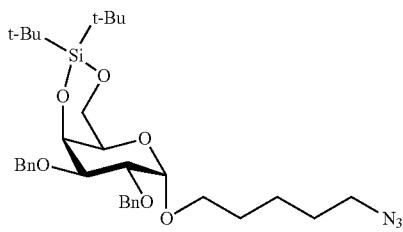

4,6-O-di-tert-butylsilanediyl-2,3-O-di-benzyl-1-O-(5-azidopenty)-α-D-galactopyranoside (7)

Compound 6 was synthesized as described. A mixture of compound 6 (5 g, 8.23 mmol), 5-azidopentan-1-ol (2.3 g, 16.46 mmol), and activated pulverized MS-4Å in dry CH$_2$Cl$_2$ (50 ml) was stirred at room temperature for 3 hours. The solution was cooled to 0° C., and N-iodosuccinimide (1.8 g, 16.46 mmol) was added. After that, the solution was cooled to −40° C., followed by adding 0.5 M trifluoromethanesulfonic acid in ether (4.9 mL, 2.47 mmol). The reaction was stirred at −40° C. for 1 hour. After reaction, Et$_3$N was added into the solution to quench the acid. The solution was warmed to room temperature and filtered through celite. The filtrate was then quenched with 20% Na$_2$S$_2$O$_{3(aq)}$ and washed with saturated NaHCO$_{3(aq)}$ and brine. The organic layer was dried over MgSO$_4$ and concentrated. The residue was purified by silica gel column chromatography (EtOAc/hexane=1/10) to give compound 7 (86%, 4.33 g)

$^1$H NMR (600 MHz, CDCl$_3$) δ 7.43 (d, J=7.5 Hz, 2H), 7.39-7.24 (m, 8H), 4.87 (d, J=11.9 Hz, 1H), 4.77-4.69 (m, 3H), 4.66 (d, J=11.9 Hz, 1H), 4.52 (d, J=2.8 Hz, 1H), 4.22 (dd, J=12.5, 2.0 Hz, 1H), 4.09 (dd, J=12.5, 1.6 Hz, 1H), 3.98 (dd, J=10.0, 3.7 Hz, 1H), 3.82 (dd, J=10.0, 3.0 Hz, 1H), 3.64-3.56 (m, 2H), 3.43 (dt, J=10.0, 6.4 Hz, 1H), 3.23 (t, J=6.9 Hz, 2H), 1.68-1.55 (m, 4H), 1.47-1.36 (m, 2H), 1.06 (s, 9H), 1.00 (s, 9H). $^{13}$C NMR (150 MHz, CDCl$_3$) δ 139.04, 138.73, 128.31, 128.17, 127.64, 127.60, 127.43, 98.04, 77.70, 74.37, 73.62, 71.17, 71.00, 67.86, 67.26, 51.33, 28.94, 28.67, 27.66, 27.31, 23.46, 23.43, 20.66. HRMS (ESI-TOF) calcd. for C$_{33}$H$_{49}$N$_3$O$_6$SiNa [M+Na]$^+$: 634.3283, found: 634.3245.

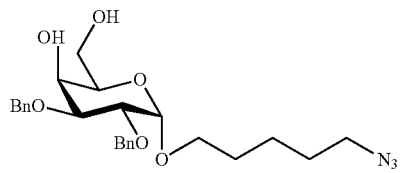

2,3-O-di-benzyl-1-O-(5-azidopenty)-α-D-galactopyranoside (8)

Compound 7 (4 g, 6.53 mmol) was dissolved in THF (40 mL), followed by adding 1M tetra-n-butylammonium fluoride (19.59 mL, 19.59 mmol). The reaction was stirred at room temperature overnight. The solvent was then removed under reduced pressure. The residue was purified by silica gel column chromatography (EtOAc/hexane=1/1) to give compound 8 (2.46 g, 81%): $^1$H NMR (600 MHz, CDCl$_3$) δ 7.39-7.27 (m, 10H), 4.84-4.78 (m, 3H), 4.70 (d, J=11.5 Hz, 1H), 4.64 (d, J=12.1 Hz, 1H), 4.08 (d, J=2.6 Hz, 1H), 3.93-3.87 (m, 2H), 3.85 (dd, J=9.8, 3.5 Hz, 1H), 3.82-3.74 (m, 2H), 3.66 (dt, J=9.9, 6.7 Hz, 1H), 3.42 (dt, J=9.9, 6.4 Hz, 1H), 3.25 (t, J=6.9 Hz, 2H), 1.71-1.58 (m, 4H), 1.50-1.39 (m, 2H). $^{13}$C NMR (150 MHz, CDCl$_3$) δ 138.44, 138.07, 128.54, 128.41, 127.96, 127.88, 127.82, 97.41, 77.38, 75.80, 73.31, 72.89, 69.10, 69.06, 67.94, 63.08, 51.33, 28.93, 28.66, 23.47. HRMS (ESI-TOF) calcd. for C$_{33}$H$_{49}$N$_3$O$_6$SiNa [M+Na]$^+$: 494.2262, found: 494.2273.

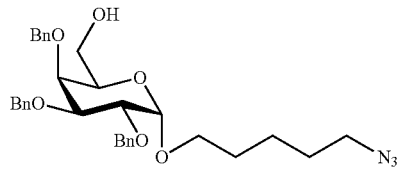

2,3,4-O-tri-benzyl-1-O-(5-azidopenty)-α-D-galactopyranoside (9)

A mixture of compound 8 (3 g, 6.36 mmol) and camphorsulfonic acid (1.47 g, 6.36 mmol) was dissolved in DMF (30 mL), followed by adding benzaldehyde dimethyl acetal (1.93 mL, 12.72 mmol). The reaction was stirred at room temperature for 3 hours. After reaction, the solution was diluted with EtOAc and washed with saturated NaHCO$_{3(aq)}$ twice and brine. The organic layer was dried over MgSO$_4$ and concentrated. The residue was purified by silica gel column chromatography (EtOAc/hexane=1/4). Purified compound (0.5 g, 0.89 mmol) was dissolved in CH$_2$Cl$_2$ (0.5 mL) and cooled to 0° C., followed by sequentially adding 1M borane. THF (3.57 mL, 3.57 mmol) and trimethylsilyl trifluoromethanesulfonate (80 µL, 0.36 mmol). The reaction was stirred at 0° C. for 3 hours. Et$_3$N and MeOH were then added into the solution to quench the reaction. (Notice: To avoid the explosive bubble, MeOH must be added slowly into the solution until the bubble no longer produced.) The solvent was removed under reduced pressure. The residue was purified by silica gel column chromatography (EtOAc/hexane=1/4) to give compound 9 (0.36 g, 72%): $^1$H NMR (600 MHz, CDCl$_3$) δ 7.44-7.26 (m, 15H), 4.97 (d, J=11.6 Hz, 1H), 4.89 (d, J=11.7 Hz, 1H), 4.83 (dd, J=7.9, 4.1 Hz, 2H), 4.76 (d, J=11.7 Hz, 1H), 4.67 (d, J=12.0 Hz, 1H), 4.64

(d, J=11.6 Hz, 1H), 4.05 (dd, J=10.1, 3.7 Hz, 2H), 3.95 (dd, J=10.1, 2.9 Hz, 1H), 3.90 (d, J=1.8 Hz, 1H), 3.75 (t, J=6.0 Hz, 1H), 3.70 (dd, J=11.2, 6.5 Hz, 1H), 3.63 (dt, J=9.8, 6.8 Hz, 1H), 3.48 (dd, J=11.2, 5.1 Hz, 1H), 3.42 (dt, J=9.9, 6.4 Hz, 1H), 3.23 (t, J=6.9 Hz, 2H), 1.69-1.57 (m, 4H), 1.47-1.37 (m, 2H). $^{13}$C NMR (150 MHz, CDCl$_3$) δ 138.78, 138.64, 138.20, 128.64, 128.51, 128.45, 128.37, 128.03, 127.93, 127.72, 127.61, 127.55, 97.63, 79.11, 76.69, 74.98, 74.47, 73.53, 73.38, 70.39, 67.92, 62.46, 51.35, 28.95, 28.66, 23.49. HRMS (ESI-TOF) calcd. for C$_{32}$H$_{39}$N$_3$O$_6$Na [M+Na]$^+$: 584.2731, found: 584.2741.

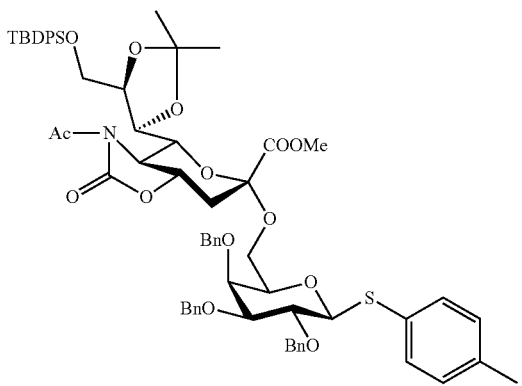

Methyl-(5-acetamino-9-O-tert-butyldiphenylsilyl-7,
8-O-isopropylidene-5-N,4-O-carbonyl-3,5-dideoxy-
2-O-(p-methylphenyl-2,3,4-tri-O-benzyl-deoxy-1-
thio-β-D-glucopyranoside)-D-glycero-α-D-galacto-
non-2-ulopyranoside)onate (10)

A mixture of compound 3 and 4 (1 g, 1.27 mmol, α/β mixture), compound 5 (0.47 g, 0.85 mmol), and activated pulverized MS-4Å in dry CH$_2$Cl$_2$ (10 mL) was stirred at room temperature for 3 hours. The solution was cooled to −70° C. and followed by adding trimethylsilyl trifluoromethanesulfonate (336 μL, 1.52 mmol). The reaction was stirred at −70° C. for 1 hour. Et$_3$N was added into the solution to quench reaction. The solution was filtered through celite. The filtrate was washed with saturated NaHCO$_{3(aq)}$ and brine. The organic layer was then dried over MgSO$_4$ and concentrated. The residue was purified by silica gel column chromatography (EtOAc/hexane=1/8) to give compound 10 (898 mg, 91%, a form): $^1$H NMR (600 MHz, CDCl$_3$) δ 7.75-7.64 (m, 4H), 7.47-7.22 (m, 23H), 6.99 (d, J=8.0 Hz, 2H), 4.98 (d, J=11.4 Hz, 1H), 4.94 (d, J=7.0 Hz, 1H), 4.80 (d, J=10.2 Hz, 1H), 4.75-4.68 (m, 3H), 4.63 (d, J=11.4 Hz, 1H), 4.54 (d, J=9.7 Hz, 1H), 4.41 (q, J=6.3 Hz, 1H), 4.24-4.14 (m, 3H), 4.11-4.04 (m, 1H), 3.95-3.82 (m, 4H), 3.57 (dd, J=9.2, 2.8 Hz, 1H), 3.50-3.44 (m, 2H), 3.30 (s, 3H), 2.84 (dd, J=12.0, 3.2 Hz, 1H), 2.50 (s, 3H), 2.27 (s, 3H), 1.97 (t, J=12.5 Hz, 1H), 1.37 (s, 3H), 1.36 (s, 3H), 1.02 (s, 9H). $^{13}$C NMR (150 MHz, CDCl$_3$) δ 172.52, 168.56, 154.11, 139.05, 138.37, 138.30, 137.00, 135.65, 133.74, 133.37, 131.83, 130.66, 129.74, 129.59, 128.39, 128.31, 128.12, 127.84, 127.68, 127.62, 127.43, 127.23, 109.40, 98.88, 88.55, 83.99, 78.04, 77.44, 77.11, 76.56, 76.16, 75.61, 74.57, 74.18, 73.04, 72.63, 62.32, 62.13, 59.69, 52.55, 36.86, 26.80, 26.07, 25.74, 25.12, 21.10, 19.16. HRMS (ESI-TOF) calcd. for C$_{66}$H$_{75}$NO$_{14}$SSiNa [M+Na]$^+$: 1188.4570, found: 1188.4586.

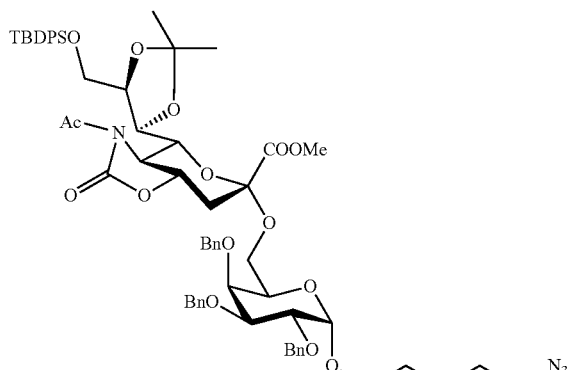

Methyl-(5-acetamino-9-O-tert-butyldiphenylsilyl-7,
8-O-isopropylidene-5-N,4-O-carbonyl-3,5-dideoxy-
2-O-(2,3,4-O-tri-benzyl-1-O-(5-azidopenty)-α-D-
galactopyranoside)-D-glycero-α-D-galacto-non-2-
ulopyranoside)onate (11)

A mixture of compound 3 and 4 (1 g, 1.26 mmol, a/p mixture), compound 9 (0.47 g, 0.84 mmol), and activated pulverized MS-4Å in dry CH$_2$Cl$_2$ (10 mL) was stirred at room temperature for 3 hours. The solution was cooled to −70° C., followed by adding trimethylsilyl trifluoromethanesulfonate (335 μL, 1.51 mmol). The reaction was stirred at −70° C. for 1 hour. Et$_3$N was added into the solution to quench reaction. The solution was filtered through celite. The filtrate was washed with saturated NaHCO$_{3(aq)}$ and brine. The organic layer was then dried over MgSO$_4$ and concentrated. The residue was purified by silica gel column chromatography (EtOAc/hexane=1/8) to give compound 11 (872 mg, 91%): $^1$H NMR (600 MHz, CDCl$_3$) δ 7.77-7.57 (m, 4H), 7.43-7.16 (m, 21H), 5.00-4.93 (m, 2H), 4.85-4.76 (m, 1H), 4.74 (d, J=11.7 Hz, 1H), 4.65 (d, J=12.0 Hz, 1H), 4.57 (d, J=11.2 Hz, 1H), 4.37 (q, J=6.3 Hz, 1H), 4.29-4.19 (m, 2H), 4.13 (dd, J=10.8, 6.2 Hz, 1H), 4.02 (dd, J=9.6, 3.7 Hz, 1H), 3.95-3.90 (m, 3H), 3.89-3.81 (m, 3H), 3.61 (dt, J=9.9, 6.7 Hz, 1H), 3.41 (t, J=8.3 Hz, 1H), 3.37-3.29 (m, 4H), 3.20 (t, J=6.9 Hz, 2H), 2.87 (dd, J=11.9, 3.3 Hz, 1H), 2.50 (s, 3H), 1.97 (dd, J=13.3, 12.0 Hz, 1H), 1.64-1.54 (m, 6H), 1.44 (s, 3H), 1.43-1.35 (m, 5H), 1.03 (s, 9H). $^{13}$C NMR (150 MHz, CDCl$_3$) δ 172.46, 168.52, 154.11, 139.07, 138.88, 138.70, 135.63, 133.73, 133.53, 129.73, 129.64, 128.31, 128.15, 127.87, 127.76, 127.67, 127.63, 127.54, 127.41, 127.35, 127.25, 109.32, 99.18, 97.49, 78.89, 77.96, 76.72, 76.55, 74.67, 74.47, 74.42, 73.25, 73.04, 68.32, 67.84, 62.65, 62.38, 59.71, 52.59, 51.30, 36.81, 28.86, 28.70, 26.83, 26.20, 25.84, 25.14, 23.39, 19.24. HRMS (ESI-TOF) calcd. for C$_{64}$H$_{78}$N$_4$O$_{15}$SiNa [M+Na]$^+$: 1193.5125, found: 1193.5151.

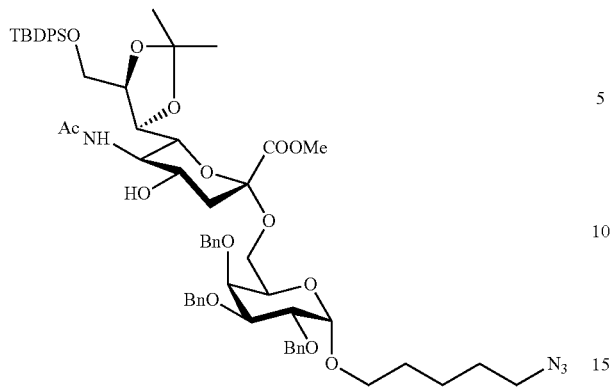
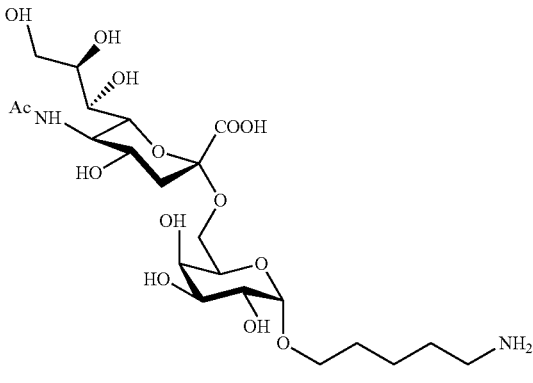

Methyl-(5-acetamino-9-O-tert-butyldiphenylsilyl-7,8-O-isopropylidene-3,5-dideoxy-2-O-(2,3,4-O-tri-benzyl-1-O-(5-azidopenty)-α-D-galactopyranoside)-D-glycero-α-D-galacto-non-2-ulopyranoside)onate (12)

5-O-acetamino-3,5-dideoxy-2-O-(1-O-(5-azidopenty)-α-D-galactopyranoside)-D-glycero-α-D-galacto-non-2-ulopyranosylonic acid (13)

Compound 11 (1 g, 0.85 mmol) was dissolved in $CH_2Cl_2$/MeOH (10 mL, 1:2), followed by adding 0.5M NaOMe in MeOH (1.7 mL, 0.85 mmol). The reaction was stirred at room temperature for 1 hour. IR-120 resin was then added into the solution to quench the reaction. The solvent was removed under reduced pressure, and the residue was purified by silica gel column chromatography (EtOAc/hexane=2/1) to give compound 12 (760 mg, 78%): $^1$H NMR (600 MHz, $CDCl_3$) δ 7.73-7.63 (m, 4H), 7.46-7.19 (m, 21H), 5.34 (d, J=8.0 Hz, 1H), 4.93 (d, J=11.3 Hz, 1H), 4.84-4.77 (m, 2H), 4.76 (d, J=3.6 Hz, 1H), 4.72 (d, J=11.7 Hz, 1H), 4.64 (d, J=12.0 Hz, 1H), 4.58 (d, J=11.3 Hz, 1H), 4.34-4.25 (m, 2H), 4.14-4.08 (m, 2H), 4.00 (dd, J=10.0, 3.6 Hz, 1H), 3.95-3.89 (m, 3H), 3.87-3.78 (m, 3H), 3.61-3.54 (m, 2H), 3.44-3.37 (m, 4H), 3.36-3.29 (m, 2H), 3.19 (t, J=7.0 Hz, 2H), 2.62 (dd, J=12.8, 4.4 Hz, 1H), 1.97 (s, 3H), 1.69 (t, J=12.4 Hz, 1H), 1.63-1.52 (m, 4H), 1.43-1.34 (m, 5H), 1.30 (s, 3H), 1.06 (s, 9H). $^{13}$C NMR (150 MHz, $CDCl_3$) δ 172.10, 168.65, 139.03, 138.91, 138.74, 135.62, 135.58, 133.53, 133.47, 129.88, 129.79, 128.30, 128.15, 127.88, 127.82, 127.76, 127.70, 127.59, 127.37, 127.26, 109.57, 98.79, 97.49, 78.83, 77.47, 76.55, 75.12, 74.59, 74.47, 73.24, 72.97, 72.58, 69.42, 68.64, 67.78, 62.62, 62.10, 53.90, 52.20, 51.30, 40.51, 28.85, 28.67, 26.94, 26.26, 25.83, 23.42, 23.38, 19.33. HRMS (ESI-TOF) calcd. for $C_{63}H_{80}N_4O_{14}SiNa$ $[M+Na]^+$: 1167.5333, found: 1167.5366.

Compound 12 (100 mg, 0.087 mmol) was dissolved in acetonitrile (2 ml) and cooled to 0° C., followed by adding 48% $BF_3$—$OEt_2$ (336 μL, 1.305 mmol). The reaction was stirred at 0° C. for 3 hours. The solution was washed with saturated $NaHCO_{3(aq)}$ and brine. The organic layer was then dried over $MgSO_4$ and concentrated. The residue was dissolved in MeOH, and 2~3 drops of concentrated NaOH in MeOH were added. The reaction was stirred at room temperature overnight. The solvent was removed under reduced pressure. The residue was purified by reverse phase column (MeOH/$H_2O$=1/1 to 4/1). The purified compound then proceeded through hydrogenation with PdOH as catalysis in MeOH/$H_2O$ under hi-pressure hydrogen at room temperature overnight. After reaction, the solution was filtered through celite and concentrated under reduced pressure. The residue was purified by Sephadex LH-20 to obtain compound 13 (31.4 mg, 65%, over three steps): $^1$H NMR (600 MHz, $D_2O$) δ 4.94 (d, J=3.5 Hz, 1H), 4.03 (dd, J=8.2, 3.9 Hz, 1H), 4.01-3.98 (m, 1H), 3.94-3.87 (m, 3H), 3.87-3.80 (m, 3H), 3.78-3.59 (m, 6H), 3.56 (dt, J=10.0, 6.2 Hz, 1H), 3.04 (t, J=7.5 Hz, 2H), 2.74 (dd, J=12.4, 4.7 Hz, 1H), 2.06 (s, 3H), 1.77-1.66 (m, 5H), 1.50 (dd, J=15.3, 7.7 Hz, 2H). $^{13}$C NMR (150 MHz, $D_2O$) δ 175.00, 173.38, 100.28, 98.32, 72.51, 71.74, 69.47, 69.35, 69.26, 68.20, 68.18, 68.14, 68.00, 63.75, 62.58, 51.83, 40.12, 39.41, 28.02, 26.56, 22.36, 21.99. HRMS (ESI-TOF) calcd. for $C_{22}H_{41}N_2O_{14}$ $[M+H]^+$: 557.2558, found: 557.2567.

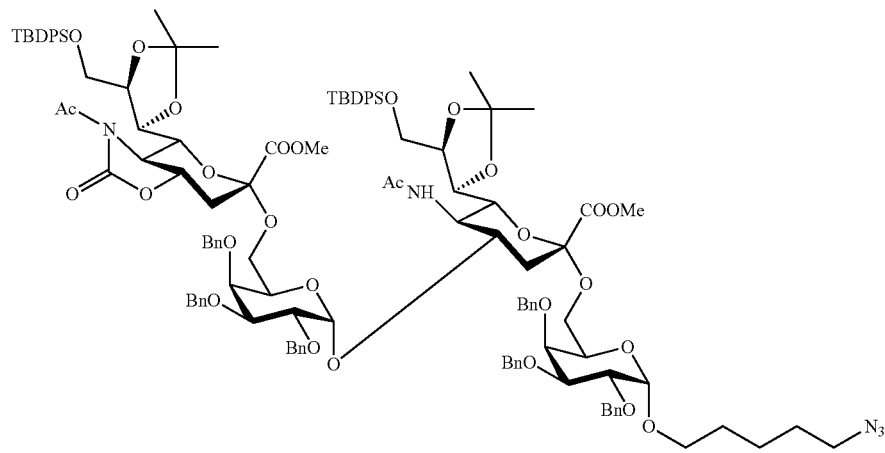

Methyl-(5-acetamino-9-O-tert-butyldiphenylsilyl-7, 8-O-isopropylidene-5-N,4-O-carbonyl-2-(2,3,4-O-tri-benzyl-1-O-(methyl-(5-acetamino-9-O-tert-butyl-diphenylsilyl-7,8-O-isopropylidene-3,5-dideoxy-2-O-(2,3,4-O-tri-benzyl-1-O-(5-azidopenty)-α-D-galactopyranoside)-D-glycero-α-D-galacto-non-2-ulopyranoside)onate)-α-D-galactopyranoside)-3,5-dideoxy-D-glycero-α-D-galacto-non-2-ulopyranoside)onate (14)

A mixture of compound 10 (458 mg, 0.39 mmol), compound 12 (300 mg, 0.26 mmol), and activated pulverized MS-4Å in dry $CH_2Cl_2$ (0.5 mL) was stirred at room temperature for 3 hours. The solution was cooled to 0° C., and N-iodosuccinimide (105 mg, 0.47 mmol) was added. After that, the solution was cooled to −40° C., followed by adding 0.5M trifluoromethanesulfonic acid in ether (0.52 mlL, 0.26 mmol). The reaction was stirred at −40° C. for 1 hour. After reaction, $Et_3N$ was added into the solution to quench the reaction. The solution was filtered through celite. The filtrate was then quenched with 20% $Na_2S_2O_{3(aq)}$ and wash with saturated $NaHCO_{3(aq)}$ and brine. The organic layer was dried over $MgSO_4$ and concentrated. The residue was purified by silica gel column chromatography (EtOAc/hexane=1/5 to 1/3) to give compound 14 (364 mg, 64%): $^1$H NMR (600 MHz, $CDCl_3$) δ 7.70-7.62 (m, 8H), 7.43-7.15 (m, 42H), 5.91 (d, J=7.5 Hz, 1H), 4.98 (d, J=7.0 Hz, 1H), 4.90 (d, J=11.1 Hz, 2H), 4.84-4.76 (m, 5H), 4.73 (d, J=11.7 Hz, 1H), 4.70-4.60 (m, 4H), 4.52 (dd, J=11.1, 6.9 Hz, 2H), 4.39 (dd, J=12.9, 6.6 Hz, 1H), 4.33-4.25 (m, 3H), 4.21-4.15 (m, 4H), 4.12 (d, J=6.6 Hz, 1H), 4.06 (dd, J=10.6, 5.9 Hz, 1H), 4.01 (dd, J=10.0, 3.6 Hz, 1H), 3.97-3.76 (m, 11H), 3.58 (dd, J=16.6, 6.7 Hz, 1H), 3.46 (s, 3H), 3.46-3.40 (m, 1H), 3.40-3.36 (m, 1H), 3.34-3.26 (m, 4H), 3.17 (t, J=7.0 Hz, 2H), 2.85 (d, J=9.0 Hz, 1H), 2.77 (dd, J=12.6, 4.5 Hz, 1H), 2.51 (s, 3H), 2.00 (t, J=12.3 Hz, 1H), 1.68 (s, 3H), 1.58-1.52 (m, 5H), 1.44 (s, 3H), 1.41 (s, 3H), 1.39 (s, 3H), 1.39-1.34 (m, 2H), 1.32-1.25 (m, 3H), 1.02 (s, 18H). $^{13}$C NMR (150 MHz, $CDCl_3$) δ 172.50, 171.03, 168.60, 168.34, 153.99, 139.05, 138.97, 138.79, 138.77, 138.56, 138.50, 135.66, 135.62, 135.58, 133.83, 133.74, 133.47, 133.40, 129.86, 129.80, 129.66, 129.60, 128.33, 128.30, 128.24, 128.13, 127.91, 127.87, 127.83, 127.76, 127.74, 127.71, 127.68, 127.58, 127.54, 127.48, 127.45, 127.40, 127.35, 127.32, 127.28, 109.48, 109.09, 99.11, 98.65, 97.45, 78.87, 78.72, 78.15, 77.90, 74.85, 74.77, 74.72, 74.67, 74.52, 74.10, 73.29, 73.20, 73.00, 72.85, 71.47, 69.35, 68.65, 67.75, 63.74, 62.65, 62.47, 61.61, 59.65, 54.37, 52.81, 52.05, 51.30, 39.19, 36.19, 28.86, 28.68, 26.86, 26.82, 26.34, 25.98, 25.60, 25.12, 23.93, 23.54, 23.39, 21.07, 19.27, 19.20, HRMS (MALDI-TOF) calcd. for $C_{122}H_{147}N_5O_{28}Si_2Na$ [M+Na]$^+$: 2208.9663, found: 2208.9660.

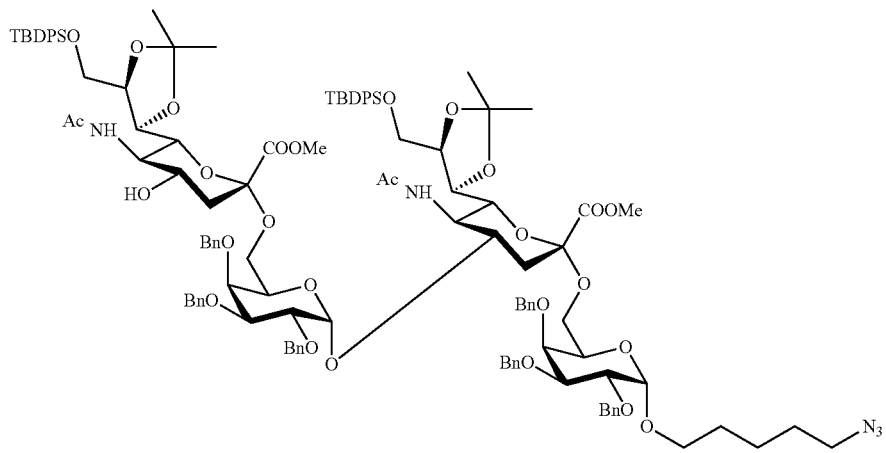

Methyl-(5-acetamino-9-O-tert-butyldiphenylsilyl-7,8-O-isopropylidene-2-(2,3,4-O-tri-benzyl-1-O-(methyl-(5-acetamino-9-O-tert-butyldiphenylsilyl-7,8-O-isopropylidene-3,5-dideoxy-2-O-(2,3,4-O-tri-benzyl-1-O-(5-azidopenty)-α-D-galactopyranoside)-D-glycero-α-D-galacto-non-2-ulopyranoside)onate)-α-D-galactopyranoside)-3,5-dideoxy-D-glycero-α-D-galacto-non-2-ulopyranoside)onate (15)

Compound 14 (100 mg, 46 μmol) was dissolved in $CH_2Cl_2$/MeOH (0.2 mL, 1:2), followed by adding 0.5M NaOMe in MeOH (92 ∝L, 46 μmol). The reaction was stirred at room temperature for 1 hour. IR-120 resin was then added into the solution to quench the reaction. The solvent was removed under reduced pressure, and the residue was purified by silica gel column chromatography (EtOAc/hexane=2/1) to give compound 15 (74.5 mg, 75%): $^1H$ NMR (600 MHz, $CDCl_3$) δ 7.71-7.61 (m, 8H), 7.44-7.16 (m, 42H), 5.96 (d, J=8.2 Hz, 1H), 5.72 (d, J=7.8 Hz, 1H), 4.89 (dd, J=22.6, 11.2 Hz, 2H), 4.84-4.70 (m, 7H), 4.69-4.62 (m, 2H), 4.52 (dd, J=19.9, 11.2 Hz, 2H), 4.30 (dt, J=12.5, 6.5 Hz, 2H), 4.22-4.11 (m, 5H), 4.06-3.90 (m, 9H), 3.88-3.69 (m, 8H), 3.66-3.56 (m, 2H), 3.47 (s, 3H), 3.45-3.39 (m, 2H), 3.35 (s, 3H), 3.33-3.27 (m, 3H), 3.17 (t, J=7.0 Hz, 2H), 2.69 (dd, J=12.7, 4.5 Hz, 1H), 2.51 (dd, J=13.2, 4.5 Hz, 1H), 1.91 (s, 3H), 1.81 (s, 3H), 1.60-1.54 (m, 5H), 1.42 (s, 3H), 1.40-1.36 (m, 2H), 1.35 (s, 3H), 1.32-1.24 (m, 8H), 1.06 (s, 9H), 1.03 (s, 9H). $^{13}C$ NMR (150 MHz, $CDCl_3$) δ 171.79, 170.96, 168.72, 168.58, 139.09, 138.95, 138.80, 138.77, 138.57, 138.44, 135.62, 135.59, 135.52, 133.82, 133.65, 133.28, 133.14, 130.00, 129.96, 129.71, 129.62, 128.34, 128.30, 128.28, 128.16, 128.13, 127.87, 127.84, 127.78, 127.74, 127.70, 127.57, 127.50, 127.45, 127.42, 127.36, 127.32, 127.26, 109.27, 109.19, 98.77, 98.62, 97.45, 97.34, 78.84, 78.78, 77.87, 77.41, 76.58, 76.36, 75.28, 75.09, 74.87, 74.70, 74.39, 73.51, 73.44, 73.19, 73.05, 72.87, 72.34, 71.88, 69.81, 69.19, 68.59, 67.74, 63.61, 62.85, 62.68, 61.60, 54.62, 52.37, 52.12, 51.30, 39.16, 38.54, 28.85, 28.68, 26.97, 26.94, 26.86, 26.64, 26.29, 26.02, 25.41, 23.57, 23.38, 23.34, 19.31, 19.24. HRMS (MALDI-TOF) calcd. for $C_{121}H_{149}N_5O_{27}Si_2Na$ [M+Na]$^+$: 2182.9817, found: 2182.9830.

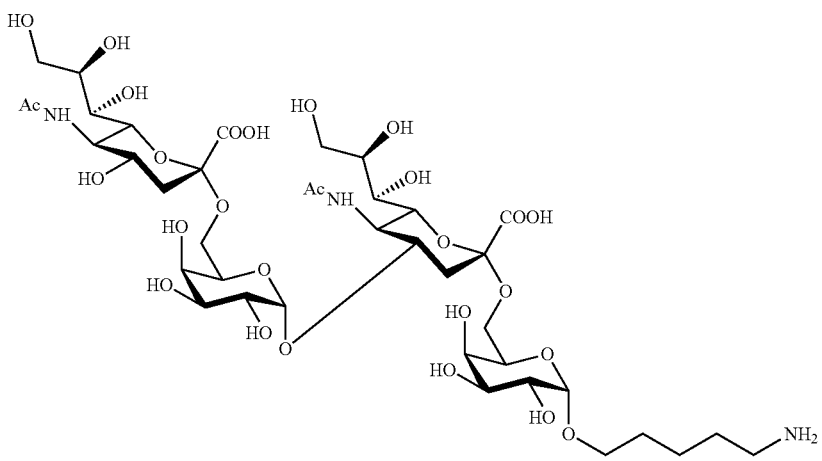

5-O-acetamino-3,5-dideoxy-2-O-(1-O-(5-O-acetamino-3,5-dideoxy-2-O-(1-O-(5-aminopenty)-α-D-galactopyranoside)-D-glycero-α-D-galacto-non-2-ulopyranosylonate)-α-D-galactopyranoside)-D-glycero-α-D-galacto-non-2-ulopyranosylonic acid (16)

Compound 15 (100 mg, 0.046 mmol) was dissolved in acetonitrile (2 mL) cooled to 0° C., followed by adding 48% $BF_3.OEt_2$ (178 μL, 0.69 mmol). The reaction was stirred at 0° C. for 3 hours. The solution was washed with saturated NaHCO$_{3(aq)}$ and brine. The organic layer was then dried over MgSO$_4$ and concentrated. The residue was dissolved in MeOH, and 2~3 drops of concentrated NaOH in MeOH were added. The reaction was stirred at room temperature overnight. The solvent was removed under reduced pressure. The residue was purified by reverse phase column (MeOH/H$_2$O=1/1 to 4/1). The purified compound then proceeded through hydrogenation with PdOH as catalysis in MeOH/H$_2$O under hi-pressure hydrogen at room temperature overnight. After reaction, the solution was filtered through celite and concentrated under reduced pressure. The residue was purified by Sephadex LH-20 to obtain compound 16 (23.2 mg, 50%, over three steps): $^1$H NMR (600 MHz, D$_2$O) δ 5.09 (d, J=3.8 Hz, 1H), 4.93 (d, J=3.5 Hz, 1H), 4.09-3.96 (m, 4H), 3.94-3.61 (m, 21H), 3.60-3.54 (m, 2H), 3.03 (t, J=7.5 Hz, 2H), 2.90 (dd, J=12.4, 4.6 Hz, 1H), 2.74 (dd, J=12.4, 4.7 Hz, 1H), 2.09 (s, 3H), 2.04 (s, 3H), 1.77-1.60 (m, 6H), 1.51-1.40 (m, 2H). $^{13}$C NMR (150 MHz, D$_2$O) δ 174.97, 174.48, 173.45, 172.96, 100.29, 100.08, 98.37, 94.26, 72.45, 72.34, 72.07, 71.88, 71.86, 69.58, 69.55, 69.37, 69.35, 69.23, 68.89, 68.35, 68.27, 68.15, 68.07, 67.87, 63.92, 62.68, 62.61, 51.79, 49.43, 40.09, 39.43, 36.36, 28.06, 26.41, 22.40, 22.37, 22.01. HRMS (ESI-TOF) calcd. for C$_{39}$H$_{66}$N$_3$O$_{27}$ [M–H]$^-$: 1008.3884, found: 1008.3878.

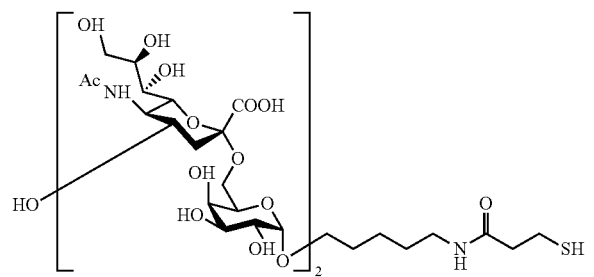

5-O-acetamino-3,5-dideoxy-2-O-(1-O-(5-O-acetamino-3,5-dideoxy-2-O-(1-O-(5-(3-mercapatopropanamido)penty)-α-D-galactopyranoside)-D-glycero-α-D-galacto-non-2-ulopyranosylonate)-α-D-galactopyranoside)-D-glycero-α-D-galacto-non-2-ulopyranosylonic acid (33)

Compound 16 (5 mg, 0.005 mmol) and 3,3'-Dithiobis(sulfosuccinimidylpropionate) (DTSSP) (11 mg, 0.0018 mmol) were dissolved in pH 7.4 PBS buffer (1 mL) at r.t. overnight. At the beginning of the reaction, the solution was adjusted by 1N NaOH(aq) and 1N HCl to keep the pH value around 7 every 20 mins for three times. After reaction, dithiothreitol (DTT) (6.9 mg, 0.045 mol) was added into the solution and the solution was stirred at 40° C. for another two hours. Compound 33 was purified through Sephadex LH-20 column chromatography: $^1$H NMR (600 MHz, D$_2$O) δ 5.08 (d, J=3.7 Hz, 1H), 4.92 (d, J=3.6 Hz, 1H), 4.09-3.50 (m, 27H), 3.23 (dd, J=12.0, 6.5 Hz, 2H), 2.98 (t, J=6.8 Hz, 1H), 2.91 (d, J=8.7 Hz, 1H), 2.75 (dd, J=12.3, 4.5 Hz, 1H), 2.68 (t, J=6.8 Hz, 1H), 2.09 (s, 3H), 2.05 (s, 3H), 1.75-1.54 (m, 8H), 1.43 (dd, J=15.1, 7.5 Hz, 2H). $^{13}$C NMR (150 MHz, D$_2$O) δ 174.98, 174.50, 174.13, 173.49, 172.97, 100.30, 100.11, 98.30, 94.47, 72.51, 72.47, 72.07, 71.89, 71.85, 69.54, 69.44, 69.35, 69.31, 69.24, 68.90, 68.39, 68.29, 68.21, 68.14, 67.87, 63.82, 62.62, 51.80, 49.49, 40.09, 39.41, 39.27, 36.62, 28.22, 28.00, 22.79, 22.43, 22.01, 20.03.

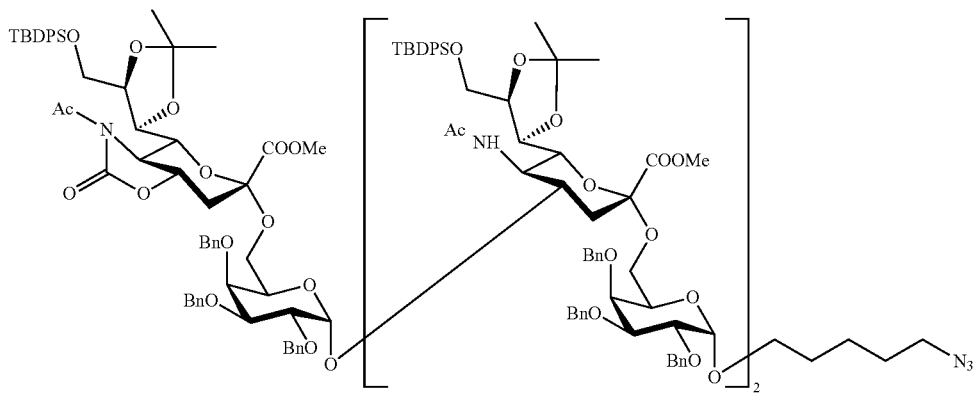

Methyl-(5-acetamino-9-O-tert-butyldiphenylsilyl-7,8-O-isopropylidene-5-N,4-O-carbonyl-2-(2,3,4-O-tri-benzyl-1-O-(methyl-(5-acetamino-9-O-tert-butyl-diphenylsilyl-7,8-O-isopropylidene-5-N,4-O-carbonyl-2-(2,3,4-O-tri-benzyl-1-O-(Methyl-(5-acetamino-9-O-tert-butyldiphenylsilyl-7,8-O-isopropylidene-3,5-dideoxy-2-O-(2,3,4-O-tri-benzyl-1-O-(5-azidopenty)-α-D-galactopyranoside)-D-glycero-α-D-galacto-non-2-ulopyranoside)onate)-α-D-galactopyranoside)-3,5-dideoxy-D-glycero-α-D-galacto-non-2-ulopyranoside)onate)-α-D-galactopyranoside)-3,5-dideoxy-D-glycero-α-D-galacto-non-2-ulopyranoside)onate (17)

A mixture of compound 10 (80 mg, 69 μmol), compound 15 (100 mg, 46 μmol), and activated pulverized MS-4Å in dry CH$_2$Cl$_2$ (0.2 mL) was stirred at room temperature for 3 hours. The solution was cooled to 0° C., and N-iodosuccinimide (19 mg, 82.8 μmol) was added. Then, the solution was cooled to −40° C., followed by adding 0.5M trifluoromethanesulfonic acid in ether (92 μL, 46 μmol). The reaction was stirred at −40° C. for 1 hour. Et$_3$N was added into the solution to quench the reaction. The solution was filter through celite. The filtrate was then quenched with 20% Na$_2$S$_2$O$_{3(aq)}$ and wash with saturated NaHCO$_{3(aq)}$ and brine. The organic layer was dried over MgSO$_4$ and concentrated. The residue was purified by silica gel column chromatography (EtOAc/hexane=1/5 to 2/5) to give compound 17 (76 mg, 52%): $^1$H NMR (600 MHz, CDCl$_3$) δ 7.70-7.60 (m, 15H), 7.42-7.18 (m, 60H), 5.90 (d, J=7.5 Hz, 1H), 5.73 (d, J=7.7 Hz, 1H), 4.98 (d, J=7.1 Hz, 1H), 4.93-4.87 (m, 3H), 4.84-4.72 (m, 10H), 4.71-4.61 (m, 8H), 4.54-4.47 (m, 3H), 4.39 (dd, J=12.9, 6.5 Hz, 1H), 4.33-4.26 (m, 4H), 4.24-4.13 (m, 7H), 4.12-4.04 (m, 6H), 4.01 (dd, J=10.0, 3.6 Hz, 1H), 3.97-3.77 (m, 19H), 3.58 (dt, J=9.9, 6.7 Hz, 1H), 3.45 (s, 3H), 3.43-3.40 (m, 1H), 3.40-3.35 (m, 4H), 3.35-3.29 (m, 2H), 3.28 (s, 3H), 3.17 (t, J=7.0 Hz, 2H), 2.85 (dd, J=11.9, 2.9 Hz, 1H), 2.78-2.74 (m, 1H), 2.71 (dd, J=12.6, 4.5 Hz, 1H), 2.51 (s, 3H), 2.00 (t, J=12.4 Hz, 1H), 1.70 (s, 3H), 1.68 (s, 3H), 1.61-1.54 (m, 5H), 1.45 (s, 3H), 1.42-1.34 (m, 11H), 1.31-1.25 (m, 6H), 1.04-0.99 (m, 27H). $^{13}$C NMR (150 MHz, CDCl$_3$) δ 172.48, 171.10, 171.02, 168.56, 168.30, 168.21, 153.92, 139.04, 138.93, 138.85, 138.82, 138.75, 138.70, 138.56, 138.49, 138.41, 135.62, 135.58, 135.56, 135.53, 133.80, 133.70, 133.53, 133.41, 133.35, 129.83, 129.75, 129.60, 129.55, 128.31, 128.26, 128.24, 128.21, 128.15, 128.08, 127.86, 127.83, 127.80, 127.73, 127.71, 127.69, 127.67, 127.66, 127.60, 127.55, 127.53, 127.44, 127.33, 127.29, 127.28, 127.22, 109.40, 109.11, 109.06, 99.08, 98.93, 98.81, 98.63, 98.57, 97.40, 78.84, 78.70, 78.62, 78.22, 78.00, 77.89, 76.55, 76.48, 76.43, 74.80, 74.74, 74.68, 74.61, 74.57, 74.48, 74.20, 74.12, 73.24, 73.15, 73.01, 72.94, 72.78, 71.59, 71.32, 69.40, 68.57, 67.70, 63.73, 62.68, 62.49, 62.41, 61.71, 61.48, 59.60, 54.30, 54.08, 52.78, 52.26, 52.00, 51.27, 39.31, 38.42, 36.21, 28.82, 28.65, 26.83, 26.77, 26.51, 26.33, 26.29, 26.01, 25.64, 25.60, 25.09, 23.56, 23.48, 23.35, 19.22, 19.16. HRMS (MALDI-TOF) calcd. for C$_{180}$H$_{216}$N$_6$O$_{41}$Si$_3$Na [M+Na]$^+$: 3224.4202, found: 3224.4131.

purified by silica gel column chromatography (EtOAc/hexane=2/1) to give compound 18 (154 mg, 78%): 1H NMR (600 MHz, CDCl$_3$) δ 7.72-7.61 (m, 14H), 7.43-7.18 (m, 61H), 5.95 (d, J=8.2 Hz, 1H), 5.73 (t, J=7.4 Hz, 2H), 4.94-4.86 (m, 3H), 4.85-4.75 (m, 7H), 4.75-4.61 (m, 9H), 4.54-4.48 (m, 3H), 4.35-4.24 (m, 3H), 4.22-3.77 (m, 33H), 3.76-3.68 (m, 2H), 3.65-3.55 (m, 2H), 3.48-3.39 (m, 9H), 3.35-3.26 (m, 7H), 3.20-3.14 (m, 2H), 2.76 (dd, J=12.6, 4.3 Hz, 1H), 2.64 (dd, J=12.6, 4.4 Hz, 1H), 2.52 (dd, J=13.2, 4.5 Hz, 1H), 1.91 (s, 3H), 1.82 (s, 3H), 1.68 (s, 3H), 1.62-1.51 (m, 5H), 1.40 (s, 6H), 1.39-1.36 (m, 2H), 1.35 (s, 3H), 1.27 (3s, 12H), 1.05 (s, 9H), 1.02 (2s, J=3.9 Hz, 18H). $^{13}$C NMR (150 MHz, CDCl$_3$) δ 171.79, 171.12, 170.98, 168.70, 168.45, 168.35, 139.07, 138.96, 138.89, 138.85, 138.79, 138.75, 138.60, 138.49, 138.41, 135.62, 135.59, 135.55, 135.52, 133.84, 133.74, 133.49, 133.45, 133.27, 133.12, 130.01, 129.97, 129.83, 129.64, 129.59, 128.36, 128.28, 128.21, 128.15, 128.11, 127.84, 127.74, 127.71, 127.69, 127.56, 127.48, 127.35, 127.32, 127.25, 109.25, 109.23, 109.10, 98.93, 98.78, 98.67, 98.56, 97.44, 78.87, 78.83, 78.63, 78.25, 77.81, 77.42, 76.58, 76.53, 76.27, 75.33, 75.04, 74.89, 74.81, 74.77, 74.71, 74.67, 74.60, 74.39, 74.22, 73.57, 73.43, 73.19, 73.14, 73.09, 72.96, 72.81, 72.23, 71.87, 71.63, 69.92, 69.42, 69.24, 68.60, 67.73, 63.71, 62.85, 62.71, 62.59, 61.84, 61.50, 54.66, 54.09, 52.35, 52.03, 51.30, 39.32, 39.15, 37.78, 30.95, 28.86, 28.69, 26.94, 26.86, 26.81, 26.68, 26.51, 26.32, 26.04, 25.71, 25.42, 23.59, 23.55, 23.38, 23.33, 19.32, 19.26, 19.18. HRMS (MALDI-TOF) calcd. for C$_{179}$H$_{218}$N$_6$O$_{40}$Si$_3$Na [M+Na]$^+$: 3198.4409, found: 3198.4446.

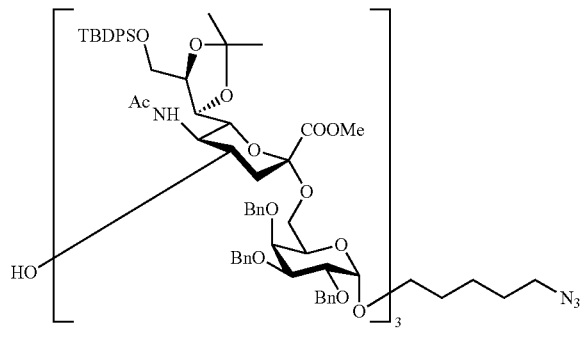

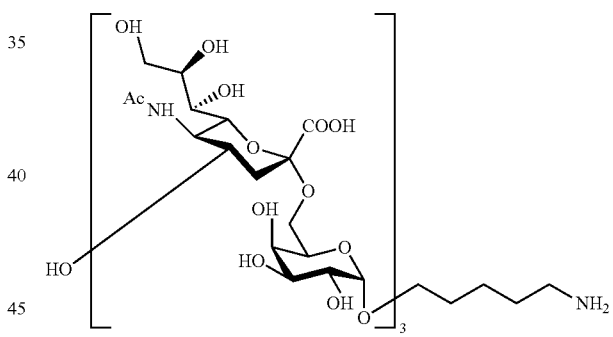

Methyl-(5-acetamino-9-O-tert-butyldiphenylsilyl-7,8-O-isopropylidene-2-(2,3,4-O-tri-benzyl-1-O-(methyl-(5-acetamino-9-O-tert-butyldiphenylsilyl-7,8-O-isopropylidene-5-N,4-O-carbonyl-2-(2,3,4-O-tri-benzyl-1-O-(Methyl-(5-acetamino-9-O-tert-butyldiphenylsilyl-7,8-O-isopropylidene-3,5-dideoxy-2-O-(2,3,4-O-tri-benzyl-1-O-(5-azidopenty)-α-D-galactopyranoside)-D-glycero-α-D-galacto-non-2-ulopyranoside)onate)-α-D-galacto pyranoside)-3,5-dideoxy-D-glycero-α-D-galacto-non-2-ulopyranoside)onate)-α-D-galactopyranoside)-3,5-dideoxy-D-glycero-α-D-galacto-non-2-ulopyranoside)onate (18)

Compound 17 (200 mg, 62.4 μmol) was dissolved in CH$_2$Cl$_2$/MeOH (2 mL, 1:2), followed by adding 0.5M NaOMe in MeOH (124.8 μL, 62.4 μmol). The reaction was stirred at room temperature for 1 hour. IR-120 resin was then added into the solution to quench the reaction. The solvent was removed under reduced pressure, and the residue was 5-O-acetamino-3,5-dideoxy-2-O-(1-O-(5-O-acetamino-3,5-dideoxy-2-O-(1-O-(5-O-acetamino-3,5-dideoxy-2-O-(1-O-(5-aminopenty)-α-D-galactopyranoside)-D-glycero-α-D-galacto-non-2-ulopyranosylonate)-α-D-galactopyranoside)-D-glycero-α-D-galacto-non-2-ulopyranosylonate)-α-D-galactopyranoside)-D-glycero-α-D-galacto-non-2-ulopyranosylonic acid (19)

Compound 18 (100 mg, 0.031 mmol) was dissolved in acetonitrile (2 mL) and cooled to 0° C., followed by adding 48% BF$_3$.OEt$_2$ (230 μL, 0.4720 mmol). The reaction was stirred at 0° C. for 3 hours. The solution was washed with saturated NaHCO$_{3(aq)}$ and brine. The organic layer was then dried over MgSO$_4$ and concentrated. The residue was dissolved in MeOH, and 2~3 drops of concentrated NaOH in MeOH were added. The reaction was stirred at room temperature overnight. The solvent was removed under reduced pressure. The residue was purified by reverse phase column (MeOH/H$_2$O=1/1 to 4/1). The purified compound then proceeded through hydrogenation with PdOH as catalysis in MeOH/H$_2$O under hi-pressure hydrogen at room temperature overnight. After reaction, the solution was filtered through celite and concentrated under reduced pressure. The residue was purified by Sephadex LH-20 to obtain compound 19 (20 mg, 45%, over three steps): $^1$H NMR (600 MHz, D$_2$O) δ 5.10 (d, J=3.8 Hz, 1H), 5.08 (d, J=3.5 Hz, 1H), 4.93 (d, J=3.4 Hz, 1H), 4.09-3.51 (m, 39H), 3.03 (t, J=7.5 Hz, 2H), 2.93-2.87 (m, 2H), 2.74 (dd, J=12.5, 4.4 Hz, 1H), 2.10 (2s, J=11.8 Hz, 6H), 2.05 (s, 3H), 1.76-1.59 (m, 7H), 1.52-1.42 (m, 2H). $^{13}$C NMR (150 MHz, D$_2$O) δ 174.98, 174.51, 173.46, 173.01, 100.36, 100.18, 98.39, 98.26, 94.87, 94.26, 73.08, 72.45, 72.33, 72.09, 72.01, 71.86, 71.82, 69.62, 69.55, 69.39, 69.36, 69.25, 69.07, 68.91, 68.38, 68.29, 68.16, 68.10, 68.04, 67.89, 67.77, 63.91, 62.88, 62.61, 51.80, 49.47, 40.03, 39.43, 36.70, 36.63, 36.27, 28.08, 26.39, 22.46, 22.42, 22.38, 22.00. HRMS (ESI-TOF) calcd. for C$_{56}$H$_{92}$N$_4$O$_{40}$ [M−2H]$^{2-}$: 730.2644, found: 730.2645.

hours. The solution was cooled to 0° C., and N-iodosuccinimide (15.5 mg, 67 μmol) was added. After that, the solution was cooled to −40° C., followed by adding 0.5M trifluoromethanesulfonic acid in ether (62 μL, 31 μmol). The reaction was stirred at −40° C. for 1 hour. The solution was filter through celite. The filtrate was then quenched with 20% Na$_2$S$_2$O$_{3(aq)}$ and wash with saturated NaHCO$_{3(aq)}$ and brine. The organic layer was dried over MgSO$_4$ and concentrated. The residue was purified by silica gel column chromatography (EtOAc/hexane=1/5 to 1/3) to give compound 20 (60 mg, 46%): $^1$H NMR (600 MHz, CDCl$_3$) δ 7.70-7.60 (m, 18H), 7.41-7.19 (m, 82H), 5.89 (d, J=7.5 Hz, 1H), 5.73 (t, J=7.8 Hz, 2H), 4.98 (d, J=7.1 Hz, 1H), 4.94-4.86 (m, 4H), 4.85-4.75 (m, 10H), 4.75-4.61 (m, 12H), 4.54-4.46 (m, 4H), 4.39 (dd, J=13.0, 6.5 Hz, 1H), 4.33-4.04 (m, 24H), 4.01 (dd, J=10.0, 3.5 Hz, 1H), 3.97-3.77 (m, 23H), 3.59 (dt, J=10.1, 6.6 Hz, 1H), 3.47-3.25 (m, 22H), 3.17 (t, J=7.0 Hz, 2H), 2.84 (dd, J=11.7, 2.7 Hz, 1H), 2.78-2.69 (m, 3H), 2.51 (s, 3H), 1.99 (t, J=12.4 Hz, 1H), 1.69 (3s, 12H), 1.60-1.54 (m, 7H), 1.44 (s, 3H), 1.42-1.38 (m, 14H), 1.29-

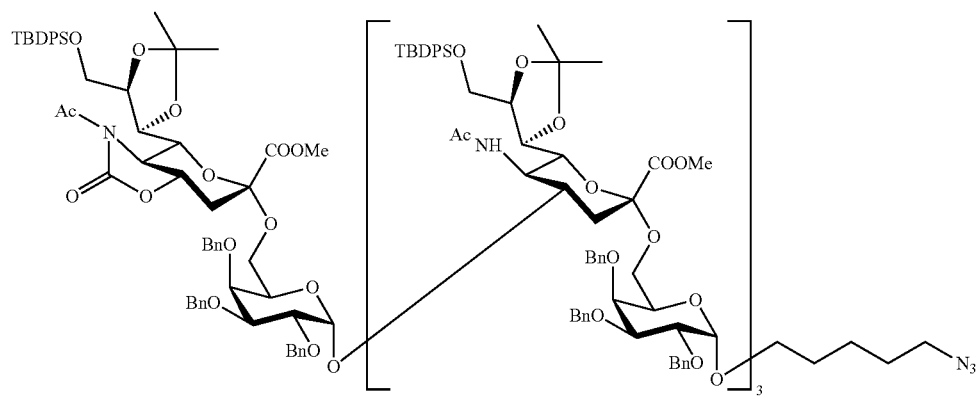

Methyl-(5-acetamino-9-O-tert-butyldiphenylsilyl-7,8-O-isopropylidene-5-N,4-O-carbonyl-2-(2,3,4-O-tri-benzyl-1-O-(methyl-(5-acetamino-9-O-tert-butyldiphenylsilyl-7,8-O-isopropylidene-5-N,4-O-carbonyl-2-(2,3,4-O-tri-benzyl-1-O-(methyl-(5-acetamino-9-O-tert-butyldiphenylsilyl-7,8-O-isopropylidene-5-N,4-O-carbonyl-2-(2,3,4-O-tri-benzyl-1-O-(Methyl-(5-acetamino-9-O-tert-butyldiphenylsilyl-7,8-O-isopropylidene-3,5-dideoxy-2-O-(2,3,4-O-tri-benzyl-1-O-(5-azidopenty)-α-D-galactopyranoside)-D-glycero-α-D-galacto-non-2-ulopyranoside)onate)-α-D-galactopyranoside)-3,5-dideoxy-D-glycero-α-D-galacto-non-2-ulopyranoside)onate)-α-D-galactopyranoside)-3,5-dideoxy-D-glycero-α-D-galacto-non-2-ulopyranoside)onate)-α-D-galactopyranoside)-3,5-dideoxy-D-glycero-α-D-galacto-non-2-ulopyranoside)onate (20)

A mixture of compound 10 (65 mg, 56 μmol), compound 18 (100 mg, 31 μmol), and activated pulverized MS-4Å in dry CH$_2$Cl$_2$ (0.2 mL) was stirred at room temperature for 3

1.25 (m, 9H), 1.01 (4s, 36H). $^{13}$C NMR (150 MHz, CDCl$_3$) δ 207.00, 172.51, 171.14, 171.07, 171.04, 168.59, 168.33, 168.24, 168.18, 153.94, 139.07, 138.95, 138.89, 138.85, 138.82, 138.79, 138.71, 138.60, 138.53, 138.51, 138.44, 135.64, 135.61, 135.59, 135.56, 135.53, 133.83, 133.73, 133.55, 133.44, 133.42, 133.38, 129.86, 129.78, 129.63, 129.57, 128.34, 128.28, 128.25, 128.18, 128.17, 128.10, 127.87, 127.85, 127.83, 127.76, 127.72, 127.66, 127.58, 127.55, 127.51, 127.48, 127.44, 127.36, 127.34, 127.31, 127.29, 127.24, 109.41, 109.16, 109.08, 99.11, 98.98, 98.80, 98.66, 98.62, 97.43, 78.87, 78.73, 78.68, 78.65, 78.25, 78.09, 78.06, 77.93, 76.57, 76.50, 76.43, 76.37, 74.75, 74.70, 74.64, 74.61, 74.59, 74.50, 74.28, 74.23, 74.11, 73.26, 73.18, 73.07, 73.03, 72.96, 72.80, 71.61, 71.53, 71.43, 69.53, 69.42, 68.59, 67.71, 63.75, 62.71, 62.55, 62.44, 61.73, 61.67, 61.49, 60.41, 59.62, 54.20, 54.12, 53.94, 52.80, 52.28, 52.26, 52.02, 51.29, 39.35, 38.57, 38.49, 36.24, 31.59, 30.94, 29.71, 28.84, 28.68, 26.95, 26.86, 26.80, 26.58, 26.52, 26.36, 26.32, 26.05, 25.72, 25.68, 25.63, 25.11, 23.61, 23.57, 23.51, 23.37, 22.66, 21.06, 19.25, 19.18, 19.17, 14.21, 14.13. HRMS (ESI-TOF) calcd. for C$_{238}$H$_{287}$N$_7$O$_{54}$Si$_4$ [M+2H]$^{2+}$: 2110.9538, found: 2110.9494.

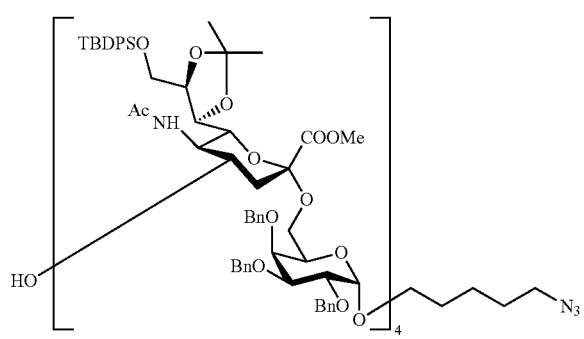

Methyl-(5-acetamino-9-O-tert-butyldiphenylsilyl-7,
8-O-isopropylidene-2-(2,3,4-O-tri-benzyl-1-O-
(methyl-(5-acetamino-9-O-tert-butyldiphenylsilyl-7,
8-O-isopropylidene-5-N,4-O-carbonyl-2-(2,3,4-O-
tri-benzyl-1-O-(methyl-(5-acetamino-9-O-tert-
butyldiphenylsilyl-7,8-O-isopropylidene-5-N,4-O-
carbonyl-2-(2,3,4-O-tri-benzyl-1-O-(Methyl-(5-
acetamino-9-O-tert-butyldiphenylsilyl-7,8-O-
isopropylidene-3,5-dideoxy-2-O-(2,3,4-O-tri-benzyl-
1-O-(5-azidopenty)-α-D-galactopyranoside)-D-
glycero-α-D-galacto-non-2-ulopyranoside)onate)-α-
D-galactopyranoside)-3,5-dideoxy-D-glycero-α-D-
galacto-non-2-ulopyranoside)onate)-α-D-
galactopyranoside)-3,5-dideoxy-D-glycero-α-D-
galacto-non-2-ulopyranoside)onate)-α-D-
galactopyranoside)-3,5-dideoxy-D-glycero-α-D-
galacto-non-2-ulopyranoside)onate (21)

Compound 20 (100 mg, 23 µmol) was dissolved in CH$_2$Cl$_2$/MeOH (0.2 mL, 1:2), followed by adding 0.5M NaOMe in MeOH (46 µL, 23 µmol). The reaction was stirred at room temperature for 1 hour. IR-120 resin was then added into the solution to quench the reaction. The solvent was removed under reduced pressure, and the residue was purified by silica gel column chromatography (EtOAc/hexane=2/1) to give compound 21 (67 mg, 70%): $^1$H NMR (600 MHz, CDCl$_3$) δ 7.71-7.60 (m, 23H), 7.44-7.18 (m, 77H), 5.96 (d, J=8.3 Hz, 1H), 5.77-5.70 (m, 3H), 4.94-4.86 (m, 5H), 4.85-4.76 (m, 12H), 4.74-4.61 (m, 15H), 4.54-4.46 (m, 5H), 4.34-4.23 (m, 6H), 4.22-3.76 (m, 54H), 3.74-3.64 (m, 5H), 3.59 (dt, J=9.8, 6.7 Hz, 2H), 3.48-3.26 (m, 26H), 3.17 (t, J=7.0 Hz, 2H), 2.76 (dd, J=12.6, 4.2 Hz, 1H), 2.71 (dd, J=12.3, 4.2 Hz, 1H), 2.65 (dd, J=12.6, 4.2 Hz, 1H), 2.51 (dd, J=13.2, 4.4 Hz, 1H), 1.90 (s, 3H), 1.83 (s, 3H), 1.69 (s, 3H), 1.68 (s, 3H), 1.64-1.54 (m, 5H), 1.42-1.39 (m, 9H), 1.38-1.36 (m, 2H), 1.35 (s, 3H), 1.29-1.25 (m, 12H), 1.06 (s, 9H), 1.02 (3s, 27H). $^{13}$C NMR (150 MHz, CDCl$_3$) δ 171.78, 171.13, 171.08, 170.97, 168.69, 168.40, 168.34, 168.25, 139.06, 138.94, 138.88, 138.84, 138.82, 138.78, 138.71, 138.60, 138.54, 138.48, 138.38, 135.60, 135.58, 135.52, 133.83, 133.72, 133.54, 133.46, 133.42, 133.25, 133.11, 130.00, 129.96, 129.82, 129.78, 129.62, 129.57, 128.35, 128.34, 128.28, 128.21, 128.17, 128.14, 128.10, 127.83, 127.76, 127.73, 127.71, 127.66, 127.64, 127.58, 127.54, 127.49, 127.46, 127.44, 127.38, 127.32, 127.31, 127.24, 109.19, 109.15, 109.09, 99.04, 98.85, 98.77, 98.66, 98.64, 98.60, 97.42, 97.34, 78.85, 78.64, 78.24, 78.06, 77.85, 77.42, 76.56, 76.48, 76.38, 76.22, 75.32, 75.01, 74.77, 74.70, 74.63, 74.58, 74.37, 74.22, 74.14, 73.51, 73.42, 73.18, 73.06, 73.03, 72.96, 72.80, 72.32, 71.84, 71.66, 71.53, 69.92, 69.50, 69.41, 69.21, 68.59, 67.71, 63.73, 62.84, 62.71, 62.55, 61.80, 61.69, 61.49, 54.66, 53.99, 53.92, 52.34, 52.27, 52.19, 52.02, 51.29, 39.27, 39.13, 38.54, 37.79, 30.94, 29.70, 29.06, 28.84, 28.67, 26.93, 26.86, 26.80, 26.67, 26.53, 26.51, 26.31, 26.04, 25.71, 25.39, 23.60, 23.54, 23.37, 23.31, 19.30, 19.24, 19.16. HRMS (ESI-TOF) calcd. for C$_{237}$H$_{289}$N$_7$O$_{53}$Si$_4$ [M+2H]$^{2+}$: 2097.9742, found: 2097.9598.

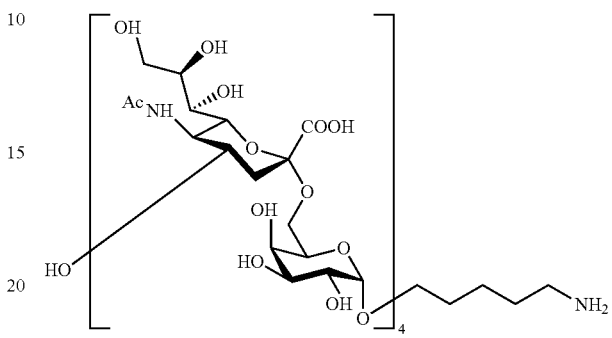

5-O-acetamino-3,5-dideoxy-2-O-(1-O-(5-O-acet-
amino-3,5-dideoxy-2-O-(1-O-(5-O-acetamino-3,5-
dideoxy-2-O-(1-O-(5-O-acetamino-3,5-dideoxy-2-
O-(1-O-(5-aminopenty)-α-D-galactopyranoside)-D-
glycero-α-D-galacto-non-2-ulopyranosylonate)-α-D-
galactopyranoside)-D-glycero-α-D-galacto-non-2-
ulopyranosylonate)-α-D-galactopyranoside)-D-
glycero-α-D-galacto-non-2-ulopyranosylonate)-α-D-
galactopyranoside)-D-glycero-α-D-galacto-non-2-
ulopyranosylonic acid (22)

Compound 21 (100 mg, 0.024 mmol) was dissolved in acetonitrile (2 mL) and cooled to 0° C., followed by adding 48% BF$_3$.OEt$_2$ (174 µL, 0.358 mmol). The reaction was stirred at 0° C. for 3 hours. The solution was washed with saturated NaHCO$_{3(aq)}$ and brine. The organic layer was then dried over MgSO$_4$ and concentrated. The residue was dissolved in MeOH, and 2~3 drops of concentrated NaOH in MeOH were added. The reaction was stirred at room temperature overnight. The solvent was removed under reduced pressure. The residue was purified by reverse phase column (MeOH/H$_2$O=1/1 to 4/1). The purified compound then proceeded through hydrogenation with PdOH as catalysis in MeOH/H$_2$O under hi-pressure hydrogen at room temperature overnight. After reaction, the solution was filtered through celite and concentrated under reduced pressure. The residue was purified by Sephadex LH-20 to obtain compound 22 (18 mg, 40%, over three steps): $^1$H NMR (600 MHz, D$_2$O) δ 5.10 (d, J=3.8 Hz, 1H), 5.07 (d, J=3.4 Hz, 2H), 4.93 (d, J=3.6 Hz, 1H), 4.08-3.53 (m, 54H), 3.03 (t, J=7.5 Hz, 2H), 2.93-2.86 (m, 3H), 2.74 (dd, J=12.4, 4.7 Hz, 1H), 2.09 (3s, J=1.8 Hz, 9H), 2.04 (s, 3H), 1.76-1.62 (m, 8H), 1.48 (p, J=7.6 Hz, 2H). $^{13}$C NMR (150 MHz, D$_2$O) δ 174.96, 174.50, 174.46, 173.47, 173.04, 173.02, 100.33, 100.22, 100.18, 100.13, 98.38, 98.25, 95.01, 94.87, 94.25, 73.25, 73.10, 72.44, 72.32, 72.09, 71.96, 71.87, 71.81, 69.61, 69.54, 69.38, 69.34, 69.24, 69.08, 69.03, 68.90, 68.38, 68.28, 68.16, 68.09, 68.03, 67.88, 67.79, 67.75, 63.89, 62.90, 62.80, 62.60, 51.79, 49.47, 40.03, 39.44, 36.80, 36.73, 36.64, 36.27, 28.08, 26.44, 22.49, 22.46, 22.41, 22.38, 22.00. HRMS (ESI-TOF) calcd. for C$_{73}$H$_{119}$N$_5$O$_{53}$ [M−2H]$^{2-}$: 956.8385, found: 956.8393.

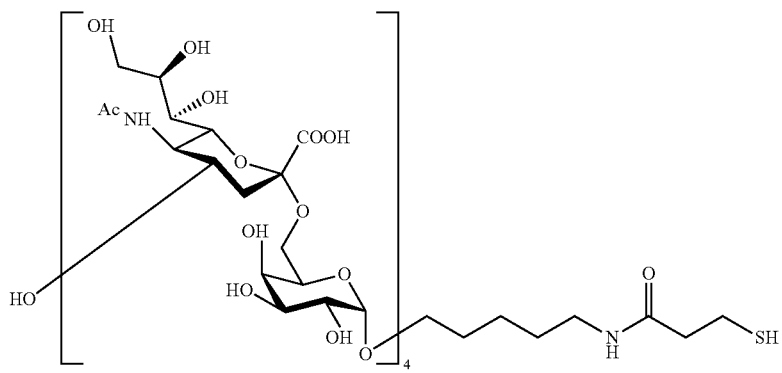

5-O-acetamino-3,5-dideoxy-2-O-(1-O-(5-O-acetamino-3,5-dideoxy-2-O-(1-O-(5-O-acetamino-3,5-dideoxy-2-O-(1-O-(5-O-acetamino-3,5-dideoxy-2-O-(1-O-(5-(3-mercapatopropanamido)penty)-α-D-galactopyranoside)-D-glycero-α-D-galacto-non-2-ulopyranosylonate)-α-D-galactopyranoside)-D-glycero-α-D-galacto-non-2-ulopyranosylonate)-α-D-galactopyranoside)-D-glycero-α-D-galacto-non-2-ulopyranosylonate)-α-D-galactopyranoside)-D-glycero-α-D-galacto-non-2-ulopyranosylonic acid (35)

Compound 22 (5 mg, 0.002 mmol) and 3,3'-Dithiobis(sulfosuccinimidylpropionate) (DTSSP) (6.0 mg, 0.010 mmol) were dissolved in pH 7.4 PBS buffer (1 mL) at r.t. overnight. At the beginning of the reaction, the solution was adjusted by 1N NaOH(aq) and 1N HCl to keep the pH value around 7 every 20 mins for three times. After reaction, dithiothreitol (DTT) (3.8 mg, 0.025 mol) was added into the solution, and the solution was stirred at 40° C. for another two hours. Compound 35 was purified through Sephadex LH-20 column chromatography: $^1$H NMR (600 MHz, D$_2$O) δ 5.10-5.04 (m, 3H), 4.92 (d, J=4.0 Hz, 1H), 4.08-3.52 (m, 54H), 3.27-3.22 (m, 2H), 2.93-2.86 (m, 3H), 2.80 (t, J=6.6 Hz, 1H), 2.74 (dd, J=12.4, 4.6 Hz, 1H), 2.56 (t, J=6.9 Hz, 1H), 2.09 (2s, J=1.9 Hz, 9H), 2.04 (s, 3H), 1.75-1.54 (m, 10H), 1.47-1.40 (m, 2H). $^{13}$C NMR (150 MHz, D$_2$O) δ 174.97, 174.51, 174.13, 173.48, 173.07, 100.24, 100.14, 98.30, 95.07, 94.89, 94.59, 73.12, 72.61, 72.45, 72.08, 71.96, 71.86, 71.82, 69.61, 69.45, 69.30, 69.21, 69.08, 68.91, 68.39, 68.21, 68.08, 67.77, 63.82, 62.79, 62.61, 51.80, 49.48, 40.04, 39.40, 39.26, 36.64, 28.22, 27.99, 22.79, 22.47, 22.01, 20.02.

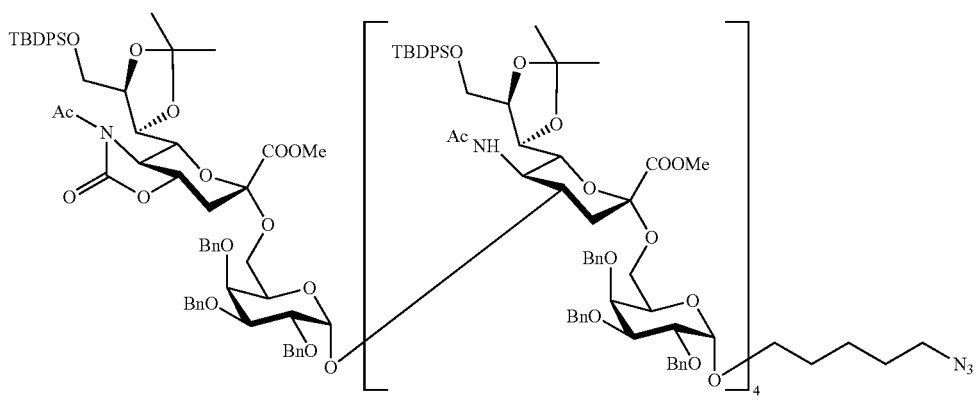

Methyl-(5-acetamino-9-O-tert-butyldiphenylsilyl-7,
8-O-isopropylidene-5-N,4-O-carbonyl-2-(2,3,4-O-
tri-benzyl-1-O-(methyl-(5-acetamino-9-O-tert-butyl-
diphenylsilyl-7,8-O-isopropylidene-5-N,4-O-
carbonyl-2-(2,3,4-O-tri-benzyl-1-O-(methyl-(5-
acetamino-9-O-tert-butyldiphenylsilyl-7,8-O-
isopropylidene-5-N,4-O-carbonyl-2-(2,3,4-O-tri-
benzyl-1-O-(methyl-(5-acetamino-9-O-tert-
butyldiphenylsilyl-7,8-O-isopropylidene-5-N,4-O-
carbonyl-2-(2,3,4-O-tri-benzyl-1-O-(Methyl-(5-
acetamino-9-O-tert-butyldiphenylsilyl-7,8-O-
isopropylidene-3,5-dideoxy-2-O-(2,3,4-O-tri-benzyl-
1-O-(5-azidopenty)-α-D-galactopyranoside)-D-
glycero-α-D-galacto-non-2-ulopyranoside)onate)-α-
D-galactopyranoside)-3,5-dideoxy-D-glycero-α-D-
galacto-non-2-ulopyranoside)onate)-α-D-
galactopyranoside)-3,5-dideoxy-D-glycero-α-D-
galacto-non-2-ulopyranoside)onate)-α-D-
galactopyranoside)-3,5-dideoxy-D-glycero-α-D-
galacto-non-2-ulopyranoside)onate)-α-D-
galactopyranoside)-3,5-dideoxy-D-glycero-α-D-
galacto-non-2-ulopyranoside)onate (23)

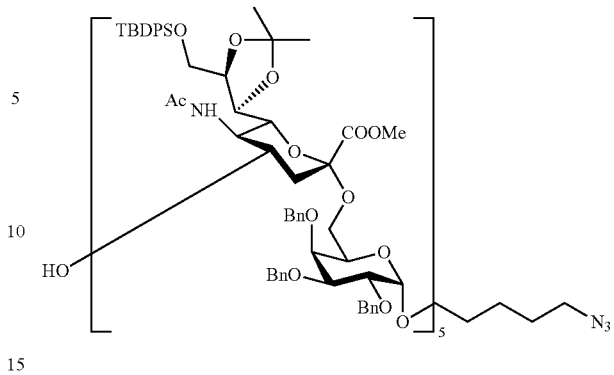

A mixture of compound 10 (56 mg, 48 µmol), compound 21 (100 mg, 24 µmol), and activated pulverized MS-4Å in dry CH$_2$Cl$_2$ (0.2 mL) was stirred at room temperature for 3 hours. The solution was cooled to 0° C., and N-iodosuccinimide (13 mg, 60 µmol) was added. Then, the solution was cooled to −40° C., followed by adding 0.5 M trifluoromethanesulfonic acid in ether (48 µL, 24 µmol). The reaction was stirred at −40° C. for 1 hour. After reaction, the solution was filter through celite. The filtrate was then quenched with 20% Na$_2$S$_2$O$_{3(aq)}$ and wash with saturated NaHCO$_{3(aq)}$ and brine. The organic layer was dried over MgSO$_4$ and concentrated. The residue was purified by silica gel column chromatography (EtOAc/hexane=1/5 to 1/3) to give compound 23 (43 mg, 35%): $^1$H NMR (600 MHz, CDCl$_3$) δ 7.70-7.58 (m, 22H), 7.40-7.14 (m, 103H), 5.88 (d, J=6.6 Hz, 1H), 5.77-5.68 (m, 3H), 5.00-4.86 (m, 7H), 4.85-4.75 (m, 12H), 4.75-4.60 (m, 15H), 4.55-4.45 (m, 5H), 4.38 (d, J=6.5 Hz, 1H), 4.32-4.23 (m, 7H), 4.21-4.03 (m, 22H), 3.98-3.77 (m, 29H), 3.68-3.56 (m, 3H), 3.48-3.25 (m, 27H), 3.17 (t, J=7.0 Hz, 2H), 2.83 (d, J=9.3 Hz, 1H), 2.78-2.67 (m, 4H), 2.51 (s, 3H), 2.03-1.96 (m, 1H), 1.70 (2s, J=14.6 Hz, 12H), 1.45-1.35 (m, 22H), 1.31-1.23 (m, 18H), 1.04-0.99 (m, 45H). $^{13}$C NMR (150 MHz, CDCl$_3$) δ 172.53, 171.14, 171.07, 171.03, 168.61, 168.36, 168.28, 168.23, 153.94, 139.08, 138.95, 138.89, 138.85, 138.82, 138.80, 138.70, 138.61, 138.54, 138.53, 138.50, 138.44, 135.62, 135.57, 135.53, 133.84, 133.73, 133.53, 133.44, 133.38, 129.87, 129.79, 129.64, 129.58, 128.36, 128.34, 128.31, 128.29, 128.27, 128.26, 128.18, 128.11, 127.86, 127.83, 127.74, 127.69, 127.60, 127.55, 127.52, 127.45, 127.38, 127.34, 127.32, 127.25, 109.39, 109.17, 109.11, 109.09, 109.03, 99.14, 98.74, 98.67, 97.43, 78.86, 78.74, 78.70, 78.65, 78.42, 78.25, 78.10, 78.04, 77.93, 76.58, 76.48, 76.39, 76.31, 76.27, 74.85, 74.75, 74.71, 74.60, 74.56, 74.48, 74.12, 74.03, 73.29, 73.18, 73.09, 73.07, 72.97, 72.81, 71.78, 71.70, 71.55, 69.56, 69.47, 69.44, 68.60, 67.72, 63.85, 62.73, 62.56, 62.46, 61.90, 61.82, 61.51, 59.63, 53.91, 53.63, 53.45, 52.81, 52.29, 52.27, 52.03, 51.30, 39.24, 38.34, 36.23, 29.71, 28.85, 28.68, 26.98, 26.95, 26.87, 26.81, 26.61, 26.58, 26.53, 26.37, 26.32, 26.05, 25.71, 25.66, 25.61, 25.12, 23.61, 23.58, 23.51, 23.38, 19.26, 19.19, 19.17. HRMS (ESI-TOF) calcd. For C$_{296}$H$_{356}$N$_8$O$_{67}$Si$_5$ [M+2H]$^{2+}$: 2617.1766, found: 2617.1804.

Methyl-(5-acetamino-9-O-tert-butyldiphenylsilyl-7,
8-O-isopropylidene-2-(2,3,4-O-tri-benzyl-1-O-
(methyl-(5-acetamino-9-O-tert-butyldiphenylsilyl-7,
8-O-isopropylidene-5-N,4-O-carbonyl-2-(2,3,4-O-
tri-benzyl-1-O-(methyl-(5-acetamino-9-O-tert-
butyldiphenylsilyl-7,8-O-isopropylidene-5-N,4-O-
carbonyl-2-(2,3,4-O-tri-benzyl-1-O-(methyl-(5-
acetamino-9-O-tert-butyldiphenylsilyl-7,8-O-
isopropylidene-5-N,4-O-carbonyl-2-(2,3,4-O-tri-
benzyl-1-O-(Methyl-(5-acetamino-9-O-tert-
butyldiphenylsilyl-7,8-O-isopropylidene-3,5-
dideoxy-2-O-(2,3,4-O-tri-benzyl-1-O-(5-
azidopenty)-α-D-galactopyranoside)-D-glycero-α-
D-galacto-non-2-ulopyranoside)onate)-α-D-
galactopyranoside)-3,5-dideoxy-D-glycero-α-D-
galacto-non-2-ulopyranoside)onate)-α-D-
galactopyranoside)-3,5-dideoxy-D-glycero-α-D-
galacto-non-2-ulopyranoside)onate)-α-D-
galactopyranoside)-3,5-dideoxy-D-glycero-α-D-
galacto-non-2-ulopyranoside)onate)-α-D-
galactopyranoside)-3,5-dideoxy-D-glycero-α-D-
galacto-non-2-ulopyranoside)onate (24)

Compound 23 (100 mg, 19 µmol) was dissolved in CH$_2$Cl$_2$/MeOH (0.2 mL, 1:2), followed by adding 0.5M NaOMe in MeOH (38 µL, 19 µmol). The reaction was stirred at room temperature for 1 hour. IR-120 resin was then added into the solution to quench the reaction. The solvent was removed under reduced pressure, and the residue was purified by silica gel column chromatography (EtOAc/hexane=2/1) to give compound 24 (71 mg, 72%): 1H NMR (600 MHz, CDCl$_3$) δ 7.71-7.58 (m, 30H), 7.42-7.18 (m, 95H), 5.96 (d, J=8.3 Hz, 1H), 5.78-5.69 (m, 4H), 4.94-4.86 (m, 7H), 4.84-4.76 (m, 15H), 4.75-4.61 (m, 20H), 4.53-4.45 (m, 6H), 4.33-4.24 (m, 7H), 4.21-3.99 (m, 34H), 3.98-3.90 (m, 13H), 3.89-3.77 (m, 24H), 3.74-3.65 (m, 5H), 3.58 (dt, J=10.1, 6.7 Hz, 2H), 3.46-3.26 (m, 34H), 3.17 (t, J=7.0 Hz, 2H), 2.75 (dd, J=11.9, 4.6 Hz, 1H), 2.73-2.68 (m, 2H), 2.64 (dd, J=12.2, 4.1 Hz, 1H), 2.50 (dd, J=13.3, 4.3 Hz, 1H), 1.90 (s, 3H), 1.84 (s, 3H), 1.70 (s, 6H), 1.68 (s, 3H), 1.61-1.54 (m, 5H), 1.40 (2s, J=5.9 Hz, 12H), 1.38-1.36 (m, 2H), 1.34 (s, 3H), 1.28-1.24 (m, 15H), 1.06 (s, 9H), 1.01 (2s, J=3.4 Hz, 36H). $^{13}$C NMR (150 MHz, CDCl$_3$) δ 171.74, 171.13, 171.07, 170.94, 168.69, 168.41, 168.34, 168.26, 168.22, 139.07, 138.95, 138.85, 138.80, 138.70, 138.61, 138.54, 138.49, 138.37, 135.60, 135.52, 133.83, 133.73, 133.53, 133.43, 133.25, 133.11, 130.00, 129.96, 129.78, 129.62, 129.57, 128.34, 128.28, 128.21, 128.17, 128.14, 128.10, 127.83, 127.73, 127.54, 127.50, 127.47, 127.43, 127.37, 127.31, 109.16, 109.09, 98.92, 98.77, 98.70, 98.66, 97.42, 97.26, 78.85, 78.65, 78.24, 78.13, 78.04, 77.85, 76.56, 76.49, 76.33, 76.20, 75.32, 75.02, 74.73, 74.59, 74.36, 74.18, 73.43, 73.17, 73.04, 72.95, 72.80, 72.41, 71.82, 71.65, 69.93, 69.53, 69.42, 69.21, 68.59, 67.71, 63.77, 62.85, 62.72, 62.60, 61.85, 61.75, 61.50, 54.71, 54.02, 53.74, 52.34, 52.28, 52.02, 51.29, 39.29, 39.08, 38.44, 37.72, 29.71, 28.84, 28.67, 26.93, 26.86, 26.81, 26.68, 26.55, 26.52, 26.31, 26.04, 25.71, 25.39, 23.60, 23.57, 23.37, 23.31, 19.31, 19.25, 19.16. HRMS (ESI-TOF) calcd. for $C_{295}H_{358}N_8O_{66}Si_5$ $[M+2H]^{2+}$: 2604.1869, found: 2604.1754.

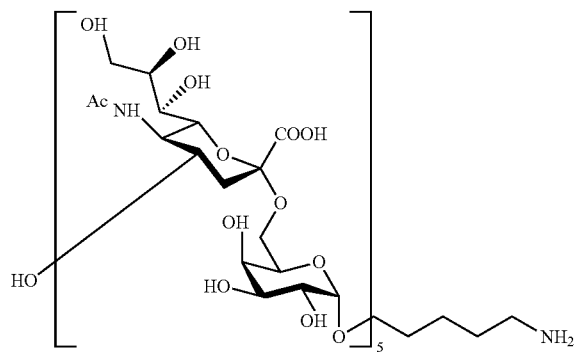

5-O-acetamino-3,5-dideoxy-2-O-(1-O-(5-O-acetamino-3,5-dideoxy-2-O-(1-O-(5-O-acetamino-3,5-dideoxy-2-O-(1-O-(5-aminopenty)-α-D-galactopyranoside)-D-glycero-α-D-galacto-non-2-ulopyranosylonate)-α-D-galactopyranoside)-D-glycero-α-D-galacto-non-2-ulopyranosylonate)-α-D-galactopyranoside)-D-glycero-α-D-galacto-non-2-ulopyranosylonate)-α-D-galactopyranoside)-D-glycero-α-D-galacto-non-2-ulopyranosylonate)-α-D-galactopyranoside)-D-glycero-α-D-galacto-non-2-ulopyranosylonic acid (25)

Compound 24 (100 mg, 0.019 mmol) was dissolved in acetonitrile (2 mL) and cooled to 0° C., followed by adding 48% $BF_3.OEt_2$ (130 ocL, 0.288 mmol). The reaction was stirred at 0° C. for 3 hours. The solution was washed with saturated $NaHCO_{3(aq)}$ and brine. The organic layer was then dried over $MgSO_4$ and concentrated. The residue was dissolved in MeOH, and 2~3 drops of concentrated NaOH in MeOH was added. The reaction was stirred at room temperature overnight. The solvent was removed under reduced pressure. The residue was purified by reverse phase column ($MeOH/H_2O$=1/1 to 4/1). The purified compound then proceeded through hydrogenation with PdOH as catalysis in $MeOH/H_2O$ under hi-pressure hydrogen at room temperature overnight. After reaction, the solution was filtered through celite and concentrated under reduced pressure. The residue was purified by Sephadex LH-20 to obtain compound 25 (17 mg, 38%, over three steps): $^1H$ NMR (600 MHz, $D_2O$) δ 5.10 (d, J=3.8 Hz, 1H), 5.08 (d, J=2.5 Hz, 3H), 4.93 (d, J=3.5 Hz, 1H), 4.09-3.54 (m, 76H), 3.03 (t, J=7.5 Hz, 2H), 2.93-2.85 (m, 4H), 2.74 (dd, J=12.3, 4.3 Hz, 1H), 2.09 (s, 14H), 2.05 (s, 3H), 1.77-1.63 (m, 9H), 1.52-1.45 (m, 1H). $^{13}C$ NMR (150 MHz, $D_2O$) δ 175.00, 174.52, 173.48, 172.99, 100.32, 100.12, 98.48, 98.33, 94.39, 94.18, 72.56, 72.39, 72.17, 72.00, 71.75, 69.82, 69.56, 69.46, 69.19, 69.10, 68.74, 68.41, 68.21, 68.04, 67.90, 62.85, 62.67, 62.41, 51.88, 49.65, 49.26, 40.08, 39.64, 39.45, 39.26, 28.08, 26.40, 22.51, 22.38, 22.25, 22.10, 21.93. HRMS (ESI-TOF) calcd. for $C_{90}H_{146}N_6O_{66}$ $[M-2H]^{2-}$: 1183.4126, found: 1183.4122.

Biological Assays

Mice Immunity:

The immunogenicity of the synthetic glycan conjugates were tested by mice serum assay. In the experimental group, female 6- to 8-week-old BALB/c mice (n=5) were intramuscular administered conjugates containing 2 μg oligosaccharide in 100 μL PBS buffer at two-week intervals. In addition, all antigens were formulated with 2 μg C34 or alum adjuvant. Blank PBS buffer was injected into mice as the control group. After seven days of the third boost, blood samples of each mice were collected for serological immune analysis by glycan microarray.

Glycan Microarray for Immunogenicity Comparison.

N. meningitidis W135 capsular disaccharide to decasaccharide compounds 13, 16, 19, 22, 25, and 70 other amine-contained oligosaccharides were printed on the NHS-coated glass slide. Detail of the printing procedure was described in supporting information. The microarray was designed 16 grids in one slide, and 20 columns×8 rows in one grid. Printed slides were allowed reacting in an atmosphere of 80% humidity for an hour followed by desiccation overnight. Before serum antibody binding, the glycan microarrays were blocked with Superblock blocking buffer (Pierce) at 4° C. for one hour, followed by washing with PBST (PBS+0.05% tween 20) buffer twice.

To investigate the immunogenicity of oligosaccharides having different lengthes, all collected sera were diluted 200 fold in PBST buffer containing 3% BSA. The diluents were incubated with the microarray at 4° C. for one hour to allow the induced antibodies binding to the oligosaccharide. Excess serum antibodies were washed out and the microarrays were incubated with goat anti-mouse IgG antibody labeled with fluorescence as the 2nd antibody at 4° C. for 1 hour. The slides were washed thoroughly and scanned at 635 nm wavelength with a microarray fluorescence chip reader.

Figure 2:
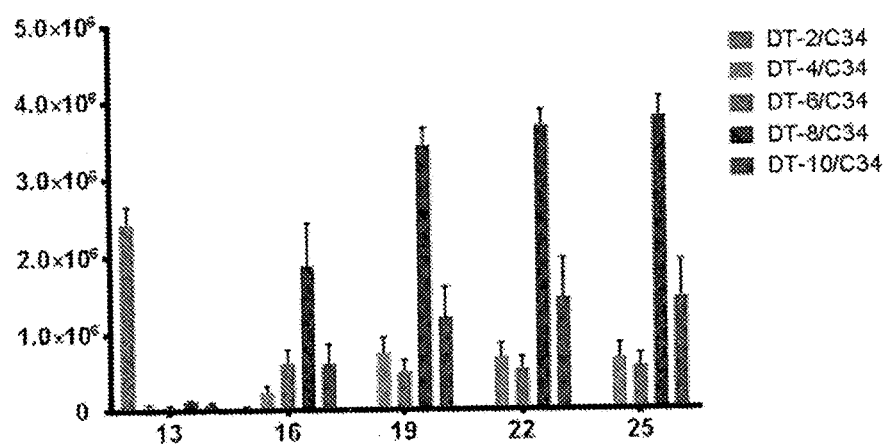
FIG. 2 shows immunogenicity comparison by microarray. Antibodies elicited by DT-4 or longer-oligosaccharide conjugates had higher binding affinity with longer oligosaccharide, and DT-8 recruited most abundant quantity of antibody.
Figure 3:
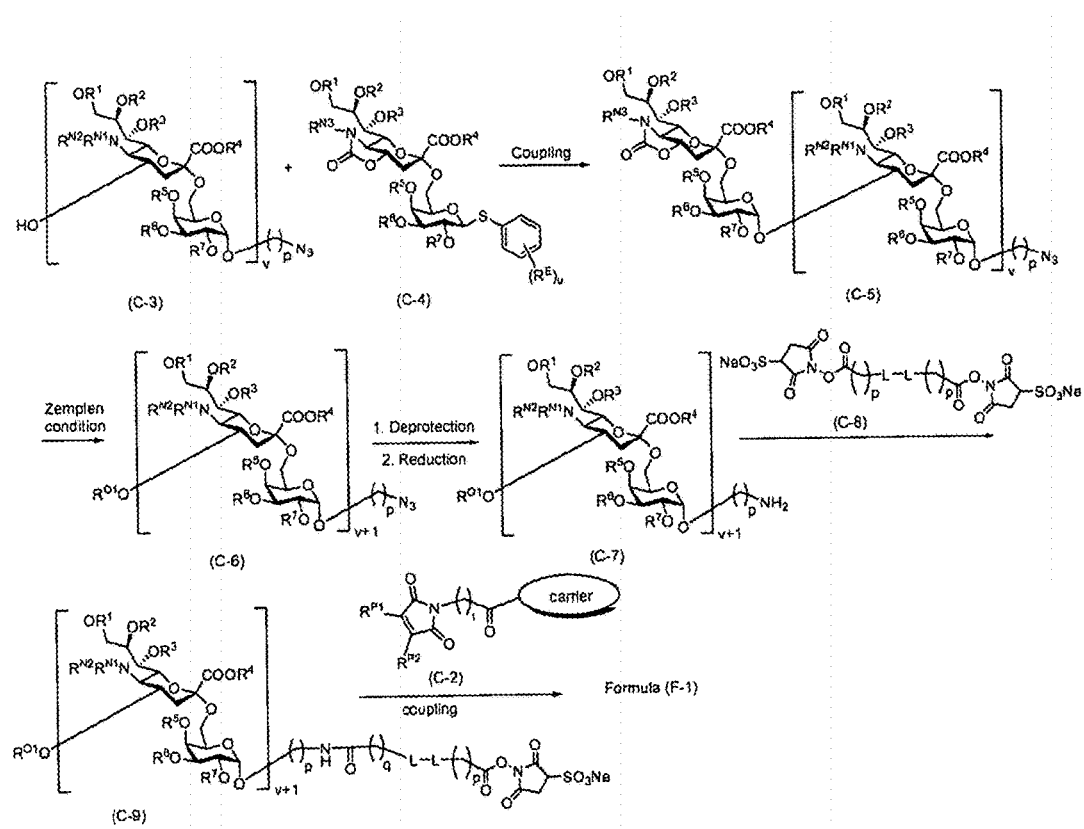
FIG. 3 shows exemplary synthesis of a compound of Formula (F-1).
Figure 6:
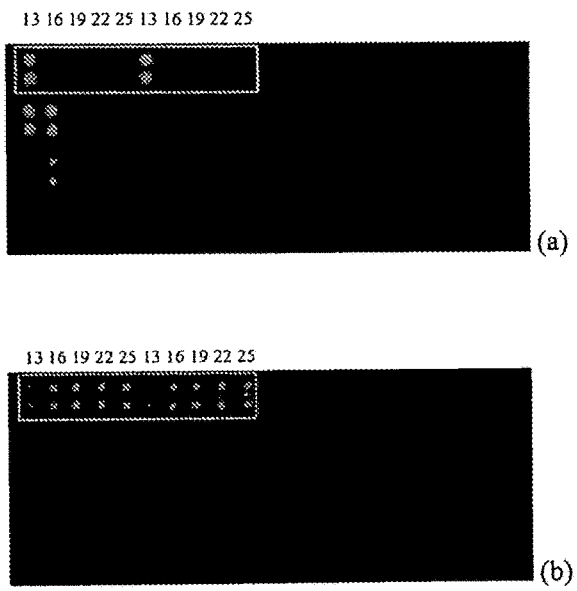
FIG. 6 shows immunogenicity comparison by microarray. (a) Antibody elicited by DT-2 bound to disaccharide compound 13 and other similar structure disaccharides on the chip. (b) Antibody elicited by DT-4 bound to compounds 16, 19, 22, and 25, and antibodies elicited by DT-6, DT-8, and DT-10 also performed the same pattern on the microarray. The antibody had high specificity against *N. meningitidis* serogroup W135 capsular oligosaccharide.

In the group employed C34 as an adjuvant, mice immunized with DT-2 elicited antibody against N. meningitidis serogroup W135 capsular disaccharide compound 13, but cannot cross react with tetrasaccharide or longer oligosaccharide. The antibody also recognized other similar disaccharide compounds on the chip, including Neu5Gc-α-(1→6)-Gal-α-(2→ and Neu5Ac-α-(1→6)-Gal-β-(2→. In contrast, the DT-4 induced antibodies can bind to N. meningitidis serogroup W135 capsular oligosaccharide compounds 16, 19, 22, and 25, but cannot recognize disaccharide compound 13 or other oligosaccharides on the slide (FIG. 6). Antibodies elicited from DT-6, DT-8, and DT-10 also performed the same pattern as DT-4 induced antibodies on the microarray. Therefore, it indicated that antibodies induced by DT-4, DT-6, DT-8, and DT-10 were very similar but different from antibodies induced by DT-2. Moreover, based on the fluorescence intensity analysis of glycan array, the common phenomenon is that DT-4, DT-6, DT-8 and DT-10 induced antibodies bound to longer oligosaccharide with higher affinity and DT-8 induced most abundant antibody titers (FIG. 2).

Figure 7:
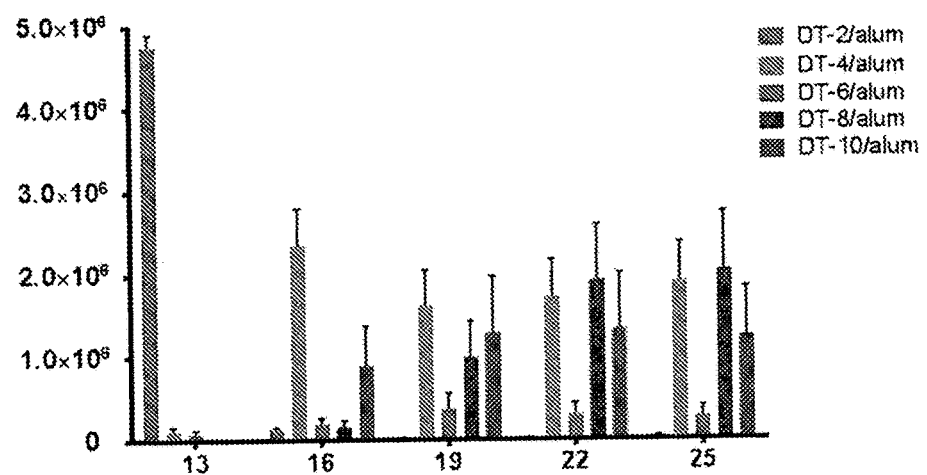
FIG. 7 shows the immunogenicity of various conjugates with alum adjuvant. With alum as adjuvant, the conjugates also performed the same pattern as with C34 adjuvant. DT-2 only recognized disaccharide compound, and DT-4 to DT-10 all recognized all oligosaccharide

In the group that employed alum as adjuvant, the antibodies induced by DT-4, DT-6, DT-8, and DT-10 also differed from DT-2 (FIG. 7), and the patterns were very similar with the vaccines that used C34 as an adjuvant. However, the induced antibodies titer of alum adjuvant was lower than C34.

When carbohydrate itself is used as an antigen, the immune system processes thymus-independent (TI) response, and IgM is the predominant antibody. On the other hand, the carbohydrate-protein conjugates elicit thymus-dependent (TD) response (a) K. E. Stein, D. A. Zopf, B. M. Johnson, C. B. Miller, W. E. Paul, J Immunol 1982, 128, 1350-1354; b) K. E. Stein, J Infect Dis 1992, 165 Suppl 1, S49-52), and the ratio of IgG and IgM changes. Here, DT-8/C34 induced serum antibodies were used for further analysis. DT-8 induced IgG and IgM antibody titers were determined by microarray. Then, the antibody titer was defined to be the most dilution fold when the fluorescence s/N ratio higher than 3. The results showed the anti-DT-8 IgG antibody titer was greater than 5×106. However, the titer of IgM antibody was only 200 (Table 2 and Table 3), indicating the use of TD-antigen resulted in switching antibody isotype.

Figure 8:
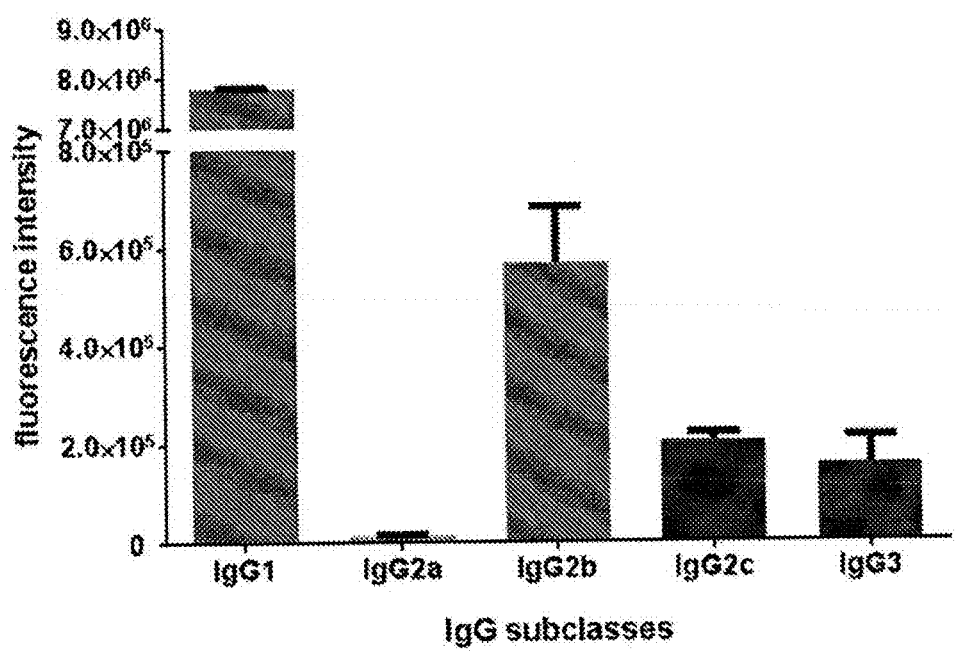
FIG. 8 shows IgG subclasses expression. As a TD-antigen, IgG1 was the major IgG subclasses group in the serum. In particular, there was a high level of IgG3 in the serum, which is the anti-carbohydrate response.
Figure 9:
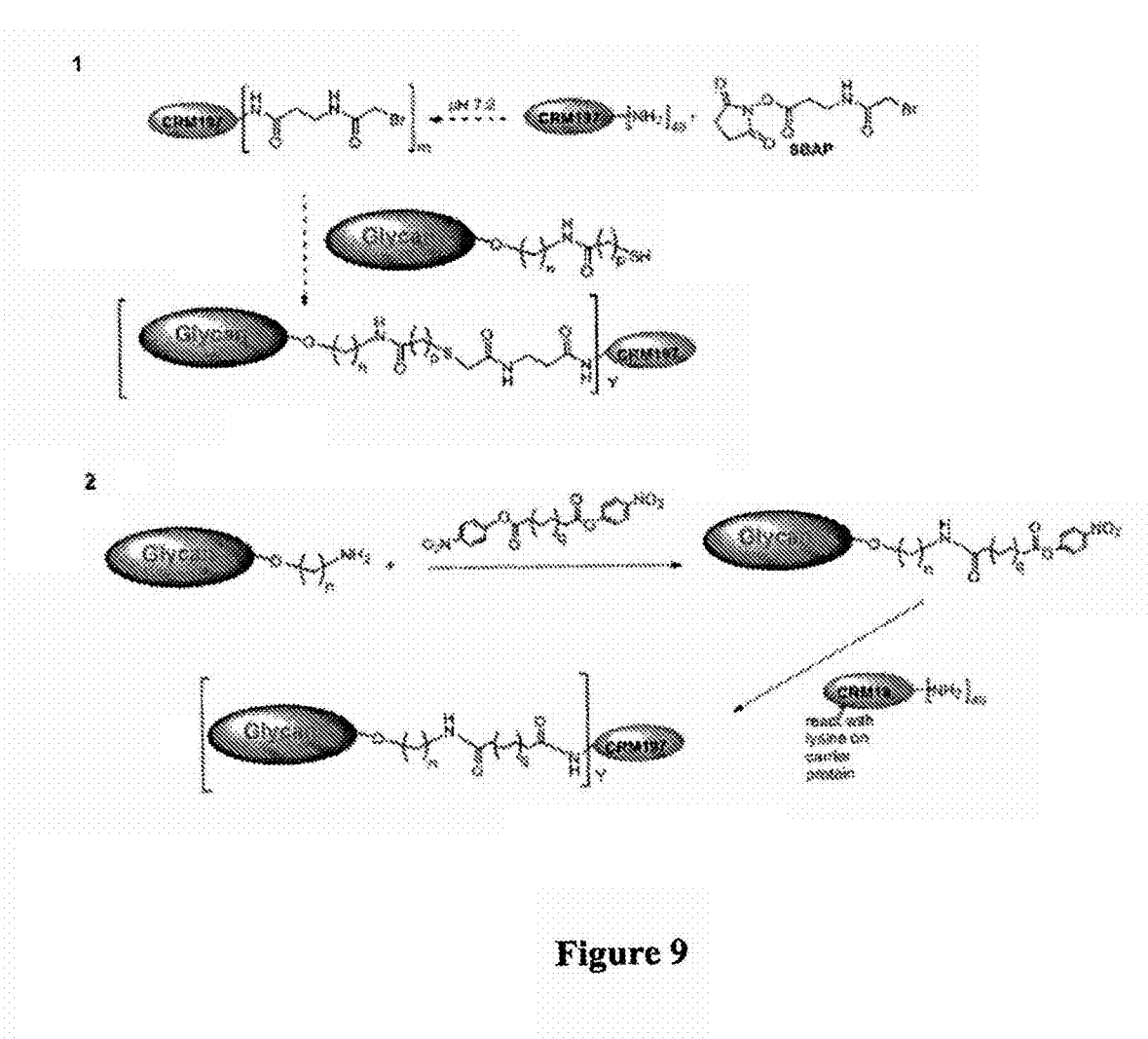
FIG. 9 shows the exemplified crosslinking reactions of an glycan conjugate with a carrier.

The IgG subclasses distribution was tested by incubating the oligosaccharide-coated microarray with $2^{nd}$ anti-mouse IgG1, IgG2a, IgG2b, IgG2c, and IgG3 antibodies after the serum antibody binding. The anti-IgG antibody in serum contained IgG1, IgG2b, IgG2c, and IgG3 but no significant IgG2a (FIG. 8). For the TD-antigen, the IgG1 subclass was highest in the serum. Particularly, IgG3, a typical anti-carbohydrate antibody (R. M. Perlmutter, D. Hansburg, D. E. Briles, R. A. Nicolotti, J. M. Davie, Journal of Immunology 1978, 121, 566-572), displayed a high level in the serum.

Serum Bactericidal Assay (SBA):

The −80° C. stock culture of *N. meningitidis* serogroup W135 strain was streaked and incubated overnight at 37° C.

TABLE 2

Mice serum IgG antibody titer.

IgG

| | dilute | | | | | | | | | |
|---|---|---|---|---|---|---|---|---|---|---|
| | 200x | | | | | 5000x | | | | |
| | DT-8-1 | DT-8-2 | DT-8-3 | DT-8-4 | DT-8-5 | DT-8-1 | DT-8-2 | DT-8-3 | DT-8-4 | DT-8-5 |
| 13 | 12.8 | 6.9 | 213.7 | 25.0 | 129.7 | 2.3 | 1.0 | 29.2 | 0.8 | 6.9 |
| 16 | 241.7 | 45.4 | 392.3 | 146.7 | 392.7 | 21.2 | 2.3 | 362.0 | 7.3 | 278.1 |
| 19 | 379.4 | 359.4 | 372.7 | 383.8 | 391.7 | 90.5 | 56.9 | 266.7 | 154.5 | 385.5 |
| 22 | 377.7 | 363.5 | 380.3 | 388.6 | 392.1 | 125.0 | 69.1 | 303.2 | 247.1 | 398.0 |
| 25 | 382.6 | 353.1 | 369.5 | 379.8 | 393.2 | 140.0 | 71.9 | 324.3 | 261.8 | 390.4 |

| | dilute | | | | | | | | | |
|---|---|---|---|---|---|---|---|---|---|---|
| | 25000x | | | | | 500000x | | | | |
| | DT-8-1 | DT-8-2 | DT-8-3 | DT-8-4 | DT-8-5 | DT-8-1 | DT-8-2 | DT-8-3 | DT-8-4 | DT-8-5 |
| 13 | 0.6 | 0.3 | 0.8 | 0.5 | 0.5 | 0.6 | 0.6 | 0.6 | 0.6 | 0.6 |
| 16 | 3.8 | 0.4 | 75.4 | 1.4 | 66.2 | 0.6 | 0.6 | 6.8 | 0.7 | 5.5 |
| 19 | 17.3 | 10.8 | 58.2 | 32.8 | 101.8 | 1.8 | 1.8 | 5.0 | 2.8 | 9.9 |
| 22 | 24.6 | 14.8 | 69.9 | 54.0 | 103.2 | 2.9 | 2.5 | 6.7 | 6.4 | 11.6 |
| 25 | 27.3 | 15.6 | 80.1 | 54.8 | 102.6 | 3.4 | 2.7 | 7.9 | 7.8 | 13.3 |

Glycan microarray was used to detect the production of IgG in the serum. The fluorescence signal to noise ratio (S/N) higher than 3 was detectable. The IgG antibody titer was higher than 500000.

TABLE 3

Mice serum IgM antibody titer.

IgM

| | dilute | | | | | | | | | |
|---|---|---|---|---|---|---|---|---|---|---|
| | 50x | | | | | 200x | | | | |
| | DT-8-1 | DT-8-2 | DT-8-3 | DT-8-4 | DT-8-5 | DT-8-1 | DT-8-2 | DT-8-3 | DT-8-4 | DT-8-5 |
| 13 | 6.3 | 8.4 | 1.0 | 0.5 | 3.6 | 1.1 | 1.3 | 0.1 | 0.6 | 0.5 |
| 16 | 7.5 | 8.6 | 8.1 | 1.2 | 0.6 | 1.0 | 1.4 | 0.9 | 0.2 | 0.1 |
| 19 | 8.6 | 8.5 | 8.0 | 6.3 | 5.8 | 1.1 | 1.0 | 0.9 | 0.2 | 0.7 |
| 22 | 8.6 | 8.3 | 9.1 | 6.6 | 5.8 | 1.0 | 1.3 | 0.9 | 0.6 | 0.8 |
| 25 | 8.4 | 7.2 | 9.1 | 7.2 | 6.3 | 1.0 | 1.2 | 0.9 | 0.7 | 0.9 |

Glycan microarray was used to detect the production of IgM in the serum. The fluorescence signal to noise ratio (S/N) higher than 3 was detectable. The IgM antibody titer was only 200. Together with the IgG antibody titer result, the oligosaccharide-protein conjugate is predominantly elicited IgG antibody.

were suspended in normal saline and adjusted to a concentration of $10^5$ cfu/ml. The antisera were two-fold serial diluted (1/2 to 1/32) with normal saline. The 10 µl of diluted antisera and 20 µl of bacteria suspension (2000 cfu) were incubated at 37° C. with 5% $CO_2$ for 15 minutes. After incubation, 25 µl of new born rabbit complement (Pel-Freez, USA) and 25 µl of normal saline were added and incubated for 1 hour at 37° C. with 5% $CO_2$. Then 2 μl of the reaction mixture was placed on the BHI-HS plate. After overnight culture, the numbers of surviving bacteria were counted. SBA titers were defined as the reciprocal of the serum dilution that resulted in ≥50% killing of the bacteria that achieved with the bacteria-complement-buffer controls.

The results showed that the bactericidal ability was roughly correlated with the antibody level in microarray. The SBA titer in mice immunized with DT-4 and DT-8 were 1/8 and 1/16 (Table 4). Note that the SBA titer of DT-10 is only 1/4.

TABLE 4

The serum bactericidal titers

| Sera | Titer |
|---|---|
| DT-2/C34 | n.d. |
| DT-4/C34 | 1/8 |
| DT-6/C34 | 1/8 |
| DT-8/C34 | 1/16 |
| DT-10/C34 | 1/4 |

Bactericidal tilter from sera of mice immunized with different length oligosaccharide conjugating with DT. Serum from mice immunized with DT-2 displayed no bactericidal activity. DT-4 or longer length oligosaccharide conjugates induced antibody with bactericidal ability.

All publications and patent applications cited in this specification are herein incorporated by reference as if each individual publication or patent application was specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The invention claimed is:

1. A homogeneous population of a glycan conjugate or a pharmaceutically acceptable salt thereof, comprising a carrier and a glycan wherein the glycan conjugate is of Formula (I-a)

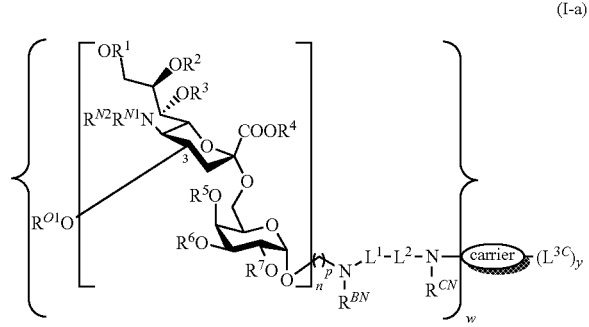

(I-a)

wherein
each instance of $R^1$, $R^2$, $R^3$, $R^4$, $R^5$, $R^6$, and $R^7$ is independently hydrogen, optionally substituted $C_{1-6}$ alkyl, or an oxygen protecting group; or optionally $R^1$ and $R^2$ are taken with the intervening atoms to form a heterocyclic ring; or optionally $R^2$ and $R^3$ are taken with the intervening atoms to form a heterocyclic ring; or optionally $R^5$ and $R^6$ are taken with the intervening atoms to form a heterocyclic ring; or optionally $R^6$ and $R^7$ are taken with the intervening atoms to form a heterocyclic ring; or $R^{N1}$ and $R^{O1}$ are taken together with the intervening atoms to form a heterocyclic ring;

each instance of $R^{N1}$, $R^{N2}$, and $R^{BN}$ is independently hydrogen, optionally substituted $C_{1-6}$ alkyl, optionally substituted acyl, or a nitrogen protecting group;

each instance of $R^{O1}$ is independently hydrogen, optionally substituted $C_{1-6}$ alkyl, or an oxygen protecting group;

each instance of L is independently a bond, —C(=O)—, —C(=O)NR$^{La}$—, —C(=O)S—, —C(=O)O—, —C(=S)NR$^{La}$—, trans-CR$^{Lb}$=CR$^{Lb}$—, cis-CR$^{Lb}$=CR$^{Lb}$—, —C≡C—, —C(R$^{Lb}$)$_2$O—, —C(R$^{Lb}$)$_2$NR$^{La}$—, —C(R$^{Lb}$)$_2$S—, —S(=O)$_2$O—, —S(=O)$_2$NR$^{La}$—, or an optionally substituted $C_{1-30}$ hydrocarbon chain, optionally wherein one or more carbon units of the hydrocarbon chain is replaced with —O—, —S—, —NR$^{La}$—, —C(=O)—, —NR$^{La}$C(=O)—, —NR$^{La}$C(=O)O—, —C(=O)NR$^{La}$—, —OC(=O)NR$^{La}$—, —SC(=O)—, —C(=O)S—, —OC(=O)—, —C(=O)O—, —NR$^{La}$C(=S)—, —C(=S)NR$^{La}$—, trans-CR$^{Lb}$=CR$^{Lb}$—, cis-CR$^{Lb}$=CR$^{Lb}$—, —C≡C—, —S(=O)$_2$O—, —OS(=O)$_2$—, —S(=O)$_2$NR$^{La}$—, or —NR$^{La}$S(=O)$_2$—, wherein each instance of $R^{La}$ is hydrogen, optionally substituted $C_{1-15}$ alkyl, or a nitrogen protecting group, or $R^{La}$ is joined with the adjacent carbon atom to form an optionally substituted heterocyclic ring, and wherein each occurrence of $R^{Lb}$ is independently selected from the group consisting of hydrogen, halogen, optionally substituted $C_{1-15}$ alkyl, optionally substituted alkenyl, optionally substituted alkynyl, optionally substituted carbocyclyl, optionally substituted heterocyclyl, optionally substituted aryl, and optionally substituted heteroaryl, or $R^{Lb}$ is joined with the adjacent carbon or nitrogen or oxygen atom to form an optionally substituted carbocyclic or heterocyclic ring, or two $R^{Lb}$ groups are joined to form an optionally substituted carbocyclic or optionally substituted heterocyclic ring;

each instance of $L^1$ is independently a bond, —O—, —S—, —NR$^{L1a}$—, —C(=O)—, —NR$^{L1a}$C(=O)—, —NR$^{L1a}$C(=O)O—, —C(=O)NR$^{L1a}$—, —OC(=O)NR$^{L1a}$—, —SC(=O)—, —C(=O)S—, —OC(=O)—, —C(=O)O—, —NR$^{L1a}$C(=S)—, —C(=S)NR$^{L1a}$—, trans-CR$^{L1b}$=CR$^{L1b}$—, cis-CR$^{L1b}$=CR$^{L1b}$—, —C≡C—, —OC(R$^{L1b}$)$_2$—, —C(R$^{L1b}$)$_2$O—, —NR$^{L1a}$C(R$^{L1b}$)$_2$—, —C(R$^{L1b}$)$_2$NR$^{L1a}$—, —SC(R$^{L1b}$)$_2$—, —C(R$^{L1b}$)$_2$S—, —S(=O)$_2$O—, —OS(=O)$_2$—, —S(=O)$_2$NR$^{L1a}$—, —NR$^{L1a}$S(=O)$_2$—, or an optionally substituted $C_{1-20}$ hydrocarbon chain, optionally wherein one or more carbon units of the hydrocarbon chain is replaced with —O—, —S—, —NR$^{L1a}$—, —C(=O)—, —NR$^{L1a}$C(=O)—, —NR$^{L1a}$C(=O)O—, —C(=O)NR$^{L1a}$—, —OC(=O)NR$^{L1a}$—, —SC(=O)—, —C(=O)S—, —OC(=O)—, —C(=O)O—, —NR$^{L1a}$C(=S)—, —C(=S)NR$^{L1a}$—, trans-CR$^{L1b}$=CR$^{L1b}$—, cis-CR$^{L1b}$=CR$^{L1b}$—, —C≡C≠, —S(=O)$_2$O—, —OS(=O)$_2$—, —S(=O)$_2$NR$^{L1a}$—, or —NR$^{L1a}$S(=O)$_2$—, wherein each instance of $R^{L1a}$ is hydrogen, optionally substituted $C_{1-6}$ alkyl, or a nitrogen protecting group, or $R^{L1a}$ is joined with the adjacent carbon atom to form an optionally substituted heterocyclic ring, and wherein each occurrence of $R^{L1b}$ is independently selected from the group consisting of hydrogen, halogen, optionally substituted $C_{1-10}$ alkyl, optionally substituted alkenyl, optionally substituted alkynyl, optionally substituted carbocyclyl, optionally substituted heterocyclyl, optionally substituted aryl, and optionally substituted heteroaryl, or $R^{L1b}$ is joined with the adjacent carbon or nitrogen or oxygen atom to form an optionally substituted carbocyclic or heterocyclic ring, or two $R^{L1b}$ groups are joined to form an optionally substituted carbocyclic or optionally substituted heterocyclic ring;

each instance of $L^2$ is independently a moiety derived from a crosslinking reagent capable of crosslinking the carrier and $L^1$-H;

each instance of $L^{3C}$ is independently a crosslinking reagent capable of crosslinking the carrier and $L^1$-H;

each instance of $R^{CN}$ is independently hydrogen, optionally substituted $C_{1-6}$ alkyl, optionally substituted acyl, or a nitrogen protecting group;

w is an integer of 1 to 100, inclusive; and y is 0 or an integer of 1 to 100, inclusive;

p is an integer of 1 to 10, inclusive; and n is an integer of 1 to 100, inclusive.

2. The glycan conjugate of claim 1, wherein w is an integer of 1 to 10, inclusive.

3. The glycan conjugate of claim 1, wherein y is 0 or an integer of 1 to 10, inclusive.

4. The glycan conjugate of any one of claims 1-3, wherein p is 5.

5. The glycan conjugate of any one of claims 1-3, wherein $R^1$, $R^2$, $R^4$, $R^5$, $R^6$, and $R^7$ are hydrogen.

6. The glycan conjugate of any one of claims 1-3, wherein $R^{N1}$ is acetyl.

7. The glycan conjugate of any one of claims 1-3, wherein $R^{N2}$ is hydrogen.

8. The glycan conjugate of any one of claim 1-3, wherein $R^{BN}$ is hydrogen.

9. The glycan conjugate of any one of claims 1-3, wherein $R^{CN}$ is hydrogen.

10. The glycan conjugate of any one of claims 1-3, wherein the carrier is a protein, a lipolized protein, a virus, a peptide comprising a T cell epitope, or a dendrimer of glycopeptides.

11. The glycan conjugate of claim 10, wherein the carrier is a toxin protein selected from the group consisting of diphtheria toxin cross-reacting material 197 (DT-CRM197), diphtheria toxoid, tetanus toxoid, and outer-membrane protein (OMP).

12. The glycan conjugate of claim 11, wherein the toxin protein is DT-CRM197.

13. A glycan conjugate of the formula:

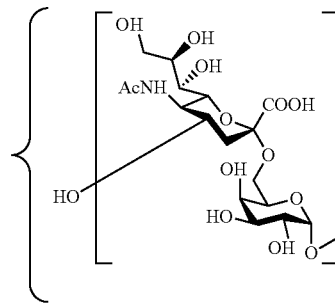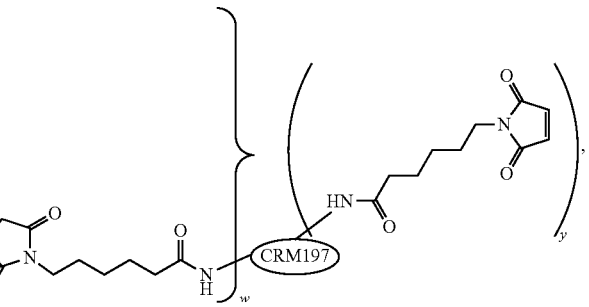

wherein n is an integer of 1 to 100, inclusive;

w is an integer of 1 to 100, inclusive; and y is 0 or an integer of 1 to 100, inclusive.

14. A glycan conjugate mixture comprising at least two of the glycan conjugates of claim 13.

15. The glycan conjugate mixture of claim 14, wherein the average value of w in the mixture is from about 1.0 to about 100.0.

16. The glycan conjugate mixture of claim 15, wherein the average value of w in the mixture is from about 1.0 to 10.0.

17. The glycan conjugate mixture of claim 16, wherein the average value of w is about 5.7, 4.9, 2.9, 2.8, or 3.1.

18. An immunogenic composition, comprising
(i) a glycan conjugate of any one of claim 1 or 13; and
(ii) a pharmaceutically acceptable excipient.

19. The immunogenic composition of claim 18, further comprising an adjuvant.

20. The immunogenic composition of claim 19, wherein the adjuvant is C34, 7DW8-5, C17, C23, C30, α-galactoceramide, Aluminum salt, Squalene, MF59, or QS-21.

21. A kit comprising a glycan conjugate according to any one of claims 1-3 or an immunogenic composition comprising a glycan conjugate according to any one of claim 1 or 13 with a pharmaceutically acceptable excipient, and instructions for use thereof.

22. A method of preparing a glycan conjugate of claim 1, comprising coupling a compound of Formula (C-1)

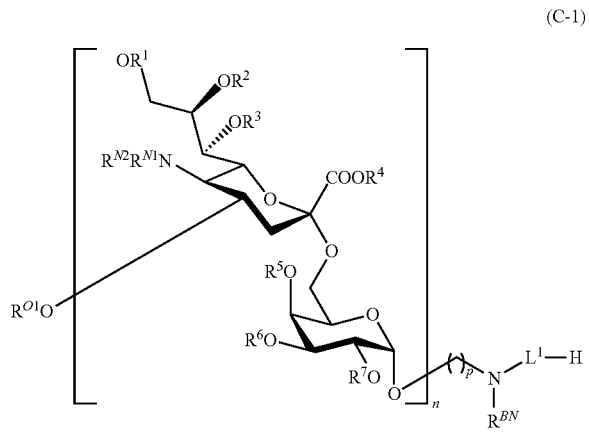

or a salt thereof, with a compound of the Formula (C-2)

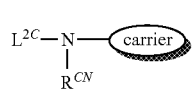
(C-2)

wherein
L$^{2C}$ is a crosslinking reagent capable of crosslinking an amino group and L$^1$-H.

23. The method of claim 22, wherein L$^{2C}$ is a crosslinking reagent capable of crosslinking an amine group and —SH.

24. The method of claim 22, wherein L$^{2C}$ is one of the following formulae:

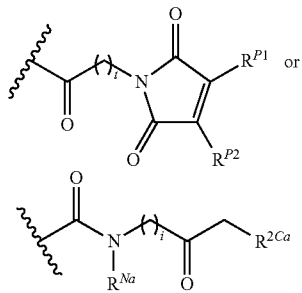

or a salt thereof,
wherein
each instance of R$^{P1}$ and R$^{P2}$ are each independently hydrogen, halogen, or optionally substituted C$_{1-6}$ alkyl;
each instance of R$^{2Ca}$ is a leaving group selected from selected from —Br, —Cl, —I, —OS(=O)$_2$R$^{2CO}$, or —OS(=O)R$^{2CO}$, wherein R$^{2CO}$ is selected from the group consisting of optionally substituted alkyl, optionally substituted alkenyl, optionally substituted alkynyl, optionally substituted carbocyclyl, optionally substituted heterocyclyl, optionally substituted aryl, and optionally substituted heteroaryl; and
each of t and i is independently an integer of 1 to 8, inclusive.

25. The method of any one of claim 22-24, wherein the molar ratio of the compound of Formula (C-1) to the compound of Formula (C-2) is from about 1 to about 100.

26. The method of any one of claims 22-25, wherein the coupling is carried out in the presence of phosphate buffered saline (PBS).

27. The method of any one of claims 22-26, further comprising glycosylating a compound of Formula (C-3)

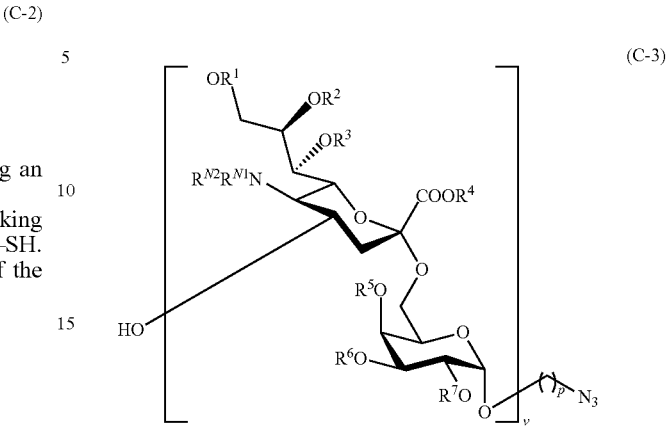

with a compound of Formula (C-4)

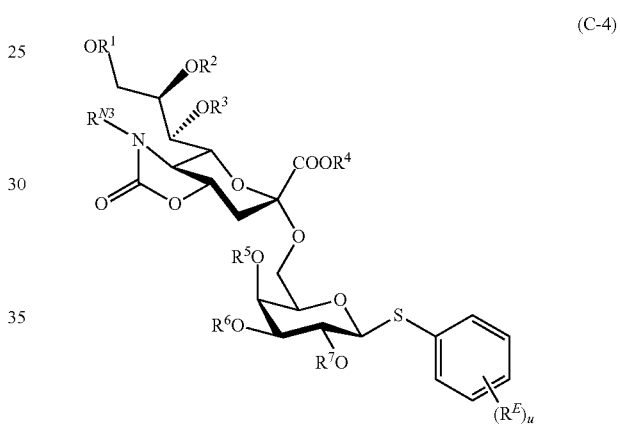

to give a compound of Formula (C-5)

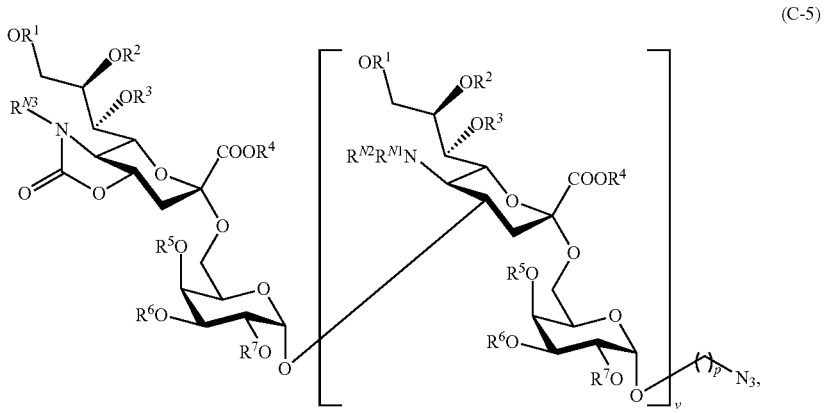

wherein
v is an integer of 1 to 99, inclusive;
u is 0, 1, 2, 3, 4, or 5;
each occurrence of R$^E$ is independently halogen, —CN, —NO$_2$, —N$_3$, optionally substituted alkyl, optionally substituted alkenyl, optionally substituted alkynyl, optionally substituted carbocyclyl, optionally substituted phenyl, optionally substituted heterocyclyl, optionally substituted heteroaryl, —OR$^{CE}$, —N(R$^{CE}$)$_2$, —SR$^E$, —C(=O)R$^{CE}$, —C(=O)OR$^{CE}$, or —C(=O)N(R$^{CE}$)$_2$, wherein each R$^{CE}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl; or an oxygen protecting group when attached to an oxygen, or a nitrogen protecting group when attached to nitrogen, or a sulfur protecting group when attached to sulfur; and R$^{N3}$ is independently hydrogen, optionally substituted alkyl, or a nitrogen protecting group.

28. The method of claim 27, further comprising reacting the compound of Formula (C-5) in the presence of a base to give a compound of Formula (C-6)

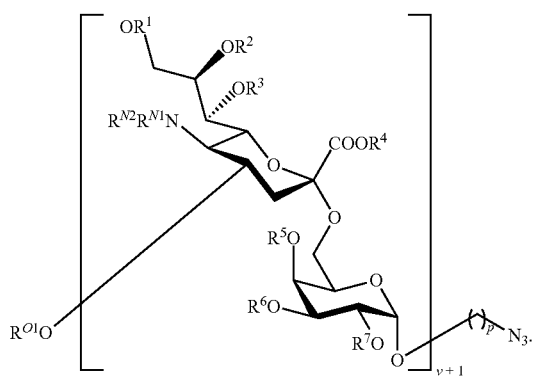

(C-6)

29. The method of claim 28, wherein the base is NaOCH3.

30. The method of claim 28, further comprising reacting the compound of Formula (C-6) with a reducing agent to give a compound of Formula (C-7)

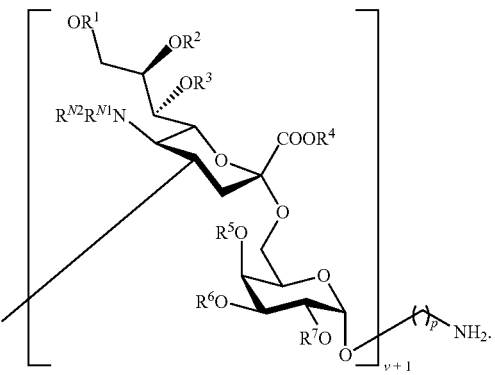

(C-7)

31. The method of any one of claim 30, further comprising (a) activating a compound of Formula (C-7) to give a compound of Formula (C-1); and (b) activating a carrier to give a compound of Formula (C-2).

32. The kit of claim 21, wherein the immunogenic composition further comprises an adjuvant.

33. The kit of claim 32, wherein the adjuvant is selected from C34, 7DW8-5, C17, C23, C30, α-galactoceramide, Aluminum salt, Squalene, MF59, or QS-21.

* * * * *